United States Patent
Kamenecka et al.

(10) Patent No.: US 9,586,928 B2
(45) Date of Patent: Mar. 7, 2017

(54) MODULATORS OF THE NUCLEAR HORMONE RECEPTOR ROR

(75) Inventors: Theodore Mark Kamenecka, Palm Beach Gardens, FL (US); Patrick R. Griffin, Jupiter, FL (US); Youseung Shin, Dublin, OH (US); Yuanjun He, Palm Beach Gardens, FL (US); Anne-Laure Blayo, Jupiter, FL (US); Brent R. Lyda, Jupiter, FL (US); Marcel Koenig, Palm Beach Gardens, FL (US); Naresh Kumar, Indianapolis, IN (US); Thomas Burris, Palm Beach Gardens, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/118,116

(22) PCT Filed: May 16, 2012

(86) PCT No.: PCT/US2012/038119
§ 371 (c)(1),
(2), (4) Date: Mar. 4, 2014

(87) PCT Pub. No.: WO2012/158784
PCT Pub. Date: Nov. 22, 2012

(65) Prior Publication Data
US 2014/0187554 A1   Jul. 3, 2014

Related U.S. Application Data

(60) Provisional application No. 61/486,459, filed on May 16, 2011.

(51) Int. Cl.
| C07D 213/74 | (2006.01) |
| C07D 213/36 | (2006.01) |
| C07D 295/096 | (2006.01) |
| C07D 295/185 | (2006.01) |
| C07D 295/195 | (2006.01) |
| C07D 295/26 | (2006.01) |

(Continued)

(52) U.S. Cl.
CPC .......... *C07D 317/50* (2013.01); *A61K 31/495* (2013.01); *A61K 31/496* (2013.01); *A61K 31/5375* (2013.01); *A61K 31/5377* (2013.01); *A61K 45/06* (2013.01); *C07D 207/09* (2013.01); *C07D 209/14* (2013.01); *C07D 211/22* (2013.01); *C07D 213/36* (2013.01); *C07D 213/61* (2013.01); *C07D 213/64* (2013.01); *C07D 213/74* (2013.01); *C07D 213/82* (2013.01); *C07D 215/12* (2013.01); *C07D 233/61* (2013.01); *C07D 277/28* (2013.01); *C07D 277/64* (2013.01); *C07D 295/096* (2013.01); *C07D 295/185* (2013.01); *C07D 295/205* (2013.01); *C07D 295/215* (2013.01); *C07D 295/26* (2013.01); *C07D 307/24* (2013.01); *C07D 317/58* (2013.01); *C07D 319/20* (2013.01); *C07D 333/20* (2013.01); *C07D 333/34* (2013.01); *C07D 401/12* (2013.01)

(58) Field of Classification Search
None
See application file for complete search history.

(56) References Cited

U.S. PATENT DOCUMENTS

| 6,281,214 B1 | 8/2001 | Akasaka et al. |
| 7,115,741 B2 * | 10/2006 | Levy .................... C07D 495/04 544/278 |

(Continued)

FOREIGN PATENT DOCUMENTS

| EP | 2368886 A1 | 9/2011 |
| WO | WO-02/058690 A2 | 8/2002 |

(Continued)

OTHER PUBLICATIONS

Kumar et al. ACS Chem. Biol. 2012, 7, 672-677.*
Ren et al. Eur. J. Org. Chem. 2010, 2372-2378.*
Cha, H.-J., et al., "Ursolic acid-induced down-regulation of MMP-9 gene is mediated through the nuclear translocation of glucocorticoid receptor in HT1080 human fibrosarcoma cells", *Oncogene*, 16(6), (1998), 771-778.
Chopra, A. R., et al., "Absence of the SRC-2 Coactivator Results in a Glycogenopathy Resembling Vov Gierke's Disease", *Science*, 322(5906), (2008), 1395-1399.
Chou, T. C., et al., "Quantitative analysis of dose-effect relationships: the combined effects of multiple drugs or enzyme inhibitors", *Advances in Enzyme Regulation*, 22, (1984), 27-55.
Fujita-Sato, S., et al., "Structural Basis of Digoxin That Antagonizes RORγt Receptor Activity and Suppresses Th17 Cell Differentiation and Interleukin (IL)-17 Production", *The Journal of Biological Chemistry*, 286(36), (2011), 31409-31417.
Huffman, M. A., et al., "Lithium Alkoxides of Cinchona Alkaloids as Chiral Controllers for Enantioselective Acetylide Addition to Cyclic N-Acyl Ketimines", *Journal of Organic Chemistry*, 60(6), (1995), 1590-1594.

(Continued)

Primary Examiner — Emily Bernhardt
(74) Attorney, Agent, or Firm — Geoffrey K. Cooper; Thomas Fitting

(57) ABSTRACT

The invention provides small molecule modulators of retinoic acid receptor-related orphan receptors such as RORα, RORβ, or RORγ, of formula

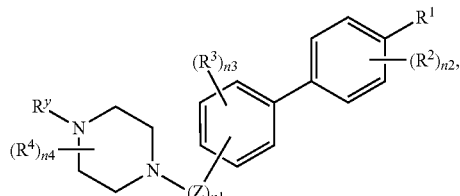

with the variable atoms as defined herein and $R^1$ comprising a hydroxyl- or alkoxyl-substituted fluoroalkyl group. Compounds of the invention can be effective modulators at concentrations ineffective to act on LXR receptors, or on other nuclear receptors, or other biological targets. Methods of modulation the RORs and methods of treating metabolic disorders, immune disorders, cancer, and CNS disorders wherein modulation of an ROR is medically indicated are also provided.

1 Claim, 17 Drawing Sheets

(51) Int. Cl.

| | | |
|---|---|---|
| C07D 277/64 | (2006.01) | |
| C07D 207/09 | (2006.01) | |
| C07D 211/22 | (2006.01) | |
| C07D 233/61 | (2006.01) | |
| C07D 317/50 | (2006.01) | |
| C07D 213/82 | (2006.01) | |
| C07D 215/12 | (2006.01) | |
| C07D 317/58 | (2006.01) | |
| C07D 319/20 | (2006.01) | |
| C07D 333/20 | (2006.01) | |
| C07D 333/34 | (2006.01) | |
| C07D 401/12 | (2006.01) | |
| C07D 277/28 | (2006.01) | |
| C07D 209/14 | (2006.01) | |
| C07D 295/205 | (2006.01) | |
| C07D 295/215 | (2006.01) | |
| C07D 213/61 | (2006.01) | |
| C07D 213/64 | (2006.01) | |
| C07D 307/24 | (2006.01) | |
| A61K 31/495 | (2006.01) | |
| A61K 31/496 | (2006.01) | |
| A61K 31/5375 | (2006.01) | |
| A61K 31/5377 | (2006.01) | |
| A61K 45/06 | (2006.01) | |

(56) References Cited

U.S. PATENT DOCUMENTS

| | | |
|---|---|---|
| 2003/0181420 A1 | 9/2003 | Bayne et al. |
| 2006/0111440 A1 | 5/2006 | Gauthier et al. |
| 2006/0258672 A1* | 11/2006 | Barbosa ............... C07D 239/42 514/253.01 |
| 2007/0154487 A1 | 7/2007 | Littman et al. |

FOREIGN PATENT DOCUMENTS

| | | |
|---|---|---|
| WO | WO-2011/115892 A1 | 9/2011 |
| WO | WO-2012/158784 A2 | 11/2012 |
| WO | WO-2012/158784 A3 | 11/2012 |

OTHER PUBLICATIONS

Huh, J. R., et al., "Digoxin and its derivatives suppress $T_H17$ cell differentiation by antagonizing RORγt activity", *Nature*, 472(7344), (2011), 486-490.
Ivanov, I., et al., "The Orphan Nuclear Receptor RORγt Directs the Differentiation Program of Proinflammatory IL-17$^+$ T Helper Cells", *Cell*, 126, (2006), 1121-1133.
Jetten, A. M., et al., "Retinoid-related orphan receptors (RORs): critical roles in development, immunity, circadian rhythm, and cellular metabolism.", *Nuclear Receptor Signaling*, 7, e003, (2009), 1-32.
Jin, L., et al., "Structural Basis for Hydroxycholesterols as Natural Ligands of Orphan Nuclear Receptor RORγ", *Molecular Endocrinology*, 25(5), (2010), 923-929.
Kassi, E., et al., "Ursolic acid triggers apoptosis and Bcl-2 downregulation in MCF-7 breast cancer cells.", (Abstract Only), *Cancer Invest.*, 27(7), (2009), 1 pg.
Kumar, N., et al., "Identification of SR3335 (ML-176): a Synthetic RORα Selective Inverse Agonist.", *ACS Chem. Biol.*, 6(3), (2011), 218-222.
Kumar, N., et al., "The Benzenesulfoamide T0901317 [N-(2,2,2-Trifluoroethyl)-N-[4-[2,2,2-trifluoro-1-hydroxy-1-(trifluoromethyl)ethyl]phenyl]-benzenesulfonamide] is a Novel Retinoic Acid Receptor-Related Orphan Receptor-α/γ Inverse Agonist.", *Mol Pharmacol.*, 77(2), (Feb. 2010), 228-236.
Nakae, S., et al., "Suppression of Immune Induction of Collagen-Induced Arthritis in IL-17-Deficient Mice", *Journal of Immunology*, 171(11), (2003), 6173-6177.
Solt, L. A., et al., "Suppression of TH17 differentiation and autoimmunity by a synthetic ROR ligand.", *Nature*, 472(7344), (2011), 491-494.
Tucker, T. J., et al., "Synthesis of a Series of 4-(Arylethynyl)-6-chloro-4-cyclopropyl-3,4-dihydroquinazolin-2(1H)-ones as Novel Non-nucleoside HIV-1 Reverse Transcriptase inhibitors", *Journal of Medicinal Chemistry*, 37(15), (1994), 2437-2444.
Wang, Y., et al., "Modulation of Retinoic Acid Receptor-related Orphan Receptor α and γ Activity by 7-Oxygenated Sterol Ligands", *The Journal of Biological Chemistry*, 285(7), (2010), 5013-5025.
Xu, T., et al., "Ursolic acid suppresses interleukin-17 (IL-17) production by selectively antagonizing the function of RORγt protein", *The Journal of Biological Chemistry*, 286(26), 22707-22710.
Yang, X. O., et al., "TH17 lineage differentiation is programmed by orphan nuclear receptors RORα and RORγ", *Immunity*, 28, (2008), 29-39.
CID 46829258, [Online]. Retrieved from the internet: <http://pubchem.ncbi.nlm.nih.gov/summary/summary.cgi?cid=46829258>, (Jul. 28, 2010), 1 pg.
CID 46829260, [Online]. Retrieved from the internet: <http://pubchem.ncbi.nlm.nih.gov/summary/summary.cgi?cid=46829260& loc=ec_rcs>, (Jul. 28, 2010), 1 pg.
"International Application Serial No. PCT/US2012/038119, International Search Report mailed Aug. 20, 2012", 3 pgs.
"International Application Serial No. PCT/US2012/038119, International Preliminary Report on Patentability mailed Nov. 28, 2013", 6 pgs.
Stehlin-Gaon, Catherine, et al., "All-trans retinoic acid is a ligand for the orphan nuclear receptor RORB", *Nature Structural Biology*, 10(10), (2003), 820-825.
Wang, Yongjun, et al., "Identification of SR1078, a Synthetic Agonist for the Orphan Nuclear Receptors RORaiph and RORγ", *ACS Chem. Biol.*, 5 (11), (Aug. 24, 2010), 1029-1034.

\* cited by examiner

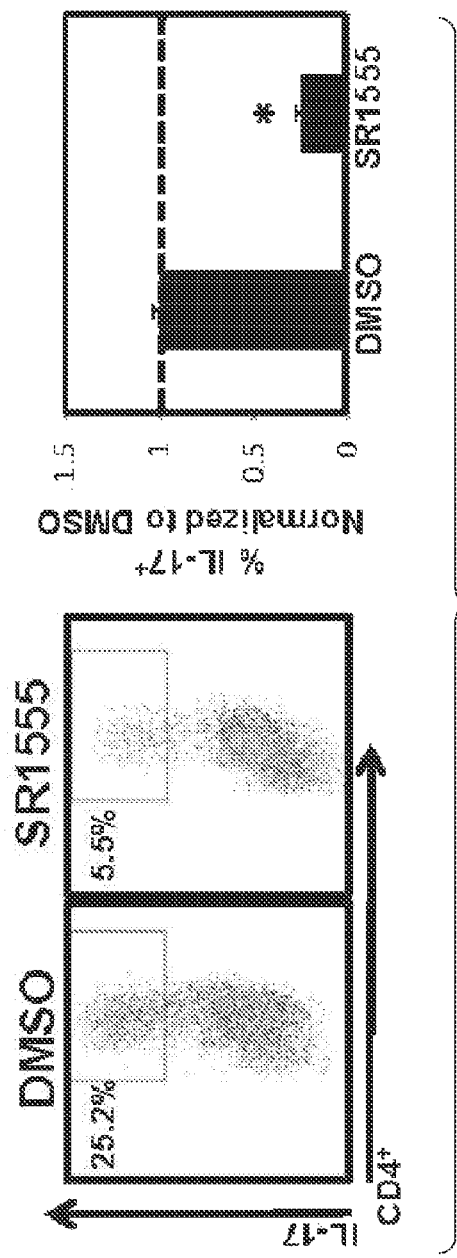
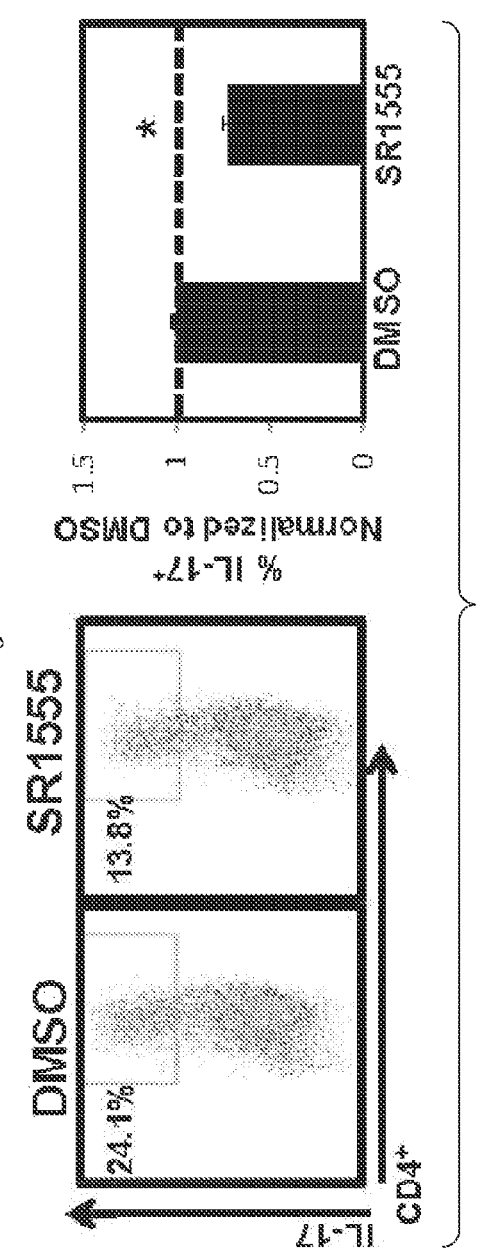
Fig. 2B
Fig. 2C

MODULATORS OF THE NUCLEAR HORMONE RECEPTOR ROR

CROSS-REFERENCE TO RELATED APPLICATIONS

This application is a national stage application under 35 U.S.C. §371 of PCT/US2012/038119, filed May 16, 2012, and published as WO 2012/158784 on Nov. 22, 2012, which claims the benefit of priority of U.S. Provisional Application Ser. No. 61/486,459, filed May 16, 2011, entitled "MODULATORS OF THE NUCLEAR HORMONE RECEPTOR ROR," which applications and publication are incorporated by reference as if reproduced herein and made a part hereof in their entirety, and the benefit of priority of each of which is claimed herein.

STATEMENT OF GOVERNMENT SUPPORT

This invention was made with government support under MH084512, MH074404, DK080201, MH092769 and GM084041 awarded by the National Institutes of Health. The government has certain rights in the invention.

BACKGROUND

Retinoic acid receptor-related orphan receptors (RORs) are nuclear receptors that are constitutively active and can modulate gene transcription in the absence of binding endogenous ligand. Crystal structures of the ligand binding domain of RORs have found cholesterol and cholesterol sulfate in the ligand binding pocket. It is not clear if these ligands act as modulators or if this finding is an artifact of the purification and crystallization process. More recently, we have shown the oxygenated derivatives of cholesterol, 7-α hydroxycholesterol as an example, are capable of modulating the activity of the RORs. However, it is still unclear if the oxysterols are endogenous ligands for the RORs. It is important to note that this subfamily of nuclear receptors was named not from any known propensity to interact with retinoids, but from sequence homology with retinoic acid receptors (RARs). Recently, it has been found that a high affinity ligand of RORα and RORγ, compound T1317, which was developed previously as a LXR modulator, upon binding to the receptors modulates the receptor's ability to interact with transcriptional cofactor proteins and results in repression of ROR target genes.

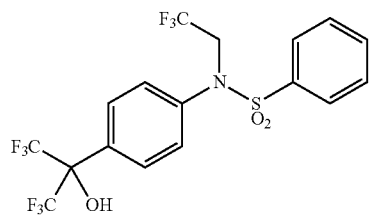

T1317

Binding of the ligand T1317 was found to repress ROR α/γ dependent transactivation of ROR-responsive reporter genes, and in HepG2 cells reduced the recruitment of steroid receptor coactivator-2 (SRC-2) by RORα at an endogenous ROR target gene. This ligand exhibited a degree of selectivity among this class of nuclear receptors, as it was reported to be inactive versus RORβ. Unlike RORα and RORγ, RORβ appears to not be constitutively active, thus antagonists and inverse agonists have no effect on this receptor's basal activity. However, we have demonstrated that radiolabeled T1317 does in fact bind to RORβ. Thus, in the presence of a yet to be discovered endogenous agonist of RORβ, T1317 and analogs of it, may prove effective at repression this receptor. Likewise, analogs of T1317 that are agonists, or agonists derived from other chemical scaffolds, are likely to be effective at modulating the activity of RORβ. Each of the three major ROR isoforms has multiple variants. See N. Kumar, et al., *Mol. Pharm.*, 77:228-236, 2010. Accordingly, RORs are an attractive target for small molecule drugs useful for therapeutic intervention for metabolic and immune disorders, cancer, and CNS disorders as well as other diseases where the RORs play a role.

SUMMARY

In various embodiments, the invention is directed to compounds having retinoic acid receptor-related orphan receptor (ROR) modulating bioactivities and methods of modulating ROR comprising contacting the receptor with an effective amount of a compound. In various embodiments, the compounds are sulfonamides and carboxamide derivatives of substituted anilines, which are small molecule modulators of one or more isoforms of ROR. In various embodiments, the compounds are agonists of an ROR. In other embodiments, the compounds are repressors or inverse agonists, or antagonists of an ROR. In various embodiments, the compounds are selective modulators of an ROR with little or no effect on the NR1H nuclear receptor subfamily, specifically LXRα and LXRβ, FXR.

In various embodiments, the invention provides a method of modulating the bioactivity of an ROR, comprising contacting the ROR with an effective amount of a compound of formula (I) as shown below, wherein the compound is an agonist or an activator, or is a repressor, inverse agonist, or antagonist, of a receptor comprising any sequence variant of any isoform of the ROR subfamily, including RORα, RORβ, or RORγ.

In various embodiments, the invention provides a ROR-modulatory compound of formula (I)
wherein

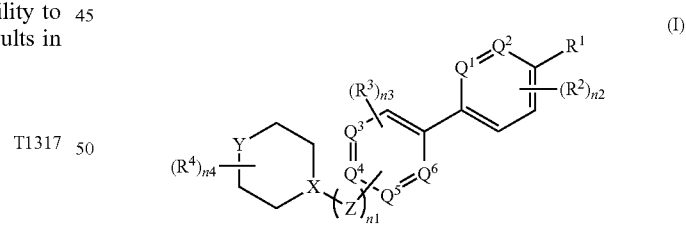

(I)

X is N or CR$^x$, wherein R$^x$ is H or (C1-C4)alkyl;

Y is C(R$^y$)$_2$, NR$^y$, or O, wherein R$^y$ is independently H, OR, or (C1-C4) alkyl optionally mono- or independently multi-substituted with R, OR, oxo, or halo; or R$^y$ is independently aryl, arylalkyl, heterocyclyl, heterocyclylalkyl, heteroaryl, or heteroarylalkyl, wherein any of said aryl, arylalkyl, heterocyclyl, heterocyclylalkyl, heteroaryl, or heteroarylalkyl is optionally mono- or independently multi-substituted with cyano, nitro, halo, (C1-C4)alkyl, (C1-C4) fluoroalkyl, cycloalkyl, heterocyclyl, aryl, or heteroaryl, any of which alkyl, fluoroalkyl, cycloalkyl, heterocyclyl, aryl, or heteroaryl is optionally mono- or independently multi-substituted with R, OR or halo; or R$^y$ is independently COR$^{yy}$ wherein $R^{yy}$ is independently (C1-C4)alkyl, OR, $NR_2$, heterocyclyl, aryl, or heteroaryl, wherein any heterocyclyl, aryl, or heteroaryl is optionally mono- or independently multi-substituted with (C1-C4)alkyl, halo, or cyano;

Z is independently CHR, O, NR, C(O), or absent, provided that when n1=2, both Z are not CO, O, or NR;

$Q^1$ and $Q^2$ are independently CH, $CR^2$, or N, provided that both $Q^1$ and $Q^2$ are not N;

$Q^3$, $Q^4$, $Q^5$, and $Q^6$ are independently CH, $CR^3$, or N, provided that no more than two of $Q^3$, $Q^4$, $Q^5$, and $Q^6$ are N;

$R^1$ is (C1-C4)alkyl optionally substituted with OR, or aryl-(C1-C4)alkyl optionally substituted with OR, or (C1-C4)fluoroalkyl optionally substituted with OR, or aryl-(C1-C4)fluoroalkyl optionally substituted with OR; or $R^1$ is OR; or $R^1$ is $NHC(O)R^a$ or $NHSO_2R^a$ wherein $R^a$ is (C1-C4) alkyl, aryl, arylalkyl, or (C1-C4)alkoxy wherein any aryl is optionally substituted with (C1-C4)alkyl or (C1-C4)alkoxy; $SO_2NR_2$; or $R^1$ is $C(O)R^b$ wherein $R^b$ is OH, $NR_2$, (C1-C4) alkoxy, aryl optionally substituted with heteroaryl; or heteroaryl;

$R^2$ is independently halo, (C1-C4)alkyl, or (C1-C4) alkoxy;

$R^3$ is independently halo, (C1-C4)alkyl, or (C1-C4) alkoxy;

$R^4$ is independently halo, (C1-C4)alkyl, or (C1-C4) alkoxy;

R is independently H, (C1-C4)alkyl, aryl, arylalkyl, alkanoyl, aroyl, or heteroaroyl;

n1 is 0, 1 or 2;
n2 is 0-4;
n3 is 0-4;
n4 is 0-8;
or any pharmaceutically acceptable salt thereof.

In various embodiments, pharmaceutical compositions comprising a compound of the invention and a pharmaceutically acceptable excipient are provided. The composition can be adapted for administration to a patient as a dosage form of the invention, such as a orally or parentally administered dosage form.

In various embodiments, pharmaceutical combinations comprising a compound of the invention and a second medicament are provided.

In various embodiments, a method of treating a metabolic or immune disorder wherein modulation of an ROR is medically indicated, is provided. In various embodiments of an inventive method of treatment of a patient, such as a human, the ROR is modulated by a compound of the invention at a dose ineffective to modulate any other nuclear receptor, such as LXRα or LXRβ, in the patient, providing an effect free of side effects resulting from modulation of nuclear receptors other than ROR. In various embodiments, the effective amount of the compound of the invention does not affect any other nuclear receptor, any G-protein coupled receptor (GPCR), any kinase, protease, or other enzyme, or any other cellular component or system at a concentration effective to modulate the effect of at least one of RORα, RORβ, or RORγ.

In various embodiments, the invention provides novel compounds for carrying out the methods of the invention.

In various embodiments, the invention provides a dosage form adapted for administration to a patient afflicted with a malcondition comprising a metabolic or an immune disorder, cancer, or a central nervous system (CNS) disorder, wherein the dosage form comprises a capsule, a tablet, a liquid or dispersed oral formulation, or a formulation adapted for parenteral administration comprising a novel compound of the invention.

Accordingly, in various embodiments the invention provides technical solutions to the problem of modulating RORs, which offers potential for the development of pharmaceutical molecular entities useful in the treatment of human diseases and disorders in which modulation of an ROR is clinically indicated, including a metabolic or an immune disorder, cancer, or a CNS disorder.

FIG. 6 depicts data showing suppression of constitutive activity of RORγ by SR2211: 293T cells were cotransfected with (a) Gal4-RORa, (b) Gal4-RORg, (c) Gal4-LXRa, (d) Gal4-FXR, or (e) Gal4-VP16, along with a UAS-luciferase plasmid. The cells were treated for 20 hr with indicated concentration of SR2211 or positive controls SR3335 (a), T1317 (c) and GW4064 (d). Relative change was determined by normalizing to cells treated with vehicle. Each data point was performed in 6 replicates and represented as mean±SEM, n=6.

FIG. 7 depicts data showing that SR2211 modulates full length RORγ in reporter assays: 293T cells were cotransfected with 5×RORE-luc and either (a) empty vector or (b) RORγ; IL-17-Luc reporter and either (c) RORα or (d) RORγ; (e) ABCA1 luciferase and LXRα followed by treatment with indicated concentration of SR2211 for 20 hr. The luciferase activity was measured. Relative change was determined by normalizing to vehicle treated cells. Each data point was measured in 4-6 replicates and presented as mean±SEM.

Figure 8A:
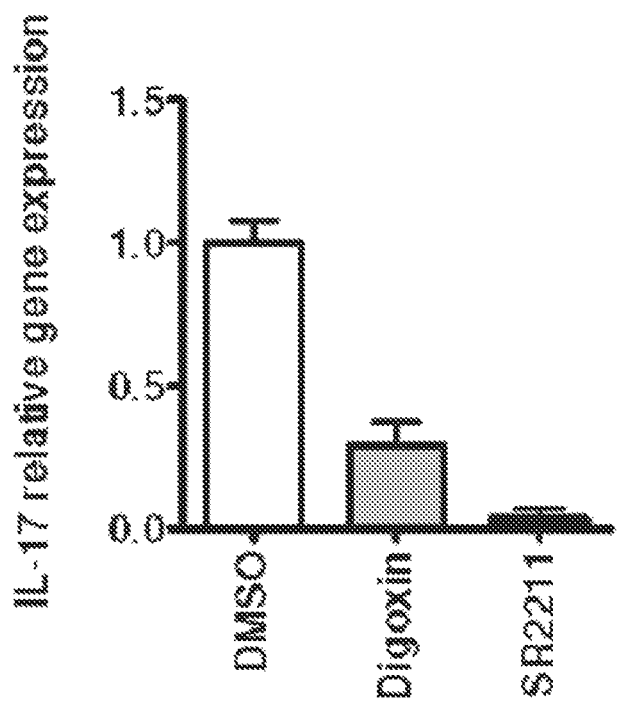
Figure 8B:
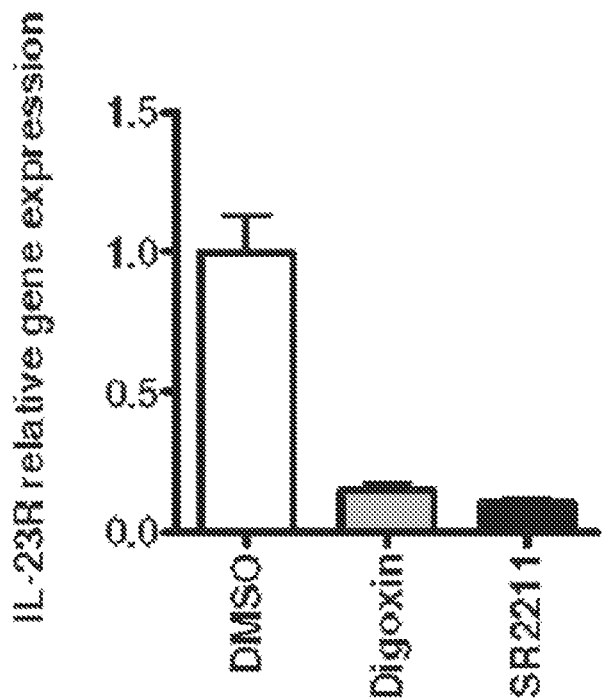

FIG. 8 depicts data showing that SR2211 modulates the expression of IL 17A and IL-23R in EL-4 cells: EL-4 cells were pre-treated with Digoxin (5 µM) or SR2211 (5 µM) or DMSO for 20 hr followed by stimulation with PMA and ionomycin for 5 hr. (a) IL-17A and (b) IL-23R mRNA expression was quantitated and normalized to GAPDH or intracellular IL-17 protein (c) expression was measured as outlined in Methods. The results are shown as mean±SEM. * $p<0.05$, *** $p<0.0005$.

DETAILED DESCRIPTION

Definitions

References in the specification to "an embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

A "small molecule" refers to an organic compound, including an organometallic compound, of a molecular weight less than about 2 kDa, that is not a polynucleotide, a polypeptide, a polysaccharide, or a synthetic polymer composed of a plurality of repeating units.

As to any of the groups described herein, which contain one or more substituents, it is understood that such groups do not contain any substitution or substitution patterns which are sterically impractical and/or synthetically nonfeasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1H$), deuterium ($^2H$), or tritium ($^3H$) in any combination. Similarly, any carbon atom or set thereof in a molecule can be any of the isotopic form of carbons, such as $^{11}C$, $^{12}C$, $^{13}C$, or $^{14}C$, or any nitrogen atom or set thereof in a molecule can be any of the isotopic forms of nitrogen, such as $^{13}N$, $^{14}N$, or $^{15}N$. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}C$ radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}N$ and $^{15}N$, $^{32}S$ and $^{34}S$, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example $^{14}C$ and $^3H$ can be prepared using neutrons generated in a nuclear reactor. Following nuclear transformation, $^{14}C$ and $^3H$ are incorporated into precursor molecules, followed by further elaboration as needed.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C (CH$_3$), —C≡C(CH$_2$CH$_3$), —CH$_2$C≡CH, —CH$_2$C≡C (CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S (=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, —CH$_2$—CH=CH—CH$_2$—SH, and —CH=CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a CA-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like. For example, the group —C(OH)(CF$_3$)$_2$ is a hydroxy-substituted haloalkyl (i.e., fluoroalkyl) group within the meaning herein. A fluoroalkyl group can be fully or partially fluorinated.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like. A fluoroalkoxy group can be fully or partially fluorinated.

A "hydroxyhaloalkyl" as the term is used herein refers to an alkyl group bearing at least one hydroxy group and at least one halo group. For example, a 1-hydroxy-1-trifluoromethyl-2,2,2-trifluoroethyl group is a hydroxyhaloalkyl group within the meaning herein.

The term "(C$_x$-C$_y$)perfluoroalkyl," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkyl, more preferred is —(C$_1$-C$_3$)perfluoroalkyl, most preferred is —CF$_3$. A perfluoroalkyl group encompasses a fully fluorinated fluoroalkyl group.

The term "(C$_x$-C$_y$)perfluoroalkylene," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkylene, more preferred is —(C$_1$-C$_3$)perfluoroalkylene, most preferred is —CF$_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" group is a group of the formula C(O)NR$_2$, wherein R can be H, alkyl, aryl, etc.

The term "azido" refers to an N$_3$ group. An "azide" can be an organic azide or can be a salt of the azide (N$_3^-$) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^-$) anion.

The term "urethane" ("carbamoyl" or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein. Lists of many suitable salts are also found in *Remington's Pharmaceutical Sciences*, 17th ed., Mack Publishing Company, Easton, Pa., (1985), 1418, and the disclosure of which is incorporated herein by reference.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemical agents within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985. As used herein, the term "prodrug" refers to any pharmaceutically acceptable form of compound of the invention which, upon administration to a patient, provides a compound of the invention. Pharmaceutically acceptable prodrugs refer to a compound that is metabolized, for example hydrolyzed or oxidized, in the host to form a compound of the invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of the invention herein possess antiviral activity against HCV, or are metabolized to a compound that exhibits such activity.

As used herein, the term "metabolite" refers to any compound produced in vivo or in vitro from the parent drug of the invention, or any of its prodrugs that are converted biologically to a parent drug of the invention and then to a further biotransformation product of the parent drug.

"Treating" or "treatment" within the meaning herein refers to an alleviation of symptoms associated with a disorder or disease, or inhibition of further progression or worsening of those symptoms, or prevention or prophylaxis of the disease or disorder. As used herein, the terms "treating" or "treat" includes (i) preventing a pathological condition from occurring (e.g., prophylaxis); (ii) inhibiting the pathologic condition or arresting its development; (iii) relieving the pathologic condition; and/or (iv) diminishing symptoms associated with the pathologic condition Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

An "effective amount" of a compound of the invention is an amount or concentration of the compound which is sufficient to modulate the effect of an ROR, e.g., RORα, RORβ, or RORγ, but does not affect a nuclear receptor of another type, e.g., LXRα or LXRβ. In various embodiments, an effective amount of a compound of the invention does not affect any nuclear receptor other than an ROR. In various embodiments, an effective amount of a compound of the invention does not affect any G-protein coupled receptor (GPCR), kinase, protease, ion channel, enzyme, or any other biological component or system other than an ROR.

As used herein, the term "therapeutically effective amount" is intended to include an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example by Chou and Talalay, *Adv. Enzyme Regul.*, 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

A "retinoic acid receptor-related orphan receptor" refers to nuclear receptors such as the sequence variants of RORα (NR1F1), RORβ (NR1F2), and RORγ (NR1F3), all having sequence homology to the retinoic acid receptor subfamily of nuclear receptors as are described in N. Kumar, et al., *Mol. Pharm.*, 77:228-236, 2010, and documents cited therein.

A "modulator" as the term is used herein refers to a molecule that alters the basal activity of the ROR either positively (activates) or negatively (represses). "Modulating" refers to the action of a modulator, either activating or repressing a receptor, such as an ROR or another nuclear receptor such as LXR, or as an agonist or antagonist of a receptor, such as a G-protein coupled receptor (GPCR), or as an inhibitor or activator of an enzyme, for example a kinase or a protease. A compound of the invention can be a modulator of an ROR, for example at an effective concentration or in an effective amount, but not be a modulator of any nuclear receptor other than an ROR, e.g., not a modulator, or not a modulator at some particular concentration or in some particular amount of LXRα or LXRβ or another type of nuclear receptor, and not an agonist or antagonist of a GPCR or an inhibitor or activator of an enzyme. This can provide selectivity of effect of a compound of the invention when administered in a quantity to a patient for treatment of a malcondition such as a immune or metabolic disorder, cancer, or a central nervous system (CNS) disorder.

The term "medically indicated" refers to a course of treatment or a use of a medicinal compound or procedure wherein the treatment or use is recommended by competent medical authority, e.g., a physician treating a patient, wherein the physician based upon factors such as the physician's knowledge, experience, analysis and intuition recommends the treatment or use as potentially beneficial to the patient.

As used herein, the term "patient" refers to a warm-blooded animal, and preferably a mammal, such as, for example, a cat, dog, horse, cow, pig, mouse, rat, or primate, including a human.

As used herein, the term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

One diastereomer or one enantiomer of a compound of the invention may display superior biological activity compared with the other. When required, separation of the diastereomeric mixture or the racemic material can be achieved by HPLC, optionally using a chiral column or by a resolution using a resolving agent such as camphonic chloride as in Tucker et al., *J. Med. Chem.*, 37, 2437 (1994), for the resolution of enantiomers. A chiral compound described herein may also be directly synthesized using a chiral catalyst or a chiral ligand, e.g., Huffman et al., *J. Org. Chem.*, 60:1590 (1995).

As used herein, "µg" denotes microgram, "mg" denotes milligram, "g" denotes gram, "µL" denotes microliter, "mL" denotes milliliter, "L" denotes liter. "nM" denotes nanomolar, "µM" denotes micromolar, "mM" denotes millimolar, "M" denotes molar, and "nm" denotes nanometer.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

Terms such as "comprising" or "including" as used in claims herein refer to an embodiment wherein additional ingredients, steps, or the like are not excluded; the terms are open-ended. However, when a composition, method, or the like is defined in an claim as "comprising" or "including" the ingredients, steps, or the like, it is understood that in various embodiments the invention so claimed is also defined as "consisting essentially of" those named ingredients, steps, or the like. The novel and essential components or characteristics of a claimed invention are themselves an embodiment of the invention; other embodiments can include additional claim elements. Accordingly, if a claim recites that the invention claimed therein "comprises" claim elements X, Y, and Z, it is also understood that in various embodiments, the invention "consists essentially of" the claim elements X, Y, and Z.

The present invention further embraces isolated compounds according to the formulas specified herein. The expression "isolated compound" refers to a preparation of a compound of a specified formula, or a mixture of compounds, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound or a mixture of compounds, which contains the named compound or mixture of compounds in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Tautomerism

Within the present invention it is to be understood that a compound or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

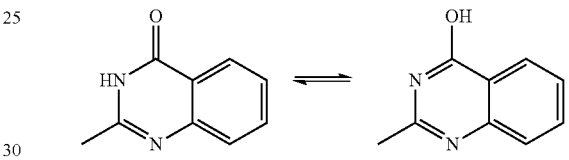

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). The Cahn-Ingold-Prelog ranking is A>B>C>D. The lowest ranking atom, D is oriented away from the viewer.

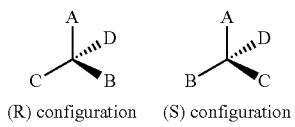

(R) configuration   (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula (I) which are biologically active in the treatment of cancer or other proliferative disease states.

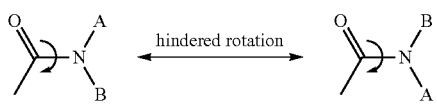

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

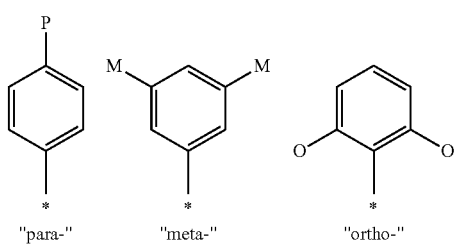

DETAILED DESCRIPTION

In various embodiments, the invention provides a method of modulating the bioactivity of an ROR, comprising contacting the ROR with an effective amount or concentration of a compound of formula (I) as shown below, wherein the compound is an agonist or an activator, or is a repressor, inverse agonist, or antagonist, of a receptor comprising any sequence variant of any isoform of the ROR subfamily, including ROR$\alpha$, ROR$\beta$, or ROR$\gamma$.

In various embodiments, the invention provides a ROR-modulatory compound of formula (I)

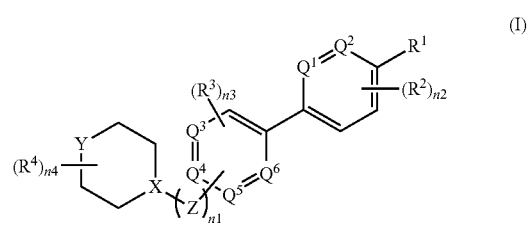

wherein

X is N or $CR^x$, wherein $R^x$ is H or (C1-C4)alkyl;

Y is $C(R^y)_2$, $NR^y$, or O, wherein $R^y$ is independently H, OR, or (C1-C4) alkyl optionally mono- or independently multi-substituted with R, OR, oxo, or halo; or $R^y$ is independently aryl, arylalkyl, heterocyclyl, heterocyclylalkyl, heteroaryl, or heteroarylalkyl, wherein any of said aryl, arylalkyl, heterocyclyl, heterocyclylalkyl, heteroaryl, or heteroarylalkyl is optionally mono- or independently multi-substituted with cyano, nitro, halo, (C1-C4)alkyl, (C1-C4) fluoroalkyl, cycloalkyl, heterocyclyl, aryl, or heteroaryl, any of which alkyl, fluoroalkyl, cycloalkyl, heterocyclyl, aryl, or heteroaryl is optionally mono- or independently multi-substituted with R, OR or halo; or $R^y$ is independently $COR^{yy}$ wherein $R^{yy}$ is independently (C1-C4)alkyl, OR, $NR_2$, heterocyclyl, aryl, or heteroaryl, wherein any heterocyclyl, aryl, or heteroaryl is optionally mono- or independently multi-substituted with (C1-C4)alkyl, halo, or cyano;

Z is independently CHR, O, NR, C(O), or absent, provided that when n1=2, both Z are not CO, O, or NR;

$Q^1$ and $Q^2$ are independently CH, $CR^2$, or N, provided that both $Q^1$ and $Q^2$ are not N;

$Q^3$, $Q^4$, $Q^5$, and $Q^6$ are independently CH, $CR^3$, or N, provided that no more than two of $Q^3$, $Q^4$, $Q^5$, and $Q^6$ are N;

$R^1$ is (C1-C4)alkyl optionally substituted with OR, or aryl-(C1-C4)alkyl optionally substituted with OR, or (C1-C4)fluoroalkyl optionally substituted with OR, or aryl-(C1-C4)fluoroalkyl optionally substituted with OR; or $R^1$ is OR; or $R^1$ is $NHC(O)R^a$ or $NHSO_2R^a$ wherein $R^a$ is (C1-C4) alkyl, aryl, arylalkyl, or (C1-C4)alkoxy wherein any aryl is optionally substituted with (C1-C4)alkyl or (C1-C4)alkoxy; $SO_2NR_2$; or $R^1$ is $C(O)R^b$ wherein $R^b$ is OH, $NR_2$, (C1-C4) alkoxy, aryl optionally substituted with heteroaryl; or heteroaryl;

$R^2$ is independently halo, (C1-C4)alkyl, or (C1-C4) alkoxy;

$R^3$ is independently halo, (C1-C4)alkyl, or (C1-C4) alkoxy;

$R^4$ is independently halo, (C1-C4)alkyl, or (C1-C4) alkoxy;

R is independently H, (C1-C4)alkyl, aryl, arylalkyl, alkanoyl, aroyl, or heteroaroyl;

n1 is 0, 1 or 2;

n2 is 0-4;

n3 is 0-4;

n4 is 0-8;

or any pharmaceutically acceptable salt thereof.

In various embodiments, group X of formula (I) can be CH, N, or O.

In various embodiments, group Y of formula (I) can be NH, N—(C1-C4)alkyl, N—(C1-C4)hydroxyalkyl, N-phenyl, N—(C1-C4)alkanoyl, N-benzyl, N-biphenylmethyl, N-heteroarylmethyl, N-heterocyclylmethyl, or N—C(O)R$^{yy}$ wherein R$^{yy}$ is NH—(C1-C4)alkyl, NH-phenyl, or NH-benzyl; wherein any Y can be substituted or unsubstituted. More specifically, Y can be any of CHOH, NH, NCH$_2$CH$_3$, NCH$_2$CH$_2$OH, NCH(CH$_2$)$_2$, NCOCH$_3$, N C$_6$H$_5$, N—CH$_2$-biphenyl-4'-C(CF$_3$)$_2$OH, N—CH$_2$-benzo[1,3]dioxole, N—CH$_2$—C$_6$H$_4$-3-CF$_3$, N—CH$_2$—C$_6$H$_4$-3-OCH$_3$, N—CH$_2$—CH$_2$-Ph. N—CH$_2$—C$_6$H$_4$-4-Br. N—CH$_2$-Ph, N—CH$_2$-pyridin-4-yl, N—CH$_2$-thiophen-2-yl, N—CH$_2$-5-fluoro-1H-indol-2-yl, N—CH$_2$-2,3-dihydro-1,4-benzodioxin-2-yl, N—CO$_2$—C—(CH$_3$)$_3$, N—CO-tetrahydrofuran-2-yl, N—CO—CH$_2$CH$_3$, N—CO—NH—CH$_2$—CH$_2$—CH$_3$, N—CO—NH-Ph, or N—CO—NH—CH$_2$-Ph.

In various embodiments, the group R$^1$ of formula (I) can be OH, (C1-C4)alkyl, (C1-C4)fluoroalkyl substituted with OH, NHC(O)—(C1-C4)alkyl, NHC(O)-aryl, NHC(O)-heteroaryl, HN—SO$_2$-aryl, HN—SO$_2$-alkylaryl, SO$_2$NR$_2$ wherein R is as defined in claim 1, C(O)O—(C1-C4)alkyl, C(O)NH-aryl, C(O)NH-alkylaryl, or C(O)NH-alkylheteroaryl. More specifically, R$^1$ can be C(CH$_3$)$_3$, HO—C—(CF$_3$)$_2$, HN—CO—CH$_3$, NH—C(O)-phenyl, HN—C(O)-4-tolyl, NH—C(O)O-4-methoxyphenyl, NH—C(O)—CH$_2$-4-methoxyphenyl, NH—C(O)O—C(CH$_3$)$_3$, OH, NH—SO$_2$-p-tolyl, HN—SO$_2$-Ph, HN—SO$_2$—CH$_2$-Ph, SO$_2$NH$_2$, COOH, CONH$_2$, CO$_2$C(CH$_3$)$_3$, COHNCH$_3$, CO—N(CH$_3$) CH$_2$-Ph, CO—NH-Ph, CO—HN—CH$_2$-Ph, tetrazol-5-yl, 1H-pyrazol-4-yl, 1H-pyrazol-3-yl, or 4-(pyrazol-3-yl)phenyl. In various embodiments, R$^1$ is HO—C—(CF$_3$)$_2$, a 1,1,1,3,3,3-hexafluoro-2-hydroxy-isopropyl group.

In various embodiments, the group Z of formula (I) can be CH$_2$ or CO and n1=1.

In various embodiments any of groups R$^2$, R$^3$, and R$^4$ of formula (I) can be independently F, CH$_3$O, or methyl In various embodiments, a compound of the invention can be any of the compounds of Table 1, below.

The ROR-modulatory compound suitable for modulating an ROR can be an agonist or an activator, or a repressor, inverse agonist, or antagonist, of a receptor comprising any sequence variant of any isoforms of ROR, including RORα, RORβ, or RORγ [NR1F1, NR1F2, and NR1F3], thereby affecting the bioactivity of one or more of the ROR NR1F subfamily of nuclear receptors at concentrations of the compound accessible in vivo upon administration of the compound to a human patient.

In various embodiments of the invention, a compound of the invention is inactive with respect to modulation of a nuclear receptor other than an ROR or with respect to modulation of a G-protein coupled receptor, an ion channel, or an enzyme; or the modulation of the ROR takes place at a concentration ineffective for modulation of a nuclear receptor other than an ROR at the concentration, or ineffective for modulation of a G-protein coupled receptor, an ion channel, or an enzyme at the concentration.

A compound of the invention that is an effective modulator (repressor or activator) of an ROR can be inactive with respect to modulation of another nuclear receptor, such as LXRα or LXRβ, or the modulation of an ROR can be selective at some concentration with respect to modulation of another nuclear receptor, such as an LXR, providing an effect free of side effects resulting from modulation of a non-target nuclear receptor. In various embodiments of an inventive method of treatment of a patient, such as a human, the ROR is modulated by a compound of the invention at a dose ineffective to modulate any other nuclear receptor, such as LXRα or LXRβ, in the patient, providing an effect free of side effects resulting from modulation of nuclear receptors other than ROR. In various embodiments, the effective amount of the compound of the invention does not affect any nuclear receptor other than an ROR, or does not affect any G-protein coupled receptor (GPCR), or any ion channel, or any kinase, protease, or other enzyme, or any other cellular component or system at a concentration effective to modulate the effect of an ROR such as RORα, RORβ, or RORγ.

In various embodiments, the invention provides a pharmaceutical composition comprising a compound of the invention and a pharmaceutically effective excipient. In various embodiments, the invention provides a pharmaceutical combination comprising a compound of the invention and a second medicament. The second medicament can comprise, for treatment of a metabolic disorder, an anti-diabetic or anti-insulin resistance agent, such as a glitazone, a sulfonylurea, metformin, insulin, an insulin mimetic, a DPP4 inhibitor, a GLP1 receptor agonist, a glucagon receptor antagonist, or an anti-obesity agent. For treatment of an immune disorder, the second medicament can comprise an anti-TNF agent or an immune-suppressive glucocorticoid. For treatment of cancer, the second medicament can comprise an anticancer agent such as a platinum compound, a *Vinca* alkaloid or analog thereof, a taxane, a nitrogen mustard, or the like.

In various embodiments, the invention provides a use of a compound of a compound of the invention in the preparation of a medicament. More specifically, the medicament can be adapted for the treatment of metabolic and immune disorders, cancer, or CNS disorders.

In various embodiments, the invention provides a method of modulating the bioactivity of an ROR, comprising contacting the ROR with an effective amount of a compound of the invention. More specifically, the modulation can take place in vivo in a mammal. The mammal can be a human or a non-human primate.

In various embodiments, the invention provides a method of modulating the bioactivity of an ROR, wherein the bioactivity of an LXR is substantially unaffected by a concentration of the compound in a tissue effective for modulation of an ROR, providing an effect free of side effects resulting from LXR modulation. Modulation of LXR can result in an increase in blood triglycerides, which is undesirable therapeutically.

In various embodiments, the invention provides a method of treating a metabolic or immune disorder, cancer, or a CNS disorder in a patient for which modulation of an ROR is medically indicated, comprising administering to the patient an effective amount of a compound of the invention at a frequency and for a duration of time to provide a beneficial result to the patient. More specifically, the metabolic disorder can comprise insulin resistance, type 2 diabetes, diabetes, and obesity.

More specifically, the immune disorder can comprise an auto immune disorder such as Hashimoto's thyroiditis, Pernicious anemia, Addison's disease, Type I diabetes, Rheumatoid arthritis, Systemic lupus erythematosus. Dermatomyositis, Sjogren syndrome, Lupus erythematosus, Multiple sclerosis, Myasthenia gravis, Reactive arthritis, Grave's disease, Crohn's disease, Lupus, etc.

More specifically, cancer can comprise prostate cancer, colon cancer, breast cancer, lung cancer, etc.

More specifically, a CNS disorder can comprise sleep disorder, anxiety, neurodegenerative disease such as Parkinson's or Alzheimer's, etc.

Pharmaceutical Use

Retinoic acid receptor-related orphan receptors (RORs) regulate a variety of physiological processes including hepatic gluconeogenesis, lipid metabolism, circadian rhythm, and immune function. Compounds of the invention have been found to be high affinity ligands, agonists or repressors (antagonists), of at least RORα and/or RORγ classes of receptors. Binding of a radiolabeled compound of the invention to RORβ has also been demonstrated. Modulation of one or more of these ROR receptors can be effective in controlling these and other physiological processes.

The role for RORα in regulation of metabolic pathways has been revealed by studies of a mutant mouse strain termed staggerer (RORα$^{sg/sg}$), wherein the RORα is rendered inactive. Such mice are less susceptible to hepatic steatosis and have a reduced body fat index relative to wild-type mice despite higher food consumption. RORα has also been implicated in regulation of glucose metabolism. RORγ has been implicated in the regulation of immune function, such as in the development of TH17 cells that are believed to play an important role in autoimmunity. Accordingly, repressors of RORγ may be able to block Th17 cell proliferation and IL-17 production. Recently, RORα has been shown to attenuate Wnt/b-catenin signaling in colon cancer. Modulation of ROR may be able to stop cancer cell growth or induce cancer cell death. In addition, ROR plays a critical role in regulation of the core clock which controls circadian rhythms. Thus, modulation of RORs can be useful in the treatment of sleep dysfunction and other CNS disorders.

In various embodiments, a compound of the invention can be present in vivo in a patient in an amount or concentration of the compound which is sufficient to modulate the effect of an ROR, e.g., RORα, RORβ, or RORγ, but does not affect a nuclear receptor of another type, e.g., LXRα or LXRβ in a living organism. In various embodiments, an effective amount of a compound of the invention does not affect any nuclear receptor other than an ROR. In various embodiments, an effective amount of a compound of the invention does not affect any G-protein coupled receptor (GPCR), kinase, protease, ion channel, enzyme, or any other biological component or system other than an ROR.

Further discussions of biological data obtained for specific compounds of the invention, such as SR1555 and SR2211, are discussed below in greater detail.

Compositions and Combinations

Another aspect of an embodiment of the invention provides compositions of the compounds of the invention, alone or in combination with another medicament. As set forth herein, compounds of the invention include stereoisomers, tautomers, solvates, prodrugs, metabolites, pharmaceutically acceptable salts and mixtures thereof. Compositions containing a compound of the invention can be prepared by conventional techniques, e.g. as described in Remington: *The Science and Practice of Pharmacy*, 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

In various embodiments, the invention provides a dosage form adapted for administration to a patient afflicted with a malcondition comprising a metabolic or an immune disorder, cancer, or a CNS disorder, wherein the dosage form comprises a capsule, a tablet, a liquid or dispersed oral formulation, or a formulation adapted for parenteral administration.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 g to about 1250 mg, preferably from about 250 g to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

Evaluation of Bioactivity

It is within ordinary skill to evaluate any compound disclosed and claimed herein for effectiveness in modulation of an ROR in various cellular and biochemical assays using the procedures described above or found in the scientific literature. Accordingly, the person of ordinary skill can prepare and evaluate any of the claimed compounds without undue experimentation. It is also within ordinary skill to evaluate any compound disclosed and claimed herein for effectiveness in modulation of the nuclear receptors LXRα and LXRβ in various cellular and biochemical assays using the procedures described above or found in the scientific literature, and in evaluating the results in light of the ROR modulatory results, evaluate the selectivity of the tested compound(s) for ROR selectivity over the LXRs, other nuclear receptors, and other biological targets and for further evaluation as a medicinal compound.

Any compound found to be an effective and selective inhibitor of an ROR can likewise be tested in animal models and in human clinical studies using the skill and experience of the investigator to guide the selection of dosages and treatment regimens.

TABLE 1

Compounds of the Invention

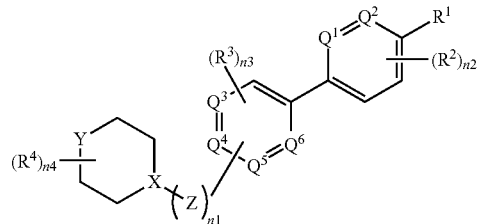

| # | Compound Structure | Generic Structure/Substituents |
|---|---|---|
| 1 | 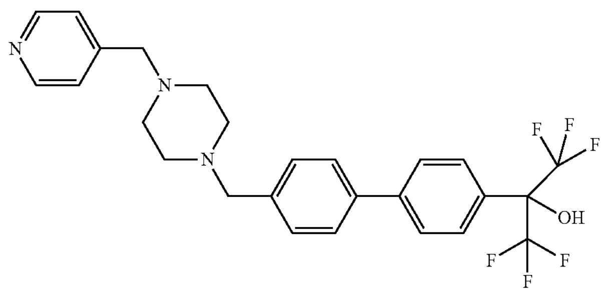 [SMILES: OC(c1ccc(-c2ccc(CN3CCN(Cc4ccncc4)CC3)cc2)cc1)(C(F)(F)F)C(F)(F)F] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 2 | 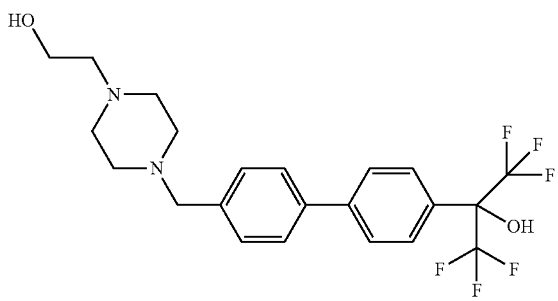 [SMILES: OCCN1CCN(Cc2ccc(-c3ccc(C(O)(C(F)(F)F)C(F)(F)F)cc3)cc2)CC1] | X = N<br>Y = NCH$_2$CH$_2$OH<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 3 | 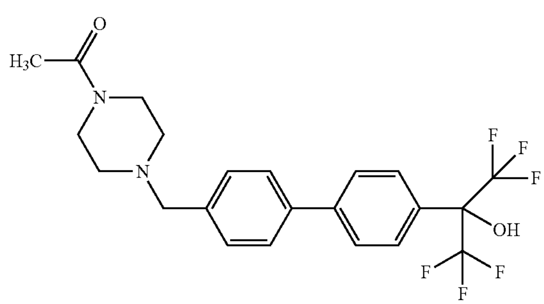 [SMILES: CC(=O)N1CCN(Cc2ccc(-c3ccc(C(O)(C(F)(F)F)C(F)(F)F)cc3)cc2)CC1] | X = N<br>Y = NCOCH$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 4 | 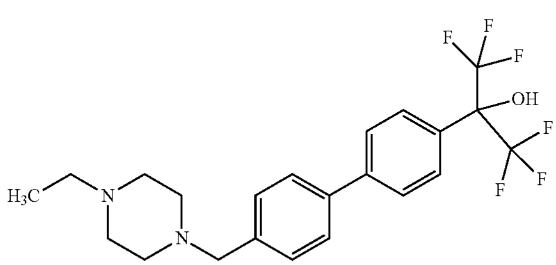 [SMILES: CCN1CCN(Cc2ccc(-c3ccc(C(O)(C(F)(F)F)C(F)(F)F)cc3)cc2)CC1] | X = N<br>Y = NCH$_2$CH$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

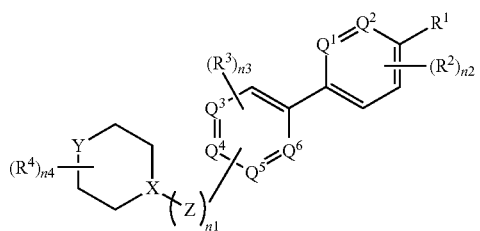

| # | Compound Structure | Generic Structure/Substituents |
|---|---|---|
| 5 | 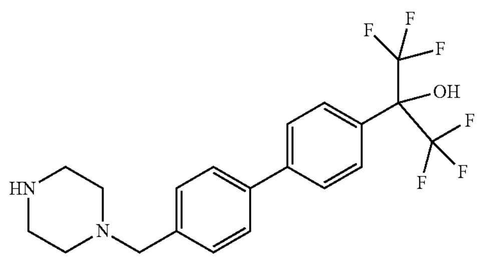 [SMILES: OC(c1ccc(-c2ccc(CN3CCNCC3)cc2)cc1)(C(F)(F)F)C(F)(F)F] | X = N<br>Y = NH<br>Z = $CH_2$<br>$R^1$ = HO—C—$(CF_3)_2$<br>$R^2$ = Absent<br>$R^3$ = Absent<br>$R^4$ = Absent<br>n = 1 |
| 6 | 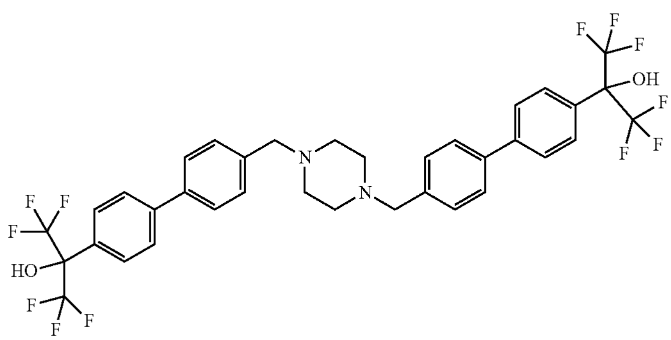 [SMILES: OC(c1ccc(-c2ccc(CN3CCN(Cc4ccc(-c5ccc(C(O)(C(F)(F)F)C(F)(F)F)cc5)cc4)CC3)cc2)cc1)(C(F)(F)F)C(F)(F)F] | X = N<br>Y = N—$CH_2$-biphenyl-4'-C$(CF_3)_2$OH<br>Z = $CH_2$<br>$R^1$ = HO—C—$(CF_3)_2$<br>$R^2$ = Absent<br>$R^3$ = Absent<br>$R^4$ = Absent<br>n = 1 |
| 7 | 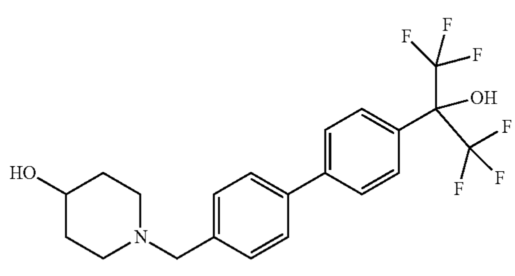 [SMILES: OC1CCN(Cc2ccc(-c3ccc(C(O)(C(F)(F)F)C(F)(F)F)cc3)cc2)CC1] | X = N<br>Y = CHOH<br>Z = $CH_2$<br>$R^1$ = HO—C—$(CF_3)_2$<br>$R^2$ = Absent<br>$R^3$ = Absent<br>$R^4$ = Absent<br>n = 1 |
| 8 | 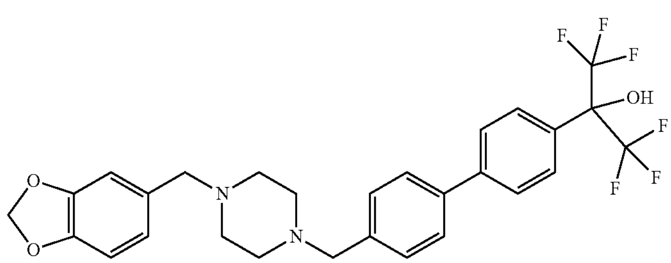 [SMILES: OC(c1ccc(-c2ccc(CN3CCN(Cc4ccc5c(c4)OCO5)CC3)cc2)cc1)(C(F)(F)F)C(F)(F)F] | X = N<br>Y = N—$CH_2$-benzo[1,3]dioxole<br>Z = $CH_2$<br>$R^1$ = HO—C—$(CF_3)_2$<br>$R^2$ = Absent<br>$R^3$ = Absent<br>$R^4$ = Absent<br>n = 1 |

TABLE 1-continued

Compounds of the Invention

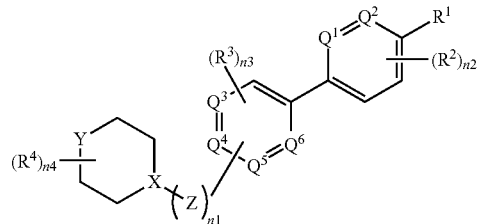

| # | Compound Structure | Generic Structure/Substituents |
|---|---|---|
| 9 | 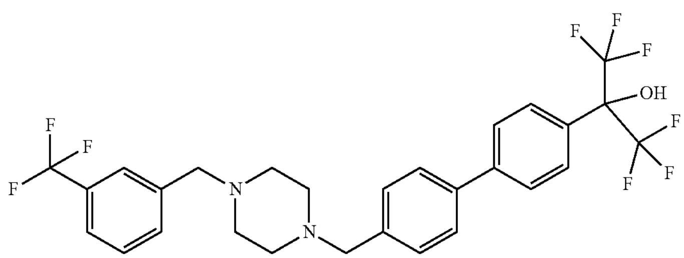 [SMILES: OC(c1ccc(-c2ccc(CN3CCN(Cc4cccc(C(F)(F)F)c4)CC3)cc2)cc1)(C(F)(F)F)C(F)(F)F] | X = N<br>Y = N—CH$_2$—C$_6$H$_4$-3-CF$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 10 | 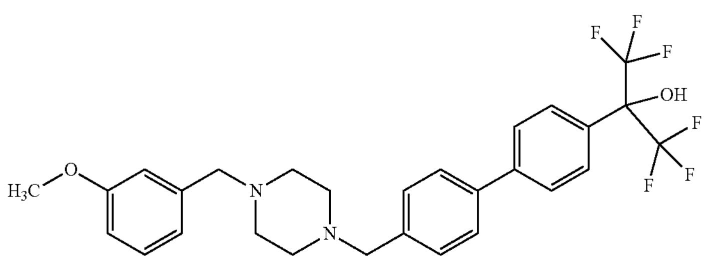 [SMILES: COc1cccc(CN2CCN(Cc3ccc(-c4ccc(C(O)(C(F)(F)F)C(F)(F)F)cc4)cc3)CC2)c1] | X = N<br>Y = N—CH$_2$—C$_6$H$_4$-3-OCH$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 11 | 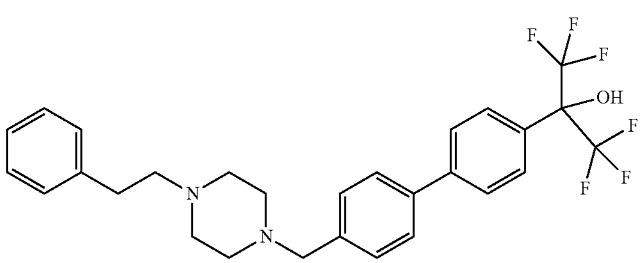 [SMILES: OC(c1ccc(-c2ccc(CN3CCN(CCc4ccccc4)CC3)cc2)cc1)(C(F)(F)F)C(F)(F)F] | X = N<br>Y = N—CH$_2$—CH$_2$—Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 12 | 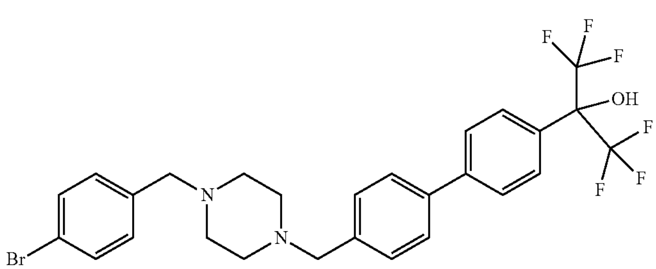 [SMILES: OC(c1ccc(-c2ccc(CN3CCN(Cc4ccc(Br)cc4)CC3)cc2)cc1)(C(F)(F)F)C(F)(F)F] | X = N<br>Y = N—CH$_2$—C6H4-4-Br<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

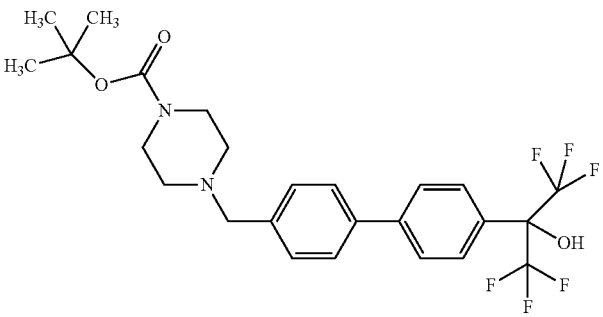 [SMILES: CC(C)(C)OC(=O)N1CCN(Cc2ccc(-c3ccc(C(O)(C(F)(F)F)C(F)(F)F)cc3)cc2)CC1]

| # | Compound Structure | Generic Structure/Substituents |
|---|---|---|
| 13 | 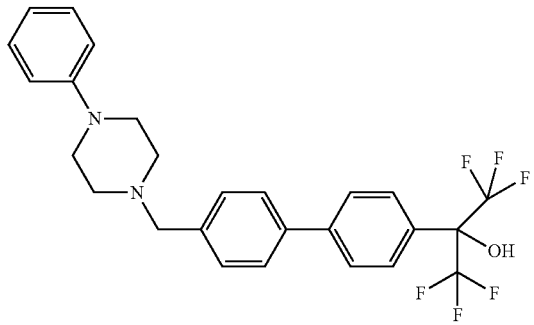 [SMILES: OC(c1ccc(-c2ccc(CN3CCN(c4ccccc4)CC3)cc2)cc1)(C(F)(F)F)C(F)(F)F] | X = N<br>Y = N—CO$_2$—C—(CH$_3$)$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 14 | 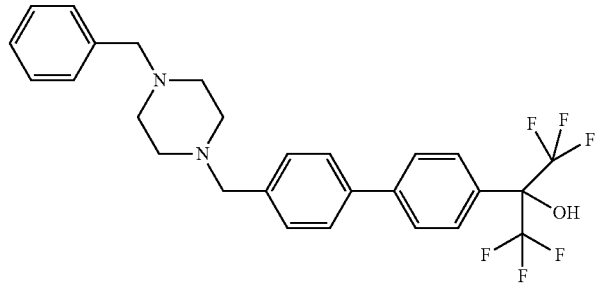 | X = N<br>Y = C$_6$H$_5$N<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 15 | 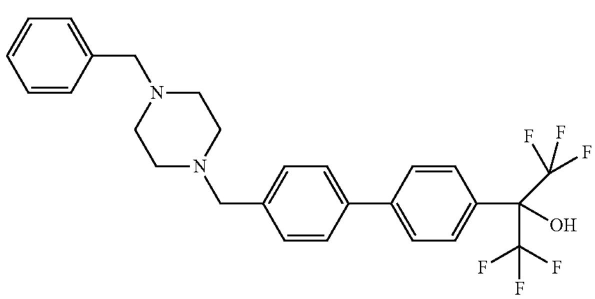 | X = N<br>Y = N—CH$_2$—Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 16 | 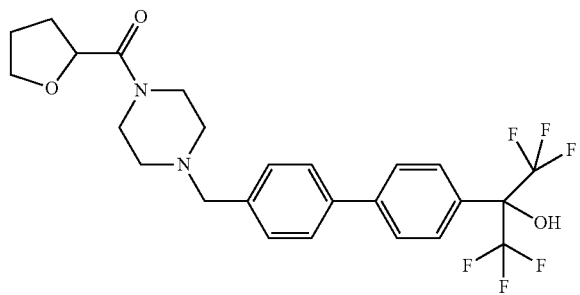 [SMILES: O=C(C1CCCO1)N1CCN(Cc2ccc(-c3ccc(C(O)(C(F)(F)F)C(F)(F)F)cc3)cc2)CC1] | X = N<br>Y = N—CO-tetrahydrofuran-2-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

US 9,586,928 B2

37                                                                                              38

TABLE 1-continued

Compounds of the Invention

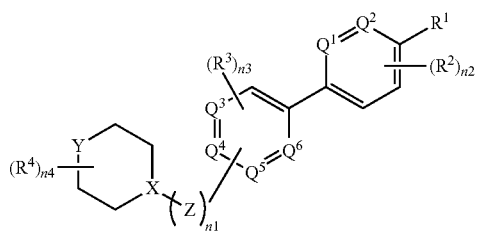

| # | Compound Structure | Generic Structure/Substituents |
|---|---|---|
| 17 | 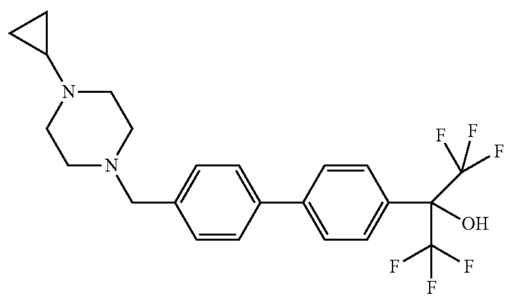 [SMILES: OC(c1ccc(-c2ccc(CN3CCN(C4CC4)CC3)cc2)cc1)(C(F)(F)F)C(F)(F)F] | X = N<br>Y = NCH(CH$_2$)$_2$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 18 | 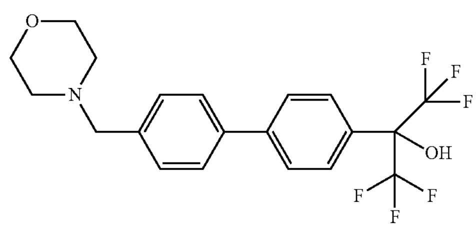 [SMILES: OC(c1ccc(-c2ccc(CN3CCOCC3)cc2)cc1)(C(F)(F)F)C(F)(F)F] | X = N<br>Y = O<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 19 | 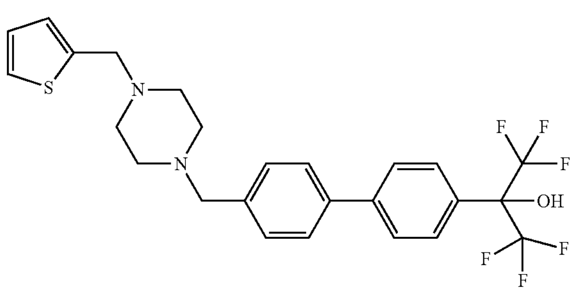 [SMILES: OC(c1ccc(-c2ccc(CN3CCN(Cc4cccs4)CC3)cc2)cc1)(C(F)(F)F)C(F)(F)F] | X = N<br>Y = N—CH$_2$-thiophen-2-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 20 | 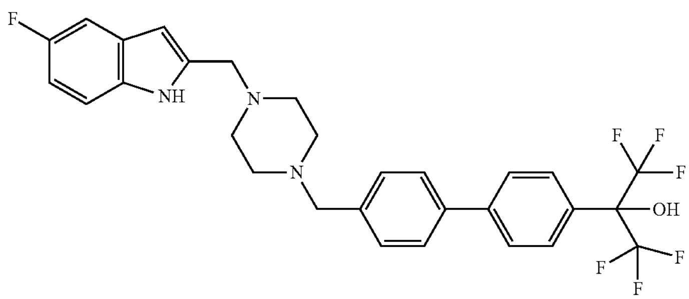 [SMILES: OC(c1ccc(-c2ccc(CN3CCN(Cc4cc5cc(F)ccc5[nH]4)CC3)cc2)cc1)(C(F)(F)F)C(F)(F)F] | X = N<br>Y = N—CH$_2$-5-fluoro-1H-indol-2-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 21 | 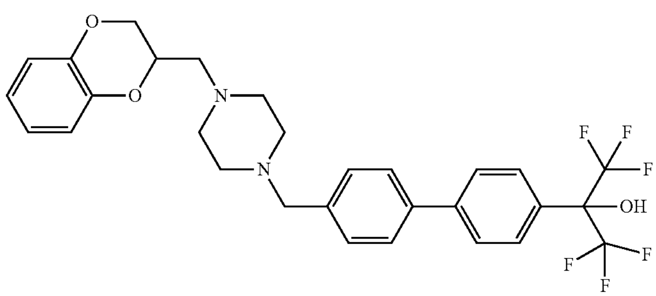 [SMILES: OC(c1ccc(-c2ccc(CN3CCN(CC4COc5ccccc5O4)CC3)cc2)cc1)(C(F)(F)F)C(F)(F)F] | X = N<br>Y = N—CH$_2$-2,3-dihydro-<br>1,4-benzodioxin-2-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 22 | 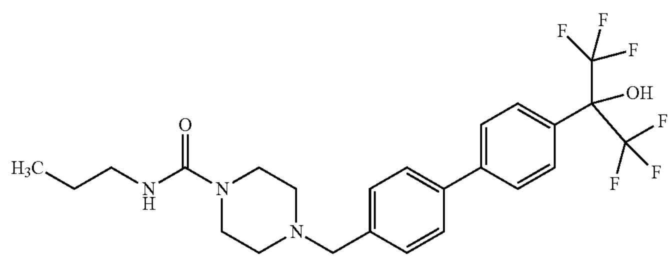 [SMILES: CCCNC(=O)N1CCN(Cc2ccc(-c3ccc(C(O)(C(F)(F)F)C(F)(F)F)cc3)cc2)CC1] | X = N<br>Y = N—CO—NH—CH$_2$—CH$_2$—CH$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 23 | 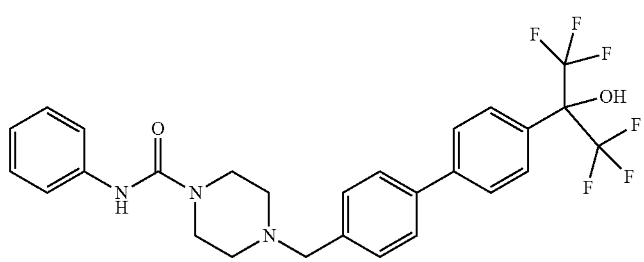 [SMILES: O=C(Nc1ccccc1)N1CCN(Cc2ccc(-c3ccc(C(O)(C(F)(F)F)C(F)(F)F)cc3)cc2)CC1] | X = N<br>Y = N—CO—NH—Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 24 | 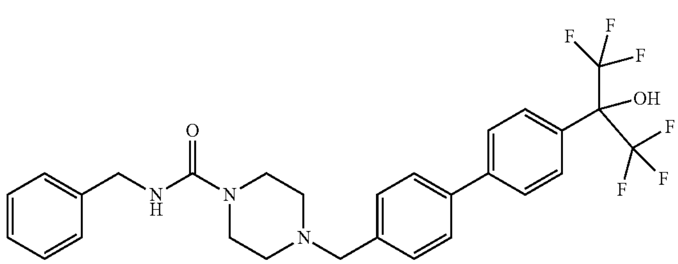 [SMILES: O=C(NCc1ccccc1)N1CCN(Cc2ccc(-c3ccc(C(O)(C(F)(F)F)C(F)(F)F)cc3)cc2)CC1] | X = N<br>Y = N—CO—NH—CH$_2$—Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 25 | 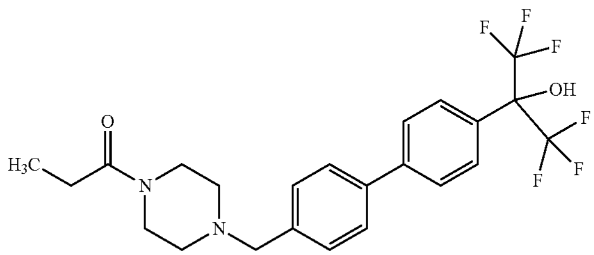 [SMILES: CCC(=O)N1CCN(Cc2ccc(-c3ccc(C(O)(C(F)(F)F)C(F)(F)F)cc3)cc2)CC1] | X = N<br>Y = N—CO—CH$_2$CH$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 26 | 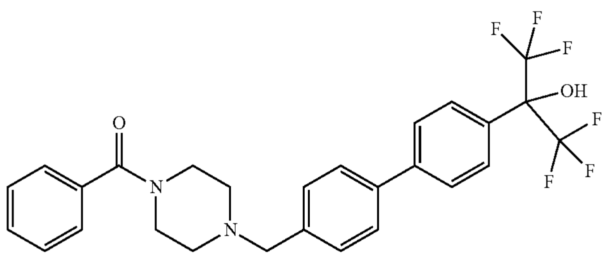 [SMILES: O=C(c1ccccc1)N1CCN(Cc2ccc(-c3ccc(C(O)(C(F)(F)F)C(F)(F)F)cc3)cc2)CC1] | X = N<br>Y = N—CO—Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 27 | 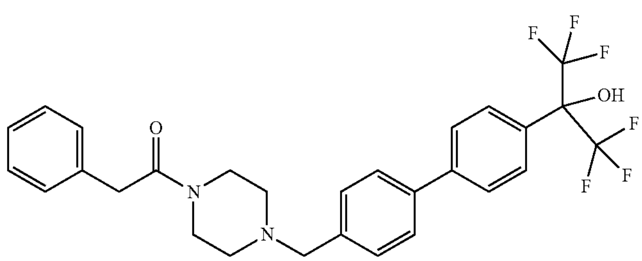 [SMILES: O=C(Cc1ccccc1)N1CCN(Cc2ccc(-c3ccc(C(O)(C(F)(F)F)C(F)(F)F)cc3)cc2)CC1] | X = N<br>Y = N—CO—CH$_2$—Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 28 | 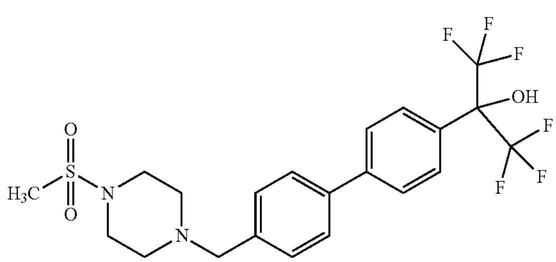 [SMILES: CS(=O)(=O)N1CCN(Cc2ccc(-c3ccc(C(O)(C(F)(F)F)C(F)(F)F)cc3)cc2)CC1] | X = N<br>Y = N—SO$_2$—CH$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 29 | 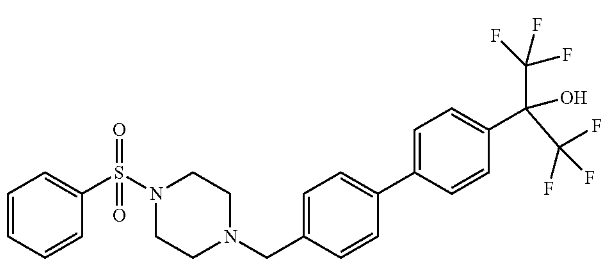 [SMILES: O=S(=O)(c1ccccc1)N1CCN(Cc2ccc(-c3ccc(C(O)(C(F)(F)F)C(F)(F)F)cc3)cc2)CC1] | X = N<br>Y = N—SO$_2$—Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

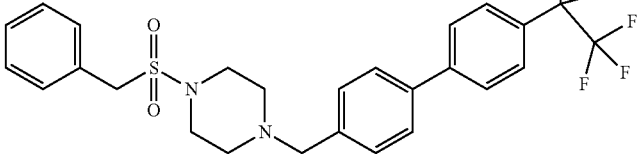

| # | Compound Structure | Generic Structure/Substituents |
|---|---|---|
| 30 | 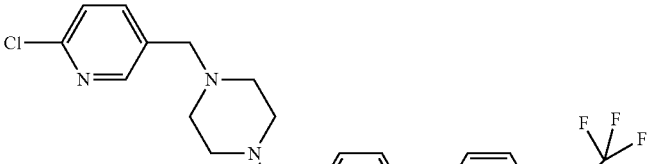 | X = N<br>Y = N—SO$_2$—CH$_2$—Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 31 | 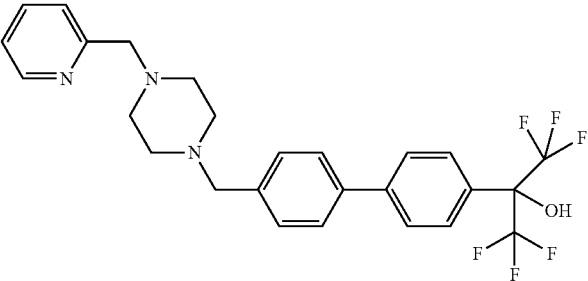 [SMILES: OC(c1ccc(-c2ccc(CN3CCN(Cc4ccccn4)CC3)cc2)cc1)(C(F)(F)F)C(F)(F)F] | X = N<br>Y = N—CH$_2$-2-chloro-pyridin-5-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 32 | 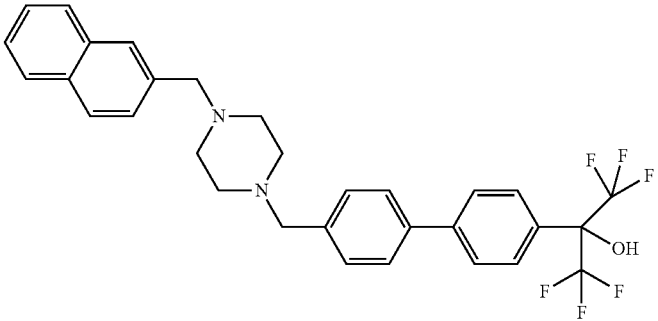 [SMILES: OC(c1ccc(-c2ccc(CN3CCN(Cc4ccc5ccccc5c4)CC3)cc2)cc1)(C(F)(F)F)C(F)(F)F] | X = N<br>Y = N—CH$_2$-pyridin-2-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 33 | | X = N<br>Y = N—C$_2$-naphthalen-2-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 34 | | X = N<br>Y = NCH$_2$CH$_2$-benzo[1,3]dioxole<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 35 | | X = N<br>Y = N—CH$_2$-2-methoxy-pyridin-5-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 36 | | X = N<br>Y = N—CH$_2$-2-trifluoromethyl-pyridin-5-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 37 | | X = N<br>Y = N—CH$_2$-Pyridin-3-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

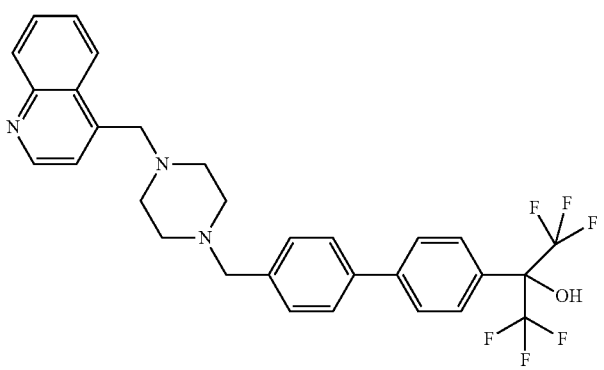 [SMILES: OC(c1ccc(-c2ccc(CN3CCN(Cc4ccnc5ccccc45)CC3)cc2)cc1)(C(F)(F)F)C(F)(F)F]

| # | Compound Structure | Generic Structure/Substituents |
|---|---|---|
| 38 | 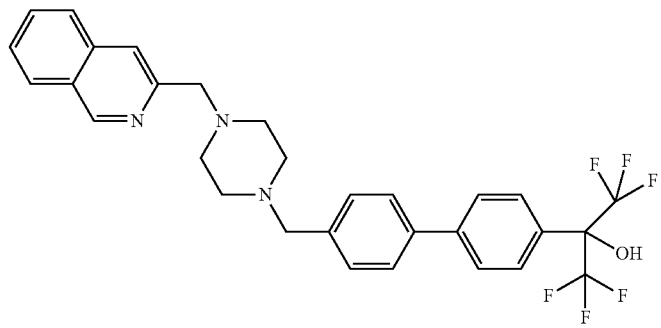 [SMILES: OC(c1ccc(-c2ccc(CN3CCN(Cc4cc5ccccc5cn4)CC3)cc2)cc1)(C(F)(F)F)C(F)(F)F] | X = N<br>Y = N—CH$_2$-quinolin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 39 | 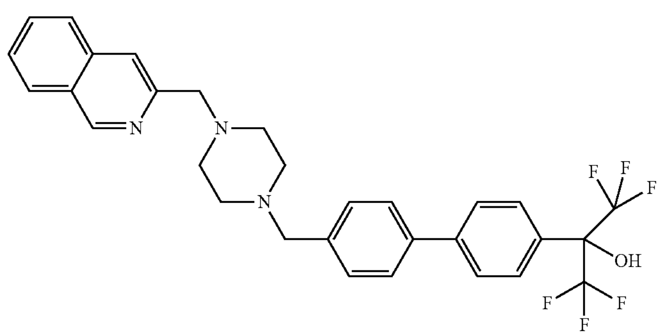 | X = N<br>Y = N—CH$_2$-isoquinolin-3-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 40 | 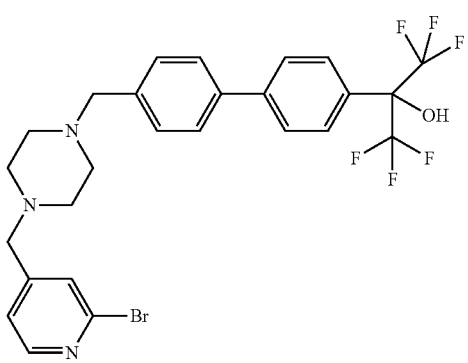 [SMILES: OC(c1ccc(-c2ccc(CN3CCN(Cc4ccnc(Br)c4)CC3)cc2)cc1)(C(F)(F)F)C(F)(F)F] | X = N<br>Y = N—CH$_2$-2-bromopyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

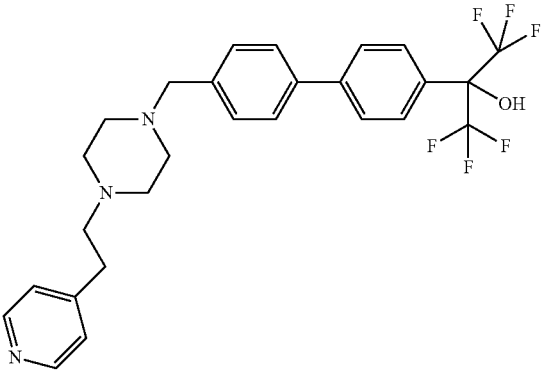 [SMILES: OC(c1ccc(-c2ccc(CN3CCN(CCc4ccncc4)CC3)cc2)cc1)(C(F)(F)F)C(F)(F)F]

| # | Compound Structure | Generic Structure/Substituents |
|---|---|---|
| 41 | 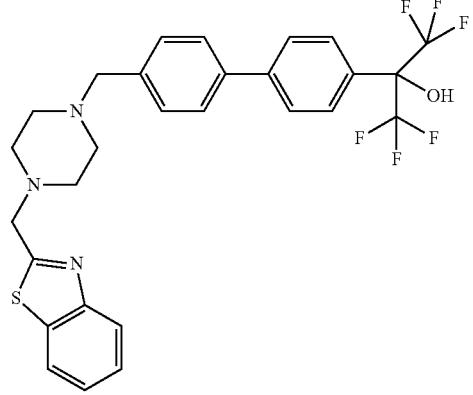 [SMILES: OC(c1ccc(-c2ccc(CN3CCN(Cc4nc5ccccc5s4)CC3)cc2)cc1)(C(F)(F)F)C(F)(F)F] | X = N<br>Y = N—CH$_2$—CH$_2$-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 42 | 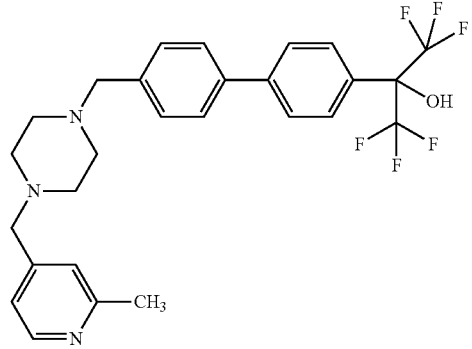 [SMILES: Cc1cc(CN2CCN(Cc3ccc(-c4ccc(C(O)(C(F)(F)F)C(F)(F)F)cc4)cc3)CC2)ccn1] | X = N<br>Y = N—CH$_2$-benzothiozol-2-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 43 | 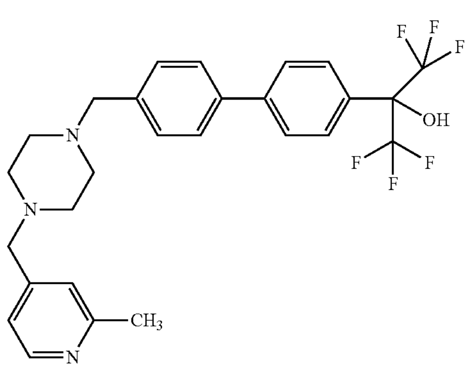 | X = N<br>Y = N—CH$_2$-2-methylpyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

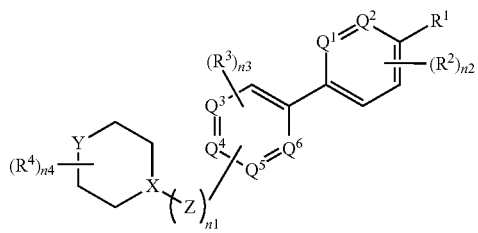

| # | Compound Structure | Generic Structure/Substituents |
|---|---|---|
| 44 | 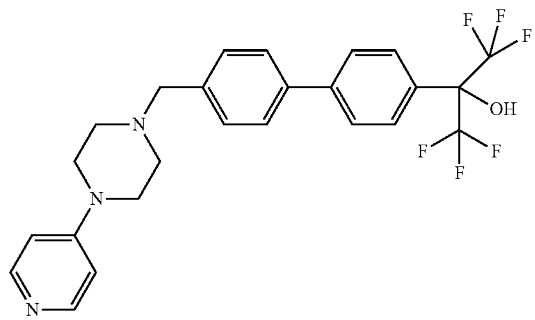 [SMILES: OC(c1ccc(-c2ccc(CN3CCN(c4ccncc4)CC3)cc2)cc1)(C(F)(F)F)C(F)(F)F] | X = N<br>Y = N-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 45 | 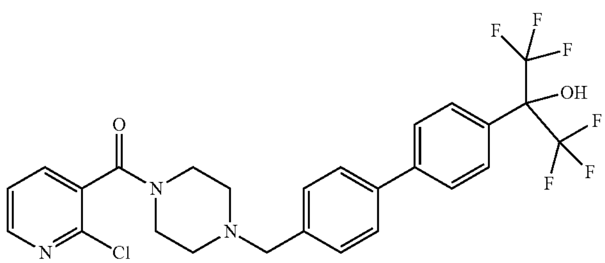 [SMILES: O=C(c1cccnc1Cl)N1CCN(Cc2ccc(-c3ccc(C(O)(C(F)(F)F)C(F)(F)F)cc3)cc2)CC1] | X = N<br>Y = N—CO-2-chloropyridin-3-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 46 | 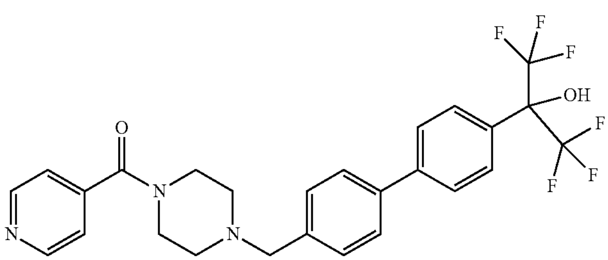 [SMILES: O=C(c1ccncc1)N1CCN(Cc2ccc(-c3ccc(C(O)(C(F)(F)F)C(F)(F)F)cc3)cc2)CC1] | X = N<br>Y = N—CO-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 47 | 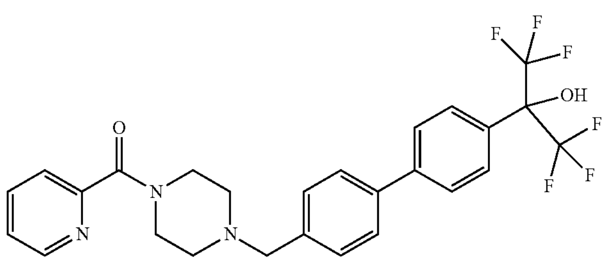 [SMILES: O=C(c1ccccn1)N1CCN(Cc2ccc(-c3ccc(C(O)(C(F)(F)F)C(F)(F)F)cc3)cc2)CC1] | X = N<br>Y = N—CO-pyridin-2-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 48 | 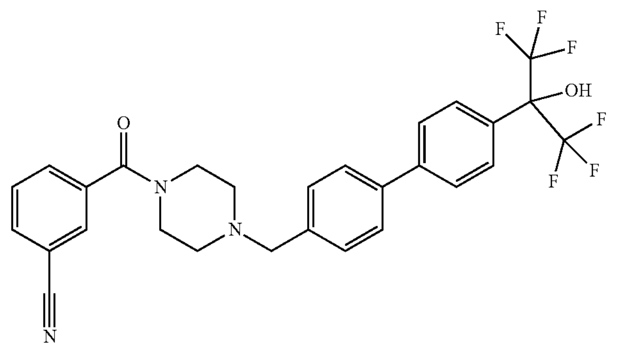 [SMILES: N#Cc1cccc(C(=O)N2CCN(Cc3ccc(-c4ccc(C(O)(C(F)(F)F)C(F)(F)F)cc4)cc3)CC2)c1] | X = N<br>Y = N—CO-benzo-3-nitrile<br>Z = $CH_2$<br>$R^1$ = HO—C—$(CF_3)_2$<br>$R^2$ = Absent<br>$R^3$ = Absent<br>$R^4$ = Absent<br>n = 1 |
| 49 | 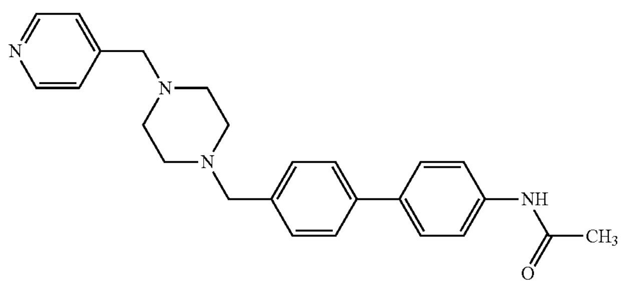 [SMILES: CC(=O)Nc1ccc(-c2ccc(CN3CCN(Cc4ccncc4)CC3)cc2)cc1] | X = N<br>Y = N—$CH_2$-pyridin-4-yl<br>Z = $CH_2$<br>$R^1$ = HN—CO—$CH_3$<br>$R^2$ = Absent<br>$R^3$ = Absent<br>$R^4$ = Absent<br>n = 1 |
| 50 | 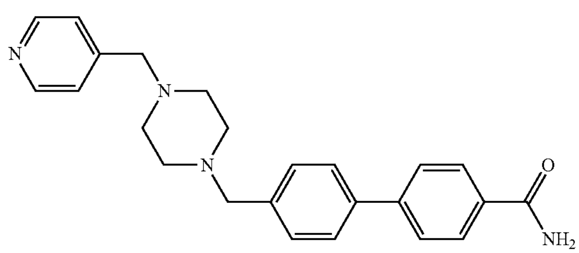 [SMILES: NC(=O)c1ccc(-c2ccc(CN3CCN(Cc4ccncc4)CC3)cc2)cc1] | X = N<br>Y = N—$CH_2$-pyridin-4-yl<br>Z = $CH_2$<br>$R^1$ = $CONH_2$<br>$R^2$ = Absent<br>$R^3$ = Absent<br>$R^4$ = Absent<br>n = 1 |
| 51 | 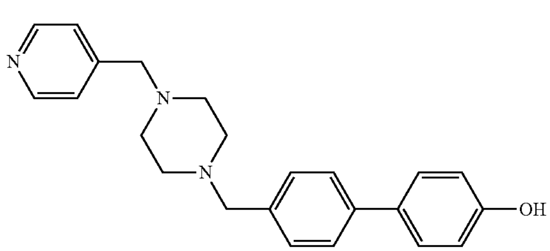 [SMILES: Oc1ccc(-c2ccc(CN3CCN(Cc4ccncc4)CC3)cc2)cc1] | X = N<br>Y = N—$CH_2$-pyridin-4-yl<br>Z = $CH_2$<br>$R^1$ = OH<br>$R^2$ = Absent<br>$R^3$ = Absent<br>$R^4$ = Absent<br>n = 1 |

TABLE 1-continued

Compounds of the Invention

| # | Compound Structure | Generic Structure/Substituents |
|---|---|---|
| 52 | | X = N<br>Y = N—CH$_2$-pyridin-4-yl<br>Z = CH$_2$<br>R$^1$ = SO$_2$NH$_2$<br>R$^2$ = Absent<br>R$^3$ = Absent<br>R$^4$ = Absent<br>n = 1 |
| 53 | | X = N<br>Y = N—CH$_2$-pyridin-4-yl<br>Z = CH$_2$<br>R$^1$ = HH—SO$_2$-p-tolyl<br>R$^2$ = Absent<br>R$^3$ = Absent<br>R$^4$ = Absent<br>n = 1 |
| 54 | | X = N<br>Y = N—CH$_2$-pyridin-4-yl<br>Z = CH$_2$<br>R$^1$ = CO$_2$C(CH$_3$)$_3$<br>R$^2$ = Absent<br>R$^3$ = Absent<br>R$^4$ = Absent<br>n = 1 |
| 55 | | X = N<br>Y = N—CH$_2$-pyridin-4-yl<br>Z = CH$_2$<br>R$^1$ = COHNCH$_3$<br>R$^2$ = Absent<br>R$^3$ = Absent<br>R$^4$ = Absent<br>n = 1 |
| 56 | | X = N<br>Y = N—CH$_2$-Pyridine<br>Z = CH$_2$<br>R$^1$ = tetrazol-5-yl<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 57 | 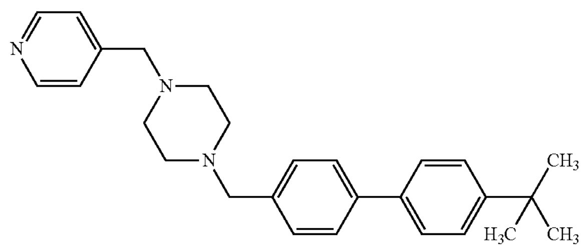 [SMILES: CC(C)(C)c1ccc(-c2ccc(CN3CCN(Cc4ccncc4)CC3)cc2)cc1] | X = N<br>Y = N—CH$_2$-pyridin-4-yl<br>Z = CH$_2$<br>R$^1$ = C(CH$_3$)$_3$<br>R$^2$ = Absent<br>R$^3$ = Absent<br>R$^4$ = Absent<br>n = 1 |
| 58 | 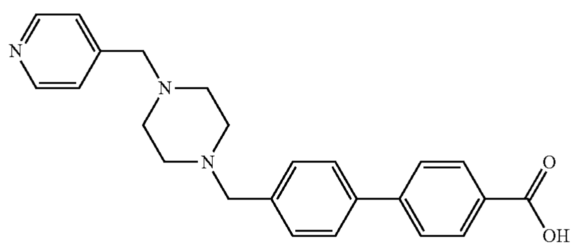 [SMILES: O=C(O)c1ccc(-c2ccc(CN3CCN(Cc4ccncc4)CC3)cc2)cc1] | X = N<br>Y = N—CH$_2$-pyridin-4-yl<br>Z = CH$_2$<br>R$^1$ = COOH<br>R$^2$ = Absent<br>R$^3$ = Absent<br>R$^4$ = Absent<br>n = 1 |
| 59 | 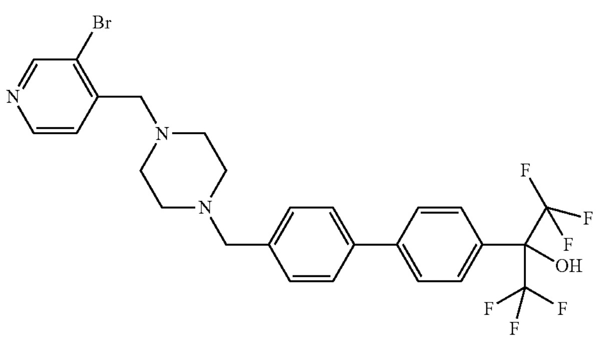 [SMILES: OC(c1ccc(-c2ccc(CN3CCN(Cc4ccncc4Br)CC3)cc2)cc1)(C(F)(F)F)C(F)(F)F] | X = N<br>Y = N—CH$_2$-3-bromopyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 60 | 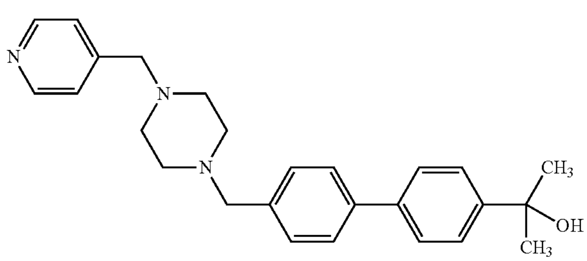 [SMILES: CC(C)(O)c1ccc(-c2ccc(CN3CCN(Cc4ccncc4)CC3)cc2)cc1] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

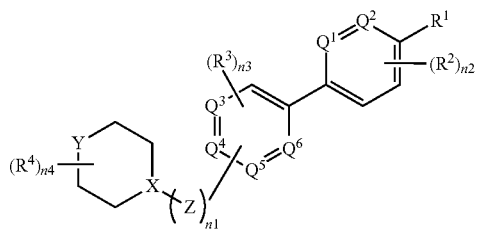

| # | Compound Structure | Generic Structure/Substituents |
|---|---|---|
| 61 | | X = N<br>Y = N—CH$_2$-2-chloro-3-fluoropyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 62 | | X = N<br>Y = N—CH$_2$-pyridin-4-yl<br>Z = CH$_2$<br>R$^1$ = 1H-pyrazol-4-yl<br>R$^2$ = Absent<br>R$^3$ = Absent<br>R$^4$ = Absent<br>n = 1 |
| 63 | | X = N<br>Y = N—CH$_2$-pyridin-4-yl<br>Z = CH$_2$<br>R$^1$ = 1H-pyrazol-3-yl<br>R$^2$ = Absent<br>R$^3$ = Absent<br>R$^4$ = Absent<br>n = 1 |
| 64 | | X = N<br>Y = N—CH$_2$-pyridin-4-yl<br>Z = CH$_2$<br>R$^1$ = 4-(pyrazol-3-yl)phenyl<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 65 | 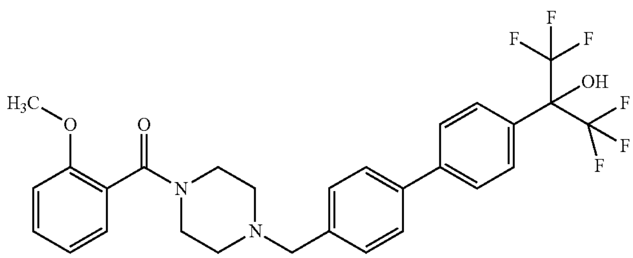 [SMILES: COc1ccccc1C(=O)N1CCN(Cc2ccc(-c3ccc(C(O)(C(F)(F)F)C(F)(F)F)cc3)cc2)CC1] | X = N<br>Y = N—CO-2-methoxyphenyl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 66 | 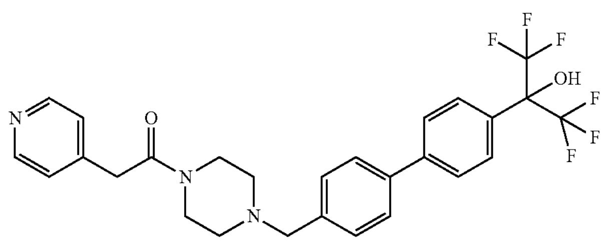 [SMILES: O=C(Cc1ccncc1)N1CCN(Cc2ccc(-c3ccc(C(O)(C(F)(F)F)C(F)(F)F)cc3)cc2)CC1] | X = N<br>Y = N—CO—CH$_2$-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 67 | 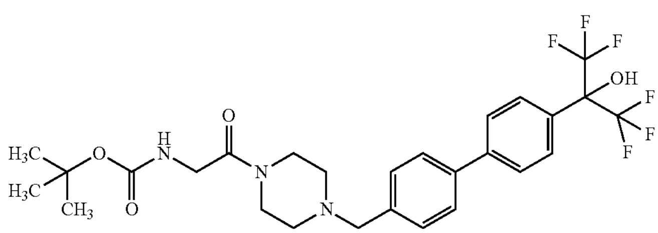 [SMILES: CC(C)(C)OC(=O)NCC(=O)N1CCN(Cc2ccc(-c3ccc(C(O)(C(F)(F)F)C(F)(F)F)cc3)cc2)CC1] | X = N<br>Y = N—CO—CH$_2$—NH—CO—O—C(CH$_3$)$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 68 | 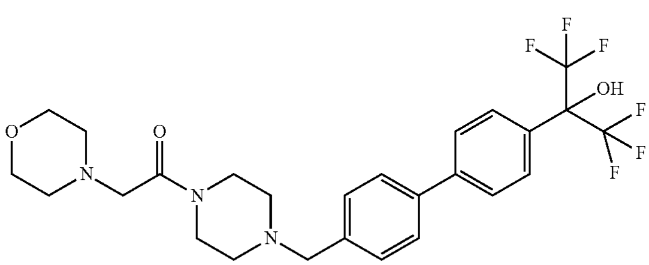 [SMILES: O=C(CN1CCOCC1)N1CCN(Cc2ccc(-c3ccc(C(O)(C(F)(F)F)C(F)(F)F)cc3)cc2)CC1] | X = N<br>Y = N—CO—CH$_2$-morpholine<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 69 | 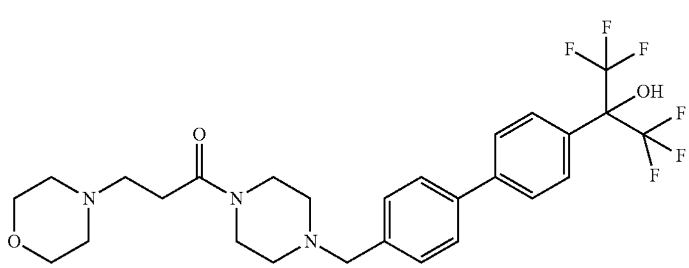 [SMILES: O=C(CCN1CCOCC1)N1CCN(Cc2ccc(-c3ccc(C(O)(C(F)(F)F)C(F)(F)F)cc3)cc2)CC1] | X = N<br>Y = N—CO—CH$_2$—CH$_2$-morpholine<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 70 | 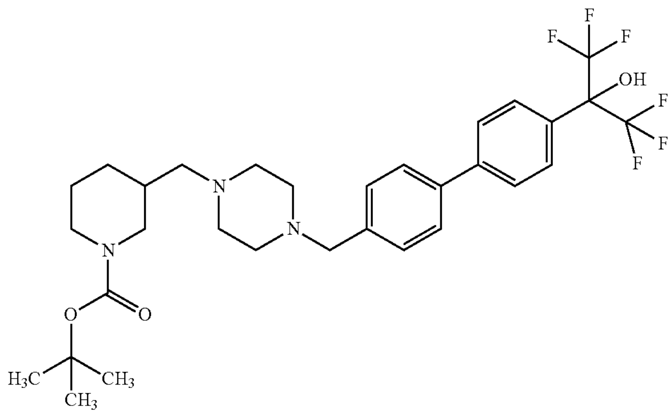 [SMILES: CC(C)(C)OC(=O)N1CCCC(CN2CCN(Cc3ccc(-c4ccc(C(O)(C(F)(F)F)C(F)(F)F)cc4)cc3)CC2)C1] | X = N<br>Y = N—CH$_2$-3-piperidine-1-carboxylic acid tert-butyl ester<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 71 | 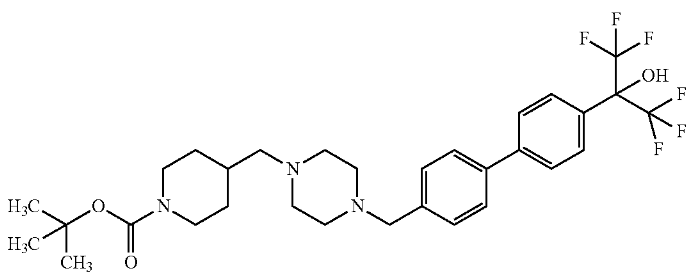 [SMILES: CC(C)(C)OC(=O)N1CCC(CN2CCN(Cc3ccc(-c4ccc(C(O)(C(F)(F)F)C(F)(F)F)cc4)cc3)CC2)CC1] | X = N<br>Y = N—CH$_2$-4-piperidine-1-carboxylic acid tert-butyl ester<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 72 | 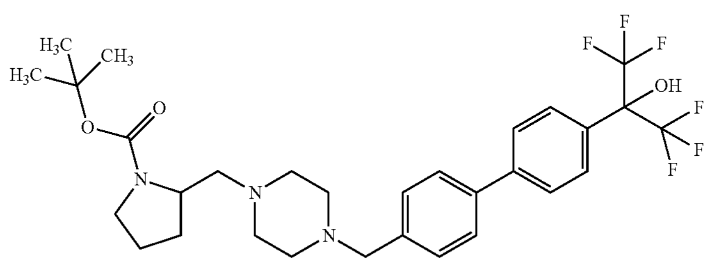 [SMILES: CC(C)(C)OC(=O)N1CCCC1CN1CCN(Cc2ccc(-c3ccc(C(O)(C(F)(F)F)C(F)(F)F)cc3)cc2)CC1] | X = N<br>Y = N—CH$_2$-2-pyrrolidine-1-carboxylic acid tert-butyl ester<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 73 | 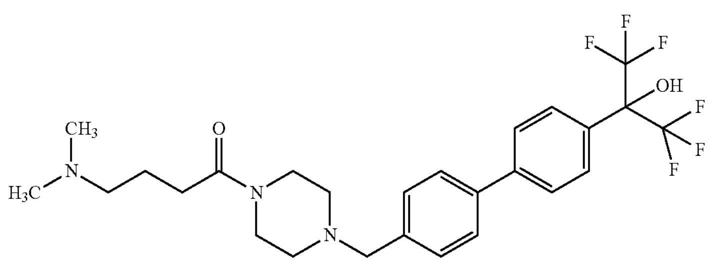 [SMILES: CN(C)CCCC(=O)N1CCN(Cc2ccc(-c3ccc(C(O)(C(F)(F)F)C(F)(F)F)cc3)cc2)CC1] | X = N<br>Y = N—CO—(CH$_2$)$_3$N(CH$_3$)$_2$<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 74 | 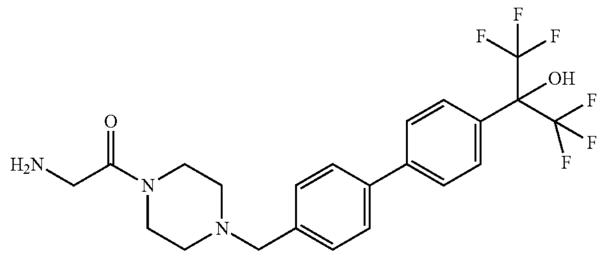 [SMILES: NCC(=O)N1CCN(Cc2ccc(-c3ccc(C(O)(C(F)(F)F)C(F)(F)F)cc3)cc2)CC1] | X = N<br>Y = N—CO—CH$_2$—NH$_2$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 75 | 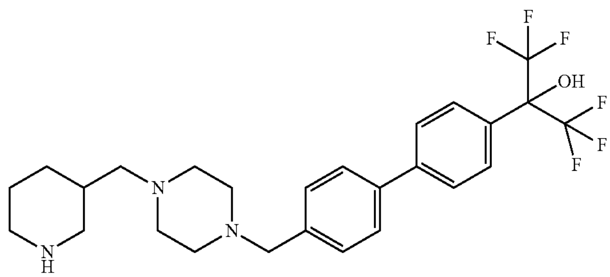 [SMILES: OC(c1ccc(-c2ccc(CN3CCN(CC4CCCNC4)CC3)cc2)cc1)(C(F)(F)F)C(F)(F)F] | X = N<br>Y = N—CH$_2$-piperidin-3-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 76 | 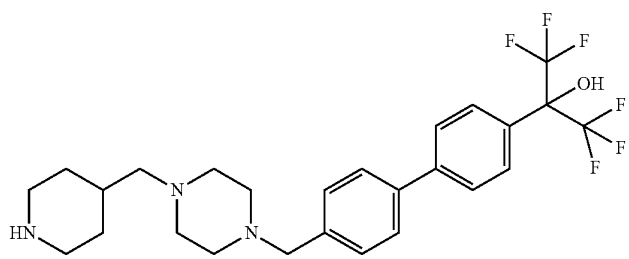 [SMILES: OC(c1ccc(-c2ccc(CN3CCN(CC4CCNCC4)CC3)cc2)cc1)(C(F)(F)F)C(F)(F)F] | X = N<br>Y = N—CH$_2$-piperidin4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 77 | 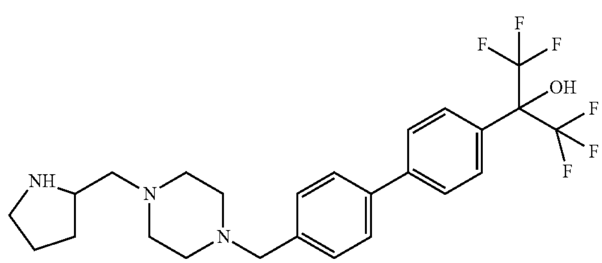 [SMILES: OC(c1ccc(-c2ccc(CN3CCN(CC4CCCN4)CC3)cc2)cc1)(C(F)(F)F)C(F)(F)F] | X = N<br>Y = N—CH$_2$-pyrrolidin2-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 78 | 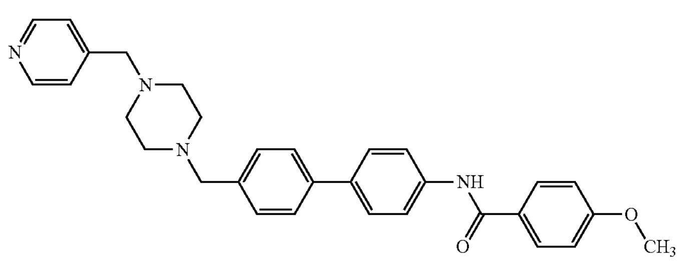 [SMILES: COc1ccc(C(=O)Nc2ccc(-c3ccc(CN4CCN(Cc5ccncc5)CC4)cc3)cc2)cc1] | X = N<br>Y = N—CH$_2$-pyridin-4-yl<br>Z = CH$_2$<br>R$^1$ = NH—CO-4-methoxyphenyl<br>R$^2$ = Absent<br>R$^3$ = Absent<br>R$^4$ = Absent<br>n = 1 |

TABLE 1-continued

Compounds of the Invention

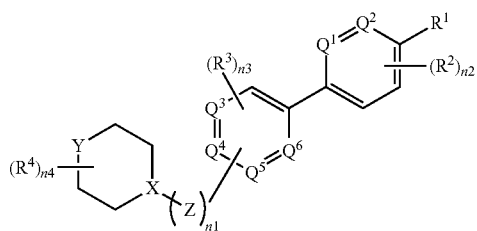

| # | Compound Structure | Generic Structure/Substituents |
|---|---|---|
| 79 | 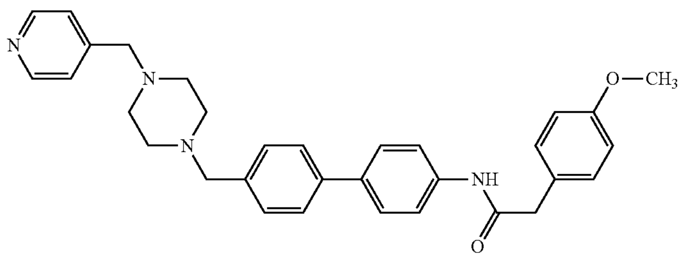 [SMILES: COc1ccc(CC(=O)Nc2ccc(-c3ccc(CN4CCN(Cc5ccncc5)CC4)cc3)cc2)cc1] | X = N<br>Y = N—CH$_2$-pyridin-4-yl<br>Z = CH$_2$<br>R$^1$ = NH—CO—CH$_2$-4-methoxyphenyl<br>R$^2$ = Absent<br>R$^3$ = Absent<br>R$^4$ = Absent<br>n = 1 |
| 80 | 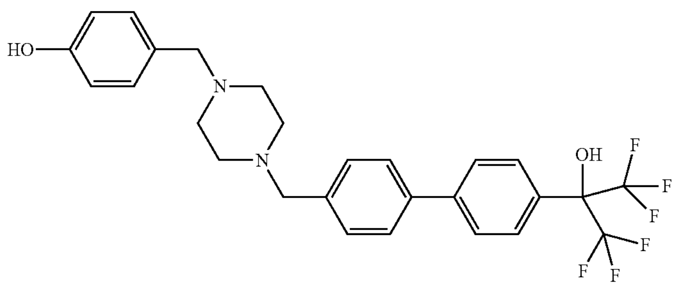 [SMILES: Oc1ccc(CN2CCN(Cc3ccc(-c4ccc(C(O)(C(F)(F)F)C(F)(F)F)cc4)cc3)CC2)cc1] | X = N<br>Y = N—CH$_2$-4-hydroxyphenyl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 81 | 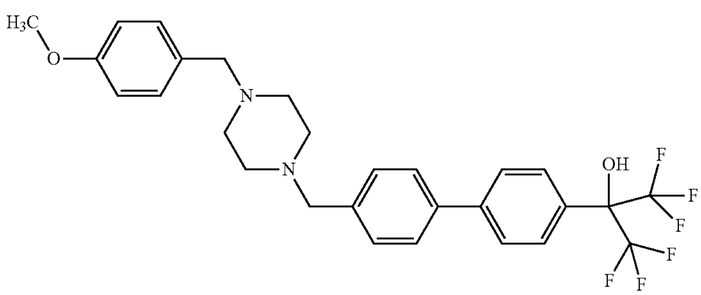 [SMILES: COc1ccc(CN2CCN(Cc3ccc(-c4ccc(C(O)(C(F)(F)F)C(F)(F)F)cc4)cc3)CC2)cc1] | X = N<br>Y = N—CH$_2$-4-methoxyphenyl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 82 | 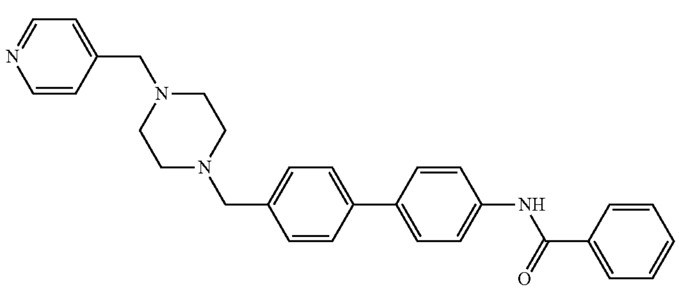 [SMILES: O=C(Nc1ccc(-c2ccc(CN3CCN(Cc4ccncc4)CC3)cc2)cc1)c1ccccc1] | X = N<br>Y = N—CH$_2$-pyridin-4-yl<br>Z = CH$_2$<br>R$^1$ = NH—CO-phenyl<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 83 | 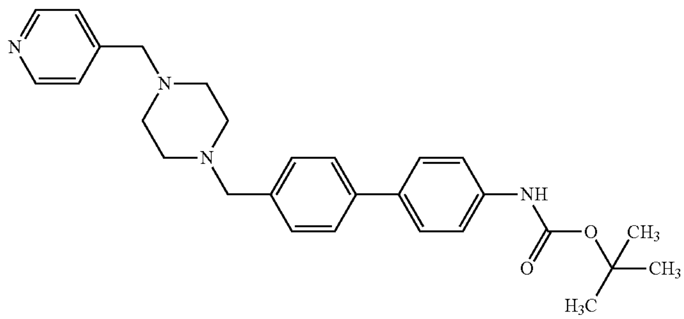 [SMILES: CC(C)(C)OC(=O)Nc1ccc(-c2ccc(CN3CCN(Cc4ccncc4)CC3)cc2)cc1] | X = N<br>Y = N—CH$_2$-pyridin-4-yl<br>Z = CH$_2$<br>R$^1$ = NH—COO—C(CH$_3$)$_3$<br>R$^2$ = Absent<br>R$^3$ = Absent<br>R$^4$ = Absent<br>n = 1 |
| 84 | 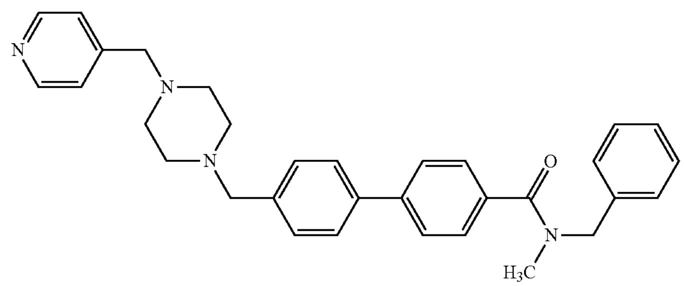 [SMILES: CN(Cc1ccccc1)C(=O)c1ccc(-c2ccc(CN3CCN(Cc4ccncc4)CC3)cc2)cc1] | X = N<br>Y = N—CH$_2$-pyridin-4-yl<br>Z = CH$_2$<br>R$^1$ = CON(CH$_3$)CH$_2$Ph<br>R$^2$ = Absent<br>R$^3$ = Absent<br>R$^4$ = Absent<br>n = 1 |
| 85 | 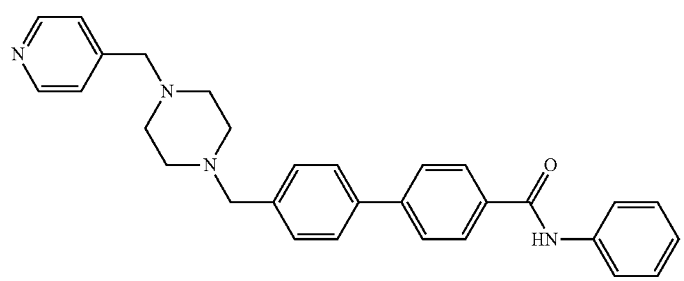 [SMILES: O=C(Nc1ccccc1)c1ccc(-c2ccc(CN3CCN(Cc4ccncc4)CC3)cc2)cc1] | X = N<br>Y = N—CH$_2$-pyridin-4-yl<br>Z = CH$_2$<br>R$^1$ = CO—NH—Ph<br>R$^2$ = Absent<br>R$^3$ = Absent<br>R$^4$ = Absent<br>n = 1 |
| 86 | 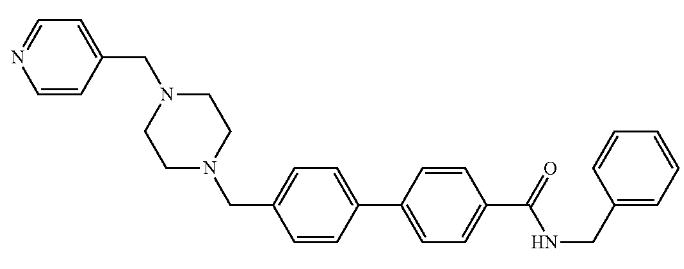 [SMILES: O=C(NCc1ccccc1)c1ccc(-c2ccc(CN3CCN(Cc4ccncc4)CC3)cc2)cc1] | X = N<br>Y = N—CH$_2$-pyridin-4-yl<br>Z = CH$_2$<br>R$^1$ = CO—HN—CH$_2$—Ph<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 87 | 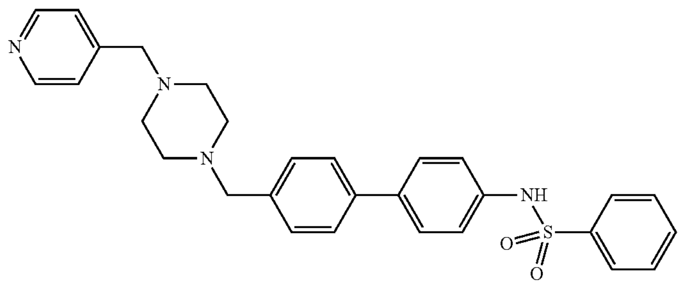 [SMILES: O=S(=O)(Nc1ccc(-c2ccc(CN3CCN(Cc4ccncc4)CC3)cc2)cc1)c1ccccc1] | X = N<br>Y = N—CH$_2$-pyridin-4-yl<br>Z = CH$_2$<br>R$^1$ = HN—O$_2$S—Ph<br>R$^2$ = Absent<br>R$^3$ = Absent<br>R$^4$ = Absent<br>n = 1 |
| 88 | 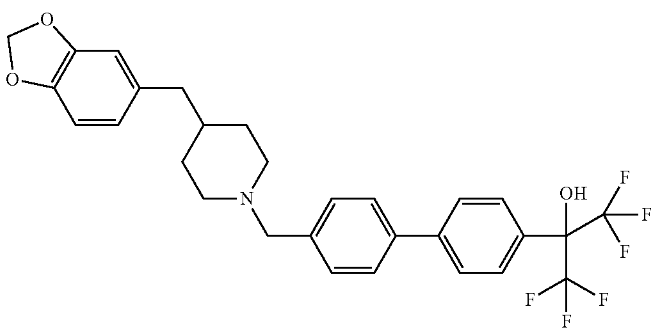 [SMILES: OC(c1ccc(-c2ccc(CN3CCC(Cc4ccc5c(c4)OCO5)CC3)cc2)cc1)(C(F)(F)F)C(F)(F)F] | X = N<br>Y = CH—CH$_2$-Benzo[1,3]dioxole<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 89 | 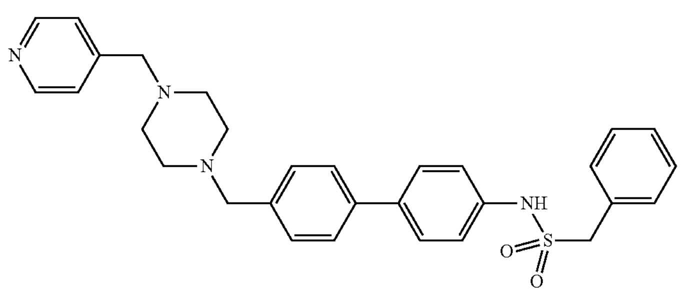 [SMILES: O=S(=O)(Cc1ccccc1)Nc1ccc(-c2ccc(CN3CCN(Cc4ccncc4)CC3)cc2)cc1] | X = N<br>Y = N—CH$_2$-pyridin-4-yl<br>Z = CH$_2$<br>R$^1$ = HN—SO$_2$—CH$_2$—Ph<br>R$^2$ = Absent<br>R$^3$ = Absent<br>R$^4$ = Absent<br>n = 1 |
| 90 | 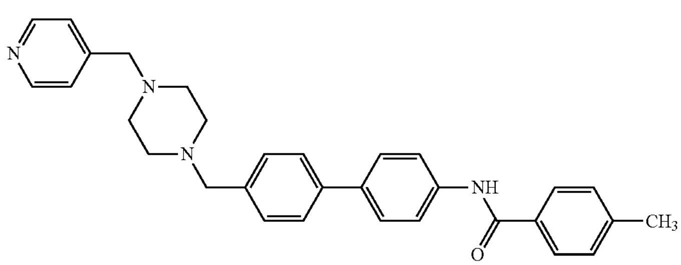 [SMILES: Cc1ccc(C(=O)Nc2ccc(-c3ccc(CN4CCN(Cc5ccncc5)CC4)cc3)cc2)cc1] | X = N<br>Y = N—CH$_2$-pyridin-4-yl<br>Z = CH$_2$<br>R$^1$ = HN—CO-4-tolyl<br>R$^2$ = Absent<br>R$^3$ = Absent<br>R$^4$ = Absent<br>n = 1 |

TABLE 1-continued

Compounds of the Invention

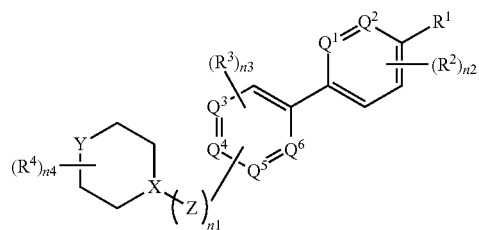

| # | Compound Structure | Generic Structure/Substituents |
|---|---|---|
| 91 | 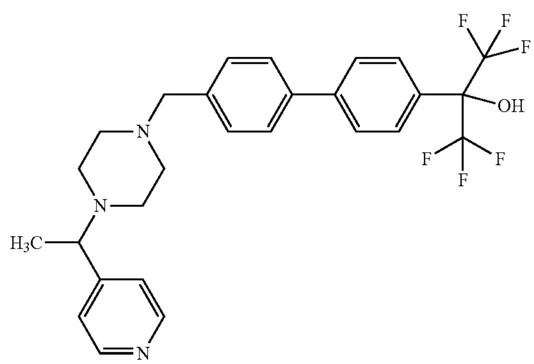 [SMILES: CC(c1ccncc1)N1CCN(Cc2ccc(-c3ccc(C(O)(C(F)(F)F)C(F)(F)F)cc3)cc2)CC1] | X = N<br>Y = N—C(CH$_3$)-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 92 | 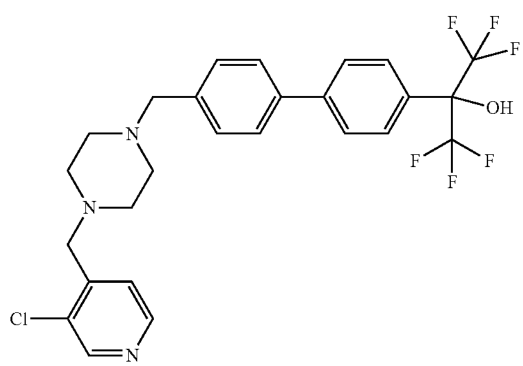 [SMILES: OC(c1ccc(-c2ccc(CN3CCN(Cc4ccncc4Cl)CC3)cc2)cc1)(C(F)(F)F)C(F)(F)F] | X = N<br>Y = N—CH$_2$-3-chloro pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 93 | 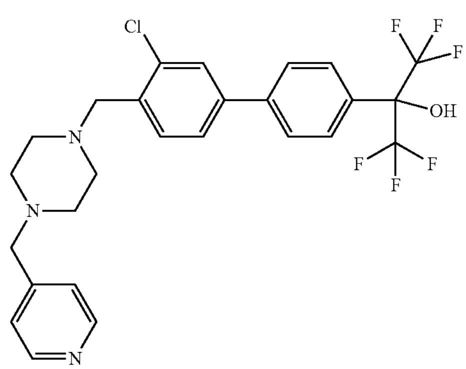 [SMILES: OC(c1ccc(-c2ccc(CN3CCN(Cc4ccncc4)CC3)c(Cl)c2)cc1)(C(F)(F)F)C(F)(F)F] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = Cl<br>R$^4$ = Absent<br>n = 1<br>n3 = 1 |

TABLE 1-continued

Compounds of the Invention

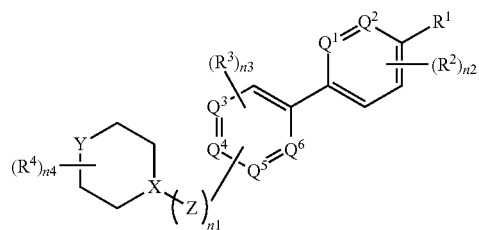

| # | Compound Structure | Generic Structure/Substituents |
|---|---|---|
| 94 | 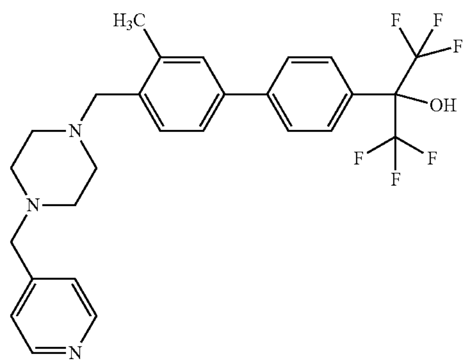 [SMILES: Cc1cc(-c2ccc(C(O)(C(F)(F)F)C(F)(F)F)cc2)ccc1CN1CCN(Cc2ccncc2)CC1] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = CH$_3$<br>R$^4$ = Absent<br>n = 1<br>n3 = 1 |
| 95 | 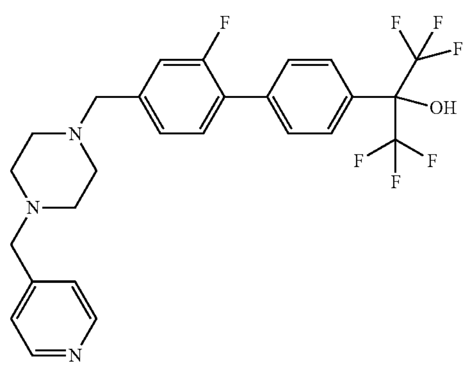 [SMILES: OC(c1ccc(-c2ccc(CN3CCN(Cc4ccncc4)CC3)cc2F)cc1)(C(F)(F)F)C(F)(F)F] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = F<br>R$^4$ = Absent<br>n = 1<br>n3 = 1 |
| 96 | 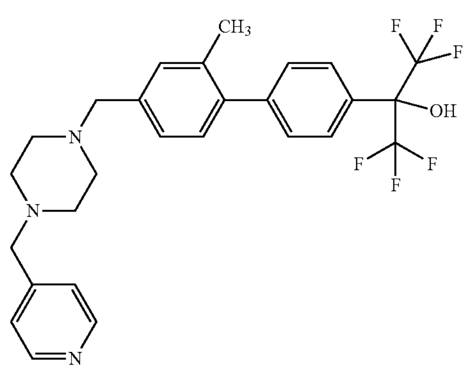 [SMILES: Cc1cc(CN2CCN(Cc3ccncc3)CC2)ccc1-c1ccc(C(O)(C(F)(F)F)C(F)(F)F)cc1] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = CH$_3$<br>R$^4$ = Absent<br>n = 1<br>n3 = 1 |

TABLE 1-continued

Compounds of the Invention

| # | Compound Structure | Generic Structure/Substituents |
|---|---|---|
| 97 | 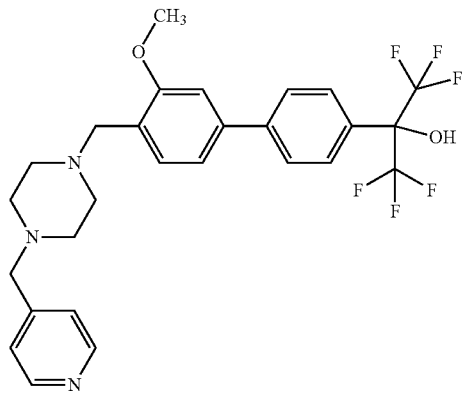 [SMILES: COc1cc(-c2ccc(C(O)(C(F)(F)F)C(F)(F)F)cc2)ccc1CN1CCN(Cc2ccncc2)CC1] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = OCH$_3$<br>R$^4$ = Absent<br>n = 1<br>n3 = 1 |
| 98 | 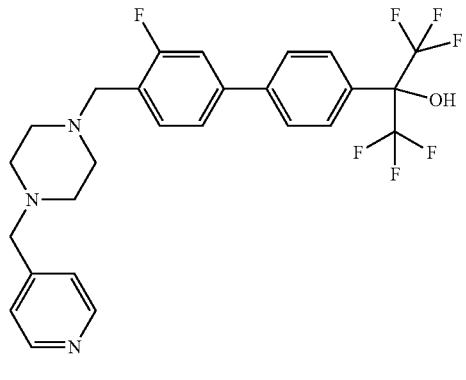 [SMILES: OC(c1ccc(-c2ccc(CN3CCN(Cc4ccncc4)CC3)c(F)c2)cc1)(C(F)(F)F)C(F)(F)F] | X = N<br>Y = N—CH$_2$-yridin-4-yl<br>Z = CH$_2$<br>R$^1$ = HO—C—(CF$_3$)$_2$<br>R$^2$ = Absent<br>R$^3$ = F<br>R$^4$ = Absent<br>n = 1<br>n3 = 1 |
| 99 | 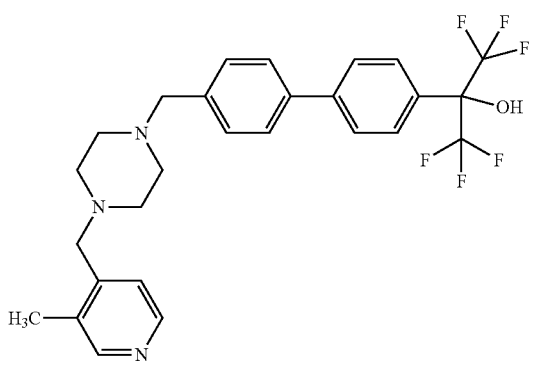 [SMILES: Cc1cnccc1CN1CCN(Cc2ccc(-c3ccc(C(O)(C(F)(F)F)C(F)(F)F)cc3)cc2)CC1] | X = N<br>Y = N—CH$_2$-3-methylpyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

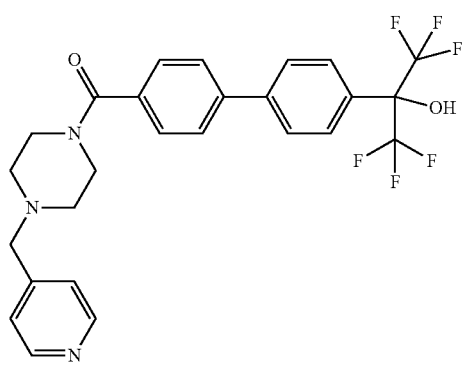 [SMILES: O=C(c1ccc(-c2ccc(C(O)(C(F)(F)F)C(F)(F)F)cc2)cc1)N1CCN(Cc2ccncc2)CC1]

| # | Compound Structure | Generic Structure/Substituents |
|---|---|---|
| 100 | 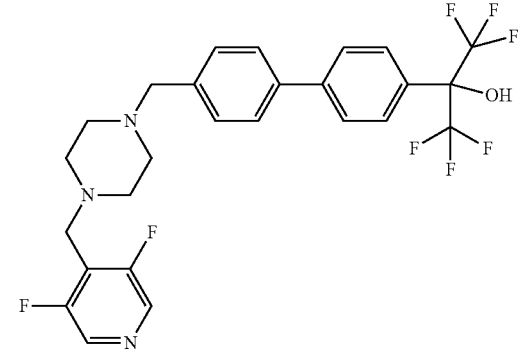 [SMILES: OC(c1ccc(-c2ccc(CN3CCN(Cc4c(F)cncc4F)CC3)cc2)cc1)(C(F)(F)F)C(F)(F)F] | X = N<br>Y = N—CH$_2$-Pyridine<br>Z = CO<br>R$^1$ = HO—C—(CF$_3$)$_2$<br>R$^2$ = Absent<br>R$^3$ = Absent<br>R$^4$ = Absent<br>n = 1 |
| 101 | 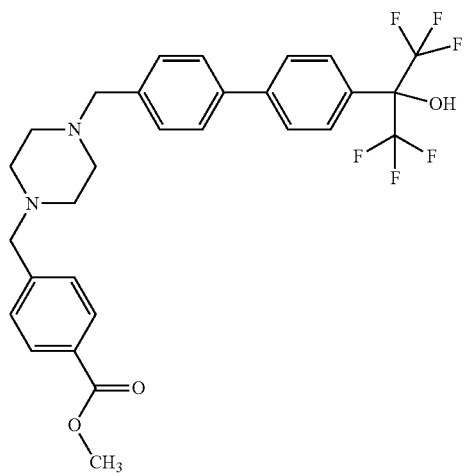 | X = N<br>Y = N—CH$_2$-3,5-difluoropyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 102 | 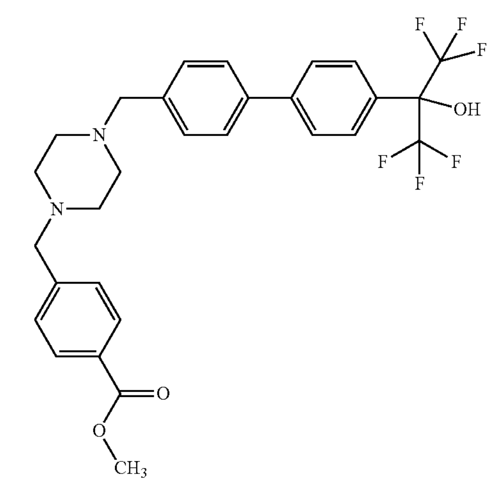 [SMILES: COC(=O)c1ccc(CN2CCN(Cc3ccc(-c4ccc(C(O)(C(F)(F)F)C(F)(F)F)cc4)cc3)CC2)cc1] | X = N<br>Y = N—CH$_2$-p-phenyl-CO$_2$CH$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

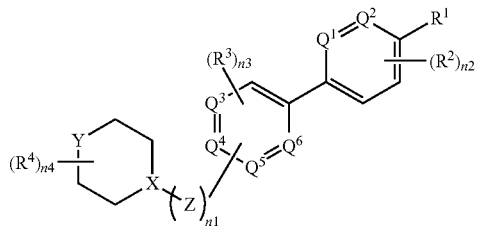

| # | Compound Structure | Generic Structure/Substituents |
|---|---|---|
| 103 | 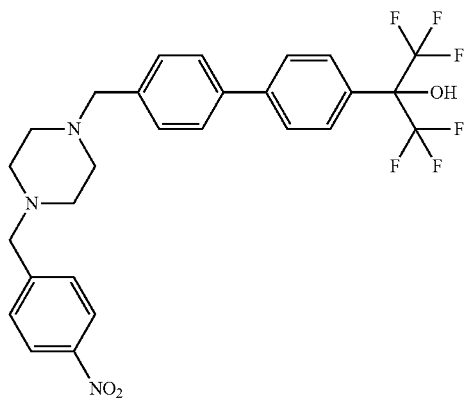 [SMILES: O=[N+]([O-])c1ccc(CN2CCN(Cc3ccc(-c4ccc(C(O)(C(F)(F)F)C(F)(F)F)cc4)cc3)CC2)cc1] | X = N<br>Y = N—CH$_2$-p-nitrophenyl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 104 | 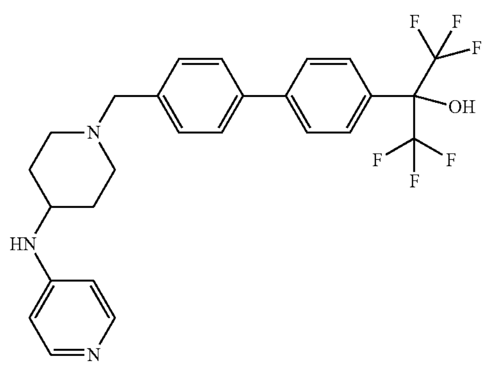 [SMILES: OC(c1ccc(-c2ccc(CN3CCC(Nc4ccncc4)CC3)cc2)cc1)(C(F)(F)F)C(F)(F)F] | X = N<br>Y = CH—HN-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 105 | 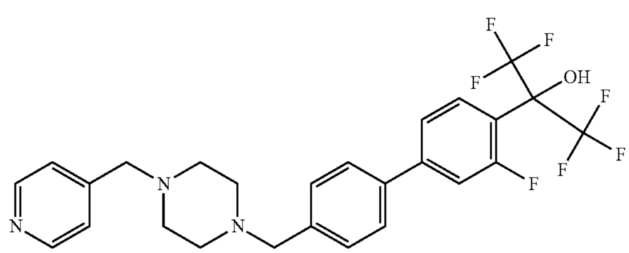 [SMILES: OC(c1ccc(-c2ccc(CN3CCN(Cc4ccncc4)CC3)cc2)cc1F)(C(F)(F)F)C(F)(F)F] | X = N<br>Y = N—CH$_2$-pyridin-4-yl<br>Z = CH$_2$<br>R$^1$ = HO—C—(CF$_3$)$_2$<br>R$^2$ = F<br>R$^3$ = Absent<br>R$^4$ = Absent<br>n = 1<br>n2 = 1 |
| 106 | 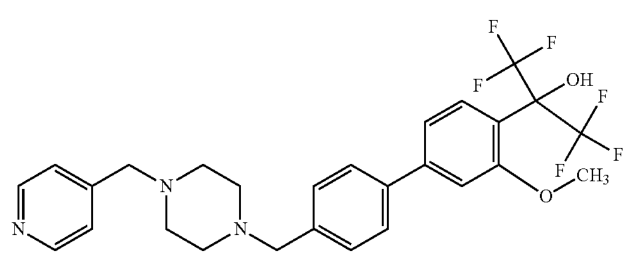 [SMILES: COc1cc(-c2ccc(CN3CCN(Cc4ccncc4)CC3)cc2)ccc1C(O)(C(F)(F)F)C(F)(F)F] | X = N<br>Y = N—CH$_2$-pyridine<br>Z = CH$_2$<br>R$^1$ = HO—C—(CF$_3$)$_2$<br>R$^2$ = OCH$_3$<br>R$^3$ = Absent<br>R$^4$ = Absent<br>n = 1<br>n2 = 1 |

TABLE 1-continued

Compounds of the Invention

| # | Compound Structure | Generic Structure/Substituents |
|---|---|---|
| 107 | 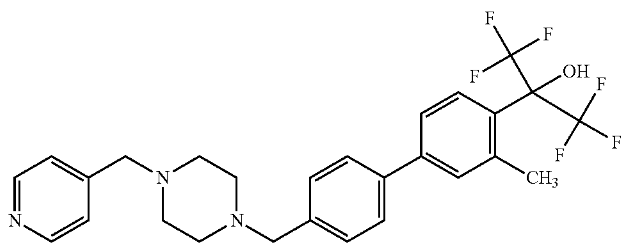 [SMILES: Cc1cc(-c2ccc(CN3CCN(Cc4ccncc4)CC3)cc2)ccc1C(O)(C(F)(F)F)C(F)(F)F] | X = N<br>Y = N—CH$_2$-pyridin-4-yl<br>Z = CH$_2$<br>R$^1$ = HO—C—(CF$_3$)$_2$<br>R$^2$ = CH$_3$<br>R$^3$ = Absent<br>R$^4$ = Absent<br>n = 1<br>n2 = 1 |
| 108 | 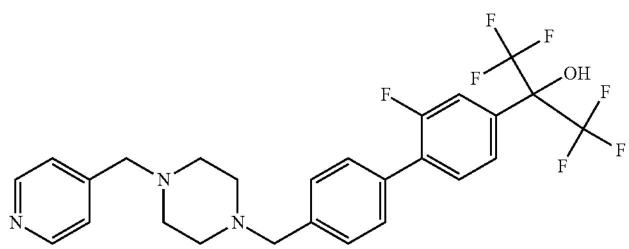 [SMILES: OC(c1ccc(-c2ccc(CN3CCN(Cc4ccncc4)CC3)cc2)c(F)c1)(C(F)(F)F)C(F)(F)F] | X = N<br>Y = N—CH$_2$-pyridin-4-yl<br>Z = CH$_2$<br>R$^1$ = HO—C—(CF$_3$)$_2$<br>R$^2$ = F<br>R$^3$ = Absent<br>R$^4$ = Absent<br>n = 1<br>n2 = 1 |
| 109 | 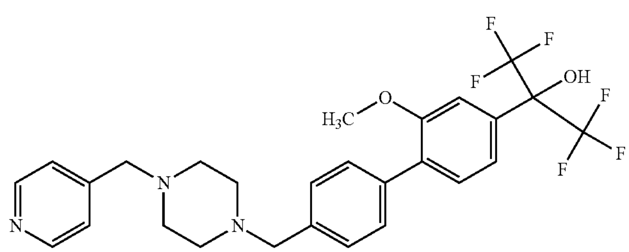 [SMILES: COc1cc(C(O)(C(F)(F)F)C(F)(F)F)ccc1-c1ccc(CN2CCN(Cc3ccncc3)CC2)cc1] | X = N<br>Y = N—CH$_2$-pyridin-4-yl<br>Z = CH$_2$<br>R$^1$ = HO—C—(CF$_3$)$_2$<br>R$^2$ = OCH$_3$<br>R$^3$ = Absent<br>R$^4$ = Absent<br>n = 1<br>n2 = 1 |
| 110 | 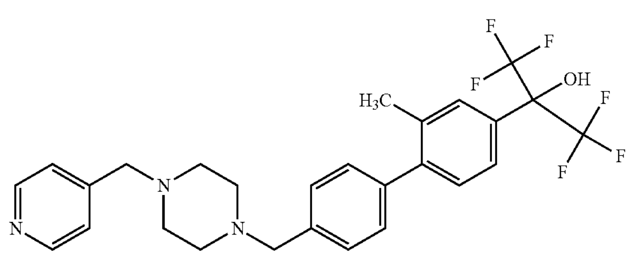 [SMILES: Cc1cc(C(O)(C(F)(F)F)C(F)(F)F)ccc1-c1ccc(CN2CCN(Cc3ccncc3)CC2)cc1] | X = N<br>Y = N—CH$_2$-pyridin-4-yl<br>Z = CH$_2$<br>R$^1$ = HO—C—(CF$_3$)$_2$<br>R$^2$ = CH$_3$<br>R$^3$ = Absent<br>R$^4$ = Absent<br>n = 1<br>n2 = 1 |
| 111 | 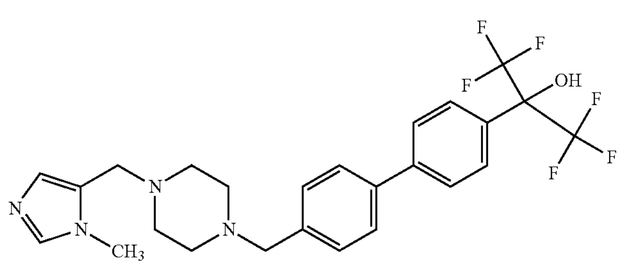 [SMILES: Cn1cncc1CN1CCN(Cc2ccc(-c3ccc(C(O)(C(F)(F)F)C(F)(F)F)cc3)cc2)CC1] | X = N<br>Y = N—CH$_2$-1-methyl-1H-imidazol-5-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 112 | 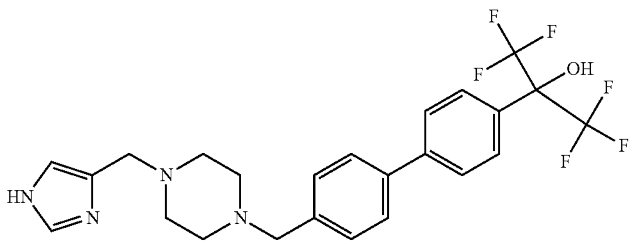 [SMILES: OC(c1ccc(-c2ccc(CN3CCN(Cc4c[nH]cn4)CC3)cc2)cc1)(C(F)(F)F)C(F)(F)F] | X = N<br>Y = N—CH$_2$-4-imidazol-5-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 113 | 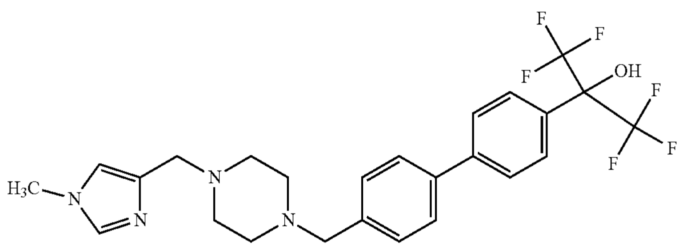 [SMILES: Cn1cnc(CN2CCN(Cc3ccc(-c4ccc(C(O)(C(F)(F)F)C(F)(F)F)cc4)cc3)CC2)c1] | X = N<br>Y = N—CH$_2$-1-methyl-1H-imidazol-5-yl<br>R$^1$ = HO—C—(CF$_3$)$_2$<br>R$^2$ = Absent<br>R$^3$ = Absent<br>R$^4$ = Absent<br>n = 1 |
| 114 | 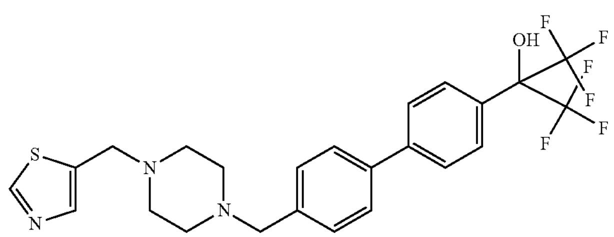 [SMILES: OC(c1ccc(-c2ccc(CN3CCN(Cc4cncs4)CC3)cc2)cc1)(C(F)(F)F)C(F)(F)F] | X = N<br>Y = N—CH$_2$-5-thiazole<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 115 | 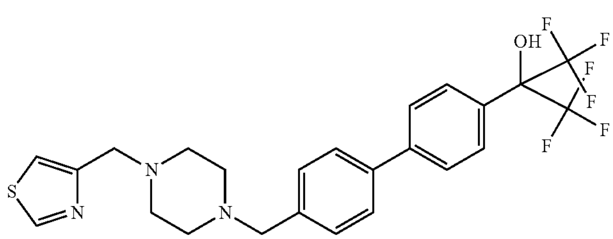 [SMILES: OC(c1ccc(-c2ccc(CN3CCN(Cc4cscn4)CC3)cc2)cc1)(C(F)(F)F)C(F)(F)F] | X = N<br>Y = N—CH$_2$-thiazol-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 116 | 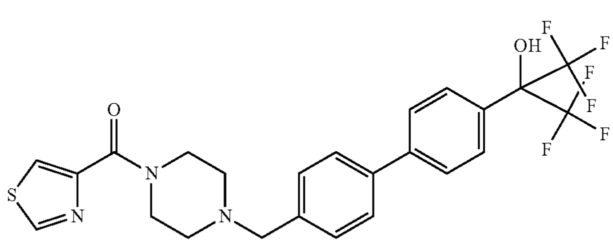 [SMILES: O=C(c1cscn1)N1CCN(Cc2ccc(-c3ccc(C(O)(C(F)(F)F)C(F)(F)F)cc3)cc2)CC1] | X = N<br>Y = N—CO-4-thiazol-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

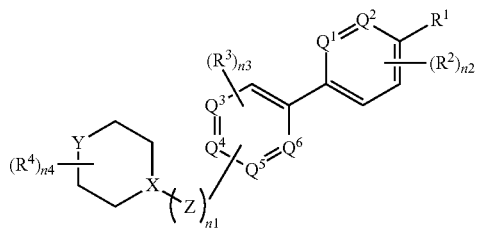

| # | Compound Structure | Generic Structure/Substituents |
|---|---|---|
| 117 | 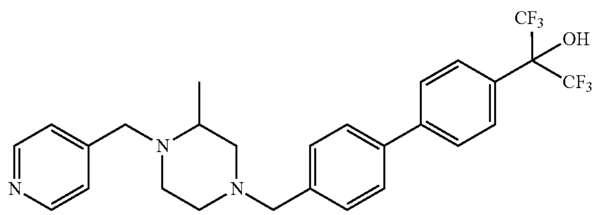 [SMILES: CC1CN(Cc2ccc(-c3ccc(C(O)(C(F)(F)F)C(F)(F)F)cc3)cc2)CCN1Cc1ccncc1] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = Absent<br>R$^4$ = CH$_3$<br>n = 1<br>n4 = 1 |
| 118 | 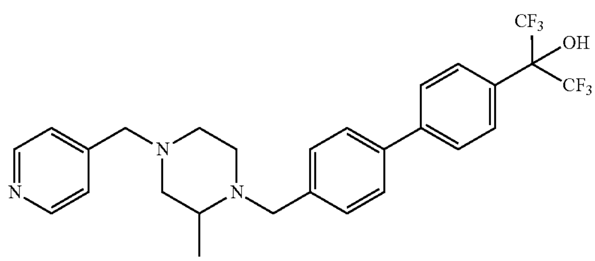 [SMILES: CC1CN(Cc2ccncc2)CCN1Cc1ccc(-c2ccc(C(O)(C(F)(F)F)C(F)(F)F)cc2)cc1] | X = N<br>Y = N—CH$_2$-pyridin-4-yl<br>R$^1$ = HO—C—(CF$_3$)$_2$<br>R$^2$ = Absent<br>R$^3$ = Absent<br>R$^4$ = CH$_3$<br>n = 1<br>n4 = 1 |
| 119 | 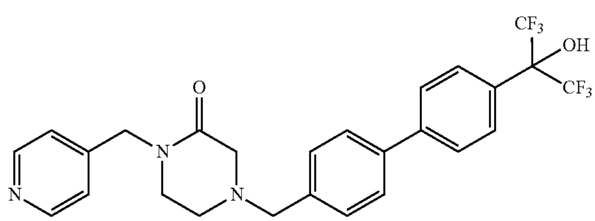 [SMILES: O=C1CN(Cc2ccc(-c3ccc(C(O)(C(F)(F)F)C(F)(F)F)cc3)cc2)CCN1Cc1ccncc1] | X = N<br>Y = N—CH$_2$-pyridin-4-yl<br>R$^1$ = HO—C—(CF$_3$)$_2$<br>R$^2$ = Absent<br>R$^3$ = Absent<br>R$^4$ = oxo<br>n = 1<br>n4 = 1 |
| 120 | 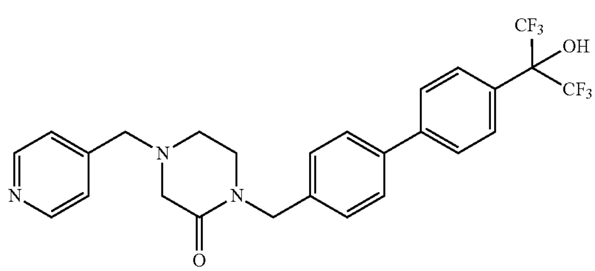 [SMILES: O=C1CN(Cc2ccncc2)CCN1Cc1ccc(-c2ccc(C(O)(C(F)(F)F)C(F)(F)F)cc2)cc1] | X = N<br>Y = N—CH$_2$-pyridin-4-yl<br>R$^1$ = HO—C—(CF$_3$)$_2$<br>R$^2$ = Absent<br>R$^3$ = Absent<br>R$^4$ = oxo<br>n = 1<br>n4 = 1 |
| 121 | 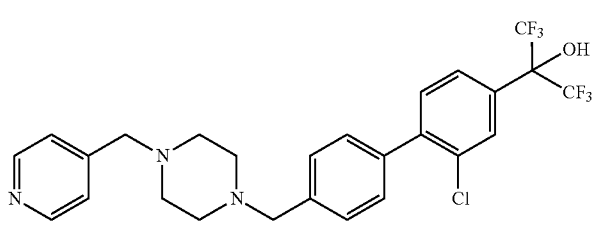 [SMILES: OC(c1ccc(-c2ccc(CN3CCN(Cc4ccncc4)CC3)cc2)c(Cl)c1)(C(F)(F)F)C(F)(F)F] | X = N<br>Y = N—CH$_2$-pyridin-4-yl<br>R$^1$ = HO—C—(CF$_3$)$_2$<br>R$^2$ = Cl<br>R$^3$ = Absent<br>R$^4$ = Absent<br>n = 1<br>n2 = 1 |

TABLE 1-continued

Compounds of the Invention

| # | Compound Structure | Generic Structure/Substituents |
|---|---|---|
| 122 | 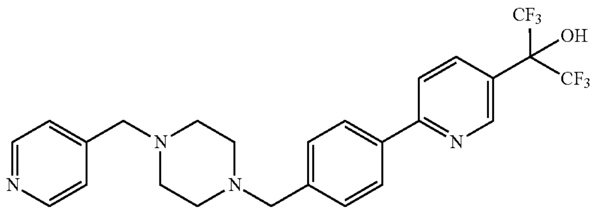 [SMILES: OC(c1ccc(-c2ccc(CN3CCN(Cc4ccncc4)CC3)cc2)nc1)(C(F)(F)F)C(F)(F)F] | X = N<br>Y = N—CH$_2$-pyridine-4-yl<br>Z = CH$_2$<br>Q$^1$ = CH$_2$<br>R$^1$ = HO—C—(CF$_3$)$_2$<br>R$^2$ = Absent<br>R$^3$ = Absent<br>R$^4$ = Absent<br>n = 1 |
| 123 | 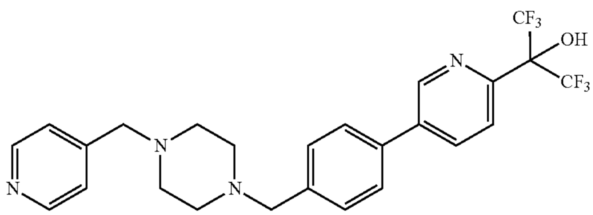 [SMILES: OC(c1ccc(-c2ccc(CN3CCN(Cc4ccncc4)CC3)cc2)cn1)(C(F)(F)F)C(F)(F)F] | X = N<br>Y = N—CH$_2$-pyridin-4-yl<br>Z = CH$_2$<br>Q$^2$ = N<br>R$^1$ = HO—C—(CF$_3$)$_2$<br>R$^2$ = Absent<br>R$^3$ = Absent<br>R$^4$ = Absent<br>n = 1 |
| 124 | 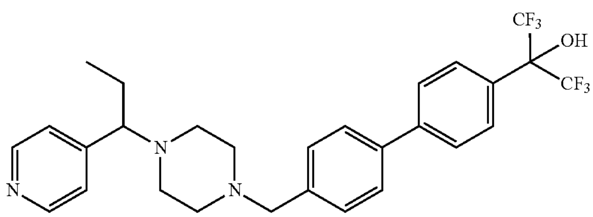 [SMILES: CCC(c1ccncc1)N1CCN(Cc2ccc(-c3ccc(C(O)(C(F)(F)F)C(F)(F)F)cc3)cc2)CC1] | X = N<br>Y = N-1-(4-pyridinyl)-prop-1-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 125 | 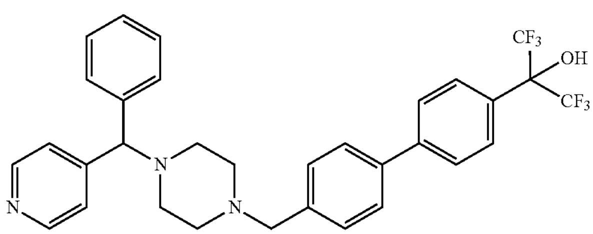 [SMILES: OC(c1ccc(-c2ccc(CN3CCN(C(c4ccccc4)c4ccncc4)CC3)cc2)cc1)(C(F)(F)F)C(F)(F)F] | X = N<br>Y = N-α-(4-pyridinyl)-benzyl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 126 | 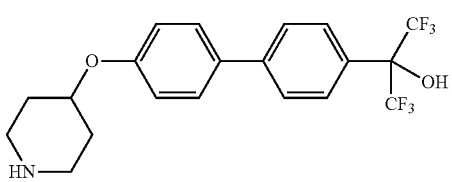 | X = CH<br>Y = NH<br>Z = O<br>R$^1$ = HO—C—(CF$_3$)$_2$<br>R$^2$ = Absent<br>R$^3$ = Absent<br>R$^4$ = Absent<br>n = 1 |
| 127 | 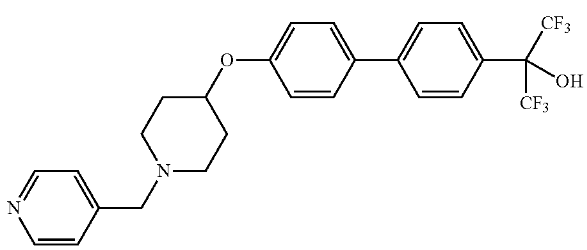 | X = CH<br>Y = N—CH$_2$-pyridin-4-yl<br>Z = O<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 128 | 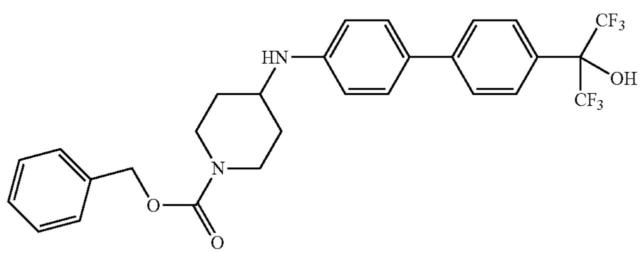 | X = CH<br>Y = N—C(O)OCH$_2$—Ph<br>Z = NH<br>R$^1$ = HO—C—(CF$_3$)$_2$<br>R$^2$ = Absent<br>R$^3$ = Absent<br>R$^4$ = Absent<br>n = 1 |
| 129 | 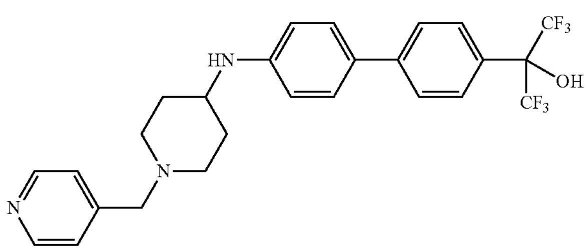 [SMILES: OC(c1ccc(-c2ccc(OC3CCN(Cc4ccncc4)CC3)cc2)cc1)(C(F)(F)F)C(F)(F)F] | X = CH<br>Y = N—CH$_2$-pyridin-4-yl<br>Z = NH<br>R$^1$ = HO—C—(CF$_3$)$_2$<br>R$^2$ = Absent<br>R$^3$ = Absent<br>R$^4$ = Absent<br>n = 1 |
| 130 | 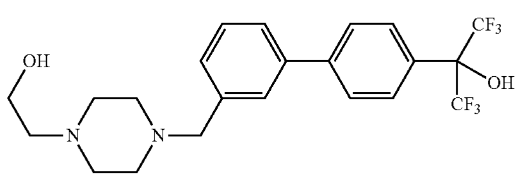 [SMILES: OCCN1CCN(Cc2cccc(-c3ccc(C(O)(C(F)(F)F)C(F)(F)F)cc3)c2)CC1] | X = N<br>Y = N—CH$_2$CH$_2$OH<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 131 | 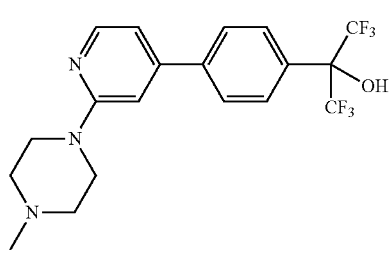 [SMILES: CN1CCN(c2cc(-c3ccc(C(O)(C(F)(F)F)C(F)(F)F)cc3)ccn2)CC1] | X = N<br>Y = N—CH$_3$<br>Z = absent<br>Q$^4$ = N<br>R$^1$ = HO—C—(CF$_3$)$_2$<br>R$^2$ = Absent<br>R$^3$ = Absent<br>R$^4$ = Absent<br>n = 1 |
| 132 | 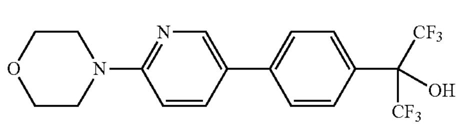 | X = N<br>Y = O<br>Z = absent<br>Q$^3$ = N<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 133 | 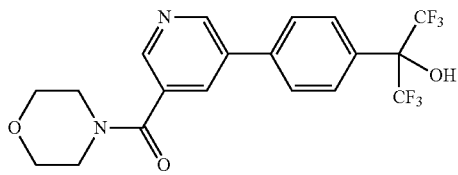 [SMILES: O=C(c1cncc(-c2ccc(C(O)(C(F)(F)F)C(F)(F)F)cc2)c1)N1CCOCC1] | X = N<br>Y = O<br>Z = C(O)<br>Q³ = N<br>R¹ = HO—C—(CF₃)₂<br>R² = Absent<br>R³ = Absent<br>R⁴ = Absent<br>n = 1 |
| 134 | 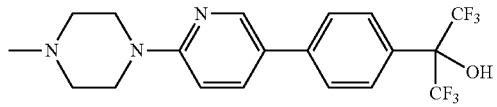 | X = N<br>Y = N—CH₃<br>Z = absent<br>Q³ = N<br>R¹ = HO—C—(CF₃)₂<br>R² = Absent<br>R³ = Absent<br>R⁴ = Absent<br>n = 1 |
| 135 | 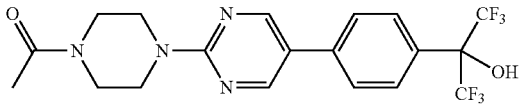 | X = N<br>Y = N—C(O)CH₃<br>Z = absent<br>Q³ = Q⁵ = N<br>R¹ = HO—C—(CF₃)₂<br>R² = Absent<br>R³ = Absent<br>R⁴ = Absent<br>n = 1 |
| 136 | 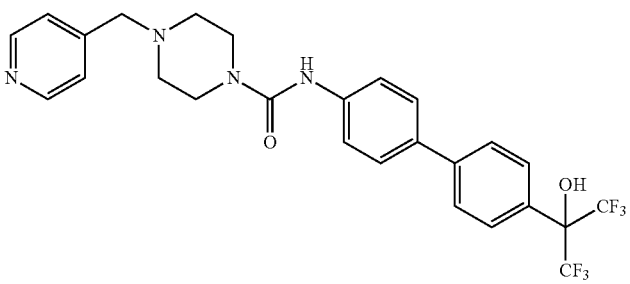 [SMILES: O=C(Nc1ccc(-c2ccc(C(O)(C(F)(F)F)C(F)(F)F)cc2)cc1)N1CCN(Cc2ccncc2)CC1] | X = N<br>Y = N—CH₂-pyridin-4-yl<br>Z = CO—NH<br>R¹ = HO—C—(CF₃)₂<br>R² = Absent<br>R³ = Absent<br>R⁴ = Absent<br>n = 1 |
| 137 | 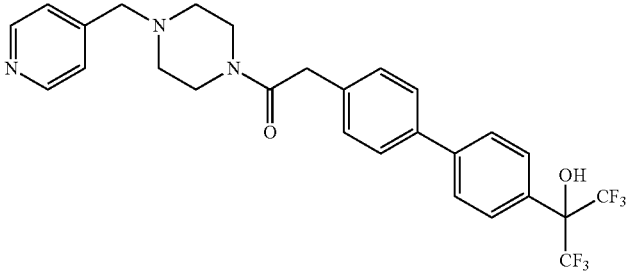 [SMILES: O=C(Cc1ccc(-c2ccc(C(O)(C(F)(F)F)C(F)(F)F)cc2)cc1)N1CCN(Cc2ccncc2)CC1] | X = N<br>Y = N—CH₂-pyridin-4-yl<br>Z = CO—CH₂<br>R¹ = HO—C—(CF₃)₂<br>R² = Absent<br>R³ = Absent<br>R⁴ = Absent<br>n = 1 |

TABLE 1-continued

Compounds of the Invention

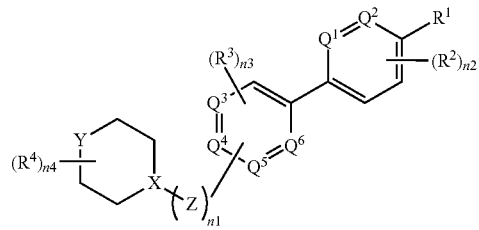

| # | Compound Structure | Generic Structure/Substituents |
|---|---|---|
| 138 | 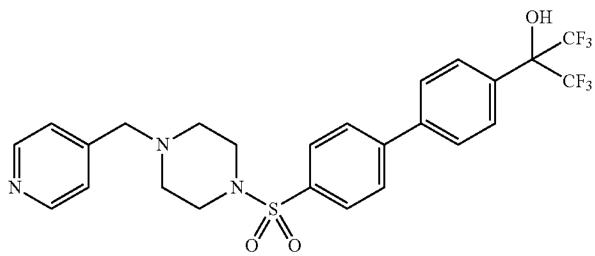 [SMILES: O=S(=O)(c1ccc(-c2ccc(C(O)(C(F)(F)F)C(F)(F)F)cc2)cc1)N1CCN(Cc2ccncc2)CC1] | X = N<br>Y = N—CH$_2$-pyridin-4-yl<br>Z = SO$_2$<br>R$^1$ = HO—C—(CF$_3$)$_2$<br>R$^2$ = Absent<br>R$^3$ = Absent<br>R$^4$ = Absent<br>n = 1 |
| 139 | 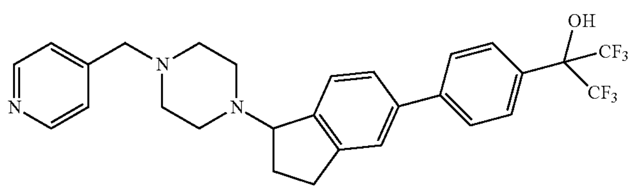 [SMILES: OC(c1ccc(-c2ccc3c(c2)CCC3N2CCN(Cc3ccncc3)CC2)cc1)(C(F)(F)F)C(F)(F)F] | X = N<br>Y = N—CH$_2$-pyridin-4-yl<br>Z = CH—CH$_2$—CH$_2$—R$^3$<br>R$^1$ = HO—C—(CF$_3$)$_2$<br>R$^2$ = Absent<br>R$^3$ = bond<br>R$^4$ = Absent<br>n = 1 |
| 140 | 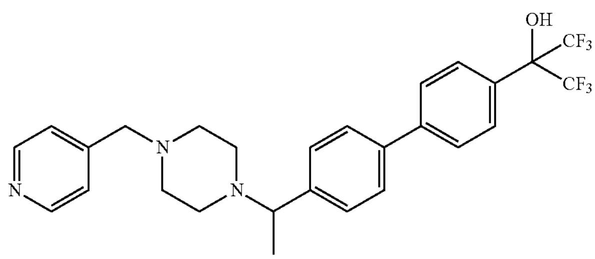 [SMILES: CC(c1ccc(-c2ccc(C(O)(C(F)(F)F)C(F)(F)F)cc2)cc1)N1CCN(Cc2ccncc2)CC1] | X = N<br>Y = N—CH$_2$-pyridin-4-yl<br>Z = CH(CH$_3$)<br>R$^1$ = HO—C—(CF$_3$)$_2$<br>R$^2$ = Absent<br>R$^3$ = Absent<br>R$^4$ = Absent<br>n = 1 |
| 141 | 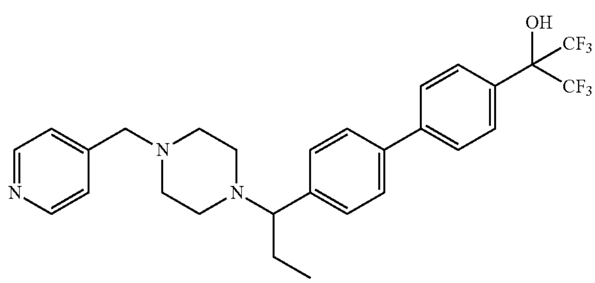 [SMILES: CCC(c1ccc(-c2ccc(C(O)(C(F)(F)F)C(F)(F)F)cc2)cc1)N1CCN(Cc2ccncc2)CC1] | X = N<br>Y = N—CH$_2$-pyridin-4-yl<br>Z = CH(CH$_2$—CH$_3$)<br>R$^1$ = HO—C—(CF$_3$)$_2$<br>R$^2$ = Absent<br>R$^3$ = Absent<br>R$^4$ = Absent<br>n = 1 |
| 142 | 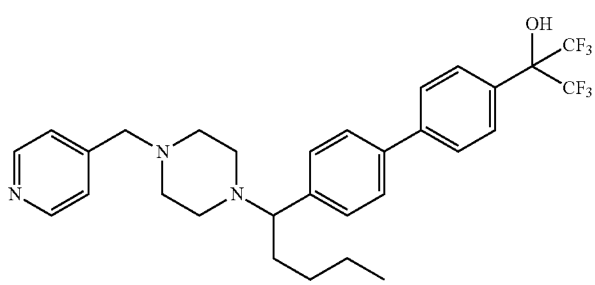 [SMILES: CCCCC(c1ccc(-c2ccc(C(O)(C(F)(F)F)C(F)(F)F)cc2)cc1)N1CCN(Cc2ccncc2)CC1] | X = N<br>Y = N—CH$_2$-4-pyridin-4-yl<br>Z = CH((CH$_2$)$_3$—CH$_3$)<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

| # | Compound Structure | Generic Structure/Substituents |
|---|---|---|
| 143 | 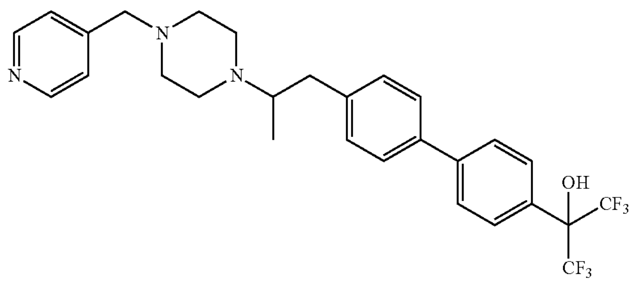 [SMILES: CC(Cc1ccc(-c2ccc(C(O)(C(F)(F)F)C(F)(F)F)cc2)cc1)N1CCN(Cc2ccncc2)CC1] | X = N<br>Y = N—CH$_2$-pyridin-4-yl<br>Z = CH(CH$_3$)—CH$_2$<br>R$^1$ = HO—C—(CF$_3$)$_2$<br>R$^2$ = Absent<br>R$^3$ = Absent<br>R$^4$ = Absent<br>n = 1 |
| 144 | 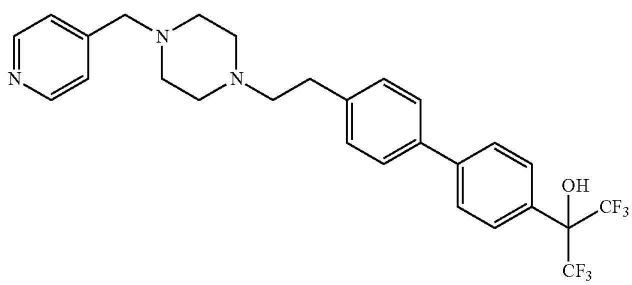 [SMILES: OC(c1ccc(-c2ccc(CCN3CCN(Cc4ccncc4)CC3)cc2)cc1)(C(F)(F)F)C(F)(F)F] | X = N<br>Y = N—CH$_2$-pyridin-4-yl<br>Z = CH$_2$—CH$_2$<br>R$^1$ = HO—C—(CF$_3$)$_2$<br>R$^2$ = Absent<br>R$^3$ = Absent<br>R$^4$ = Absent<br>n = 1 |
| 145 | 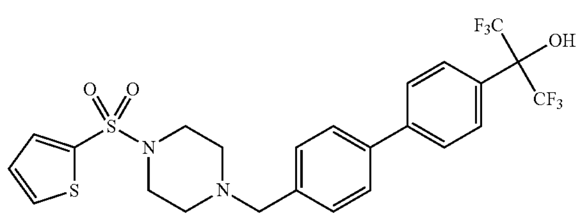 [SMILES: O=S(=O)(c1cccs1)N1CCN(Cc2ccc(-c3ccc(C(O)(C(F)(F)F)C(F)(F)F)cc3)cc2)CC1] | X = N<br>Y = N—SO$_2$-2-thiophene<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 146 | 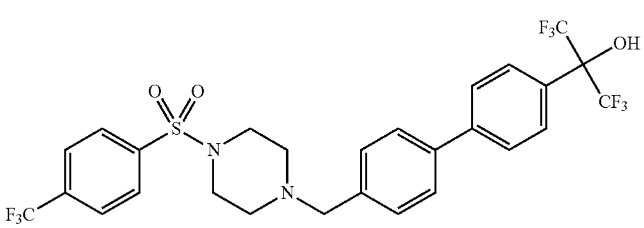 [SMILES: O=S(=O)(c1ccc(C(F)(F)F)cc1)N1CCN(Cc2ccc(-c3ccc(C(O)(C(F)(F)F)C(F)(F)F)cc3)cc2)CC1] | X = N<br>Y = N—SO$_2$-4-CF$_3$—Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 147 | 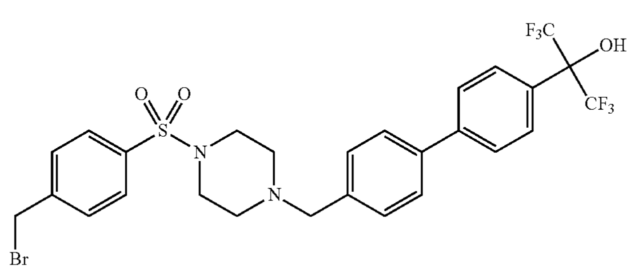 [SMILES: O=S(=O)(c1ccc(CBr)cc1)N1CCN(Cc2ccc(-c3ccc(C(O)(C(F)(F)F)C(F)(F)F)cc3)cc2)CC1] | X = N<br>Y = N—SO$_2$-4-BrCH$_2$Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

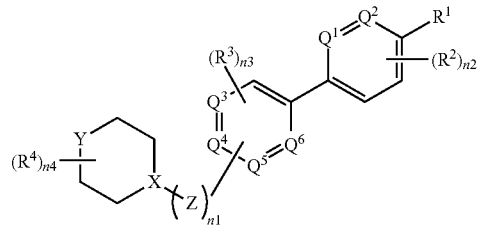

| # | Compound Structure | Generic Structure/Substituents |
|---|---|---|
| 148 | 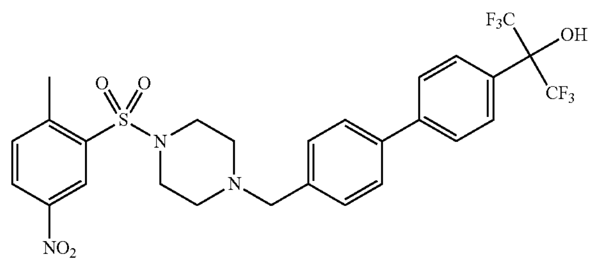 [SMILES: Cc1ccc([N+](=O)[O-])cc1S(=O)(=O)N1CCN(Cc2ccc(-c3ccc(C(O)(C(F)(F)F)C(F)(F)F)cc3)cc2)CC1] | X = N<br>Y = N—SO$_2$-2-Me,5-NO$_2$Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 149 | 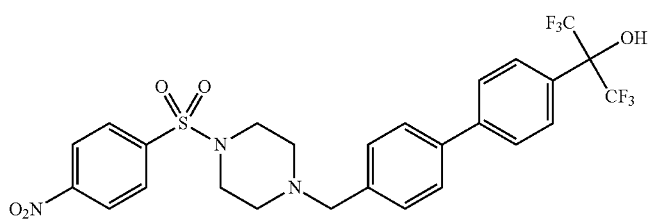 [SMILES: O=[N+]([O-])c1ccc(S(=O)(=O)N2CCN(Cc3ccc(-c4ccc(C(O)(C(F)(F)F)C(F)(F)F)cc4)cc3)CC2)cc1] | X = N<br>Y = N—SO$_2$-4-NO$_2$Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 150 | 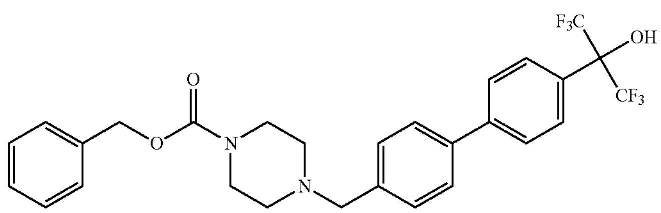 [SMILES: O=C(OCc1ccccc1)N1CCN(Cc2ccc(-c3ccc(C(O)(C(F)(F)F)C(F)(F)F)cc3)cc2)CC1] | X = N<br>Y = N—CH$_2$CH$_2$Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 151 | 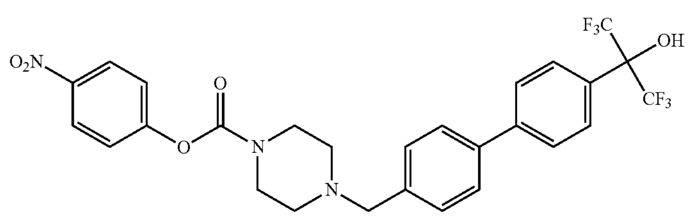 [SMILES: O=C(Oc1ccc([N+](=O)[O-])cc1)N1CCN(Cc2ccc(-c3ccc(C(O)(C(F)(F)F)C(F)(F)F)cc3)cc2)CC1] | X = N<br>Y = N—CO$_2$-4-NO$_2$Ph<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 152 | 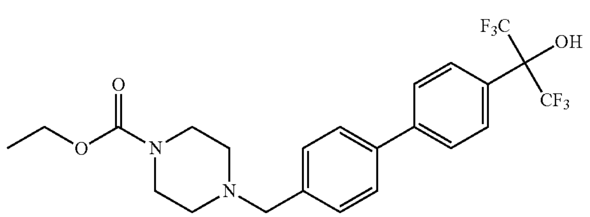 [SMILES: CCOC(=O)N1CCN(Cc2ccc(-c3ccc(C(O)(C(F)(F)F)C(F)(F)F)cc3)cc2)CC1] | X = N<br>Y = N—CO$_2$CH$_2$CH$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

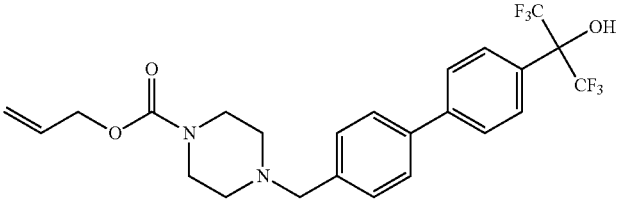 [SMILES: C=CCOC(=O)N1CCN(Cc2ccc(-c3ccc(C(O)(C(F)(F)F)C(F)(F)F)cc3)cc2)CC1]

| # | Compound Structure | Generic Structure/Substituents |
|---|---|---|
| 153 | 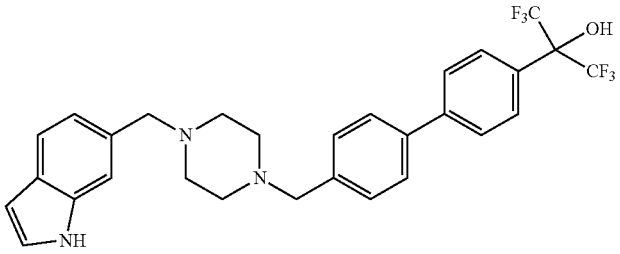 [SMILES: OC(c1ccc(-c2ccc(CN3CCN(Cc4ccc5cc[nH]c5c4)CC3)cc2)cc1)(C(F)(F)F)C(F)(F)F] | X = N<br>Y = N—CO$_2$CH$_2$CHCH$_2$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 154 | 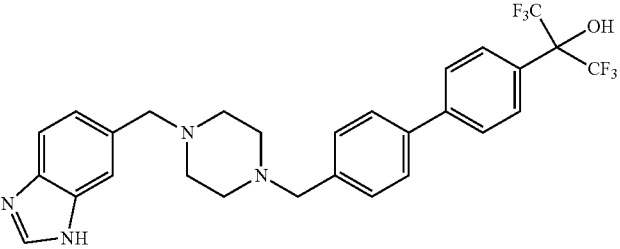 [SMILES: OC(c1ccc(-c2ccc(CN3CCN(Cc4ccc5nc[nH]c5c4)CC3)cc2)cc1)(C(F)(F)F)C(F)(F)F] | X = N<br>Y = NCH$_2$-5-indolyl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 155 | 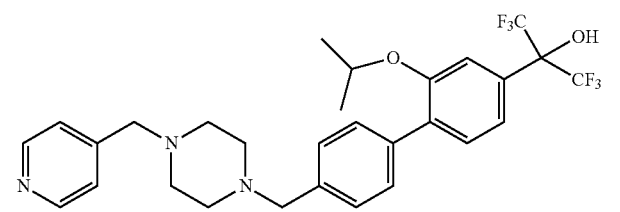 [SMILES: CC(C)Oc1cc(C(O)(C(F)(F)F)C(F)(F)F)ccc1-c1ccc(CN2CCN(Cc3ccncc3)CC2)cc1] | X = N<br>Y = NCH$_2$5-benzimidazolyl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 156 | 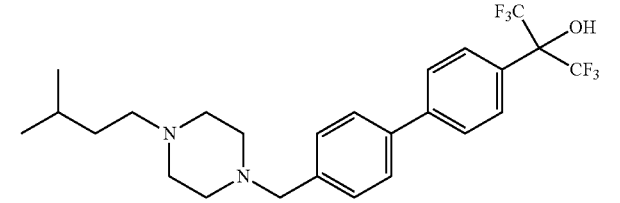 | X = N<br>Y = N—CH$_2$-pyridin-4-yl<br>Z = CH$_2$<br>R$^1$ = HO—C—(CF$_3$)$_2$<br>R$^2$ = OiPr<br>R$^3$ = Absent<br>R$^4$ = Absent<br>n = 1<br>n2 = 1 |
| 157 | 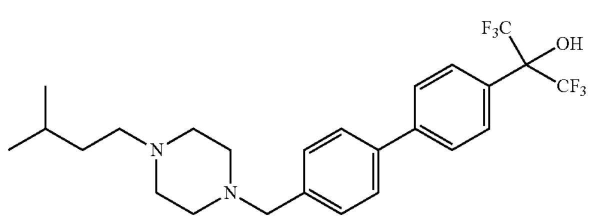 [SMILES: CC(C)CCN1CCN(Cc2ccc(-c3ccc(C(O)(C(F)(F)F)C(F)(F)F)cc3)cc2)CC1] | X = N<br>Y = NCH$_2$CH$_2$CH(CH$_3$)$_2$<br>Z = CH$_2$<br>R$^1$ = HO—C—(CF$_3$)$_2$<br>R$^2$ = Absent<br>R$^3$ = Absent<br>R$^4$ = Absent<br>n = 1 |

TABLE 1-continued

Compounds of the Invention

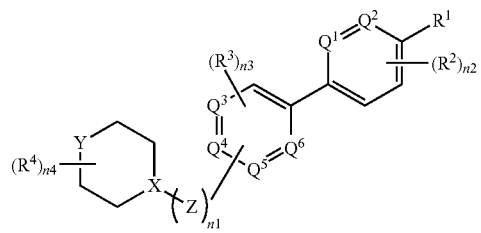

| # | Compound Structure | Generic Structure/Substituents |
|---|---|---|
| 158 | 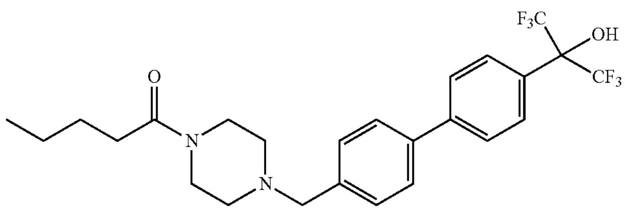 [SMILES: CCCCC(=O)N1CCN(Cc2ccc(-c3ccc(C(O)(C(F)(F)F)C(F)(F)F)cc3)cc2)CC1] | X = N<br>Y = NCOCH$_2$CH$_2$CH$_2$CH$_3$<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 159 | 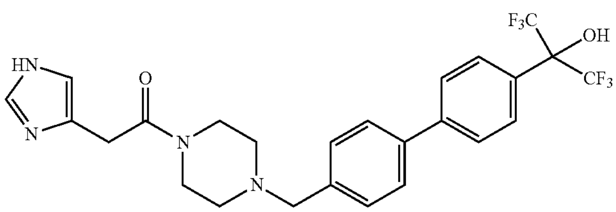 [SMILES: O=C(Cc1c[nH]cn1)N1CCN(Cc2ccc(-c3ccc(C(O)(C(F)(F)F)C(F)(F)F)cc3)cc2)CC1] | X = N<br>Y = NCOCH$_2$imidazolyl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 160 | 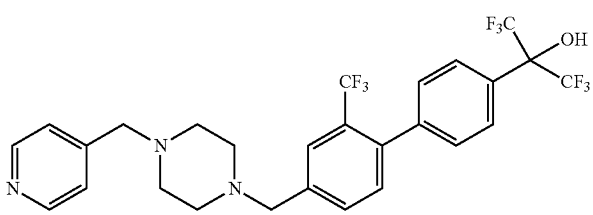 [SMILES: OC(c1ccc(-c2ccc(CN3CCN(Cc4ccncc4)CC3)cc2C(F)(F)F)cc1)(C(F)(F)F)C(F)(F)F] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = CF$_3$<br>R$^4$ = Absent<br>n = 1<br>n2 = 1 |
| 161 | 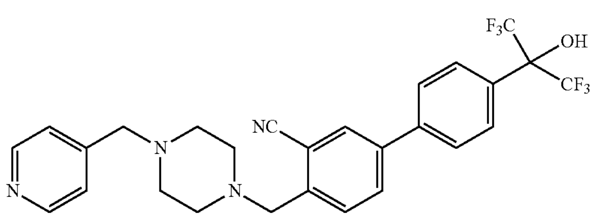 [SMILES: N#Cc1cc(-c2ccc(C(O)(C(F)(F)F)C(F)(F)F)cc2)ccc1CN1CCN(Cc2ccncc2)CC1] | X = N<br>Y = N—CH$_2$-pyridin-4-yl<br>Z = CH$_2$<br>R$^1$ = HO—C—(CF$_3$)$_2$<br>R$^2$ = Absent<br>R$^3$ = CN<br>R$^4$ = Absent<br>n = 1<br>n2 = 1 |
| 162 | 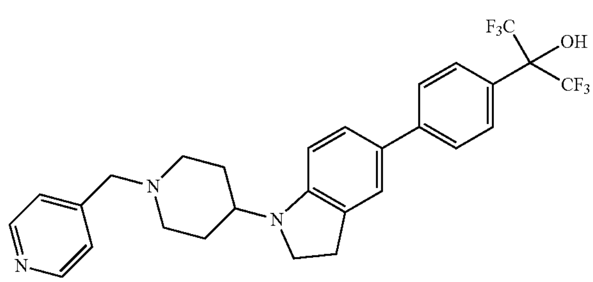 [SMILES: OC(c1ccc(-c2ccc3c(c2)CCN3C2CCN(Cc3ccncc3)CC2)cc1)(C(F)(F)F)C(F)(F)F] | X = CH<br>Y = N—CH$_2$-pyridin-4-yl<br>Z = N—CH$_2$—CH$_2$—R$^3$<br>R$^1$ = HO—C—(CF$_3$)$_2$<br>R$^2$ = Absent<br>R$^3$ = bond<br>R$^4$ = Absent<br>n = 1 |

TABLE 1-continued

Compounds of the Invention

| # | Compound Structure | Generic Structure/Substituents |
|---|---|---|
| 163 | 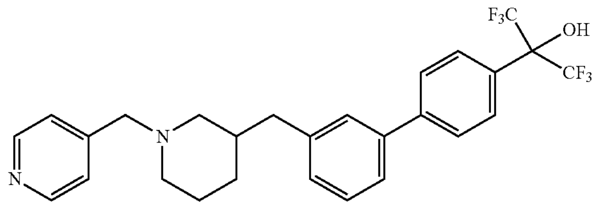 [SMILES: OC(c1ccc(-c2cccc(CC3CCCN(Cc4ccncc4)C3)c2)cc1)(C(F)(F)F)C(F)(F)F] | X = CH<br>Y = N—CH$_2$-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 |
| 164 | | X = CH<br>Y = N—CH$_2$-pyridin-4-yl<br>Z = CH$_2$<br>R$^1$ = HO—C—(CF$_3$)$_2$<br>R$^2$ = Absent<br>R$^3$ = Absent<br>R$^4$ = Absent<br>n = 1 | note:
Ph = phenyl; CO = carbonyl; Bn = benzyl; Q1-Q5 = C unless otherwise indicated.

Synthetic Procedures
The following abbreviations are used throughout this document.
DCM Dichloromethane
DIPEA, $^i$Pr$_2$EtN N,N-Diisopropylethylamine
DMAP 4-(N,N-dimethylamino)pyridine
DMF N,N-Dimethylformamide
DMSO Dimethylsulfoxide
EDAC 1-Ethyl-3-(3-dimethylaminopropyl)carbodiimide hydrochloride
eq Equivalents
Et$_2$O Diethyl ether
EtOAc Ethyl acetate
h, hr Hours
HATU O-(7-Azabenzotriazole-1-yl)-N, N,N',N'-tetramethyluronium hexafluorophosphate
HCl Hydrochloric acid
mg Milligrams
min Minutes
μL Microliters
mL Milliliters
μmole Micromole
mmole Millimoles
MS Mass spectroscopy
MeOH Methanol
NMM N-Methylmorpholine
rt Room temperature
sat. Saturated
TEA Triethylamine
TFA Trifluoroacetic acid
THF Tetrahydrofuran Example 1

1,1,1,3,3,3-Hexafluoro-2-(4'-((4-(pyridin-4-ylmethyl)piperazin-1-yl)methyl)-[1,1'-biphenyl]-4-yl)propan-2-ol

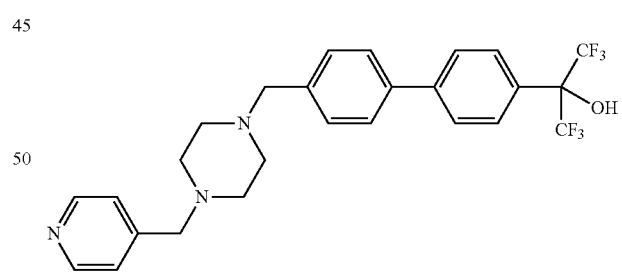

Step 1:
1,1,1,3,3,3-Hexafluoro-2-(4-iodophenyl)propan-2-ol

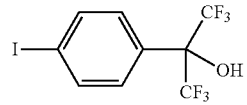

To a solution of 2-(4-aminophenyl)-1,1,1,3,3,3-hexafluoropropan-2-ol (10.0 g, 38.6 mmol) in DMF (50 mL) was dropwise added a solution of sodium nitrite (2.8 g, 40.5 mmol) in water (15.5 mL) and a 6M solution of hydrochloric acid (19.3 mL, 115.7 mmol), while maintaining the reaction temperature at 0~5° C. The reaction mixture was stirred for 30 min, and then potassium iodide (6.4 g, 38.6 mmol) was added portionwise at 0~5° C. The resulting reaction mixture was stirred overnight at rt. The reaction mixture was extracted with EtOAc, and the combined organic layers were washed with saturated sodium thiosulphate and dried over $Na_2SO_4$. The solvent was evaporated in vacuo to obtain the crude, which was purified by flash chromatography on silica gel (~5% EtOAc/Hex) to obtain the title compound.

Step 2: tert-Butyl 4-((4'-(1,1,1,3,3,3-hexafluoro-2-hydroxypropan-2-yl)-[1,1'-biphenyl]-4-yl)methyl)piperazine-1-carboxylate

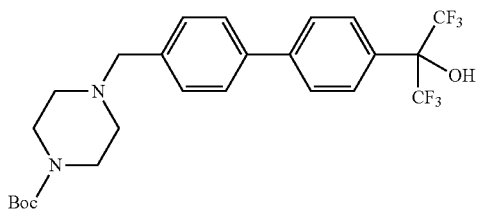 [SMILES: CC(C)(C)OC(=O)N1CCN(Cc2ccc(-c3ccc(C(O)(C(F)(F)F)C(F)(F)F)cc3)cc2)CC1]

The mixture of tert-butyl piperazine-1-carboxylate (0.65 g, 3.49 mmol), (4-(bromomethyl)phenyl)boronic acid (0.75 g, 3.49 mmol) and DIEA (0.7 mL, 4.12 mmol) in DMF (8 mL) was stirred for h at rt. To this mixture was added 1,1,1,3,3,3-hexafluoro-2-(4-iodophenyl)propan-2-ol (1.07 g, 3.49 mmol), P(PPh$_3$)$_4$ (0.5 g, 0.52 mmol), $K_2CO_3$ (1.2 g, 10.47 mmol) and dioxane/$H_2O$ (4:1, 150 mL). The mixture was degassed for 5 min and heated for 2 h at 80° C. oil bath. The completion of reaction was monitored by anal. HPLC and LC/MS. The mixture was cooled and extracted with EtOAc. The combine organic layers were washed with saturated $NaHCO_3$ and dried over $Na_2SO_4$. The solvent was removed in vacuo to obtain the crude, which was purified by flash chromatography on silica gel to obtain the title compound. ESI-MS (m/z): 519 [M+1]$^+$.

Step 3: 1,1,1,3,3,3-Hexafluoro-2-(4'-(piperazin-1-ylmethyl)-[1,1'-biphenyl]-4-yl)propan-2-ol

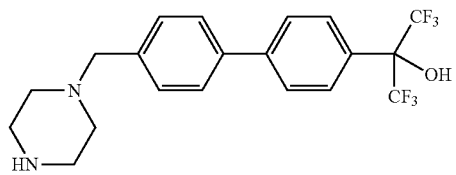 [SMILES: OC(c1ccc(-c2ccc(CN3CCNCC3)cc2)cc1)(C(F)(F)F)C(F)(F)F]

Tert-butyl 4-((4'-(1,1,1,3,3,3-hexafluoro-2-hydroxypropan-2-yl)-[1,1'-biphenyl]-4-yl)methyl)piperazine-1-carboxylate was dissolved in 30% TFA/DCM at rt and the reaction was stirred for 2 h at rt. The completion of reaction was monitored by analytical HPLC and LC/MS. The solvent was removed to obtain the crude, which was dissolved in EtOAc. The organic phase was washed with saturated $NaHCO_3$ and dried over $Na_2SO_4$. The solvent was removed in vacuo to obtain the crude, which was used in the next step with no further purification. ESI-MS (m/z): 419 [M+1]$^+$.

Step 4: 1,1,1,3,3,3-Hexafluoro-2-(4'-((4-(pyridin-4-ylmethyl)piperazin-1-yl)methyl)-[1,1'-biphenyl]-4-yl)propan-2-ol The mixture 1,1,1,3,3,3-hexafluoro-2-(4'-(piperazin-1-ylmethyl)-[1,1'-biphenyl]-4-yl)propan-2-ol (30 mg, 0.0717 mmol) and isonicotinaldehyde (15 mg, 0.14 mmol) in dry DMF (1 mL) was stirred at rt for 30 min, then NaBH(OAc)$_3$ (23 mg, 0.11 mmol) was added at rt. The mixture was stirred at rt overnight. The completion of reaction was monitored by analytical HPLC and LC/MS. The reaction was quenched with MeOH. The mixture was purified by prep-HPLC (MeOH/Acetonitrile/water) to obtain the title compound as TFA salt. ESI-MS (m/z): 510 [M+1]$^+$.

Example 2

1,1,1,3,3,3-Hexafluoro-2-(4'-((4-(2-hydroxyethyl)piperazin-1-yl)methyl)-[1,1'-biphenyl]-4-yl)propan-2-ol

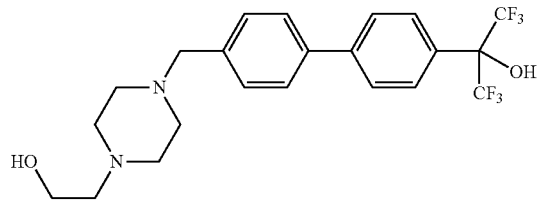 [SMILES: OCCN1CCN(Cc2ccc(-c3ccc(C(O)(C(F)(F)F)C(F)(F)F)cc3)cc2)CC1]

The title compound was prepared following the same general protocol as described in Step 2, Example 1, using 2-(piperazin-1-yl)ethanol instead of tert-butyl piperazine-1-carboxylate. ESI-MS (m/z): 463 [M+1]$^+$.

Example 3

1-(4-((4'-(1,1,1,3,3,3-Hexafluoro-2-hydroxypropan-2-yl)-[1,1'-biphenyl]-4-yl)methyl)piperazin-1-yl)ethanone

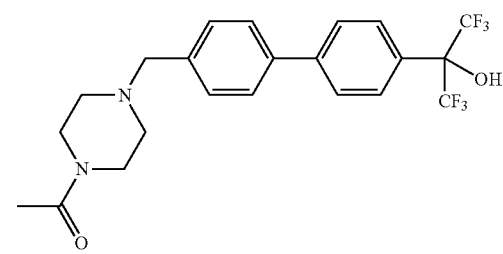 [SMILES: CC(=O)N1CCN(Cc2ccc(-c3ccc(C(O)(C(F)(F)F)C(F)(F)F)cc3)cc2)CC1]

Step 1:
1,1,1,3,3,3-Hexafluoro-2-(4-iodophenyl)propan-2-ol

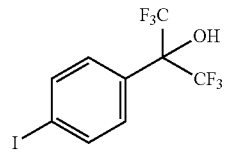 [SMILES: OC(c1ccc(I)cc1)(C(F)(F)F)C(F)(F)F]

To 2-(4-Amino-phenyl)-1,1,1,3,3,3-hexafluoropropan-2-ol (commercially available) in DMF was added a solution of sodium nitrite (1.2 eq) in water and 6M hydrochloric acid (3 eq), while maintaining the temperature between 0~5° C. in an ice bath. The reaction mixture was stirred for 30 min, and then potassium iodide (1.5 eq) was added in portions. The resulting reaction mixture was stirred overnight at rt. The reaction mixture was diluted with Et$_2$O, washed several times with a solution of saturated sodium thiosulphate and treated with Na$_2$SO$_4$. The solvent was evaporated in vacuo leaving a crude oil and the product, 1,1,1,3,3,3-Hexafluoro-2-(4-iodophenyl)propan-2-ol, was isolated by flash chromatography on silica gel (~5% EtOAc/Hex) to obtain the title compound.

Step 2: 1,1,1,3,3,3-hexafluoro-2-(4'-((1-(acetyl) piperazine)methyl)-[1,1'-biphenyl]-4-yl)propan-2-ol

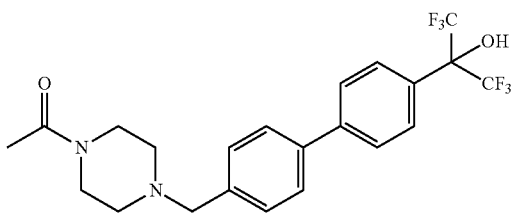 [SMILES: CC(=O)N1CCN(Cc2ccc(-c3ccc(C(O)(C(F)(F)F)C(F)(F)F)cc3)cc2)CC1]

To 4-bromomethylphenylboronic acid was added 1,4-dioxane, followed by addition of K$_2$CO$_3$ (4.0 eq), of 1-acetyl-piperazine (1.1 eq) and potassium iodide (2% weight). The mixture was allowed to stir overnight at rt (~23° C.) under argon balloon. To the mixture was then added water (1:4, water/dioxane) and Pd(PPh$_3$)$_4$ (5 mol %). The mixture was then purged of air via vacuum line and argon balloon, fitted with air cooled condenser, and heated at reflux under argon balloon for 1.5 h. The reaction mixture was allowed to cool and was then subsequently extracted with excess EtOAc, keeping the organic phase, which was washed with brine and dried over Na$_2$SO$_4$, and concentrated in vacuo. The crude residue was purified by reverse-phase preparative HPLC to provide the TFA salt of the title compound as a colorless solid. $^1$H NMR (400 MHz, DMSO-d$_6$) δ 7.92-7.65 (m, 7H), 7.66 (d, J=8.0 Hz, 2H), 4.61-4.49 (m, 3H), 4.11-4.09 (m, 1H), 3.50-2.91 (m, 6H), 2.08 (s, 3H); $^{13}$C NMR (100 MHz, DMSO-d$_6$) δ 168.53. 158.49 (q, J=33.7 Hz, CF$_3$COOH), 140.86, 140.08, 131.96, 130.23, 129.12, 127.43, 127.25, 126.96, 122.91, 117.97 (CF$_3$COOH), 76.78 (q, J=30 Hz, CF$_3$), 58.43, 50.71, 50.33, 42.49, 37.71, 20.85; ESI-MS (m/z): 460.94 [M+1]$^+$.

Example 4

2-(4'-((4-Ethylpiperazin-1-yl)methyl)-[1,1'-biphenyl]-4-yl)-1,1,1,3,3,3-hexafluoropropan-2-ol

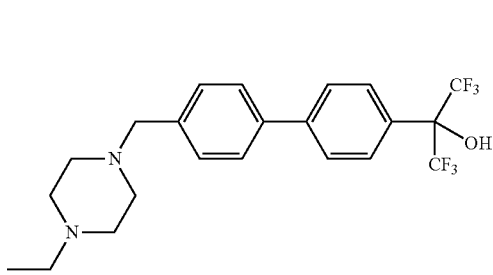 [SMILES: CCN1CCN(Cc2ccc(-c3ccc(C(O)(C(F)(F)F)C(F)(F)F)cc3)cc2)CC1]

The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and 1-ethylpiperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 447 [M+1]$^+$.

Example 8

2-(4'-((4-(Benzo[d][1,3]dioxol-5-ylmethyl)piperazin-1-yl)methyl)-[1,1'-biphenyl]-4-yl)-1,1,1,3,3,3-hexafluoropropan-2-ol

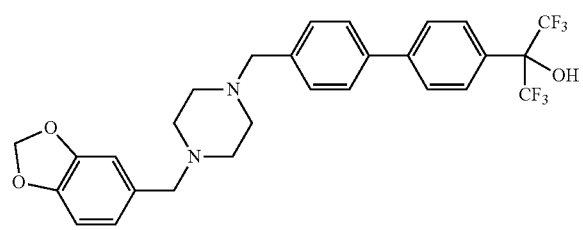 [SMILES: OC(c1ccc(-c2ccc(CN3CCN(Cc4ccc5c(c4)OCO5)CC3)cc2)cc1)(C(F)(F)F)C(F)(F)F]

The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and 1-(benzo[d][1,3]dioxol-5-ylmethyl)piperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 553 [M+1]$^+$.

Example 9

(1,1,1,3,3,3-Hexafluoro-2-(4'-((4-(3-(tri fluoromethyl)benzyl)piperazin-1-yl)methyl)-1,1'-biphenyl-4-yl)propan-2-ol

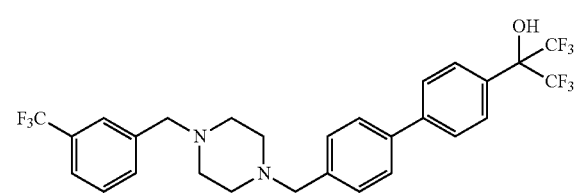 [SMILES: OC(c1ccc(-c2ccc(CN3CCN(Cc4cccc(C(F)(F)F)c4)CC3)cc2)cc1)(C(F)(F)F)C(F)(F)F]

The mixture of 1,1,1,3,3,3-hexafluoro-2-(4'-(piperazin-1-ylmethyl)-[1,1'-biphenyl]-4-yl)propan-2-ol (49 mg, 0.11 mmol; see Example 1, step 3 for preparation), 1-(bromomethyl)-3-(trifluoromethyl)benzene (32 mg, 0.1 mmol) and DIEA (0.1 mL) in DMF (2 mL) was stirred at rt overnight. The mixture was purified by prep-HPLC (MeOH/acetonitrile/water) to obtain the title compound as TFA salt. ESI-MS (m/z): 577 [M+H]+

Example 10

1,1,1,3,3,3-Hexafluoro-2-(4'-((4-(3-methoxybenzyl)piperazin-1-yl)methyl)-[1,1'-biphenyl]-4-yl)propan-2-ol

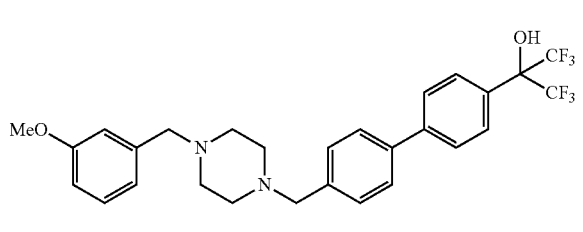 [SMILES: COc1cccc(CN2CCN(Cc3ccc(-c4ccc(C(O)(C(F)(F)F)C(F)(F)F)cc4)cc3)CC2)c1]

The title compound was prepared following the same general protocol as described in Example 9, using 1-(bromomethyl)-3-methoxybenzene instead of 1-(bromomethyl)-3-(trifluoromethyl)benzene. ESI-MS (m/z): 539 [M+1]+.

Example 11

1,1,1,3,3,3-Hexafluoro-2-(4'-((4-phenethylpiperazin-1-yl)methyl)-[1,1'-biphenyl]-4-yl)propan-2-ol

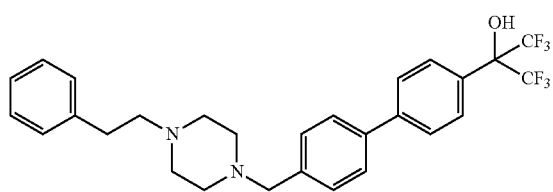 [SMILES: OC(c1ccc(-c2ccc(CN3CCN(CCc4ccccc4)CC3)cc2)cc1)(C(F)(F)F)C(F)(F)F]

The title compound was prepared following the same general protocol as described in Example 9, using 1 (2-bromoethyl)benzene instead of 1-(bromomethyl)-3-(trifluoromethyl)benzene. ESI-MS (m/z): 523 [M+1]+.

Example 12

2-(4'-((4-(4-Bromobenzyl)piperazin-1-yl)methyl)-[1,1'-biphenyl]-4-yl)-1,1,1,3,3,3-hexafluoropropan-2-ol

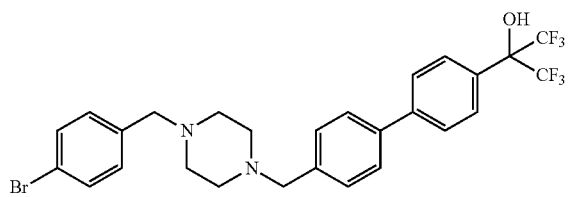 [SMILES: OC(c1ccc(-c2ccc(CN3CCN(Cc4ccc(Br)cc4)CC3)cc2)cc1)(C(F)(F)F)C(F)(F)F]

The title compound was prepared following the same general protocol as described in Example 9, using 1-bromo-4-(bromomethyl)benzene instead of 1-(bromomethyl)-3-(trifluoromethyl)benzene. ESI-MS (m/z): 587, 589 [M+1]+.

Example 14

1,1,1,3,3,3-Hexafluoro-2-(4'-((4-phenylpiperazin-1-yl)methyl)-[1,1'-biphenyl]-4-yl)propan-2-ol

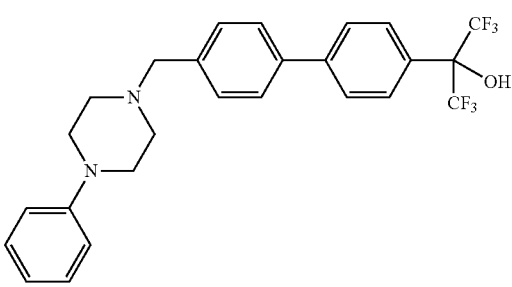 [SMILES: OC(c1ccc(-c2ccc(CN3CCN(c4ccccc4)CC3)cc2)cc1)(C(F)(F)F)C(F)(F)F]

Step 1: 4'-(1,1,1,3,3,3-Hexafluoro-2-hydroxypropan-2-yl)-[1,1'-biphenyl]-4-carbaldehyde

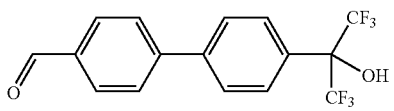

The mixture of 1,1,1,3,3,3-hexafluoro-2-(4-iodophenyl)propan-2-ol (1.07 g, 3.49 mmol), (4-formylphenyl)boronic acid (0.63 g, 4.19 mmol), P(PPh3)4 (0.5 g, 0.52 mmol), K2CO3 (1.2 g, 10.47 mmol) and dioxane/H2O (4:1, 150 mL) was degassed for 5 min and heated for 2 h at 80° C. oil bath. The completion of reaction was monitored by anal. HPLC. The mixture was cooled and extracted with EtOAc. The combine organic layers were washed with saturated NaHCO3 and dried over Na2SO4. The solvent was removed in vacuo to obtain the crude, which was purified by flash chromatography on silica gel to obtain the title compound.

Step 2: 1,1,1,3,3,3-Hexafluoro-2-(4'-((4-phenylpiperazin-1-yl)methyl)-[1,1'-biphenyl]-4-yl)propan-2-ol The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and 1-phenylpiperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 495 [M+1]+.

Example 15

2-(4'-((4-Benzylpiperazin-1-yl)methyl)-[1,1'-biphenyl]-4-yl)-1,1,1,3,3,3-hexafluoropropan-2-ol

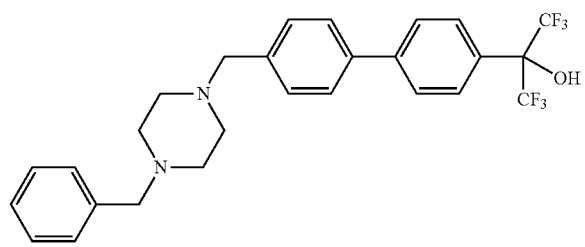 [SMILES: OC(c1ccc(-c2ccc(CN3CCN(Cc4ccccc4)CC3)cc2)cc1)(C(F)(F)F)C(F)(F)F]

The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and 1-benzylpiperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 509 [M+1]$^+$.

Example 16

(4-((4'-(1,1,1,3,3,3-Hexafluoro-2-hydroxypropan-2-yl)-[1,1'-biphenyl]-4-yl)methyl)piperazin-1-yl)(tetrahydrofuran-2-yl)methanone

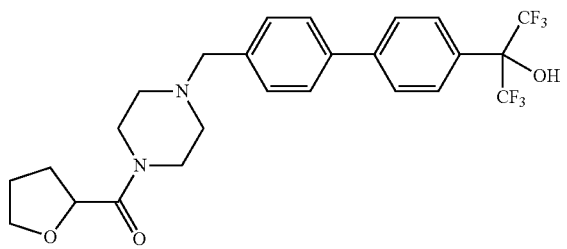 [SMILES: O=C(C1CCCO1)N1CCN(Cc2ccc(-c3ccc(C(O)(C(F)(F)F)C(F)(F)F)cc3)cc2)CC1]

The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and piperazin-1-yl(tetrahydrofuran-2-yl)methanone instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 517 [M+1]$^+$.

Example 17

2-(4'-((4-Cyclopropylpiperazin-1-yl)methyl)-[1,1'-biphenyl]-4-yl)-1,1,1,3,3,3-hexafluoropropan-2-ol

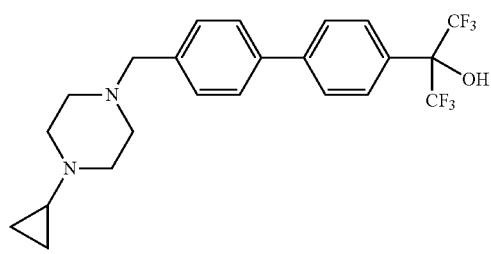 [SMILES: OC(c1ccc(-c2ccc(CN3CCN(C4CC4)CC3)cc2)cc1)(C(F)(F)F)C(F)(F)F]

The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and 1-cyclopropylpiperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 459 [M+1]$^+$.

Example 18

1,1,1,3,3,3-Hexafluoro-2-(4'-(morpholinomethyl)-[1,1'-biphenyl]-4-yl)propan-2-ol

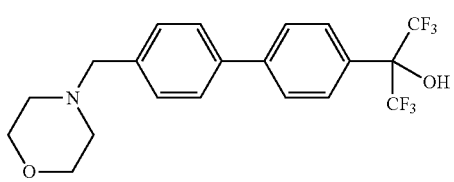 [SMILES: OC(c1ccc(-c2ccc(CN3CCOCC3)cc2)cc1)(C(F)(F)F)C(F)(F)F]

The title compound was prepared following the same general protocol as described in Step 2, Example 1, using morpholine instead of tert-butyl piperazine-1-carboxylate. ESI-MS (m/z): 420 [M+1]$^+$.

Example 19

1,1,1,3,3,3-Hexafluoro-2-(4'-((4-(thiophen-2-ylmethyl)piperazin-1-yl)methyl)-[1,1'-biphenyl]-4-yl)propan-2-ol

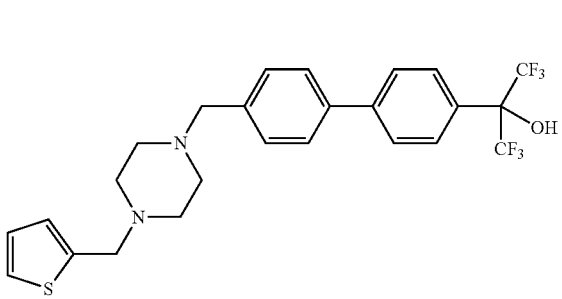 [SMILES: OC(c1ccc(-c2ccc(CN3CCN(Cc4cccs4)CC3)cc2)cc1)(C(F)(F)F)C(F)(F)F]

The title compound was prepared following the same general protocol as described in Step 4, Example 1, using thiophene-2-carbaldehyde instead of isonicotinaldehyde. ESI-MS (m/z): 515 [M+1]$^+$.

Example 20

1,1,1,3,3,3-Hexafluoro-2-(4'-((4-((5-fluoro-1H-indol-2-yl)methyl)piperazin-1-yl)methyl)-[1,1'-biphenyl]-4-yl)propan-2-ol

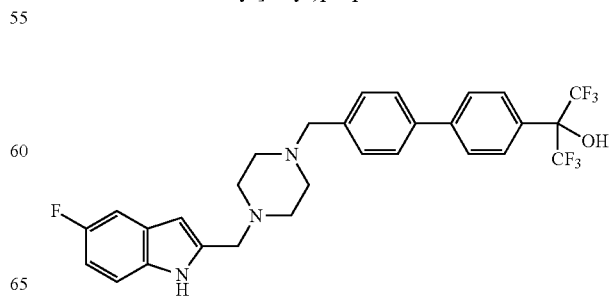

The title compound was prepared following the same general protocol as described in Step 4, Example 1, using 5-fluoro-1H-indole-2-carbaldehyde instead of isonicotinaldehyde. ESI-MS (m/z): 565 [M+1]$^+$.

Example 21

2-(4'-((4-((2,3-Dihydrobenzo[b][1,4]dioxin-2-yl)methyl)piperazin-1-yl)methyl)-[1,1'-biphenyl]-4-yl)-1,1,1,3,3,3-hexafluoropropan-2-ol

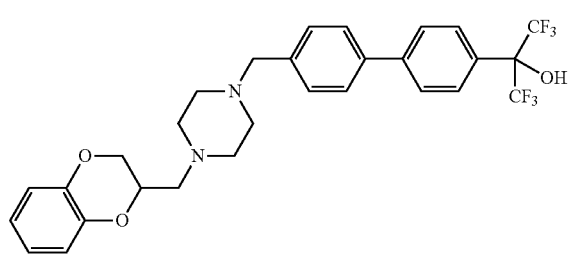 [SMILES: OC(c1ccc(-c2ccc(CN3CCN(CC4COc5ccccc5O4)CC3)cc2)cc1)(C(F)(F)F)C(F)(F)F]

The title compound was prepared following the same general protocol as described in Step 4, Example 1, using 2,3-dihydrobenzo[b][1,4]dioxine-2-carbaldehyde instead of isonicotinaldehyde. ESI-MS (m/z): 567 [M+1]$^+$.

Example 22

4-((4'-(1,1,1,3,3,3-Hexafluoro-2-hydroxypropan-2-yl)-[1,1'-biphenyl]-4-yl)methyl)-N-propylpiperazine-1-carboxamide

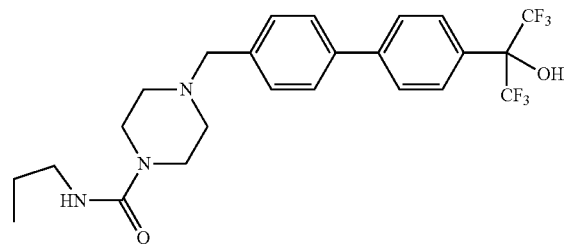 [SMILES: CCCNC(=O)N1CCN(Cc2ccc(-c3ccc(C(O)(C(F)(F)F)C(F)(F)F)cc3)cc2)CC1]

The mixture of 1,1,1,3,3,3-hexafluoro-2-(4'-(piperazin-1-ylmethyl)-[1,1'-biphenyl]-4-yl)propan-2-ol (21 mg, 0.05 mmol) and 1-isocyanatopropane (4.3 mg, 0.05 mmol) in DCM (0.3 mL) was stirred at rt overnight. The reaction completion was monitored by analytical HPLC and LC/MS. The solvent was removed in vacuo and the crude was purified by prep-HPLC (MeOH/Acetonitrile/water) to obtain the title compound as TFA salt. ESI-MS (m/z): 504 [M+1]$^+$.

Example 23

4-((4'-(1,1,1,3,3,3-Hexafluoro-2-hydroxypropan-2-yl)-[1,1'-biphenyl]-4-yl)methyl)-N-phenylpiperazine-1-carboxamide

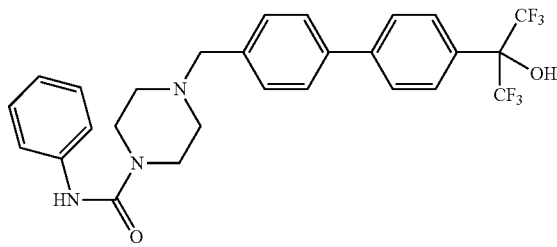 [SMILES: O=C(Nc1ccccc1)N1CCN(Cc2ccc(-c3ccc(C(O)(C(F)(F)F)C(F)(F)F)cc3)cc2)CC1]

The title compound was prepared following the same general protocol as described in Example 22, using isocyanatobenzene instead of 1-isocyanatopropane. ESI-MS (m/z): 538 [M+]$^+$.

Example 24

N-Benzyl-4-((4'-(1,1,1,3,3,3-hexafluoro-2-hydroxypropan-2-yl)-[1,1'-biphenyl]-4-yl)methyl)piperazine-1-carboxamide

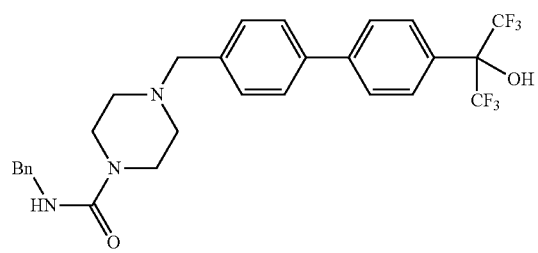 [SMILES: O=C(NCc1ccccc1)N1CCN(Cc2ccc(-c3ccc(C(O)(C(F)(F)F)C(F)(F)F)cc3)cc2)CC1]

The title compound was prepared following the same general protocol as described in Example 22, using (isocyanatomethyl)benzene instead of 1-isocyanatopropane. ESI-MS (m/z): 538 [M+1]$^+$.

Example 25

1-(4-((4'-(1,1,1,3,3,3-Hexafluoro-2-hydroxypropan-2-yl)-[1,1'-biphenyl]-4-yl)methyl)piperazin-1-yl)propan-1-one

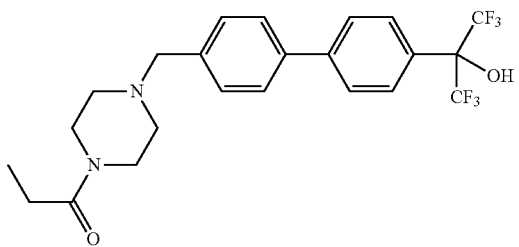 [SMILES: CCC(=O)N1CCN(Cc2ccc(-c3ccc(C(O)(C(F)(F)F)C(F)(F)F)cc3)cc2)CC1]

The mixture of 1,1,1,3,3,3-hexafluoro-2-(4'-(piperazin-1-ylmethyl)-[1,1'-biphenyl]-4-yl)propan-2-ol (21 mg, 0.05 mmol), EtCOCl (propionyl chloride, 8.7 uL, 0.1 mmol) and polymer bound dimethylamine (resin 1) (~0.1 g, ~0.1 mmol) in DCM (1 mL) was stirred at rt for 15 h. The reaction completion was monitored by analytical HPLC. Then polymer bound tris-(2-aminoethyl)amine (resin-2) (~30 mgm ~0.1 mmol) was added to the above mixture and the resulting mixture was stirred at rt for 20 h. The mixture was filtered and the filtrate was concentrated to brown oil as the title compound. ESI-MS (m/z): 475 [M+1]⁺.

Example 26

(4-((4'-(1,1,1,3,3,3-Hexafluoro-2-hydroxypropan-2-yl)-[1,1'-biphenyl]-4-yl)methyl)piperazin-1-yl)(phenyl)methanone

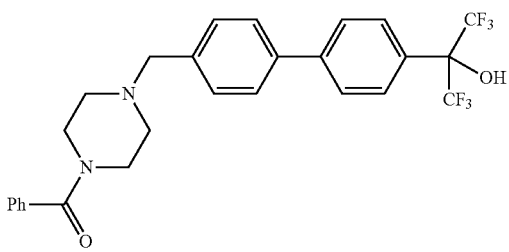 [SMILES: O=C(c1ccccc1)N1CCN(Cc2ccc(-c3ccc(C(O)(C(F)(F)F)C(F)(F)F)cc3)cc2)CC1]

The title compound was prepared following the same general protocol as described in Example 25, using benzoyl chloride instead of propionyl chloride. ESI-MS (m/z): 523 [M+1]⁺.

Example 27

1-(4-((4'-(1,1,1,3,3,3-Hexafluoro-2-hydroxypropan-2-yl)-[1,1'-biphenyl]-4-yl)methyl)piperazin-1-yl)-2-phenylethanone

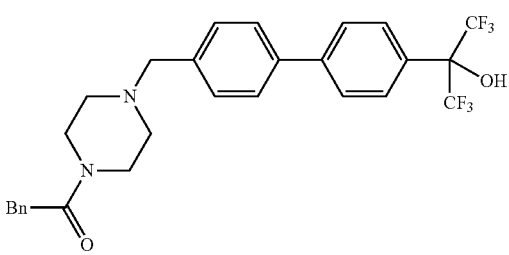 [SMILES: O=C(Cc1ccccc1)N1CCN(Cc2ccc(-c3ccc(C(O)(C(F)(F)F)C(F)(F)F)cc3)cc2)CC1]

The title compound was prepared following the same general protocol as described in Example 25, using 2-phenylacetyl chloride instead of propionyl chloride. ESI-MS (m/z): 537 [M+1]⁺.

Example 28

1,1,1,3,3,3-Hexafluoro-2-(4'-((4-(methylsulfonyl)piperazin-1-yl)methyl)-[1,1'-biphenyl]-4-yl)propan-2-ol

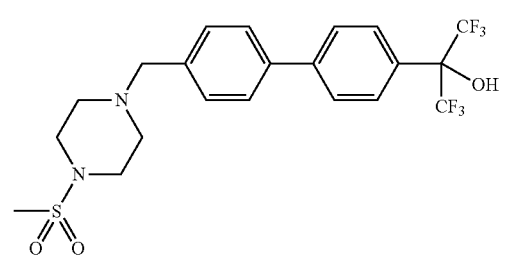 [SMILES: CS(=O)(=O)N1CCN(Cc2ccc(-c3ccc(C(O)(C(F)(F)F)C(F)(F)F)cc3)cc2)CC1]

The title compound was prepared following the same general protocol as described in Example 25, using methanesulfonyl chloride instead of propionyl chloride. ESI-MS (m/z): 483 [M+1]⁺.

Example 29

1,1,1,3,3,3-Hexafluoro-2-(4'-((4-(phenylsulfonyl)piperazin-1-yl)methyl)-[1,1'-biphenyl]-4-yl)propan-2-ol

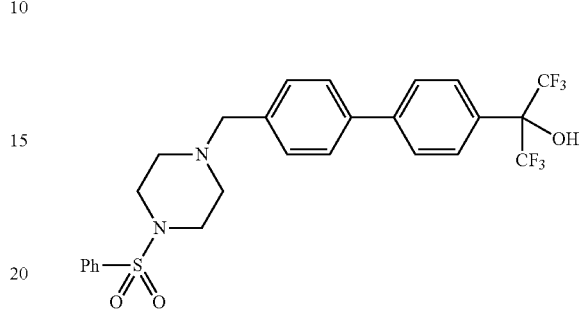

The title compound was prepared following the same general protocol as described in Example 25, using benzenesulfonyl chloride instead of propionyl chloride. ESI-MS (m/z): 545 [M+1]⁺.

Example 30

2-(4'-((4-(Benzylsulfonyl)piperazin-1-yl)methyl)-[1,1'-biphenyl]-4-yl)-1,1,1,3,3,3-hexafluoropropan-2-ol

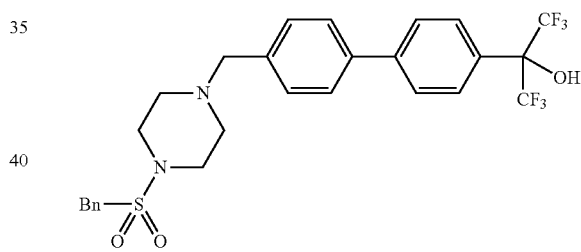

The title compound was prepared following the same general protocol as described in Example 25, using phenylmethanesulfonyl chloride instead of propionyl chloride. ESI-MS (m/z): 573 [M+1]⁺.

Example 40

2-(4'-((4-((2-Bromopyridin-4-yl)methyl)piperazin-1-yl)methyl)-[1,1'-biphenyl]-4-yl)-1,1,1,3,3,3-hexafluoropropan-2-ol

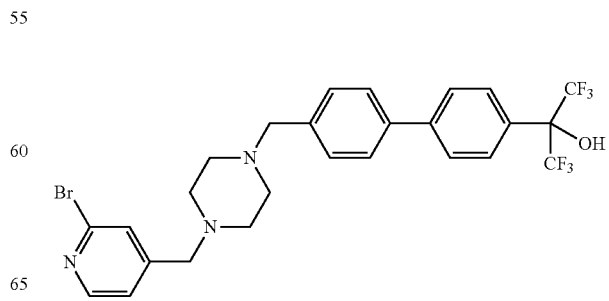

The title compound was prepared following the same general protocol as described in Step 4, Example 1, using 2-bromoisonicotinaldehyde instead of isonicotinaldehyde. ESI-MS (m/z): 588, 590 [M]$^+$, [M+2]$^+$.

Example 41

1,1,1,3,3,3-Hexafluoro-2-(4'-((4-(2-(pyridin-4-yl)ethyl)piperazin-1-yl)methyl)-[1,1'-biphenyl]-4-yl)propan-2-ol

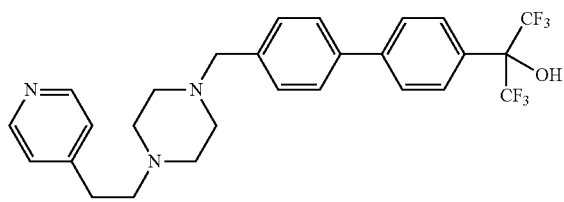 [SMILES: OC(c1ccc(-c2ccc(CN3CCN(CCc4ccncc4)CC3)cc2)cc1)(C(F)(F)F)C(F)(F)F]

The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and 1-(2-(pyridin-4-yl)ethyl)piperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 524 [M+1]$^+$.

Example 42

2-(4'-((4-(Benzo[d]thiazol-2-ylmethyl)piperazin-1-yl)methyl)-[1,1'-biphenyl]-4-yl)-1,1,1,3,3,3-hexafluoropropan-2-ol

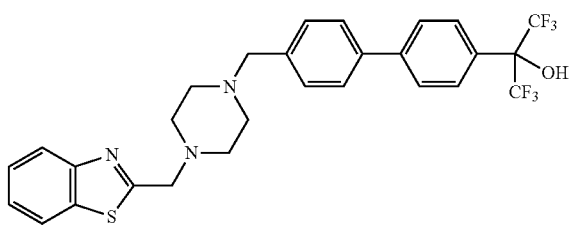 [SMILES: OC(c1ccc(-c2ccc(CN3CCN(Cc4nc5ccccc5s4)CC3)cc2)cc1)(C(F)(F)F)C(F)(F)F]

The title compound was prepared following the same general protocol as described in Step 4, Example 1, using benzo[d]thiazole-2-carbaldehyde instead of isonicotinaldehyde. ESI-MS (m/z): 566 [M+1]$^+$.

Example 43

1,1,1,3,3,3-Hexafluoro-2-(4'-((4-((2-methylpyridin-4-yl)methyl)piperazin-1-yl)methyl)-[1,1'-biphenyl]-4-yl)propan-2-ol

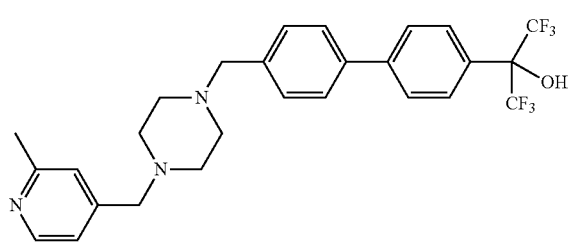 [SMILES: Cc1cc(CN2CCN(Cc3ccc(-c4ccc(C(O)(C(F)(F)F)C(F)(F)F)cc4)cc3)CC2)ccn1]

To a 5 mL Microwave vial was 2-(4'-((4-((2-bromopyridin-4-yl)methyl)piperazin-1-yl)methyl)-[1,1'-biphenyl]-4-yl)-1,1,1,3,3,3-hexafluoropropan-2-ol (58.7 mg, 0.10 mmol), 2,4,6-trimethyl-1,3,5,2,4,6-trioxatriborinane (15.0 mg, 0.12 mmol), Pd(PPh$_3$)$_4$ (17.3 mg, 0.015 mmol), potassium carbonate (41 mg, 0.30 mmol) and dioxane with water (4:1, 5 mL). The mixture was degassed for 2 min and sealed. The mixture was heated in a microwave reactor for 6 h at 100° C. and the analytical HPLC and LC/MS indicated the completion of the reaction. The mixture was filtered from Celite pad and MeOH was added to wash the Celite pad. The solvent was removed and the crude was purified by prep-HPLC (MeOH/Acetonitrile/water) to obtain the title product as TFA salt. ESI-MS (m/z): 524 [M+1]$^+$

Example 44

1,1,1,3,3,3-Hexafluoro-2-(4'-((4-(pyridin-4-yl)piperazin-1-yl)methyl)-[1,1'-biphenyl]-4-yl)propan-2-ol

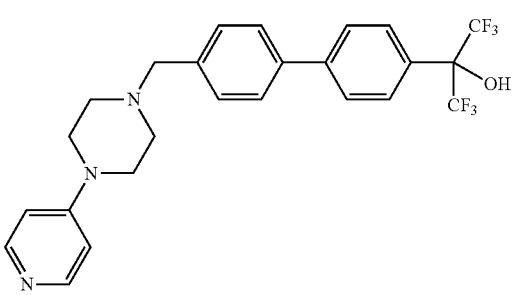 [SMILES: OC(c1ccc(-c2ccc(CN3CCN(c4ccncc4)CC3)cc2)cc1)(C(F)(F)F)C(F)(F)F]

The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and 1-(pyridin-4-yl)piperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 496 [M+1]$^+$.

Example 59

2-(4'-((4-((3-Bromopyridin-4-yl)methyl)piperazin-1-yl)methyl)-[1,1'-biphenyl]-4-yl)-1,1,1,3,3,3-hexafluoropropan-2-ol

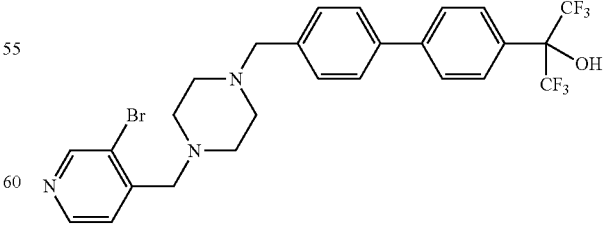

The title compound was prepared following the same general protocol as described in Step 4. Example 1, using 3-bromoisonicotinaldehyde instead of isonicotinaldehyde. ESI-MS (m/z): 588, 590 [M]$^+$, [M+2]$^+$.

Example 61

2-(4'-((4-((2-Chloro-3-fluoropyridin-4-yl)methyl) piperazin-1-yl)methyl)-[1,1'-biphenyl]-4-yl)-1,1,1,3,3,3-hexafluoropropan-2-ol

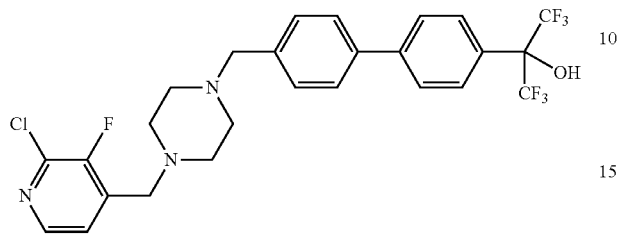

The title compound was prepared following the same general protocol as described in Step 4, Example 1, using 2-chloro-3-fluoroisonicotinaldehyde instead of isonicotinaldehyde. ESI-MS (m/z): 562 [M+]+.

Example 81

1,1,1,3,3,3-Hexafluoro-2-(4'-((4-(4-methoxybenzyl) piperazin-1-yl)methyl)-[1,1'-biphenyl]-4-yl)propan-2-ol

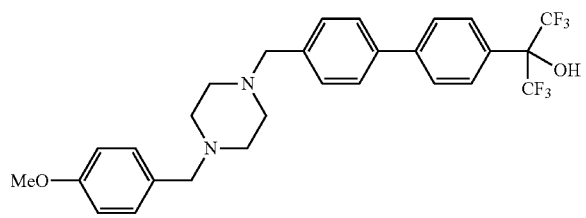 [SMILES: COc1ccc(CN2CCN(Cc3ccc(-c4ccc(C(O)(C(F)(F)F)C(F)(F)F)cc4)cc3)CC2)cc1]

The title compound was prepared following the same general protocol as described in Step 4, Example 1, using 4-methoxybenzaldehyde instead of isonicotinaldehyde. ESI-MS (m/z): 539 [M+1]+.

Example 88

2-(4'-((4-(Benzo[d][1.3]dioxol-5-ylmethyl)piperidin-1-yl)methyl)-[1,1'-biphenyl]-4-yl)-1,1,1,3,3,3-hexafluoropropan-2-ol

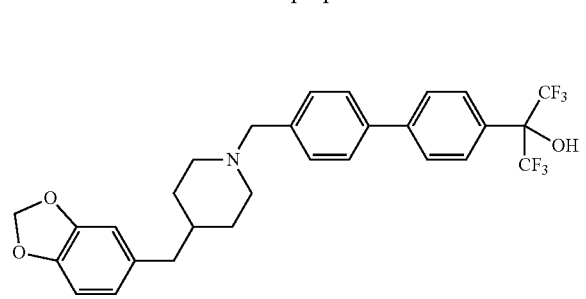

The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and 4-(benzo[d][1,3]dioxol-5-ylmethyl)piperidine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 552 [M+1]+.

Example 91

1,1,1,3,3,3-Hexafluoro-2-(4'-((4-(1-(pyridin-4-yl) ethyl)piperazin-1-yl)methyl)-[1,1'-biphenyl]-4-yl) propan-2-ol

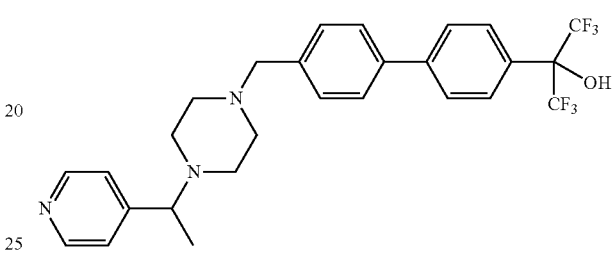

The mixture 1,1,1,3,3,3-hexafluoro-2-(4'-(piperazin-1-ylmethyl)-[1,1'-biphenyl]-4-yl)propan-2-ol (41.8 mg, 0.1 mmol) and 1-(pyridin-4-yl)ethanone (48 mg, 0.4 mmol) in dry 1,2-dichloroethane (1 mL) was stirred at 60° C. overnight, then the mixture was cooled to rt and NaBH(OAc)$_3$ (85 mg, 0.4 mmol) was added at rt. The mixture was stirred at rt overnight. The completion of reaction was monitored by analytical HPLC and LCMS. The reaction was quenched with MeOH. The mixture was purified by prep-HPLC (MeOH/Acetonitrile/water) to obtain the title compound as TFA salt. ESI-MS (m/z): 524 [M+1]+

Example 92

2-(4'-((4-((2-Bromopyridin-4-yl)methyl)piperazin-1-yl)methyl)-[1,1'-biphenyl]-4-yl)-1,1,1,3,3,3-hexafluoropropan-2-ol

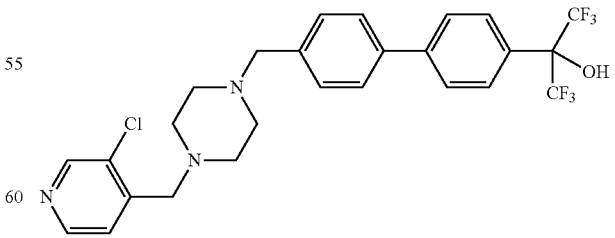

The title compound was prepared following the same general protocol as described in Step 4, Example 1, using 3-chloroisonicotinaldehyde instead of isonicotinaldehyde. ESI-MS (m/z): 544 [M+1]+.

Example 93

2-(3'-Chloro-4'-((4-(pyridin-4-ylmethyl)piperazin-1-yl)methyl)-[1,1'-biphenyl]-4-yl)-1,1,1,3,3,3-hexafluoropropan-2-ol

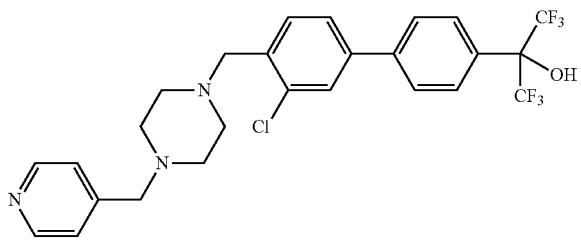

Step 1: 3-Chloro-4'-(1,1,1,3,3,3-hexafluoro-2-hydroxypropan-2-yl)-[1,1'-biphenyl]-4-carbaldehyde

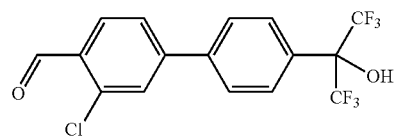 [SMILES: O=Cc1ccc(-c2ccc(C(O)(C(F)(F)F)C(F)(F)F)cc2)cc1Cl]

The title compound was prepared following the same general protocol as described in Step 1, Example 14.

Step 2: tert-Butyl 4-(pyridin-4-ylmethyl)piperazine-1-carboxylate

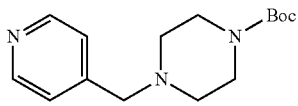

The title compound was prepared following the same general protocol as described in Step 4, Example 1, using tert-butyl piperazine-1-carboxylate instead of 1,1,1,3,3,3-hexafluoro-2-(4'-(piperazin-1-ylmethyl)-[1,1'-biphenyl]-4-yl)propan-2-ol. ESI-MS (m/z): 278. [M+1]⁺.

Step 3: 1-(Pyridin-4-ylmethyl)piperazine

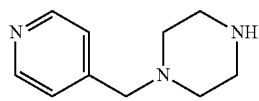 [SMILES: c1cc(CN2CCNCC2)ccn1]

Tert-butyl 4-(pyridin-4-ylmethyl)piperazine-1-carboxylate (0.2 g, 0.725 mmol) was dissolved in TFA/DCM (30%, 2 mL) and stirred at rt for 2 h. The completion of reaction was monitored by anal. HPLC. The solvent was removed to obtain the title compound as TFA salt with no further purification. ESI-MS (m/z): 178, [M+1]⁺.

Step 4: 2-(3'-Chloro-4'-((4-(pyridin-4-ylmethyl)piperazin-1-yl)methyl)-[1,1'-biphenyl]-4-yl)-1,1,1,3,3,3-hexafluoropropan-2-ol The title compound was prepared following the same general protocol as described in Step 4, Example 1, using 3-chloro-4'-(1,1,1,3,3,3-hexafluoro-2-hydroxypropan-2-yl)-[1,1'-biphenyl]-4-carbaldehyde and 1-(pyridin-4-ylmethyl)piperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 544 [M+1]⁺.

Example 94

1,1,1,3,3,3-Hexafluoro-2-(3'-methyl-4'-((4-(pyridin-4-ylmethyl)piperazin-1-yl)methyl)-[1,1'-biphenyl]-4-yl)propan-2-ol

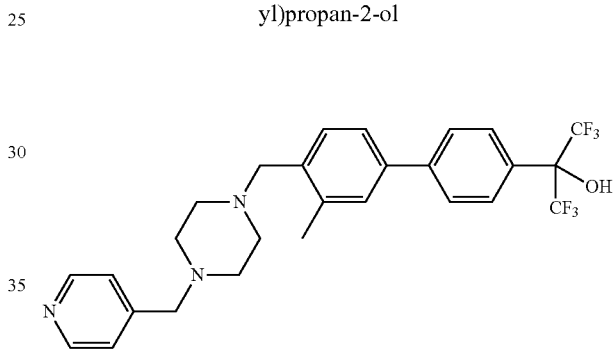

Step 1: 4'-(1,1,1,3,3,3-Hexafluoro-2-hydroxypropan-2-yl)-3-methyl-[1,1'-biphenyl]-4-carbaldehyde

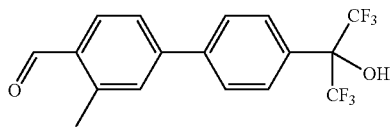

The title compound was prepared following the same general protocol as described in Step 1, Example 14.

Step 2: 1,1,1,3,3,3-Hexafluoro-2-(3'-methyl-4'-((4-(pyridin-4-ylmethyl)piperazin-1-yl)methyl)-[1,1'-biphenyl]-4-yl)propan-2-ol The title compound was prepared following the same general protocol as described in Step 4, Example 1, using 1-4'-(1,1,1,3,3,3-hexafluoro-2-hydroxypropan-2-yl)-3-methyl-[1,1'-biphenyl]-4-carbaldehyde and (pyridin-4-ylmethyl)piperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 524 [M+1]⁺.

Example 95

1,1,1,3,3,3-Hexafluoro-2-(2'-fluoro-4'-((4-(pyridin-4-ylmethyl)piperazin-1-yl)methyl)-[1,1'-biphenyl]-4-yl)propan-2-ol

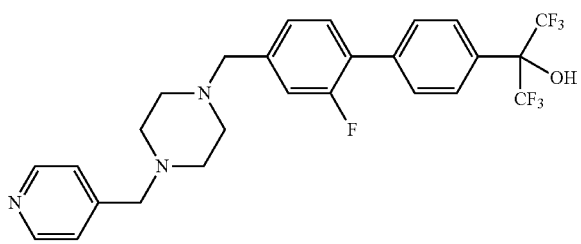 [SMILES: OC(c1ccc(-c2ccc(CN3CCN(Cc4ccncc4)CC3)cc2F)cc1)(C(F)(F)F)C(F)(F)F]

Step 1: 3'-Fluoro-4'-(1,1,1,3,3,3-hexafluoro-2-hydroxypropan-2-yl)-[1,1'-biphenyl]-4-carbaldehyde

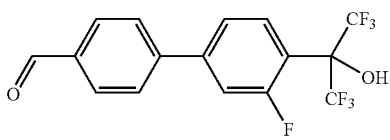 [SMILES: O=Cc1ccc(-c2ccc(C(O)(C(F)(F)F)C(F)(F)F)c(F)c2)cc1]

The title compound was prepared following the same general protocol as described in Step 1, Example 14.

Step 2: 1,1,1,3,3,3-Hexafluoro-2-(2'-fluoro-4'-((4-(pyridin-4-ylmethyl)piperazin-1-yl)methyl)-[1,1'-biphenyl]-4-yl)propan-2-ol The title compound was prepared following the same general protocol as described in Step 4, Example 1, using 3'-fluoro-4'-(1,1,1,3,3,3-hexafluoro-2-hydroxypropan-2-yl)-[1,1'-biphenyl]-4-carbaldehyde and (pyridin-4-ylmethyl)piperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 528 [M+1]$^+$.

Example 96

1,1,1,3,3,3-Hexafluoro-2-(2'-methyl-4'-((4-(pyridin-4-ylmethyl)piperazin-1-yl)methyl)-[1,1'-biphenyl]-4-yl)propan-2-ol

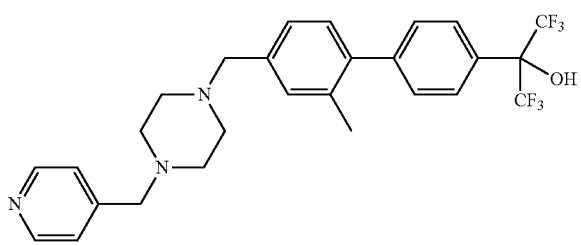 [SMILES: Cc1cc(CN2CCN(Cc3ccncc3)CC2)ccc1-c1ccc(C(O)(C(F)(F)F)C(F)(F)F)cc1]

Step 1: 4'-(1,1,1,3,3,3-Hexafluoro-2-hydroxypropan-2-yl)-3'-methyl-[1,1'-biphenyl]-4-carbaldehyde

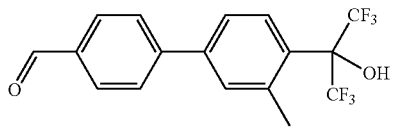 [SMILES: Cc1cc(-c2ccc(C=O)cc2)ccc1C(O)(C(F)(F)F)C(F)(F)F]

The title compound was prepared following the same general protocol as described in Step 1, Example 14.

Step 2: 4'-(1,1,1,3,3,3-Hexafluoro-2-hydroxypropan-2-yl)-3'-methyl-[1,1'-biphenyl]-4-carbaldehyde The title compound was prepared following the same general protocol as described in Step 4, Example 1, using 4'-(1,1,1,3,3,3-hexafluoro-2-hydroxypropan-2-yl)-3'-methyl-[1,1'-biphenyl]-4-carbaldehyde and (pyridin-4-ylmethyl)piperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 524 [M+1]$^+$.

Example 97

1,1,1,3,3,3-Hexafluoro-2-(3'-methoxy-4'-((4-(pyridin-4-ylmethyl)piperazin-1-yl)methyl)-[1,1'-biphenyl]-4-yl)propan-2-ol

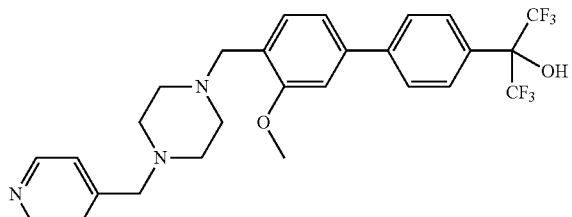

Step 1: 4'-(1,1,1,3,3,3-Hexafluoro-2-hydroxypropan-2-yl)-3-methoxy-[1,1'-biphenyl]-4-carbaldehyde

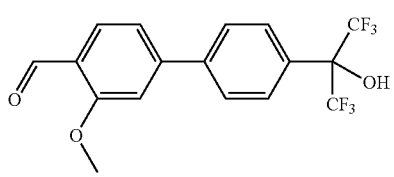 [SMILES: COc1cc(-c2ccc(C(O)(C(F)(F)F)C(F)(F)F)cc2)ccc1C=O]

The title compound was prepared following the same general protocol as described in Step 1, Example 14.

Step 2: 1,1,1,3,3,3-Hexafluoro-2-(3'-methoxy-4'-((4-(pyridin-4-ylmethyl)piperazin-1-yl)methyl)-[1,1'-biphenyl]-4-yl)propan-2-ol The title compound was prepared following the same general protocol as described in Step 4, Example 1, using 4'-(1,1,1,3,3,3-hexafluoro-2-hydroxypropan-2-yl)-3- methoxy-[1,1'-biphenyl]-4-carbaldehyde and (pyridin-4-ylmethyl)piperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 540 [M+1]$^+$.

Example 98

1,1,1,3,3,3-Hexafluoro-2-(3'-fluoro-4'-((4-(pyridin-4-ylmethyl)piperazin-1-yl)methyl)-[1,1'-biphenyl]-4-yl)propan-2-ol

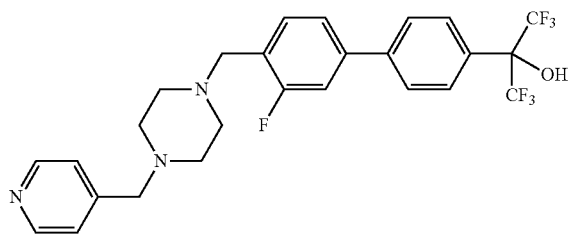 [SMILES: OC(c1ccc(-c2ccc(CN3CCN(Cc4ccncc4)CC3)c(F)c2)cc1)(C(F)(F)F)C(F)(F)F]

Step 1: 3-Fluoro-4'-(1,1,1,3,3,3-hexafluoro-2-hydroxypropan-2-yl)-[1,1'-biphenyl]-4-carbaldehyde

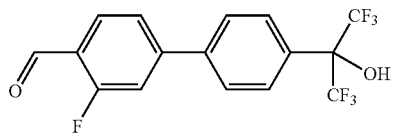

The title compound was prepared following the same general protocol as described in Step 1, Example 14.

Step 2: 1,1,1,3,3,3-Hexafluoro-2-(3'-fluoro-4'-((4-(pyridin-4-ylmethyl)piperazin-1-yl)methyl)-[1,1'-biphenyl]-4-yl)propan-2-ol The title compound was prepared following the same general protocol as described in Step 4, Example 1, using 3-fluoro-4'-(1,1,1,3,3,3-hexafluoro-2-hydroxypropan-2-yl)-[1,1'-biphenyl]-4-carbaldehyde and (pyridin-4-ylmethyl)piperazine instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 528 [M+1]$^+$.

Example 99

1,1,1,3,3,3-Hexafluoro-2-(4'-((4-((3-methylpyridin-4-yl)methyl)piperazin-1-yl)methyl)-[1,1'-biphenyl]-4-yl)propan-2-ol

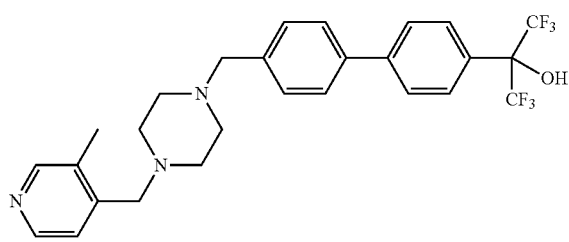 [SMILES: Cc1cnccc1CN1CCN(Cc2ccc(-c3ccc(C(O)(C(F)(F)F)C(F)(F)F)cc3)cc2)CC1]

The title compound was prepared following the same general protocol as described in Example 43. ESI-MS (m/z): 524 [M+1]$^+$.

Example 100

(4'-(1,1,1,3,3,3-Hexafluoro-2-hydroxypropan-2-yl)-[1,1'-biphenyl]-4-yl)(4-(pyridin-4-ylmethyl)piperazin-1-yl)methanone

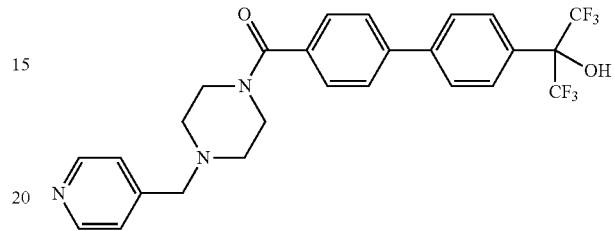

Step 1: tert-Butyl 4'-(1,1,1,3,3,3-hexafluoro-2-hydroxypropan-2-yl)-[1,1'-biphenyl]-4-carboxylate

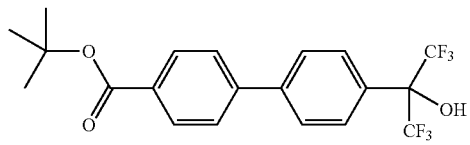

The title compound was prepared following the same general protocol as described in Step 1, Example 14.

Step 2: 4'-(1,1,1,3,3,3-Hexafluoro-2-hydroxypropan-2-yl)-[1,1'-biphenyl]-4-carboxylic acid

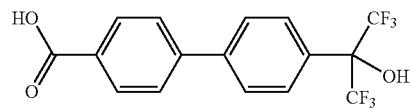

Tert-butyl 4'-(1,1,1,3,3,3-hexafluoro-2-hydroxypropan-2-yl)-[1,1'-biphenyl]-4-carboxylate (0.17 g, 0.405 mmol) was dissolved in TFA/DCM (30%, 2 mL) and stirred at rt for 2 h. The completion of reaction was monitored by analytical HPLC. The solvent was removed to obtain the title compound.

Step 3: (4'-(1,1,1,3,3,3-Hexafluoro-2-hydroxypropan-2-yl)-[1,1'-biphenyl]-4-yl)(4-(pyridin-4-ylmethyl)piperazin-1-yl)methanone To a mixture of 4'-(1,1,1,3,3,3-hexafluoro-2-hydroxypropan-2-yl)-[1,1'-biphenyl]-4-carboxylic acid (36.4 mg, 0.1 mmol) in DMF (1 mL) was added DIEA (26 mg, 0.2 mmol) and HATU (46 mg, 0.12 mmol). The mixture was stirred for 5 min, and then 1-(pyridin-4-ylmethyl)piperazine (20 mg, 0.12 mmol) was added. The reaction mixture was stirred at rt for 30 min. The completion reaction was monitored by anal. HPLC. The solvent was removed in vacuo to obtain the crude which was purified by prep-HPLC (MeOH/Acetonitrile/water) to obtain the title compound as TFA salt. ESI-MS (m/z): 524 [M+1]⁺.

Example 101

2-(4'-((4-((3,5-Difluoropyridin-4-yl)methyl)piperazin-1-yl)methyl)-[1,1'-biphenyl]-4-yl)-1,1,1,3,3,3-hexafluoropropan-2-ol

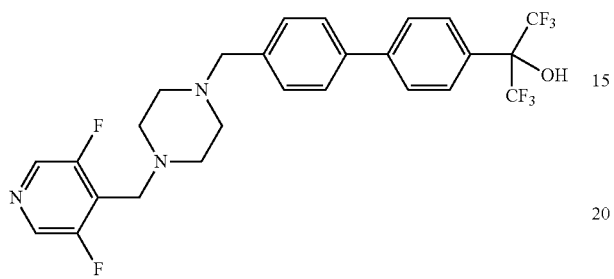

The title compound was prepared following the same general protocol as described in Step 4, Example 1, using 3,5-difluoroisonicotinaldehyde instead of isonicotinaldehyde. ESI-MS (m/z): 546 [M+1]⁺.

Example 102

Methyl 4-((4-((4'-(1,1,1,3,3,3-hexafluoro-2-hydroxypropan-2-yl)-[1,1'-biphenyl]-4-yl)methyl)piperazin-1-yl)methyl)benzoate

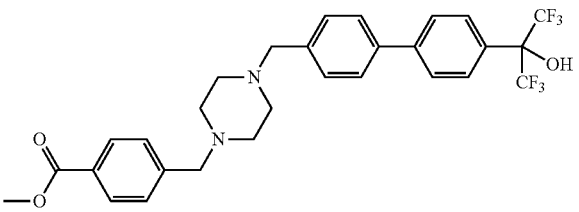 [SMILES: COC(=O)c1ccc(CN2CCN(Cc3ccc(-c4ccc(C(O)(C(F)(F)F)C(F)(F)F)cc4)cc3)CC2)cc1]

The title compound was prepared following the same general protocol as described in Step 4, Example 1, using methyl 4-formylbenzoate instead of isonicotinaldehyde. ESI-MS (m/z): 567 [M+1]⁺.

Example 103

1,1,1,3,3,3-Hexafluoro-2-(4'-((4-(4-nitrobenzyl)piperazin-1-yl)methyl)-[1,1'-biphenyl]-4-yl)propan-2-ol

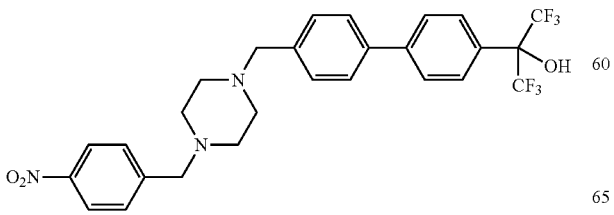

The title compound was prepared following the same general protocol as described in Step 4. Example 1, using 4-nitrobenzaldehyde instead of isonicotinaldehyde. ESI-MS (m/z): 554 [M+1]⁺.

Example 104

1,1,1,3,3,3-Hexafluoro-2-(4'-((4-(pyridin-4-ylamino)piperidin-1-yl)methyl)-[1,1'-biphenyl]-4-yl)propan-2-ol

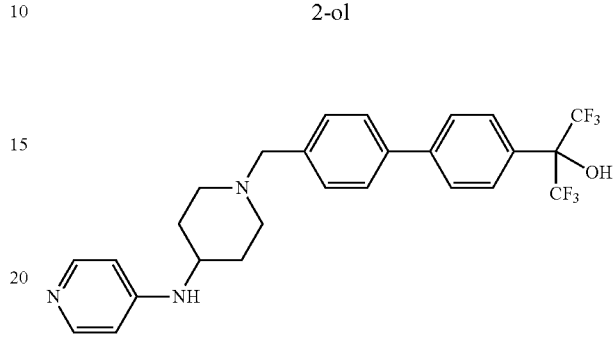

Step 1: tert-Butyl 4-(pyridin-4-ylamino)piperidine-1-carboxylate

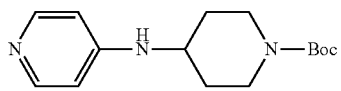 [SMILES: CC(C)(C)OC(=O)N1CCC(Nc2ccncc2)CC1]

A mixture of tert-butyl 4-aminopiperidine-1-carboxylate (0.84 g, 4.19 mmol) and 4-chloropyridine hydrochloride (0.84 g, 5.60 mmol) in n-BuOH/water/NEt₃ (1:1:1, 3 mL) was heated at 100° C. oil bath overnight. The reaction mixture was cooled to rt and diluted with DCM, then washed with saturated NaHCO₃ and brine. The organic layer was dried over Na₂SO₄ and the solvent was removed in vacuo. The crude was purified by flash chromatography in silica gel (EtOAc/DCM 0~50%) to obtain the title compound. ESI-MS (m/z): 278 [M+1]⁺.

Step 2: N-(Piperidin-4-yl)pyridin-4-amine

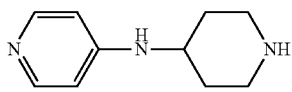 [SMILES: c1cc(NC2CCNCC2)ccn1]

Tert-butyl 4-(pyridin-4-ylmethyl)piperazine-1-carboxylate obtained from step 1 was dissolved in TFA/DCM (30%, 2 mL) and stirred at rt for 2 h. The completion of reaction was monitored by analytical HPLC. The solvent was removed to obtain the title compound as TFA salt with no further purification. ESI-MS (m/z): 178 [M+1].

Step 3: 1,1,1,3,3,3-Hexafluoro-2-(4'-((4-(pyridin-4-ylamino)piperidin-1-yl)methyl)-[1,1'-biphenyl]-4-yl)propan-2-ol The title compound was prepared following the same general protocol as described in Step 4, Example 1, using 4'-(1,1,1,3,3,3-hexafluoro-2-hydroxypropan-2-yl)-[1,1'-biphenyl]-4-carbaldehyde and N-(piperidin-4-yl)pyridin-4-amine TFA salt instead of 1,1,1,3,3,3-hexafluoro-2-(4'-(piperazin-1-ylmethyl)-[1,1'-biphenyl]-4-yl)propan-2-ol and isonicotinaldehyde. ESI-MS (m/z): 510 [M+1]$^+$.

Example 105

1,1,1,3,3,3-Hexafluoro-2-(3-fluoro-4'-((4-(pyridin-4-ylmethyl)piperazin-1-yl)methyl)-[1,1'-biphenyl]-4-yl)propan-2-ol

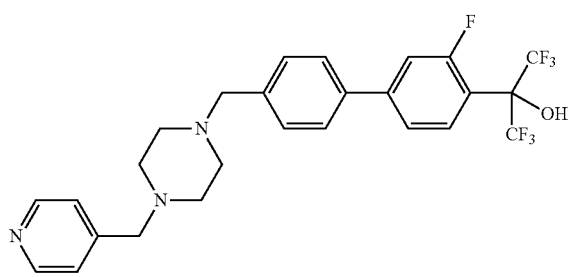 [SMILES: OC(c1ccc(-c2ccc(CN3CCN(Cc4ccncc4)CC3)cc2)cc1F)(C(F)(F)F)C(F)(F)F]

Step 1: 2-(4-Amino-2-fluorophenyl)-1,1,1,3,3,3-hexafluoropropan-2-ol

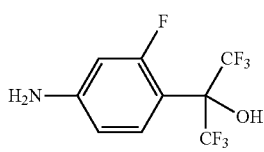

The title compound was prepared following the same general protocol as described in Step 1, Example 110, using 3-fluoroaniline instead of o-toluidine. ESI-MS (m/z): 278 [M+1]$^+$.

Step 2: 1,1,1,3,3,3-Hexafluoro-2-(2-fluoro-4-iodophenyl)propan-2-ol

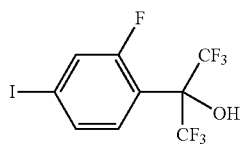

The title compound was prepared following the same general protocol as described in Step 1, Example 1, using 2-(4-amino-2-fluorophenyl)-1,1,1,3,3,3-hexafluoropropan-2-ol instead of 2-(4-aminophenyl)-1,1,1,3,3,3-hexafluoropropan-2-ol.

Step 3: 1,1,1,3,3,3-Hexafluoro-2-(3-fluoro-4'-((4-(pyridin-4-ylmethyl)piperazin-1-yl)methyl)-[1,1'-biphenyl]-4-yl)propan-2-ol The title compound was prepared following the same general protocol as described in Step 1, Example 14, using 1-(4-pyridinyl-methyl)-piperazine-4-benzyl-para-boronic pinacol ester and 1,1,1,3,3,3-hexafluoro-2-(2-fluoro-4-iodophenyl)propan-2-ol instead of (4-formylphenyl)boronic acid and 1,1,1,3,3,3-hexafluoro-2-(4-iodophenyl)propan-2-ol. ESI-MS (m/z): 528 [M+1]$^+$.

Example 106

1,1,1,3,3,3-Hexafluoro-2-(3-methoxy-4'-((4-(pyridin-4-ylmethyl)piperazin-1-yl)methyl)-[1,1'-biphenyl]-4-yl)propan-2-ol

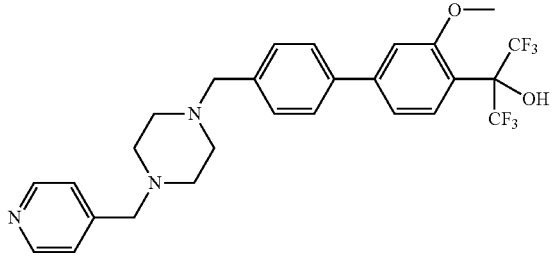 [SMILES: COc1cc(-c2ccc(CN3CCN(Cc4ccncc4)CC3)cc2)ccc1C(O)(C(F)(F)F)C(F)(F)F]

Step 1: 2-(4-Amino-2-methoxyphenyl)-1,1,1,3,3,3-hexafluoropropan-2-ol

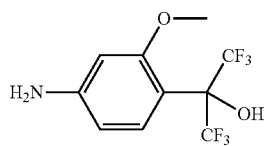

The title compound was prepared following the same general protocol as described in Step 1, Example 110, using 3-methoxyaniline instead of o-toluidine. ESI-MS (m/z): 290 [M+1]$^+$.

Step 2: 1,1,1,3,3,3-Hexafluoro-2-(4-iodo-2-methoxyphenyl)propan-2-ol

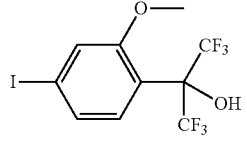

The title compound was prepared following the same general protocol as described in Step 1, Example 1, using 1,1,1,3,3,3-hexafluoro-2-(4-iodo-2-methoxyphenyl)propan-2-ol instead of 2-(4-aminophenyl)-1,1,1,3,3,3-hexafluoropropan-2-ol.

Step 3: 1,1,1,3,3,3-Hexafluoro-2-(3-methoxy-4'-((4-(pyridin-4-ylmethyl)piperazin-1-yl)methyl)-[1,1'-biphenyl]-4-yl)propan-2-ol The title compound was prepared following the same general protocol as described in Step 1. Example 14, using 1-(4-pyridinyl-methyl)-piperazine-4-benzyl-para-boronic pinacol ester and 1,1,1,3,3,3-hexafluoro-2-(4-iodo-2- methoxyphenyl)propan-2-ol instead of (4-formylphenyl)boronic acid and 1,1,1,3,3,3-hexafluoro-2-(4-iodophenyl)propan-2-ol. ESI-MS (m/z): 540 [M+1]+.

Example 107

1,1,1,3,3,3-Hexafluoro-2-(3-methyl-4'-((4-(pyridin-4-ylmethyl)piperazin-1-yl)methyl)-[1,1'-biphenyl]-4-yl)propan-2-ol

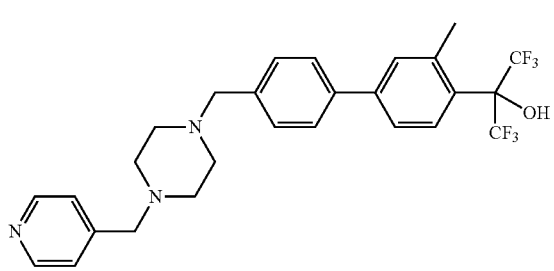 [SMILES: Cc1cc(-c2ccc(CN3CCN(Cc4ccncc4)CC3)cc2)ccc1C(O)(C(F)(F)F)C(F)(F)F]

Step 1: 2-(4-Amino-2-methylphenyl)-1,1,1,3,3,3-hexafluoropropan-2-ol

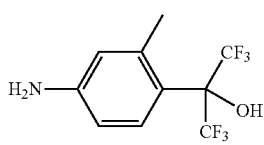

The title compound was prepared following the same general protocol as described in Step 1, Example 110, using m-toluidine instead of o-toluidine. ESI-MS (m/z): 274 [M+1]+.

Step 2: 1,1,1,3,3,3-Hexafluoro-2-(4-iodo-2-methylphenyl)propan-2-ol

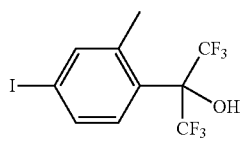

The title compound was prepared following the same general protocol as described in Step 1, Example 1, using 2-(4-amino-2-methylphenyl)-1,1,1,3,3,3-hexafluoropropan-2-ol instead of 2-(4-aminophenyl)-1,1,1,3,3,3-hexafluoropropan-2-ol.

Step 3: 1,1,1,3,3,3-Hexafluoro-2-(3-methyl-4'-((4-(pyridin-4-ylmethyl)piperazin-1-yl)methyl)-[1,1'-biphenyl]-4-yl)propan-2-ol The title compound was prepared following the same general protocol as described in Step 1, Example 14, using 1-(4-pyridinyl-methyl)-piperazine-4-benzyl-para-boronic pinacol ester and 1,1,1,3,3,3-hexafluoro-2-(4-iodo-2-methylphenyl)propan-2-ol instead of (4-formylphenyl)boronic acid and 1,1,1,3,3,3-hexafluoro-2-(4-iodophenyl)propan-2-ol. ESI-MS (m/z): 524 [M+1]+.

Example 108

1,1,1,3,3,3-Hexafluoro-2-(2-methoxy-4'-((4-(pyridin-4-ylmethyl)piperazin-1-yl)methyl)-[1,1'-biphenyl]-4-yl)propan-2-ol

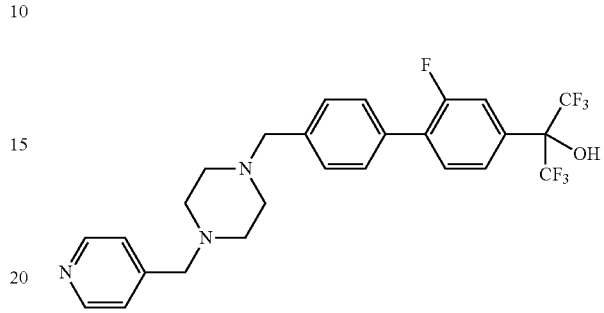

Step 1: 2-(4-Amino-3-fluorophenyl)-1,1,1,3,3,3-hexafluoropropan-2-ol

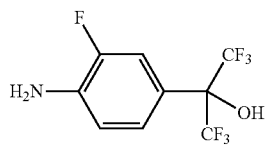

To 2-fluoroaniline (9.90 mmol) in a pressure vessel was added hexafluoroacetone sesquihydrate (10.9 mmol, 1.1 eq) neat and p-toluenelsuphonic acid (0.990 mmol, 0.1 eq). The vessel was then purged with argon, sealed and heated on an oil bath overnight (12 h) at 900° C. The reaction contents were then diluted with ethyl acetate and washed with NaHCO3 (3×100 mL; sat.). The ethyl acetate phase was then washed with brine (100 mL), dried over Na2SO4, and concentrated to a solid residue. The desired product was then isolated by silica gel using hexanes/ethyl acetate and following recrystallization from 10:1 hexanes/ethyl acetate to afford 2-(4-Amino-3-fluorophenyl)-1,1,1,3,3,3-hexafluoropropan-2-ol as white prisms. ESI-MS (m/z): 278 [M+1]+.

Step 2

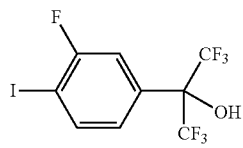

To a solution of 2-(4-Amino-3-fluorophenyl)-1,1,1,3,3,3-hexafluoropropan-2-ol (2.48 mmol) in DMF (2.5 mL) was added sodium nitrite (2.98 mmol, 1.2 eq) in water (1.5 mL) and 6M hydrochloric acid (3 eq), while maintaining the temperature between 0~5° C. Stirring was continued for 30 min, and then potassium iodide (3.72 mmol, 1.5 eq) was added in small portions. The resulting mixture was then allowed to stir overnight at room temperature. The reaction mixture was then diluted with Et2O (200 mL), washed with a saturated sodium thiosulphate (3×150 mL) and dried over Na2SO4. The solvent was removed in vacuo leaving a dark crude oil which was separated on silica gel (EtOAc/Hex) to obtain 1,1,1,3,3,3-Hexafluoro-2-(3-fluoro-4-iodophenyl) propan-2-ol.

Step 3

To 4-bromomethylphenylboronic acid pinacol ester (1.68 mmol) was added MeCN (5 mL), followed by addition of $K_2CO_3$ (5.04 mmol, 3.0 eq), 1-(pyridinyl-4-methyl)-piperazine (2.02 mmol, 1.2 eq), and NaI (2 mole %). The mixture was allowed to stir overnight at rt (~23° C.) under an argon balloon. The remaining reaction mixture was then diluted with $H_2O$ (50 mL) and extracted with $CHCl_3$ (3×100 mL). The organic washes were combined, dried over $Na_2SO_4$, concentrated to a solid residue and again extracted with 12:1 hexanes/$CH_2Cl_2$ (3×100 mL) and concentrated in vacuo to a yellow crystalline. The product 1-(4-pyridinyl-methyl)-piperazine-4-benzyl-para-boronic pinacol ester was isolated by recrystallization from hexanes and used without further purification within the following synthetic step.

Step 4

A mixture of 1,1,1,3,3,3-Hexafluoro-2-(3-fluoro-4-iodophenyl)propan-2-ol (0.183 mmol), 1-(4-pyridinyl-methyl)-piperazine-4-benzyl-para-boronic pinacol ester (2.20 mmol, 1.2 eq), Pd(PPh$_3$)$_4$ (5 mol %), $K_2CO_3$ (0.550 mmol, 3 eq) and 3:1 dioxane/$H_2O$ (4 mL) in a 20 mL pressure vessel was degassed for 5 min, purged with argon, sealed and heated for 2 h at 80° C. oil bath. Upon completion, as determined by reverse-phase HPLC, the mixture was allowed to cool and was then extracted with EtOAc (3×25 mL). The combine organic layers were washed with saturated NaHCO$_3$ (2×25 mL) and dried over Na$_2$SO$_4$. The solvent was removed in vacuo leaving a brown solid crude which was then isolated by flash chromatography on silica gel (CH$_2$Cl$_2$/MeOH) to obtain the title compound. ESI-MS (m/z): 528 [M+1]+; 1H-NMR (400 MHz, CHCl$_3$ 7.26) δ 8.46 (d, J=5.2 Hz, 2H), 7.62 (s, 1H), 7.59 (s, 1H), 7.53-7.49 (m, 3H), 7.40 (d, J=8.0 Hz, 2H), 7.30 (d, J=5.2 Hz, 2H), 3.58 (s, 2H), 3.53 (s, 2H), 2.51 (b, 8H).

Example 109

1,1,1,3,3,3-Hexafluoro-2-(2-methoxy-4'-((4-(pyridin-4-ylmethyl)piperazin-1-yl)methyl)-[1,1'-biphenyl]-4-yl)propan-2-ol

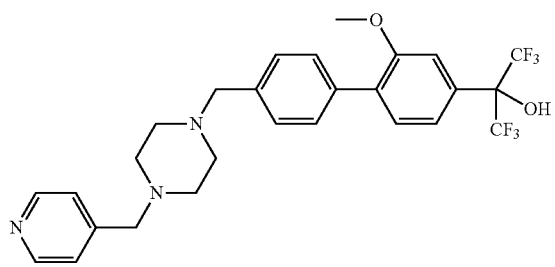 [SMILES: COc1cc(C(O)(C(F)(F)F)C(F)(F)F)ccc1-c1ccc(CN2CCN(Cc3ccncc3)CC2)cc1]

Step 1: 2-(4-Amino-3-methoxyphenyl)-1,1,1,3,3,3-hexafluoropropan-2-ol

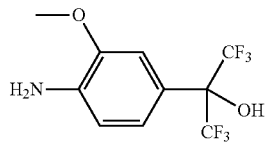

The title compound was prepared following the same general protocol as described in Step 1, Example 110, using 2-methoxyaniline instead of o-toluidine. ESI-MS (m/z): 290 [M+1]+.

Step 2: 1,1,1,3,3,3-Hexafluoro-2-(4-iodo-3-methoxyphenyl)propan-2-ol

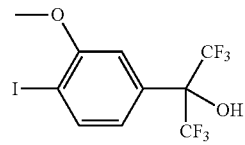

The title compound was prepared following the same general protocol as described in Step 1, Example 1, using 2-(4-amino-3-methoxyphenyl)-1,1,1,3,3,3-hexafluoropropan-2-ol instead of 2-(4-aminophenyl)-1,1,1,3,3,3-hexafluoropropan-2-ol.

Step 3: 1,1,1,3,3,3-Hexafluoro-2-(2-methoxy-4'-((4-(pyridin-4-ylmethyl)piperazin-1-yl)methyl)-[1,1'-biphenyl]-4-yl)propan-2-ol The title compound was prepared following the same general protocol as described in Step 1, Example 14, using 1-(4-pyridinyl-methyl)-piperazine-4-benzyl-para-boronic pinacol ester and 1,1,1,3,3,3-hexafluoro-2-(4-iodo-3-methoxyphenyl)propan-2-ol instead of (4-formylphenyl)boronic acid and 1,1,1,3,3,3-hexafluoro-2-(4-iodophenyl)propan-2-ol. ESI-MS (m/z): 540 [M+1]+.

Example 110

1,1,1,3,3,3-Hexafluoro-2-(2-methyl-4'-((4-(pyridin-4-ylmethyl)piperazin-1-yl)methyl)-[1,1'-biphenyl]-4-yl)propan-2-ol

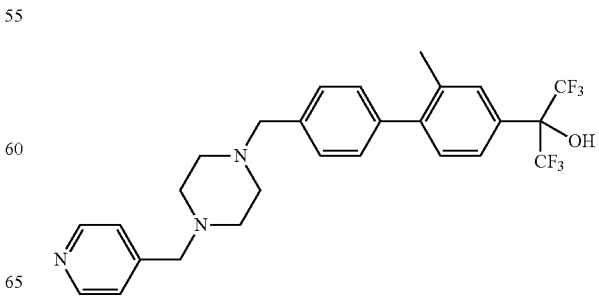

Step 1: 2-(4-Amino-3-methyl-phenyl)-1,1,1,3,3,3-hexafluoropropan-2-ol

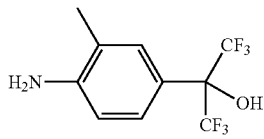

To 1.00 g (1.00 mL, 9.33 mmol) of o-toluidine in a pressure tube was added 1.41 mL (1.1 eq. 10.3 mmol) of hexafluoroacetone sesquihydrate neat and 0.180 g (0.1 eq, 0.933 mmol) p-toluenylsuphonic acid. The tube was then purged with argon, sealed and heated on an oil bath overnight (12 h) at 90° C. The reaction contents were then diluted with 200 mL ethyl acetate and washed 3×150 mL NaHCO$_3$ (sat.). The ethyl acetate phase was then washed with 50 mL brine, dried with Na$_2$SO$_4$, and concentrated to a solid residue. The desired product was then isolated by silica gel using hexanes/ethyl acetate and following recrystallization from 10:1 hexanes/ethyl acetate to afford of 2-(4-amino-3-methyl-phenyl)-1,1,1,3,3,3-hexafluoropropan-2-ol as white prisms. ESI-MS (m/z): 274 [M+1]$^+$.

Step 2: 1,1,1,3,3,3-Hexafluoro-2-(4-iodo-3-methyl-phenyl)propan-2-ol

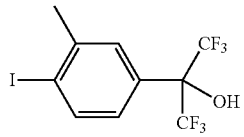

The title compound was prepared following the same general protocol as described in Step 1. Example 1, using 2-(4-amino-3-methylphenyl)-1,1,1,3,3,3-hexafluoropropan-2-ol instead of 2-(4-aminophenyl)-1,1,1,3,3,3-hexafluoropropan-2-ol.

Step 3: 1-(4-Pyridinyl-methyl)-piperazine-4-benzyl-para-boronic pinacol ester

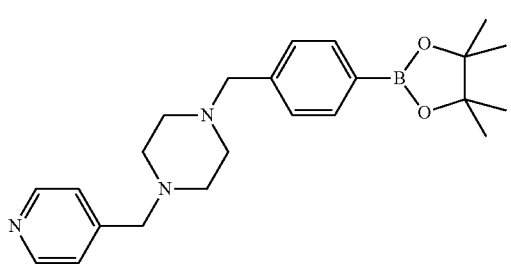 [SMILES: CC1(C)OB(c2ccc(CN3CCN(Cc4ccncc4)CC3)cc2)OC1(C)C]

To 0.500 g (1.68 mmol) of 4-bromomethylphenylboronic acid pinacol ester was added 5 mL of dry DMF, followed by addition of 0.705 g K$_2$CO$_3$ (3.0 eq, 10.1 mmol), 0.328 g (1.1 eq, 1.85 mmol) of 1-(pyridinyl-4-methyl)-piperazine and 10 mg (2% weight) NaI. The mixture was allowed to stir overnight at rt (~23° C.) under argon balloon. The remaining reaction mixture in DMF was then diluted with 200 mL CHCl$_3$ and washed 3×200 mL portions of H$_2$O maintained at pH≈10 and dried over Na$_2$SO$_4$. The washed organic phase was then concentrated to a solid residue and extracted with 12:1 hexanes/CH$_2$Cl$_2$ and again concentrated. The product 1-(4-pyridinyl-methyl)-piperazine-4-benzyl-para-boronic pinacol ester was isolated by recrystallization from 12:1 hexanes/CH$_2$Cl$_2$ and used without further purification within the subsequent synthetic step.

Step 4: 1,1,1,3,3,3-Hexafluoro-2-(2-methyl-4'-((4-(pyridin-4-ylmethyl)piperazin-1-yl)methyl)-[, 1,1'-biphenyl]-4-yl)propan-2-ol The title compound was prepared following the same general protocol as described in Step 1, Example 14, using 1-(4-pyridinyl-methyl)-piperazine-4-benzyl-para-boronic pinacol ester and 1,1,1,3,3,3-hexafluoro-2-(4-iodo-3-methyl-phenyl)propan-2-ol instead of (4-formylphenyl)boronic acid and 1,1,1,3,3,3-hexafluoro-2-(4-iodophenyl)propan-2-ol. ESI-MS (m/z): 524 [M+1]$^+$.

Examples 111 and 113

1,1,1,3,3,3-Hexafluoro-2-(4'-((4-((1-methyl-1H-imidazol-4-yl)methyl)piperazin-1-yl)methyl)-[1,1'-biphenyl]-4-yl)propan-2-ol and 1,1,1,3,3,3-hexafluoro-2-(4'-((4-((1-methyl-1H-imidazol-5-yl)methyl)piperazin-1-yl)methyl)-[1,1'-biphenyl]-4-yl)propan-2-ol

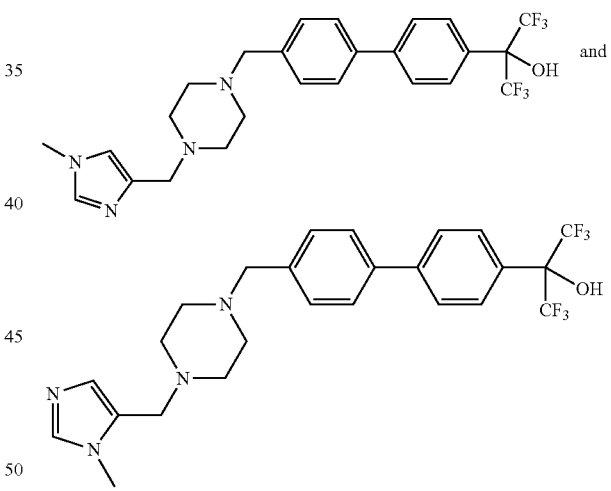

Step 1: 1-Methyl-1H-imidazole-4-carbaldehyde & 1-methyl-1H-imidazole-5-carbaldehyde

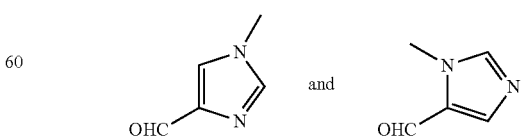

1H-Imidazole-4(5)-carbaldehyde, 0.230 g (2.40 mmol) was dissolved into 2.00 mL MeOH and 0.200 mL H$_2$O in a round bottom flask. To the stirring solution was added 0.118 g NaOH (1.2 eq, 2.87 mmol) and 0.149 mL (0.340 g, 1 eq, 2.40 mmol) of methyl iodide (iodomethane). The mixture was allowed to stir overnight (14 h) at 36° C. The reaction was then diluted with 50 mL CHCl$_3$ and washed with 3×20 mL deionized water. The aqueous phase was then extracted with 2×50 mL CHCl$_3$. The organic layers were then combined and dried over Na$_2$SO$_4$ and concentrated to a crude pink oil. The products 1-methyl-1H-imidazole-4-carbaldehyde & 1-methyl-1H-imidazole-5-carbaldehyde were isolated by silica gel using CH$_2$Cl$_2$/MeOH as a regio-isomer mixture and used in the next synthetic step without further purification.

Step 2: 1,1,1,3,3,3-Hexafluoro-2-(4'-((4-((1-methyl-1H-imidazol-4-yl)methyl)piperazin-1-yl)methyl)-[1, 1'-biphenyl]-4-yl)propan-2-ol and 1,1,1,3,3,3-hexafluoro-2-(4'-((4-((1-methyl-1H-imidazol-5-yl)methyl)piperazin-1-yl)methyl)-[1,1'-biphenyl]-4-yl) propan-2-ol The title compound was prepared following the same general protocol as described in Step 4, Example 1, using 1H1-methyl-1H-imidazole-4-carbaldehyde & 1-methyl-1H-imidazole-5-carbaldehyde instead of isonicotinaldehyde. ESI-MS (m/z): 513 [M+1]$^+$.

Example 112

2-(4'-((4-(((1H-Imidazol-5-yl)methyl)piperazin-1-yl) methyl)-[1,1'-biphenyl]-4-yl)-1,1,1,3,3,3-hexafluoropropan-2-ol

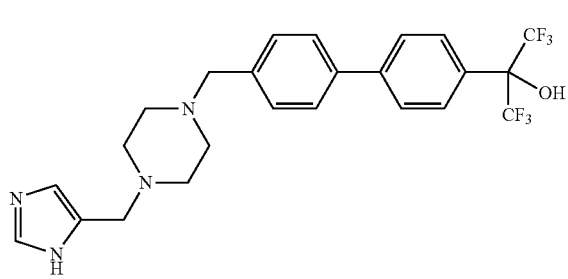 [SMILES: OC(c1ccc(-c2ccc(CN3CCN(Cc4cnc[nH]4)CC3)cc2)cc1)(C(F)(F)F)C(F)(F)F]

The title compound was prepared following the same general protocol as described in Step 4, Example 1, using 1H-imidazole-5-carbaldehyde instead of isonicotinaldehyde. ESI-MS (m/z): 499 [M+1]f.

Example 114

1,1,1,3,3,3-Hexafluoro-2-(4'-((4-(thiazol-5-ylmethyl) piperazin-1-yl)methyl)-[1,1'-biphenyl]-4-yl)propan-2-ol

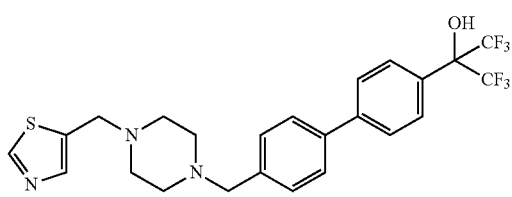 [SMILES: OC(c1ccc(-c2ccc(CN3CCN(Cc4cncs4)CC3)cc2)cc1)(C(F)(F)F)C(F)(F)F]

The title compound was prepared following the same general protocol as described in Step 4. Example 1, using thiazole-5-carbaldehyde instead of isonicotinaldehyde. ESI-MS (m/z): 516 [M+H]$^+$ Experiment 115

1,1,1,3,3,3-Hexafluoro-2-(4'-((4-(thiazol-4-ylmethyl) piperazin-1-yl)methyl)-[1,1'-biphenyl]-4-yl)propan-2-ol

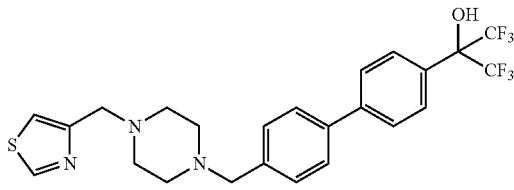 [SMILES: OC(c1ccc(-c2ccc(CN3CCN(Cc4cscn4)CC3)cc2)cc1)(C(F)(F)F)C(F)(F)F]

The title compound was prepared following the same general protocol as described in Step 4, Example 1, using thiazole-4-carbaldehyde instead of isonicotinaldehyde. ESI-MS (m/z): 516 [M+H]+

Example 116

(4-((4'-(1,1,1,3,3,3-Hexafluoro-2-hydroxypropan-2-yl)-[1,1'-biphenyl]-4-yl)methyl)piperazin-1-yl)(thiazol-4-yl)methanone

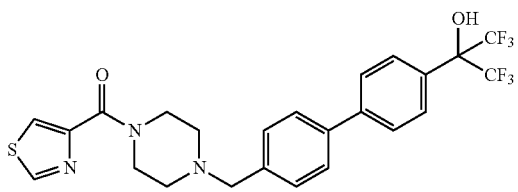 [SMILES: O=C(c1cscn1)N1CCN(Cc2ccc(-c3ccc(C(O)(C(F)(F)F)C(F)(F)F)cc3)cc2)CC1]

To a solution of 1,1,1,3,3,3-hexafluoro-2-(4'-(piperazin-1-ylmethyl)-[1,1'-biphenyl]-4-yl)propan-2-ol (50 mg, 0.12 mmol) in DCM/DMF (1/1) were added the 4-thiazolecarboxylic acid (17 mg, 0.13 mmol), EDC (25 mg, 0.13 mmol), and HOBt (20 mg, 0.13 mmol). The reaction mixture was stirred at room temperature overnight and then diluted with ethyl acetate. This organic phase was washed with brine, dried over MgSO$_4$ and concentrated in vacuo. The crude was purified by preparative HPLC to afford a white powder (33 mg). ESI-MS (m/z): 530 [M+H]$^+$ Example 126

1,1,1,3,3,3-Hexafluoro-2-(4'-(piperidin-4-yloxy)-[1, 1'-biphenyl]-4-yl)propan-2-ol

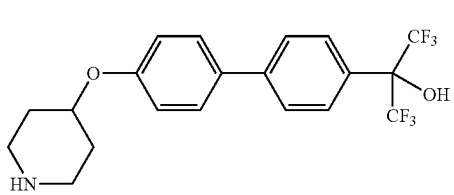 [SMILES: OC(c1ccc(-c2ccc(OC3CCNCC3)cc2)cc1)(C(F)(F)F)C(F)(F)F]

Step 1: 1,1,1,3,3,3-Hexafluoro-2-(4-(4,4,5,5-tetramethyl-1,3,2-dioxaborolan-2-yl)phenyl)propan-2-ol

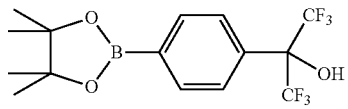

The mixture of 1,1,1,3,3,3-hexafluoro-2-(4-iodophenyl)propan-2-ol (2.5 g, 6.757 mmol), 4,4,4',4',5,5,5',5'-octamethyl-2,2'-bi(1,3,2-dioxaborolane) (2.06 g, 8.11 mmol), PdCl$_2$(PPh$_3$)$_2$ (0.474 g, 0.68 mmol) and KOAc (1.99 g, 20.27 mmol) in DMF (20 mL) was degassed for 2 min and then stirred for 16 h at 80° C. oil bath. The Reaction mixture was cooled to rt and poured into saturated NaHCO$_3$ and then extracted with EtOAc. The organic layers were combined, washed with brine and dried over Na$_2$SO$_4$. The solvent removed in vacuo and the crude was purified by flash chromatography on silica gel (EtOAc/Hex (0~10%) to obtain the title compound.

Step 2: tert-Butyl 4-((4'-(1,1,1,3,3,3-hexafluoro-2-hydroxypropan-2-yl)-[1,1'-biphenyl]-4-yl)oxy)piperidine-1-carboxylate

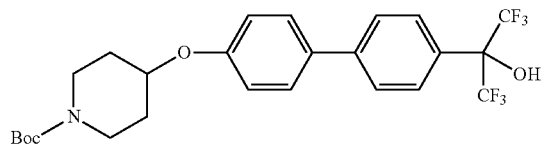 [SMILES: CC(C)(C)OC(=O)N1CCC(Oc2ccc(-c3ccc(C(O)(C(F)(F)F)C(F)(F)F)cc3)cc2)CC1]

To a mixture of 1,1,1,3,3,3-hexafluoro-2-(4-(4,4,5,5-tetramethyl-1,3,2-dioxaborolan-2-yl)phenyl)propan-2-ol (242 mg, 0.655 mmol) and tert-butyl 4-(4-bromophenoxy)piperidine-1-carboxylate (212 mg, 0.595 mmol) in DMF (2.5 mL) was added potassium phosphate (2N, 0.9 mL, 1.8 mmol), 2-(dicyclohexylphosphino)biphenyl (38.5 mg, 0.119 mmol) and palladium(II) acetate (13 mg, 0.06 mmol). The mixture was degassed and stirred for 16 h at 70° C. The Reaction mixture was cooled to rt and poured into saturated NaHCO$_3$ and then extracted with EtOAc. The organic layers were combined, washed with brine and dried over Na$_2$SO$_4$. The solvent removed in vacuo and the crude was purified by flash chromatography on silica gel (EtOAc/Hex (0~100%) to obtain the title compound. ESI-MS (m/z): 504 [M+1]$^+$.

Step 3: 1,1,1,3,3,3-Hexafluoro-2-(4'-(piperidin-4-yloxy)-[1,1'-biphenyl]-4-yl)propan-2-ol Tert-butyl 4-(pyridin-4-ylmethyl)piperazine-1-carboxylate obtained from step 2 was dissolved in TFA/DCM (30%, 2 mL) and stirred t rt for 2 h. The completion of reaction was monitored by anal. HPLC. The solvent was removed to obtain the crude which was purified by prep-HPLC (MeOH/Acetonitrile/water) to obtain the title compound as TFA salt. ESI-MS (m/z): 420 [M+1]$^+$.

Example 127

1,1,1,3,3,3-Hexafluoro-2-(4'-((1-(pyridin-4-ylmethyl)piperidin-4-yl)oxy)-[1,1'-biphenyl]-4-yl)propan-2-ol

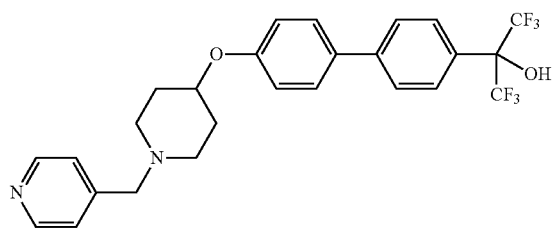

The title compound was prepared following the same general protocol as described in Step 4, Example 1, using 1,1,1,3,3,3-hexafluoro-2-(4'-(piperidin-4-yloxy)-[1,1'-biphenyl]-4-yl)propan-2-ol instead of 1,1,1,3,3,3-hexafluoro-2-(4'-(piperazin-1-ylmethyl)-[1,1'-biphenyl]-4-yl)propan-2-ol. ESI-MS (m/z): 511, [M+1]$^+$.

Example 128

Benzyl 4-((4'-(1,1,1,3,3,3-hexafluoro-2-hydroxypropan-2-yl)-[1,1'-biphenyl]-4-yl)amino)piperidine-1-carboxylate

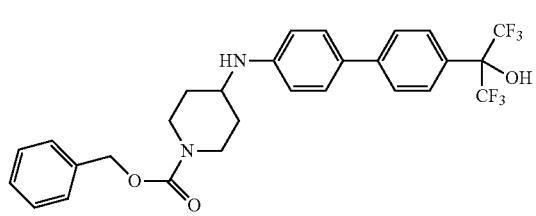 [SMILES: O=C(OCc1ccccc1)N1CCC(Nc2ccc(-c3ccc(C(O)(C(F)(F)F)C(F)(F)F)cc3)cc2)CC1]

Step 1: Benzyl 4-((4-bromophenyl)amino)piperidine-1-carboxylate

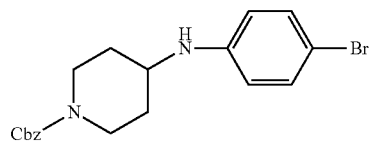 [SMILES: O=C(OCc1ccccc1)N1CCC(Nc2ccc(Br)cc2)CC1]

To a mixture of benzyl 4-oxopiperidine-1-carboxylate (1.356 g, 5.813 mmol) and 4-bromoaniline (1.0 g, 5.813 mmol) in THF (10 mL) was added titanium isopropoxide (1.98 g, 6.976 mmol). The mixture was stirred at rt for 24 h. The reaction was cooled to 0° C. and NaBH(OAc)$_3$ (3.69 g, 17.44 mmol) was added portionwise. The resulting mixture was stirred for another 5 h at rt. The mixture was then diluted with EtOAc and water, filtered through Celite pad. The resulting filtrate was then washed over brine, dried over Na$_2$SO$_4$, concentrated and flash chromatography on silica gel (EtOAc/Hex 10~100%) to yield the title compound. ESI-MS (m/z): 389, 391 [M]$^+$. [M+2]$^+$.

Step 2: Benzyl 4-((4'-(1,1,1,3,3,3-hexafluoro-2-hydroxypropan-2-yl)-[1,1'-biphenyl]-4-yl)amino)piperidine-1-carboxylate

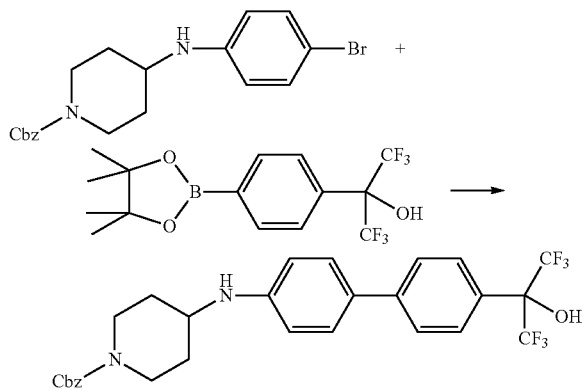

The title compound was prepared following the same general protocol as described in Step 2, Example 126, using benzyl 4-((4-bromophenyl)amino)piperidine-1-carboxylate instead of tert-butyl 4-(4-bromophenoxy)piperidine-1-carboxylate. ESI-MS (m/z): 553 [M+1]$^+$.

Example 129

1,1,1,3,3,3-Hexafluoro-2-(4'-((1-(pyridin-4-ylmethyl)piperidin-4-yl)amino)-[1,1'-biphenyl]-4-yl)propan-2-ol

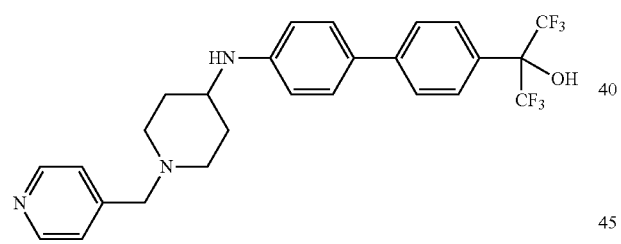

Step 1: 1,1,1,3,3,3-Hexafluoro-2-(4'-(piperidin-4-ylamino)-[1,1'-biphenyl]-4-yl)propan-2-ol

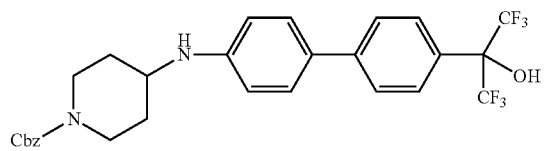 [SMILES: O=C(OCc1ccccc1)N1CCC(Nc2ccc(-c3ccc(C(O)(C(F)(F)F)C(F)(F)F)cc3)cc2)CC1]

To a mixture of benzyl 4-((4'-(1,1,1,3,3,3-hexafluoro-2-hydroxypropan-2-yl)-[1,1'-biphenyl]-4-yl)amino)piperidine-1-carboxylate (0.3 g, 0.54 mmol) in EtOH (10 mL) was added Pd/C (30 mg) and H$_2$ balloon. The mixture was stirred at rt overnight. The mixture was filtered through Celite Pad. The filtrate was concentrated to obtain the title compound. ESI-MS (m/z): 419, [M+1]$^+$.

Step 2: 1,1,1,3,3,3-hexafluoro-2-(4'-((1-(pyridin-4-ylmethyl)piperidin-4-yl)amino)-[1,1'-biphenyl]-4-yl)propan-2-ol The title compound was prepared following the same general protocol as described in Step 4, Example 1, using 1,1,1,3,3,3-hexafluoro-2-(4'-(piperidin-4-ylamino)-[1,1'-biphenyl]-4-yl)propan-2-ol instead of 1,1,1,3,3,3-hexafluoro-2-(4'-(piperazin-1-ylmethyl)-[1,1'-biphenyl]-4-yl)propan-2-ol. ESI-MS (m/z): 510 [M+1]$^+$.

Example 130

1,1,1,3,3,3-Hexafluoro-2-(3'-((4-(2-hydroxyethylpiperazin-1-yl)methyl)-[1,1'-biphenyl]-4-yl)propan-2-ol

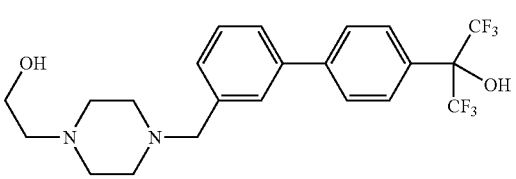 [SMILES: OCCN1CCN(Cc2cccc(-c3ccc(C(O)(C(F)(F)F)C(F)(F)F)cc3)c2)CC1]

The title compound was prepared following the same general protocol as described in Step 2, Example 1, using 2-(piperazin-1-yl)ethanol and 2-(3-(bromomethyl)phenyl)-4,4,5,5-tetramethyl-1,3,2-dioxaborolane instead of tert-butyl piperazine-1-carboxylate and 2-(4-(bromomethyl)phenyl)-4,4,5,5-tetramethyl-1,3,2-dioxaborolane. ESI-MS (m/z): 463 [M+1]$^+$.

Example 131

1,1,1,3,3,3-Hexafluoro-2-(4-(2-(4-methylpiperazin-1-yl)pyridin-4-yl)phenyl)propan-2-ol

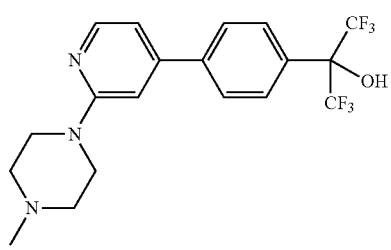 [SMILES: CN1CCN(c2cc(-c3ccc(C(O)(C(F)(F)F)C(F)(F)F)cc3)ccn2)CC1]

The title compound was prepared following the same general protocol as described in Step 1, Example 14, using 1-methyl-4-(5-(4,4,5,5-tetramethyl-1,3,2-dioxaborolan-2-yl)pyridin-3-yl)piperazine instead of (4-formylphenyl)boronic acid. ESI-MS (m/z): 420 [M+1]$^+$.

Example 132

1,1,1,3,3,3-Hexafluoro-2-(4-(6-morpholinopyridin-3-yl)phenyl)propan-2-ol

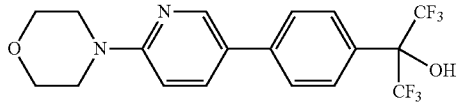

The title compound was prepared following the same general protocol as described in Step 1, Example 14, using 4-(5-(4,4,5,5-tetramethyl-1,3,2-dioxaborolan-2-yl)pyridin-2-yl)morpholine instead of (4-formylphenyl)boronic acid. ESI-MS (m/z): 407 [M+1]$^+$.

Example 133

(5-(4-(1,1,1,3,3,3-Hexafluoro-2-hydroxypropan-2-yl)phenyl)pyridin-3-yl)(morpholino)methanone

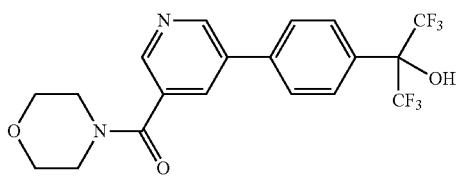 [SMILES: O=C(c1cncc(-c2ccc(C(O)(C(F)(F)F)C(F)(F)F)cc2)c1)N1CCOCC1]

The title compound was prepared following the same general protocol as described in Step 1, Example 14, using morpholino(5-(4,4,5,5-tetramethyl-1,3,2-dioxaborolan-2-yl)pyridin-3-yl)methanone instead of (4-formylphenyl)boronic acid. ESI-MS (m/z): 435 [M+1]$^+$.

Example 134

1,1,1,3,3,3-Hexafluoro-2-(4-(6-(4-methylpiperazin-1-yl)pyridin-3-yl)phenyl)propan-2-ol

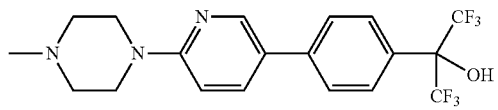

The title compound was prepared following the same general protocol as described in Step 1, Example 14, using 1-methyl-4-(5-(4,4,5,5-tetramethyl-1,3,2-dioxaborolan-2-yl)pyridin-2-yl)piperazine instead of (4-formylphenyl)boronic acid. ESI-MS (m/z): 420 [M+1]$^+$.

Example 135

1-(4-(5-(4-(1,1,1,3,3,3-Hexafluoro-2-hydroxypropan-2-yl)phenyl)pyrimidin-2-yl)piperazin-1-yl)ethanone

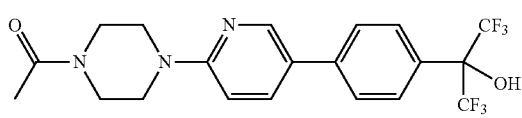

The title compound was prepared following the same general protocol as described in Example 17, using 1-(piperazin-1-yl)ethanone instead of 1-cyclopropylpiperazine. ESI-MS (m/z): 449 [M+1]$^+$.

Example 136

N-(4'-(1,1,1,3,3,3-hexafluoro-2-hydroxypropan-2-yl)-[1,1'-biphenyl]-4-yl)-4-(pyridin-4-ylmethyl)piperazine-1-carboxamide

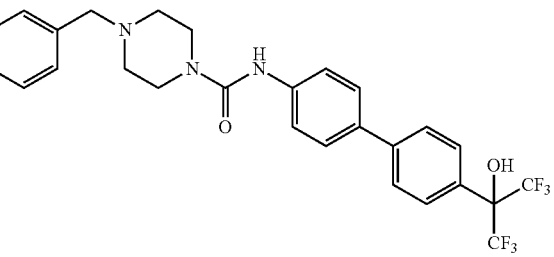

Step 1: N-(4-bromophenyl)piperazine-1-carboxamide

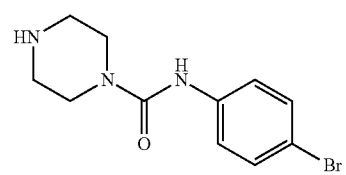 [SMILES: O=C(Nc1ccc(Br)cc1)N1CCNCC1]

A solution of Boc-piperazine (300 mg, 1.61 mmol) and 4-bromophenylisocyanate (335 mg, 1.69 mmol) in DCM (20 ml) was stirred at rt overnight. The solution was diluted with ethyl acetate, washed with a saturated aqueous solution of NaHCO$_3$ and brine. The organic phase was dried over Na$_2$SO$_4$ and concentrated. The obtained oil was dissolved in a mixture DCM/TFA 1/1 (5 ml). The solution was stirred at rt for 1 h. The title compound was precipitated as a TFA salt in diethyl ether to afford a beige powder (682 mg, 100%). ESI-MS (m/z): 284/286 [MH]$^+$.

Step 2: N-(4-bromophenyl)-4-(pyridin-4-ylmethyl)piperazine-1-carboxamide

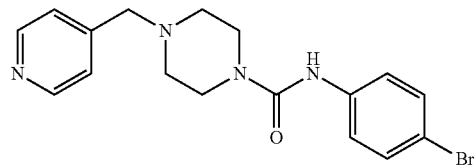 [SMILES: O=C(Nc1ccc(Br)cc1)N1CCN(Cc2ccncc2)CC1]

A solution of N-(4-bromophenyl)piperazine-1-carboxamide (597 mg, 1.5 mmol) and isonicotinaldehyde (141 μl, 1.5 mmol) in dry DCE (10 mL) was stirred at rt for 30 min, then NaBH(OAc)$_3$ (445 mg, 2.1 mmol) was added at rt. The mixture was stirred at rt overnight. The solution was diluted with ethyl acetate, washed with a saturated aqueous solution of NaHCO$_3$ and brine. The organic phase was dried over Na$_2$SO$_4$ and concentrated. The obtained oil was purified by flash chromatography on silica gel (DCM/MeOH/TEA 60/40/1) to afford a yellow oil (427 mg, 76%). ESI-MS (m/z): 375/377 [MH]$^+$.

Step 3: N-(4'-(1,1,1,3,3,3-hexafluoro-2-hydroxypropan-2-yl)-[1,1'-biphenyl]-4-yl)-4-(pyridin-4-ylmethyl)piperazine-1-carboxamide To a solution of 1,1,1,3,3,3-hexafluoro-2-(4-(4,4,5,5-tetramethyl-1,3,2-dioxaborolan-2-yl)phenyl)propan-2-ol (44 mg, 0.12 mmol) and N-(4-bromophenyl)-4-(pyridin-4-ylmethyl)piperazine-1-carboxamide (30 mg, 0.08 mmol) in dioxane/water (4/1, 1.5 ml) was added potassium carbonate (22 mg, 0.16 mmol) and tetrakis(triphenylphosphine)palladium(0) (9 mg, 0.008 mmol). The mixture was degassed and stirred for 1 h at 100° C. under microwave irradiation. The resulting mixture was purified by preparative HPLC to afford the title compound as a TFA salt. ESI-MS (m/z): 539 [M+1]+.

Example 137

2-(4'-(1,1,1,3,3,3-hexafluoro-2-hydroxypropan-2-yl)-[1,1'-biphenyl]-4-yl)-1-(4-(pyridin-4-ylmethyl)piperazin-1-yl)ethanone

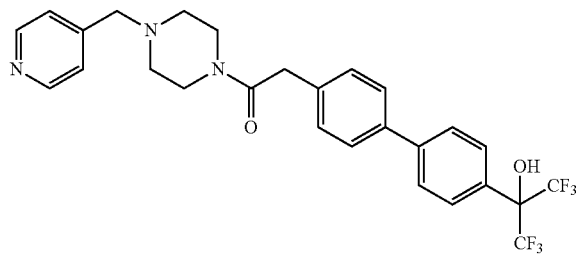 [SMILES: O=C(Cc1ccc(-c2ccc(C(O)(C(F)(F)F)C(F)(F)F)cc2)cc1)N1CCN(Cc2ccncc2)CC1]

Step 1: 2-(4-bromophenyl)-1-(piperazin-1-yl)ethanone

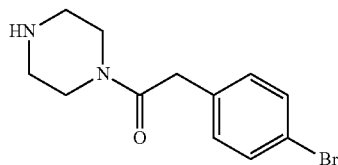

A solution of Boc-piperazine (600 mg, 3.22 mmol), 4-bromobenzoic acid (680 mg, 3.38 mmol), HATU (1.28 g, 3.38 mmol) and DIEA (1.2 ml, 6.76 mmol) in DMF (20 ml) was stirred at rt overnight. The solution was diluted with ethyl acetate, washed with a saturated aqueous solution of NaHCO3 and brine. The organic phase was dried over Na2SO4 and concentrated. The obtained powder was dissolved in a mixture DCM/TFA 1/1 (5 ml). The solution was stirred at rt for 1 h. The title compound was precipitated as a TFA salt in diethyl ether to afford a beige powder (1.22 g, 99%/0). ESI-MS (m/z): 269/271 [MH]+.

Step 2: 2-(4-bromophenyl)-1-(4-(pyridin-4-ylmethyl)piperazin-1-yl)ethanone

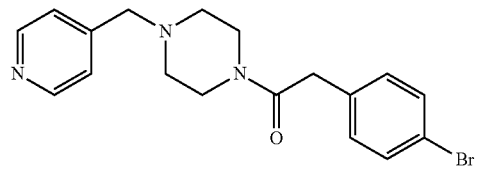 [SMILES: O=C(Cc1ccc(Br)cc1)N1CCN(Cc2ccncc2)CC1]

The title compound was obtained following the same procedure as described in Step 2, Example 136, using the 2-(4-bromophenyl)-1-(piperazin-1-yl)ethanone instead of the N-(4-bromophenyl)piperazine-1-carboxamide. ESI-MS (m/z): 374/375 [MH]+.

Step 3: 2-(4'-(1,1,1,3,3,3-hexafluoro-2-hydroxypropan-2-yl)-[1,1'-biphenyl]-4-yl)-1-(4-(pyridin-4-ylmethyl)piperazin-1-yl)ethanone The title compound was obtained following the same procedure as described in Step 3, Example 136, using the 2-(4-bromophenyl)-1-(4-(pyridin-4-ylmethyl)piperazin-1-yl)ethanone instead of the N-(4-bromophenyl)-4-(pyridin-4-ylmethyl)piperazine-1-carboxamide. ESI-MS (m/z): 538 [MH]+.

Example 138

1,1,1,3,3,3-hexafluoro-2-(4'-((4-(pyridin-4-ylmethyl)piperazin-1-yl)sulfonyl)-[1,1'-biphenyl]-4-yl)propan-2-ol

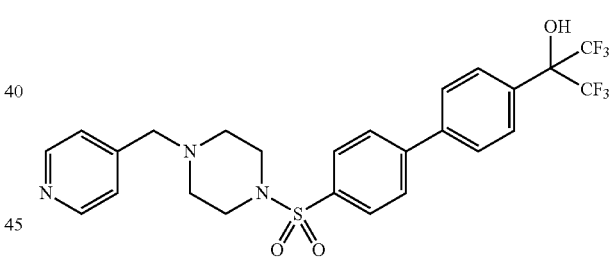

Step 1: 1-((4-bromophenyl)sulfonyl)piperazine

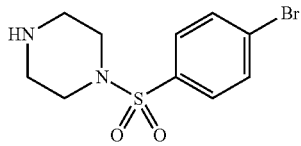 [SMILES: O=S(=O)(c1ccc(Br)cc1)N1CCNCC1]

A solution of Boc-piperazine (300 mg, 1.61 mmol), 4-bromobenzenesulfonyl chloride (432 mg, 1.69 mmol) and DIEA (0.56 ml, 3.22 mmol) in DCM (20 ml) was stirred at rt overnight. The solution was diluted with ethyl acetate, washed with a saturated aqueous solution of NaHCO3 and brine. The organic phase was dried over Na2SO4 and concentrated. The obtained oil was dissolved in a mixture DCM/TFA 1/1 (5 ml). The solution was stirred at rt for 1 h.

The title compound was precipitated as a TFA salt in diethyl ether to afford a beige powder (675 mg, 100%). ESI-MS (m/z): 305/307 [MH]+.

Step 2: 1-((4-bromophenyl)sulfonyl)-4-(pyridin-4-ylmethyl)piperazine

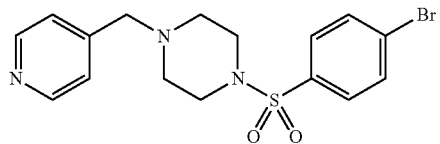 [SMILES: O=S(=O)(c1ccc(Br)cc1)N1CCN(Cc2ccncc2)CC1]

The title compound was obtained following the same procedure as described in Step 2, Example 136, using the 1-((4-bromophenyl)sulfonyl)piperazine instead of the N-(4-bromophenyl)piperazine-1-carboxamide. ESI-MS (m/z): 396/398 [MH]+.

Step 3: 1,1,1,3,3,3-hexafluoro-2-(4'-((4-(pyridin-4-ylmethyl)piperazin-1-yl)sulfonyl)-[1,1'-biphenyl]-4-yl)propan-2-ol The title compound was obtained following the same procedure as described in Step 3, Example 136, using the 1-((4-bromophenyl)sulfonyl)-4-(pyridin-4-ylmethyl)piperazine instead of the N-(4-bromophenyl)-4-(pyridin-4-ylmethyl)piperazine-1-carboxamide. ESI-MS (m/z): 560 [MH]+.

Example 139

1,1,1,3,3,3-hexafluoro-2-(4-(1-(4-(pyridin-4-ylmethyl)piperazin-1-yl)-2,3-dihydro-H 1-inden-5-yl)phenyl)propan-2-ol

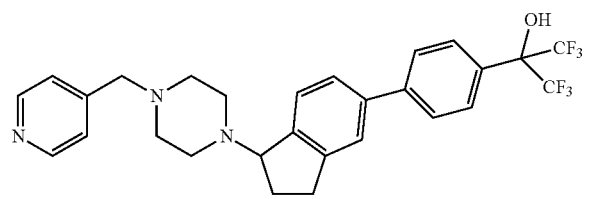 [SMILES: OC(c1ccc(-c2ccc3c(c2)CCC3N2CCN(Cc3ccncc3)CC2)cc1)(C(F)(F)F)C(F)(F)F]

Step 1: 1-(5-bromo-2,3-dihydro-1H-inden-1-yl)piperazine

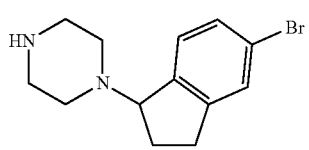 [SMILES: Brc1ccc2c(c1)CCC2N1CCNCC1]

A solution of Boc-piperazine (1 g, 5.37 mmol), 5-bromo-1-indanone (1.70 g, 1.69 mmol) and titanium isopropoxide (4.9 ml, 16.11 mmol) in anhydrous THF (20 ml) was stirred at 75° C. for 48 h under argon in presence of molecular sieves. Sodium cyanoborohydride (1 g, 16.11 mmol) and methanol (20 ml) were added to the solution. The mixture was heated at reflux for 4 h. After cooling to rt, the solution was diluted with ethyl acetate, washed with a saturated aqueous solution of NaHCO₃ and brine. The organic phase was dried over Na₂SO₄ and concentrated. The obtained oil was dissolved in a mixture DCM/TFA 1/1 (5 ml). The solution was stirred at rt for 1 h. The title compound was precipitated as a TFA salt in diethyl ether to afford a beige powder (1.72 g, 81%). ESI-MS (m/z): 281/283 [MH]+.

Step 2: 1-(5-bromo-2,3-dihydro-1H-inden-1-yl)-4-(pyridin-4-ylmethyl)piperazine

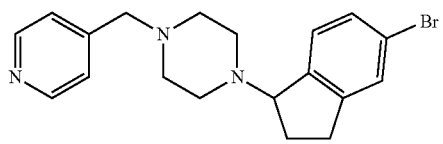 [SMILES: Brc1ccc2c(c1)CCC2N1CCN(Cc2ccncc2)CC1]

The title compound was obtained following the same procedure as described in Step 2, Example 136, using the 1-(5-bromo-2,3-dihydro-1H-inden-1-yl)piperazine instead of the N-(4-bromophenyl)piperazine-1-carboxamide. ESI-MS (m/z): 372/374 [MH]+.

Step 3: 1,1,1,3,3,3-hexafluoro-2-(4-(1-(4-(pyridin-4-ylmethyl)piperazin-1-yl)-2,3-dihydro-1H-inden-5-yl)phenyl)propan-2-ol The title compound was obtained following the same procedure as described in Step 3, Example 136, using the 1-(5-bromo-2,3-dihydro-1H-inden-1-yl)-4-(pyridin-4-ylmethyl)piperazine instead of the N-(4-bromophenyl)-4-(pyridin-4-ylmethyl)piperazine-1-carboxamide. ESI-MS (m/z): 536 [MH]+.

Example 140

1,1,1,3,3,3-hexafluoro-2-(4'-(1-(4-(pyridin-4-ylmethyl)piperazin-1-yl)ethyl)-[1,1'-biphenyl]-4-yl)propan-2-ol

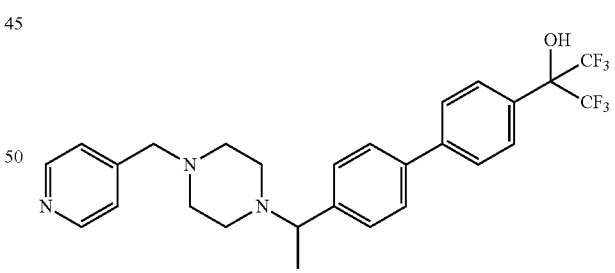

Step 1: 1-(1-(4-bromophenyl)ethyl)piperazine

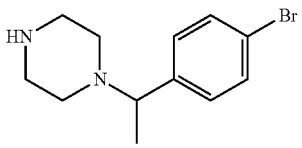

A solution of Boc-piperazine (1 g, 5.37 mmol), 4-bromoacetophenone (1.70 g, 8.05 mmol) and acetic acid (400 μl) in methanol (20 ml) was cooled at 0° C. Sodium cyanoborohydride (1 g, 16.11 mmol) was added to the solution. The resulting mixture was heated at reflux for 1 week. After cooling to rt, the solution was diluted with ethyl acetate, washed with a saturated aqueous solution of NaHCO₃ and brine. The organic phase was dried over Na₂SO₄ and concentrated. The obtained oil was dissolved in a mixture DCM/TFA 1/1 (5 ml). The solution was stirred at rt for 1 h. The title compound was precipitated as a TFA salt in diethyl ether to afford a beige powder (1.64 g, 79%). ESI-MS (m/z): 269/271 [MH]⁺.

Step 2: 1-(1-(4-bromophenyl)ethyl)-4-(pyridin-4-ylmethyl)piperazine

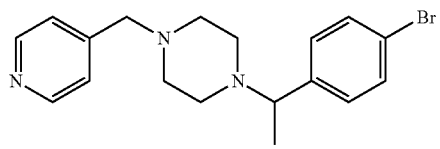 [SMILES: CC(c1ccc(Br)cc1)N1CCN(Cc2ccncc2)CC1]

The title compound was obtained following the same procedure as described in Step 2, Example 136, using the 1-(1-(4-bromophenyl)ethyl)piperazine instead of the N-(4-bromophenyl)piperazine-1-carboxamide. ESI-MS (m/z): 360/362 [MH]⁺.

Step 3: 1,1,1,3,3,3-hexafluoro-2'-(4'-(1-(4-(pyridin-4-ylmethyl)piperazin-1-yl)ethyl)-[1,1'-biphenyl]-4-yl)propan-2-ol The title compound was obtained following the same procedure as described in Step 3, Example 136, using the 1-(1-(4-bromophenyl)ethyl)-4-(pyridin-4-ylmethyl)piperazine instead of the N-(4-bromophenyl)-4-(pyridin-4-ylmethyl)piperazine-1-carboxamide. ESI-MS (m/z): 524 [MH]⁺.

Example 141

1,1,1,3,3,3-hexafluoro-2-(4'-(1-(4-(pyridin-4-ylmethyl)piperazin-1-yl)propyl)-[1,1'-biphenyl]-4-yl)propan-2-ol

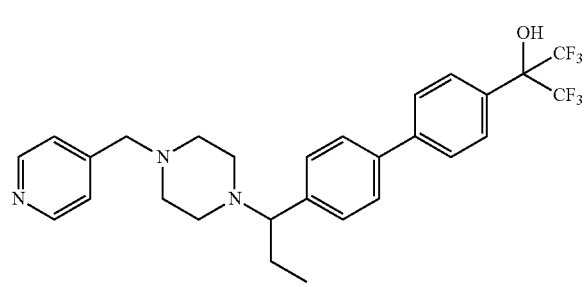 [SMILES: CCC(c1ccc(-c2ccc(C(O)(C(F)(F)F)C(F)(F)F)cc2)cc1)N1CCN(Cc2ccncc2)CC1]

Step 1: 1-(1-(4-bromophenyl)propyl)piperazine

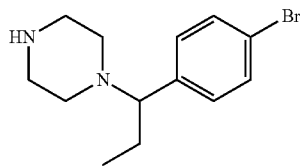 [SMILES: CCC(c1ccc(Br)cc1)N1CCNCC1]

The title compound was obtained following the same procedure as described in Step 1, Example 140, using the 4'-bromopropiophenone instead of the 4-bromoacetophenone. ESI-MS (m/z): 283/285 [MH]⁺.

Step 2: 1-(1-(4-bromophenyl)propyl)-4-(pyridin-4-ylmethyl)piperazine

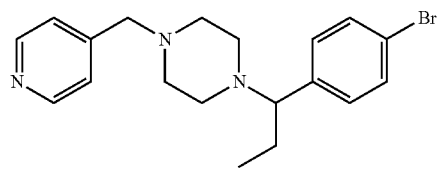 [SMILES: CCC(c1ccc(Br)cc1)N1CCN(Cc2ccncc2)CC1]

The title compound was obtained following the same procedure as described in Step 2, Example 136, using the 1-(1-(4-bromophenyl)propyl)piperazine instead of the N-(4-bromophenyl)piperazine-1-carboxamide. ESI-MS (m/z): 374/376 [MH].

Step 3: 1,1,1,3,3,3-hexafluoro-2-(4'-(1-(4-(pyridin-4-ylmethyl)piperazin-1-yl)propyl)-[1,1'-biphenyl]-4-yl)propan-2-ol The title compound was obtained following the same procedure as described in Step 3, Example 136, using the 1-(1-(4-bromophenyl)propyl)-4-(pyridin-4-ylmethyl)piperazine instead of the N-(4-bromophenyl)-4-(pyridin-4-ylmethyl)piperazine-1-carboxamide. ESI-MS (m/z): 538 [MH]⁺.

Example 142

1,1,1,3,3,3-hexafluoro-2-(4'-(1-(4-(pyridin-4-ylmethyl)piperazin-1-yl)pentyl)-[1,1'-biphenyl]-4-yl)propan-2-ol

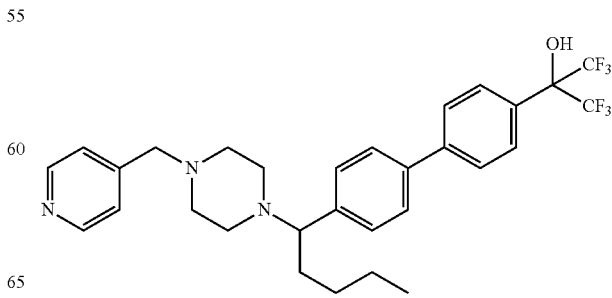

153

Step 1: 1-(1-(4-bromophenyl)pentyl)piperazine

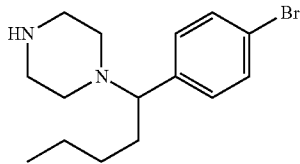 [SMILES: CCCCC(c1ccc(Br)cc1)N1CCNCC1]

The title compound was obtained following the same procedure as described in Step 1, Example 140, using the 4'-bromovalerophenone instead of the 4-bromoacetophenone. ESI-MS (m/z): 311/313 [MH]+.

Step 2: 1-(1-(4-bromophenyl)pentyl)-4-(pyridin-4-ylmethyl)piperazine

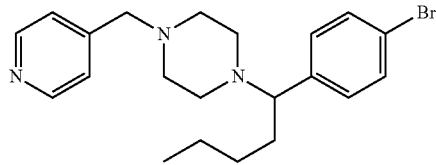 [SMILES: CCCCC(c1ccc(Br)cc1)N1CCN(Cc2ccncc2)CC1]

The title compound was obtained following the same procedure as described in Step 2, Example 136, using the 1-(1-(4-bromophenyl)pentyl)piperazine instead of the N-(4-bromophenyl)piperazine-1-carboxamide. ESI-MS (m/z): 402/404 [MH]+.

Step 3: 1,1,1,3,3,3-hexafluoro-2-(4'-(1-(4-(pyridin-4-ylmethyl)piperazin-1-yl)pentyl)-[1,1'-biphenyl]-4-yl)propan-2-ol The title compound was obtained following the same procedure as described in Step 3, Example 136, using the 1-(1-(4-bromophenyl)pentyl)-4-(pyridin-4-ylmethyl)piperazine instead of the N-(4-bromophenyl)-4-(pyridin-4-ylmethyl)piperazine-1-carboxamide. ESI-MS (m/z): 566 [MH]+.

Example 143

1,1,1,3,3,3-hexafluoro-2-(4'-(2-(4-(pyridin-4-ylmethyl)piperazin-1-yl)propyl)-[1,1'-biphenyl]-4-yl)propan-2-ol

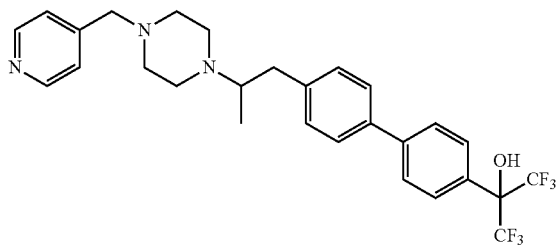 [SMILES: CC(Cc1ccc(-c2ccc(C(O)(C(F)(F)F)C(F)(F)F)cc2)cc1)N1CCN(Cc2ccncc2)CC1]

154

Step 1: 1-(1-(4-bromophenyl)propan-2-yl)piperazine

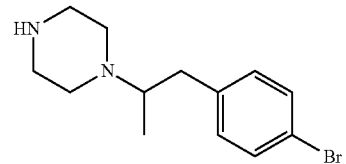 [SMILES: CC(Cc1ccc(Br)cc1)N1CCNCC1]

The title compound was obtained following the same procedure as described in Step 1, Example 140, using the 4'-bromovalerophenone instead of the 4-bromoacetophenone. ESI-MS (m/z): 283/285 [MH]+.

Step 2: 1-(1-(4-bromophenyl)propan-2-yl)-4-(pyridin-4-ylmethyl)piperazine

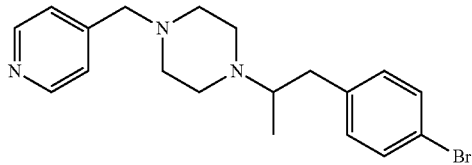 [SMILES: CC(Cc1ccc(Br)cc1)N1CCN(Cc2ccncc2)CC1]

The title compound was obtained following the same procedure as described in Step 2, Example 136, using the 1-(1-(4-bromophenyl) propan-2-yl)piperazine instead of the N-(4-bromophenyl)piperazine-1-carboxamide. ESI-MS (m/z): 374/376 [MH]+.

Step 3: 1,1,1,3,3,3-hexafluoro-2-(4'-(2-(4-(pyridin-4-ylmethyl)piperazin-1-yl)propyl)-[1,1'-biphenyl]-4-yl)propan-2-ol The title compound was obtained following the same procedure as described in Step 3, Example 136, using the 1-(1-(4-bromophenyl)propan-2-yl)-4-(pyridin-4-ylmethyl) piperazine instead of the N-(4-bromophenyl)-4-(pyridin-4-ylmethyl)piperazine-1-carboxamide. ESI-MS (m/z): 538 [MH]+.

Example 144

1,1,1,3,3,3-hexafluoro-2-(4'-(2-(4-(pyridin-4-ylmethyl)piperazin-1-yl)ethyl)-[1,1'-biphenyl]-4-yl)propan-2-ol

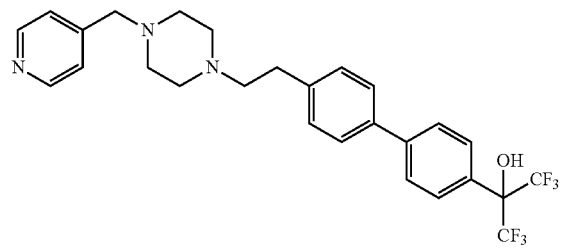 [SMILES: OC(c1ccc(-c2ccc(CCN3CCN(Cc4ccncc4)CC3)cc2)cc1)(C(F)(F)F)C(F)(F)F]

Step 1: 4-bromophenethyl methanesulfonate

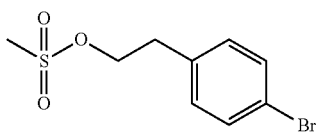

A solution of 2-(4-bromophenyl)ethanol (342 μl, 2.50 mmol), DIEA (653 μl, 3.75 mmol) and methanesulfonyl chloride (213 μl, 2.70 mmol) in DCM (12 ml) was stirred 1 h 30 at 0° C. and then overnight at rt. The solution was diluted with DCM, washed with a 0.5 N solution of HCl and brine. The organic phase was dried over $Na_2SO_4$ and concentrated to afford a yellow oil (700 mg, 100%).

Step 2: 1-(4-bromophenethyl)piperazine

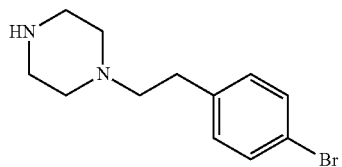 [SMILES: Brc1ccc(CCN2CCNCC2)cc1]

A solution of Boc-piperazine (560 mg, 3.01 mmol), 4-bromophenethyl methanesulfonate (700 mg, 2.5 mmol) and cesium carbonate (1.23 g, 3.75 mmol) in acetonitrile (15 ml) was stirred 4 h at 120° C. under microwave irradiation. The solution was diluted with ethyl acetate, washed with a saturated aqueous solution of $NaHCO_3$ and brine. The organic phase was dried over $Na_2SO_4$ and concentrated. The obtained oil was dissolved in a mixture DCM/TFA 1/1 (5 ml). The solution was stirred at rt for 1 h. The title compound was precipitated as a TFA salt in diethyl ether to afford a beige powder (849 mg, 100%). ESI-MS (m/z): 269/271 [MH]⁺.

Step 3: 1-(4-bromophenethyl)-4-(pyridin-4-ylmethyl)piperazine

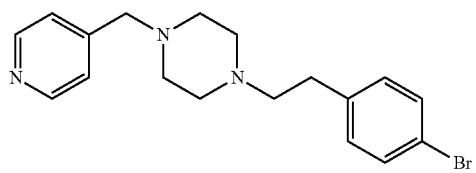

The title compound was obtained following the same procedure as described in Step 2, Example 136, using the 1-(4-bromophenethyl)piperazine instead of the N-(4-bromophenyl)piperazine-1-carboxamide. ESI-MS (m/z): 360/362 [MH]⁺.

Step 4: 1,1,1,3,3,3-hexafluoro-2-(4'-(2-(4-(pyridin-4-ylmethyl)piperazin-1-yl)ethyl)-[1,1'-biphenyl]-4-yl)propan-2-ol The title compound was obtained following the same procedure as described in Step 3, Example 136, using the 1-(4-bromophenethyl)-4-(pyridin-4-ylmethyl)piperazine instead of the N-(4-bromophenyl)-4-(pyridin-4-ylmethyl)piperazine-1-carboxamide. ESI-MS (m/z): 524 [MH]⁺.

Example 145

1,1,1,3,3,3-Hexafluoro-2-(4'-((4-(thiophen-2-ylsulfonyl)piperazin-1-yl)methyl)-[1,1'-biphenyl]-4-yl)propan-2-ol

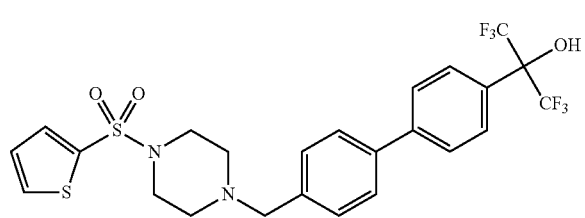 [SMILES: O=S(=O)(c1cccs1)N1CCN(Cc2ccc(-c3ccc(C(O)(C(F)(F)F)C(F)(F)F)cc3)cc2)CC1]

The title compound was prepared following the same general protocol as described in Example 25, using thiophene-2-sulfonyl chloride instead of propionyl chloride. ESI-MS (m/z): 565 [M+1]⁺.

Example 146

1,1,1,3,3,3-Hexafluoro-2-(4'-((4-((4-(trifluoromethyl)phenyl)sulfonyl)piperazin-1-yl)methyl)-[1,1'-biphenyl]-4-yl)propan-2-ol

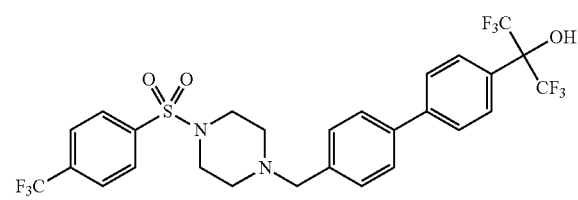 [SMILES: O=S(=O)(c1ccc(C(F)(F)F)cc1)N1CCN(Cc2ccc(-c3ccc(C(O)(C(F)(F)F)C(F)(F)F)cc3)cc2)CC1]

The title compound was prepared following the same general protocol as described in Example 25, using 4-(trifluoromethyl)benzene-1-sulfonyl chloride instead of propionyl chloride. ESI-MS (m/z): 627 [M+1]⁺.

Example 147

2-(4'-((4-((4-(Bromomethyl)phenyl)sulfonyl)piperazin-1-yl)methyl)-[1,1'-biphenyl]-4-yl)-1,1,1,3,3,3-hexafluoropropan-2-ol

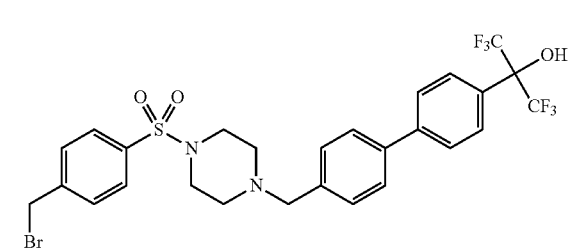 [SMILES: O=S(=O)(c1ccc(CBr)cc1)N1CCN(Cc2ccc(-c3ccc(C(O)(C(F)(F)F)C(F)(F)F)cc3)cc2)CC1]

The title compound was prepared following the same general protocol as described in Example 25, using 4-(bromomethyl)benzene-1-sulfonyl chloride instead of propionyl chloride. ESI-MS (m/z): 653 [M+1]⁺.

Example 148

1,1,1,3,33-Hexafluoro-2-(4'-((4-((2-methyl-5-nitrophenyl)sulfonyl)piperazin-1-yl)methyl)-[1,1'-biphenyl]-4-yl)propan-2-ol

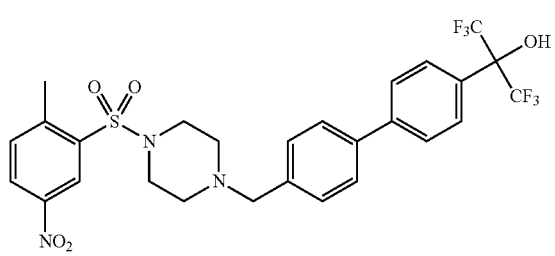 [SMILES: Cc1ccc([N+](=O)[O-])cc1S(=O)(=O)N1CCN(Cc2ccc(-c3ccc(C(O)(C(F)(F)F)C(F)(F)F)cc3)cc2)CC1]

The title compound was prepared following the same general protocol as described in Example 25, using 2-methyl-5-nitrobenzene-1-sulfonyl chloride instead of propionyl chloride. ESI-MS (m/z): 618 [M+1]⁺.

Example 149

1,1,1,3,3,3-Hexafluoro-2-(4'-((4-((4-nitrophenyl)sulfonyl)piperazin-1-yl)methyl)-[1,1'-biphenyl]-4-yl)propan-2-ol

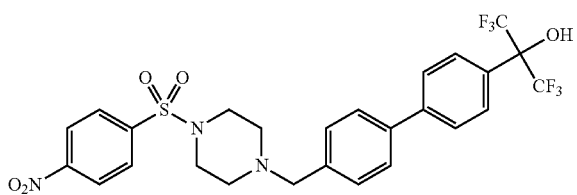

The title compound was prepared following the same general protocol as described in Example 25, using 4-nitrobenzene-1-sulfonyl chloride instead of propionyl chloride. ESI-MS (m/z): 604 [M+1]⁺.

Example 150

Benzyl 4-((4'-(1,1,1,3,3,3-hexafluoro-2-hydroxypropan-2-yl)-[1,1'-biphenyl]-4-yl)methyl)piperazine-1-carboxylate

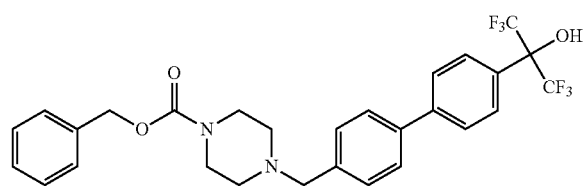 [SMILES: O=C(OCc1ccccc1)N1CCN(Cc2ccc(-c3ccc(C(O)(C(F)(F)F)C(F)(F)F)cc3)cc2)CC1]

To a solution of 4-(4'-(1,1,1,3,3,3-hexafluoro-2-hydroxypropan-2-yl)-[1,1'-biphenyl]-4-yl)piperazin-1-ium 2,2,2-trifluoroacetate (51.84 mg, 0.1 mmol) and K₂CO₃ (41.46 ml, 0.3 mmol) in THF/H₂O (1:1) was added dropwise benzyl chloroformate (0.028 mL, 0.2 mmol) while stirring at rt. The reaction was completed in 8 h and 25 mL of ethyl acetate was added and the mixture was washed with HCl (2 N) (3×20 mL) and brine (1×20 mL). The organic layer was separated, dried over MgSO₄ and concentrated under vacuum to give the title compound which was crystallized from DCM/hexanes. ESI-MS (m/z): 553 [M+1]f.

Example 151

4-Nitrophenyl 4-((4'-(1,1,1,3,3,3-hexafluoro-2-hydroxypropan-2-yl)-[1,1'-biphenyl]-4-yl)methyl)piperazine-1-carboxylate

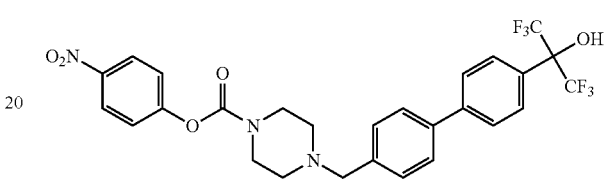

The title compound was prepared following the same general protocol as described in Example 150, using 4-nitrophenyl chloroformate instead of benzyl chloroformate. ESI-MS (m/z): 584 [M+1]⁺.

Example 152

Ethyl 4-((4'-(1,1,1,3,3,3-hexafluoro-2-hydroxypropan-2-yl)-[1,1'-biphenyl]-4-yl)methyl)piperazine-1-carboxylate

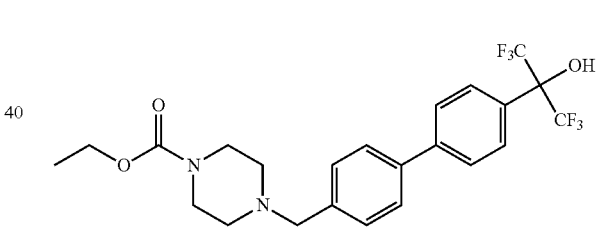

The title compound was prepared following the same general protocol as described in Example 150, using ethyl chloroformate instead of benzyl chloroformate. ESI-MS (m/z): 491 [M+1]⁺.

Example 153

Allyl 4-((4'-(1,1,1,3,3,3-hexafluoro-2-hydroxypropan-2-yl)-[1,1'-biphenyl]-4-yl)methyl)piperazine-1-carboxylate

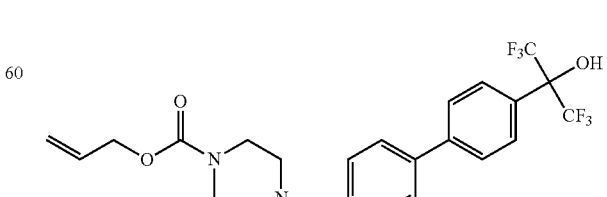

The title compound was prepared following the same general protocol as described in Example 150, using allyl chloroformate instead of benzyl chloroformate. ESI-MS (m/z): 503 [M+1]⁺.

Example 154

2-(4'-((4-((1H-indol-6-yl)methyl)piperazin-1-yl)methyl)-[1,1'-biphenyl]-4-yl)-1,1,1,3,3,3-hexafluoropropan-2-ol

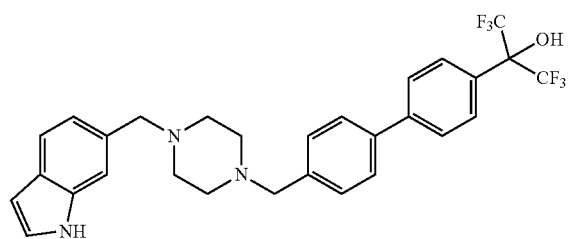 [SMILES: OC(c1ccc(-c2ccc(CN3CCN(Cc4ccc5cc[nH]c5c4)CC3)cc2)cc1)(C(F)(F)F)C(F)(F)F]

The title compound was prepared following the same general protocol as described in Step 4, Example 1, using indole-5-carboxaldehyde instead of isonicotinaldehyde. ESI-MS (m/z): 548 [M+1]⁺.

Example 155

2-(4'-((4-((1H-benzo[d]imidazol-6-yl)methyl)piperazin-1-yl)methyl)-[1,1'-biphenyl]-4-yl)-1,1,1,3,3,3-hexafluoropropan-2-ol

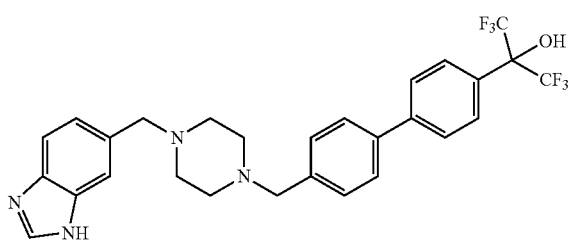 [SMILES: OC(c1ccc(-c2ccc(CN3CCN(Cc4ccc5nc[nH]c5c4)CC3)cc2)cc1)(C(F)(F)F)C(F)(F)F]

The title compound was prepared following the same general protocol as described in Step 4, Example 1, using benzimidazole-6-carboxaldehyde instead isonicotinaldehyde. ESI-MS (m/z): 549 [M+1]⁺.

Example 156

1,1,1,3,3,3-hexafluoro-2-(2-isopropoxy-4'-((4-(pyridin-4-ylmethyl)piperazin-1-yl)methyl)-[1,1'-biphenyl]-4-yl)propan-2-ol

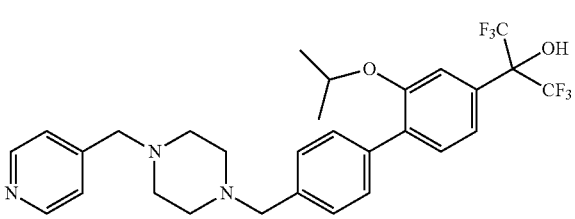 [SMILES: CC(C)Oc1cc(C(O)(C(F)(F)F)C(F)(F)F)ccc1-c1ccc(CN2CCN(Cc3ccncc3)CC2)cc1]

Step 1: 1-isopropoxy-2-nitrobenzene

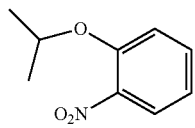

To a solution of 2-nitro-phenol (2.02 g, 14.4 mmol) in THF (5 mL) was added isopropanol (1.15 mL, 15.1 mmol). The solution was cooled on ice bath under argon for 15 min. and triphenylphosphene (4.04 g, 15.1 mmol) and DIAD (3.08 mL, 15.1 mmol) were added with vigorous stirring. The solution was allowed to warm to rt and the stirring was continued for 48 h while monitoring the reaction progress via HPLC. A cold solution of 1:1 hexanes:Et₂O was added to precipitate out triphenylphosphene oxide and filtered using excess hexanes/Et₂O. The remaining organic mixture was concentrated in vacuo to a crude, which was purified by flash chromatography on silica gel (EtOAc/Hex) to obtain the title compound.

Step 2: 2-isopropoxyaniline

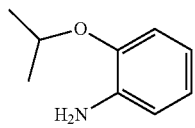

10% Pd/carbon (0.124 g, 5% wt) was added to a round bottom flask equipped with a reflux condenser/septum and containing 1-isopropoxy-2-nitrobenzene (2.480 g, 13.69 mmol) dissolved in ethanol (0.5 mL). The mixture was degassed for 15 min. and replaced with H₂(g) via balloon and refluxed for 6 h. The resulting mixture was filtered through celite using excess EtOH and concentrated to an oil crude. The title compound was isolated via flash chromatography on silica gel (MeOH:CH₂Cl₂).

Step 3: 2-(4-amino-3-isopropoxyphenyl)-1,1,1,3,3,3-hexafluoropropan-2-ol

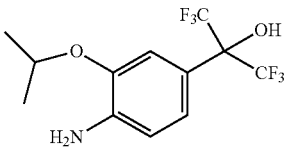 [SMILES: CC(C)Oc1cc(C(O)(C(F)(F)F)C(F)(F)F)ccc1N]

The title compound was prepared following the same general protocol as described in Step 1, Example 110, using 2-isopropoxyaniline instead of o-toluidine. ESI-MS (m/z): 318 [M+1]⁺.

Step 3: 1,1,1,3,3,3-hexafluoro-2-(4-iodo-3-isopropoxyphenyl)propan-2-ol

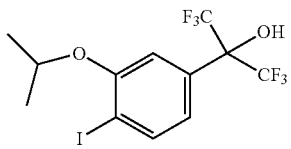 [SMILES: CC(C)Oc1cc(C(O)(C(F)(F)F)C(F)(F)F)ccc1I]

The title compound was prepared following the same general protocol as described in Step 1, Example 1, using 2-(4-amino-3-isopropoxyphenyl)-1,1,1,3,3,3-hexafluoropropan-2-ol instead of 2-(4-aminophenyl)-1,1,1,3,3,3-hexafluoropropan-2-ol.

Step 4: 1,1,1,3,3,3-hexafluoro-2-(2-isopropoxy-4'-((4-(pyridin-4-ylmethyl)piperazin-1-yl)methyl)-[1,1'-biphenyl]-4-yl)propan-2-ol The title compound was prepared following the same general protocol as described in Step 1, Example 14, using 1-(4-pyridinyl-methyl)-piperazine-4-benzyl-para-boronic pinacol ester and 1,1,1,3,3,3-hexafluoro-2-(4-iodo-3-isopropoxyphenyl)propan-2-ol instead of (4-formylphenyl)boronic acid and 1,1,1,3,3,3-hexafluoro-2-(4-iodophenyl)propan-2-ol. ESI-MS (m/z): 568 [M+1]$^+$.

Example 157

1,1,1,3,3,3-hexafluoro-2-(4'-((4-isopentylpiperazin-1-yl)methyl)-[1,1'-biphenyl]-4-yl)propan-2-ol

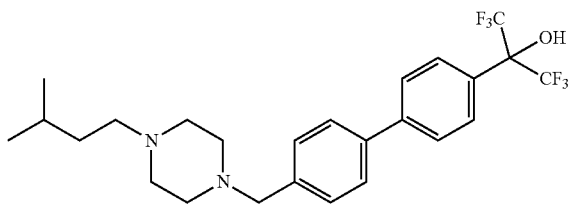 [SMILES: CC(C)CCN1CCN(Cc2ccc(-c3ccc(C(O)(C(F)(F)F)C(F)(F)F)cc3)cc2)CC1]

The title compound was prepared following the same general protocol as described in Step 4, Example 1, using isovaleraldehyde instead of isonicotinaldehyde. ESI-MS (m/z): 489 [M+1]$^+$.

Example 158

1-(4-((4'-(1,1,1,3,3,3-hexafluoro-2-hydroxypropan-2-yl)-[1,1'-biphenyl]-4-yl)methyl)piperazin-1-yl)pentan-1-one

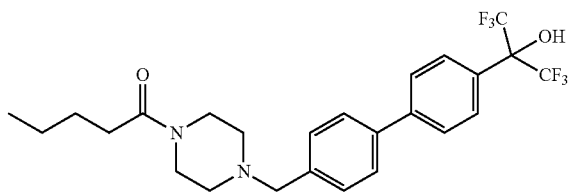 [SMILES: CCCCC(=O)N1CCN(Cc2ccc(-c3ccc(C(O)(C(F)(F)F)C(F)(F)F)cc3)cc2)CC1]

The title compound was prepared following the same general protocol as described in Example 25, using pentanoyl chloride instead of propionyl chloride. ESI-MS (m/z): 503 [M+1]$^+$.

Example 159

1-(4-((4'-(1,1,1,3,3,3-hexafluoro-2-hydroxypropan-2-yl)-[1,1'-biphenyl]-4-yl)methyl)piperazin-1-yl)-2-(1H-imidazol-4-yl)ethanone

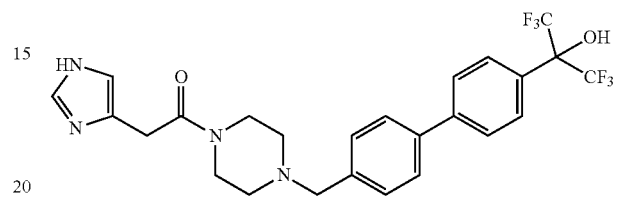

The title compound was prepared following the same general protocol as described in Step 1, Example 100, using 1,1,1,3,3,3-Hexafluoro-2-(4'-(piperazin-1-ylmethyl)-[1,1'-biphenyl]-4-yl)propan-2-ol and 1H1-imidazole-5-acetic acid instead of 1-(pyridin-4-ylmethyl)piperazine and 4'-(1,1,1,3,3,3-hexafluoro-2-hydroxypropan-2-yl)-[1,1'-biphenyl]-4-carboxylic acid. ESI-MS (m/z): 527 [M+1]$^+$.

Example 160

1,1,1,33,33-hexafluoro-2-(4'-((4-(pyridin-4-ylmethyl)piperazin-1-yl)methyl)-2'-(trifluoromethyl)-[1,1'-biphenyl]-4-yl)propan-2-ol

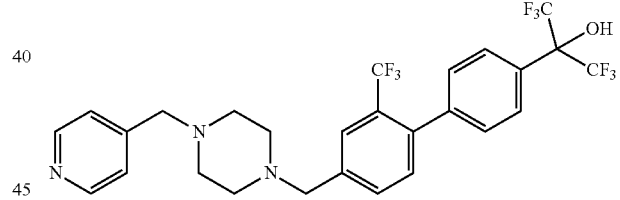

Step 1: 1-bromo-4-(bromomethyl)-2-(trifluoromethyl)benzene

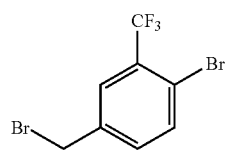

NBS (0.418 g, 2.35 mmol) and AIBN (0.032 g, 0.020 mmol) was added to a mixture of $CCl_4$ (3 mL) and 1-bromo-4-methyl-2-(trifluoromethyl)-benzene (0.468 g, 1.96 mmol) within a round bottom flask equipped with a reflux condenser. The flask was then purged via vacuum and replaced with argon. The mixture was then refluxed overnight (~10 h), diluted with DCM (100 mL), extracted with a saturated solution of sodium thiosulfate (2×100 mL) and dried over Na₂SO₄. The remaining organic mixture was concentrated in vacuo to a crude, which was purified by flash chromatography on silica gel (EtOAc/Hex) to obtain the title compound.

Step 2: 1-(4-bromo-3-(trifluoromethyl)benzyl)-4-(pyridin-4-ylmethyl)piperazine

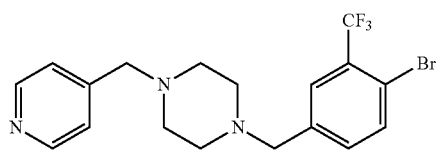

To 1-bromo-4-(bromomethyl)-2-(trifluoromethyl)benzene (0.533 g, 1.68 mmol) in MeCN (8 mL) was added 1-(pyridinyl-4-methyl)-piperazine (0.25 g, 1.40 mmol) and K₂CO₃ (0.585 g, 4.19 mmol). The mixture was stirred overnight (~10 h) while monitoring for complete by analytical HPLC. The solvent was removed by reduced pressure. The remaining crude was redissolved into EtOAc and washed with Na₂CO₃ (2×100 mL) and brine (100 mL). The title compound was isolated via flash chromatography on silica gel (MeOH:CH₂Cl₂).

Step 3: 1,1,1,3,3,3-hexafluoro-2-(4'-((4-(pyridin-4-ylmethyl)piperazin-1-yl)methyl)-2'-(trifluoromethyl)-[1,1'-biphenyl]-4-yl)propan-2-ol The title compound was prepared following the same general protocol as described in Step 2, Example 126, using 1-(4-bromo-3-(trifluoromethyl)benzyl)-4-(pyridin-4-ylmethyl)piperazine instead of tert-butyl 4-(4-bromophenoxy)piperidine-1-carboxylate. ESI-MS (m/z): 578 [M+1]⁺.

Example 161

4'-(1,1,1,3,3,3-hexafluoro-2-hydroxypropan-2-yl)-4-((4-(pyridin-4-ylmethyl)piperazin-1-yl)methyl)-[1,1'-biphenyl]-3-carbonitrile

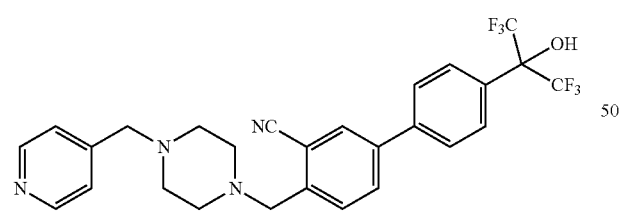

Step 1: 2-bromo-5-(bromomethyl)benzonitrile

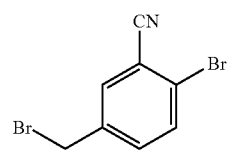

NBS (0.622 g, 3.46 mmol) and AIBN (0.026 g, 0.016 mmol) was added to a mixture of CCl₄ (5 mL) and 2-bromo-5-methyl-benzonitrile (0.616 g, 3.14 mmol) within a round bottom flask equipped with a reflux condenser. The flask was then purged via vacuum and replaced with argon. The mixture was then refluxed overnight (~10 h), diluted with DCM (100 mL), extracted with a saturated solution of sodium thiosulfate (2×100 mL) and dried over Na₂SO₄. The remaining organic mixture was concentrated in vacuo to a crude, which was purified by flash chromatography on silica gel (EtOAc/Hex) to obtain the title compound.

Step 2: 2-bromo-5-((4-(pyridin-4-ylmethyl)piperazin-1-yl)methyl)benzonitrile

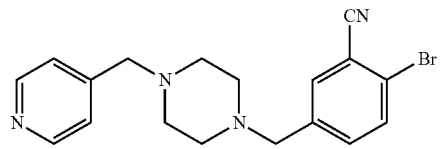 [SMILES: FC(F)(F)c1cc(CN2CCN(Cc3ccncc3)CC2)ccc1Br]

To 2-bromo-5-(bromomethyl)benzonitrile (0.527 g, 1.92 mmol) in MeCN (10 mL) was added 1-(pyridinyl-4-methyl)-piperazine (0.309 g, 1.74 mmol) and K₂CO₃ (0.723 g, 5.23 mmol). The mixture was stirred overnight (~10 h) while monitoring for complete by analytical HPLC. The solvent was removed by reduced pressure. The remaining crude was redissolved into EtOAc and washed with Na₂CO₃ (2×100 mL) and brine (100 mL). The title compound was isolated via flash chromatography on silica gel (MeOH:CH₂Cl₂).

Step 3: 4'-(1,1,1,3,3,3-hexafluoro-2-hydroxypropan-2-yl)-4-((4-(pyridin-4-ylmethyl)piperazin-1-yl)methyl)-[1,1'-biphenyl]-3-carbonitrile The title compound was prepared following the same general protocol as described in Step 2. Example 126, using 2-bromo-5-((4-(pyridin-4-ylmethyl)piperazin-1-yl)methyl)benzonitrile instead of tert-butyl 4-(4-bromophenoxy)piperidine-1-carboxylate. ESI-MS (m/z): 535 [M+1]⁺.

Example 162

1,1,1,3,3,3-hexafluoro-2-(4-(1-(1-(pyridin-4-ylmethyl)piperidin-4-yl)indolin-5-yl)phenyl)propan-2-ol

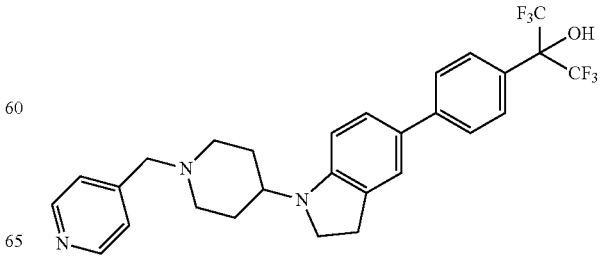

Step 1: tert-butyl 4-(5-bromoindolin-1-yl)piperidine-1-carboxylate

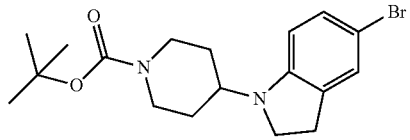 [SMILES: CC(C)(C)OC(=O)N1CCC(N2CCc3cc(Br)ccc32)CC1]

To 5-bromo-2,3-dihydro-indole (0.520 g, 2.55 mmol) in acetic acid (5 mL) was added 1-Boc-4-piperidone (0.564 g, 2.80 mmol). The flask was then purged via vacuum and argon. The mixture was allowed to stir for 30 min. at rt where NaBH(OAc)$_3$ (1.704 g, 7.64 mmol) was added in batches over 5 min. The mixture was then heated at 30° C. overnight (~12 h) and then diluted with MeOH (10 mL). Following concentration to a oil residue, EtOAc was added and the mixture was washed with water (2×100 mL) and dried over Na$_2$SO$_4$. The crude product, tert-butyl 4-(5-bromoindolin-1-yl)piperidine-1-carboxylate, was then concentrated to an oil and isolated by flash chromatography on silica gel (EtOAc/Hex). ESI-MS (m/z): 382 [M+1]$^+$.

Step 2: 5-bromo-1-(1-(pyridin-4-ylmethyl)piperidin-4-yl)indoline

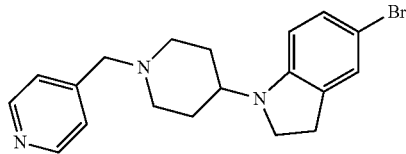 [SMILES: Brc1ccc2c(c1)CCN2C1CCN(Cc2ccncc2)CC1]

A 1:1 solution of DCM:TFA (3 mL) was added to a round bottom containing tert-butyl 4-(5-bromoindolin-1-yl)piperidine-1-carboxylate. The remaining solution was allowed to stir for 1 h where it was then aspirated until dry and then resuspended in anhydrous THF (4 mL). To this was added isonicotinaldehyde (0.0461 g, 0.480 mmol) and NaBH(OAc)$_3$ (0.214 g, 0.960 mmol) and the solution was allowed to stir overnight. MeOH (5 mL) was added to quench and all remaining solvent was removed in vacuo. The title product was isolated by flash chromatography on silica gel (MeOH:CH$_2$Cl$_2$). ESI-MS (m/z): 373 [M+1]$^+$.

Step 3: 1,1,1,3,3,3-hexafluoro-2-(4-(1-(1-(pyridin-4-ylmethyl)piperidin-4-yl)indolin-5-yl)phenyl)propan-2-ol The title compound was prepared following the same general protocol as described in Step 2, Example 126, using 5-bromo-1-(1-(pyridin-4-ylmethyl)piperidin-4-yl)indoline instead of tert-butyl 4-(4-bromophenoxy)piperidine-1-carboxylate. ESI-MS (m/z): 536 [M+1]$^+$.

Example 163

1,1,1,3,3,3-hexafluoro-2-(3'-((1-(pyridin-4-ylmethyl)piperidin-3-yl)methyl)-[1,1'-biphenyl]-4-yl)propan-2-ol

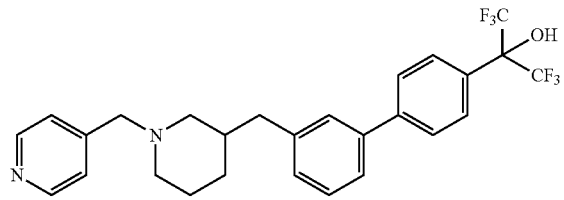 [SMILES: OC(c1ccc(-c2cccc(CC3CCCN(Cc4ccncc4)C3)c2)cc1)(C(F)(F)F)C(F)(F)F]

Step 1: (E+Z)-tert-butyl 3-(3-bromobenzylidene)piperidine-1-carboxylate

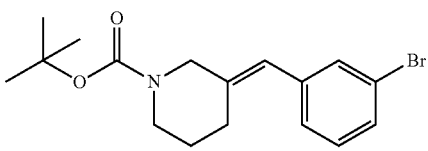 [SMILES: CC(C)(C)OC(=O)N1CCC/C(=C\c2cccc(Br)c2)C1]

To P-[(3-bromophenyl)methyl]-, diethyl ester-phosphonic acid, (0.681 g, 2.22 mmol) in anhydrous THF was added N-Boc-3-piperidone (0.372 g, 1.85 mmol). The mixture was placed into an ice bath salt slurry (−20° C.) for 15 min. under argon. Once sufficiently cool sodium tert-butoxide (0.222 g, 2.22 mmol) was added in batches. The reaction was allowed to warm to rt and stir overnight. The reaction appeared to be complete, as determined by HPLC and AcOH (4 mL) was added to quench. The mixture was then diluted into 100 mL EtOAc and extracted with NaHCO$_3$ (2×100 mL), treated with brine (50 mL). The organic partitions were dried over Na$_2$SO$_4$ and then concentrated to an oil. The title compound was then isolated by flash chromatography using silica gel (EtOAc/Hex). ESI-MS (m/z): 353 [M+1]$^+$.

Step 2: (E+Z)-tert-butyl 3-((4'-(1,1,1,3,3,3-hexafluoro-2-hydroxypropan-2-yl)-[1,1'-biphenyl]-3-yl)methylene)piperidine-1-carboxylate

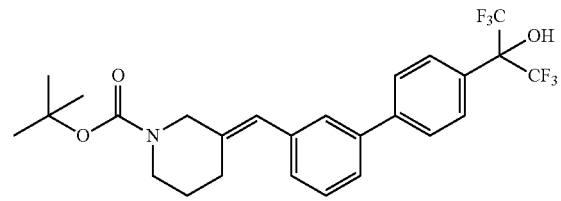 [SMILES: CC(C)(C)OC(=O)N1CCC/C(=C\c2cccc(-c3ccc(C(O)(C(F)(F)F)C(F)(F)F)cc3)c2)C1]

The title compound was prepared following the same general protocol as described in Step 2, Example 126, using (E+Z)-tert-butyl 3-(3-bromobenzylidene)piperidine-1-carboxylate instead of tert-butyl 4-(4-bromophenoxy)piperidine-1-carboxylate. ESI-MS (m/z): 516 [M+1]$^+$.

Step 3: tert-butyl 3-((4'-(1,1,1,3,3,3-hexafluoro-2-hydroxypropan-2-yl)-[1,1'-biphenyl]-3-yl)methyl)piperidine-1-carboxylate

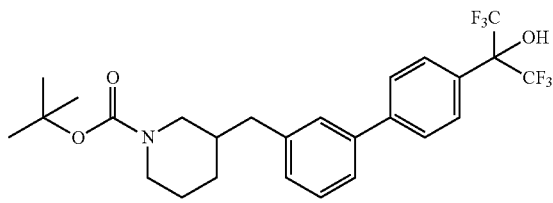 [SMILES: CC(C)(C)OC(=O)N1CCCC(Cc2cccc(-c3ccc(C(O)(C(F)(F)F)C(F)(F)F)cc3)c2)C1]

Dissolved (E+Z)-tert-butyl 3-((4'-(1,1,1,3,3,3-hexafluoro-2-hydroxypropan-2-yl)-[1,1'-biphenyl]-3-yl)methylene)piperidine-1-carboxylate (0.242 g, 0.469 mmol) into EtOH (4 mL) and AcOH (1 mL). Added 10% Pd/carbon and purged pressure flask with 50 psi $H_2$. The hydrogenation was allowed to proceed for 4 h until completed, as determined by LC-MS. The resulting mixture was then filtered through celite using excess EtOH and concentrated to an oil crude. The title compound was then isolated by flash chromatography using silica gel. ESI-MS (m/z): 518 [M+1]$^+$.

Step 4: 1,1,1,3,3,3-hexafluoro-2-(3'-((1-(pyridin-4-ylmethyl)piperidin-3-yl)methyl)-[1,1'-biphenyl]-4-yl)propan-2-ol

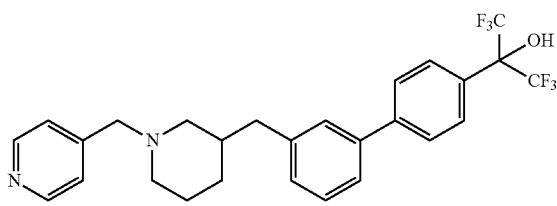 [SMILES: OC(c1ccc(-c2cccc(CC3CCCN(Cc4ccncc4)C3)c2)cc1)(C(F)(F)F)C(F)(F)F]

A 1:1 solution of DCM:TFA (5 mL) was added to a round bottom containing tert-butyl 3-((4'-(1,1,1,3,3,3-hexafluoro-2-hydroxypropan-2-yl)-[1,1'-biphenyl]-3-yl)methyl)piperidine-1-carboxylate (0.073 g, 0.14 mmol). The remaining solution was allowed to stir for 2 h where it was then aspirated until dry and then resuspended in anhydrous THF (4 mL). To this was added isonicotinaldehyde (0.020 mL, 0.21 mmol) and NaBH(OAc)$_3$ (0.095 g, 0.42 mmol) and the solution was allowed to stir overnight. MeOH (5 mL) was added to quench and all remaining solvent was removed in vacuo. The title product was isolated by reverse phase preparative HPLC (C18) (1:1/MeOH:MeCN). ESI-MS (m/z): 509 [M+1]$^+$.

Example 164

1,1,1,3,3,3-hexafluoro-2-(4'-((1-(pyridin-4-ylmethyl)piperidin-4-yl)methyl)-[1,1'-biphenyl]-4-yl)propan-2-ol

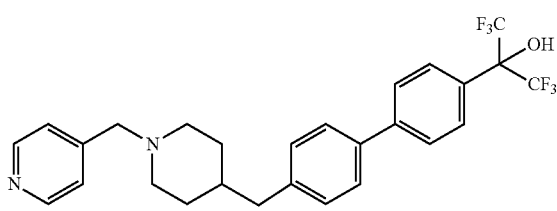 [SMILES: OC(c1ccc(-c2ccc(CC3CCN(Cc4ccncc4)CC3)cc2)cc1)(C(F)(F)F)C(F)(F)F]

The title compound was prepared following the same synthetic procedure as described in Steps 1-4, Example 163, starting from P-[(4-bromophenyl)methyl]-, diethyl ester-phosphonic acid and N-Boc-4-piperidone instead of P-[(3-bromophenyl)methyl]-, diethyl ester-phosphonic acid and N-Boc-3-piperidone. ESI-MS (m/z): 509 [M+1]$^+$.

Biological Procedures and Examples

Compounds of the invention (see, e.g., Table 1) are found to have bioactivity versus at least one ROR as an agonist or as a repressor (inverse agonist or antagonist). Compounds of the invention are found to have selective modulatory activity versus an ROR with respect to an LXR and may or may not be selective over any other nuclear receptor or any other protein target. See Tables 2A-C, below, showing inhibitory concentrations as determined by the below-described methods.

Cell Culture and Transcriptional Assays.

Luciferase reporter assays were conducted using a pBind Gal4-tagged RORα/γ LBD construct and UAS luciferase reporter cotransfected into HEK293T cells (Kumar N, Solt L A, Conkright J J, Wang Y, Istrate M A, Busby S A, Garcia-Ordonez R D, Burris T P, Griffin P R. Mol Pharmacol. 2010 February; 77(2):228-36.). Reverse transfections were performed in bulk using 1×10$^6$ cells in 10 cm plates, 9 μg of total DNA in a 1:1:1 ratio of receptor, reporter and empty vector respectively, and FuGene6 (Roche) in a 1:3 DNA:lipid ratio. Following 24 hour bulk transfection, cells were counted and plated in 384 well plates at a density of 10,000 cells/well. The cells were treated with either DMSO or various compounds as indicated four hours after replating. Following additional 20 hour incubation, luciferase levels were assayed by one-step addition of 20 μL BriteLite (Perkin Elmer) and read using an Envision multilabel plate reader (Perkin Elmer). Data was normalized to luciferase signal from UAS luciferase reporter/pBind control empty vector and displayed as fold change over UAS luciferase reporter.

RORα Modulation of Glucose 6-Phosphatase Wild-Type Promoter

For the glucose 6-phosphatase promoter, wild type promoter was used to transfect HEK293T cells with SRC-2 as co-activator in the presence or absence of full length RORα (Chopra A R, Louet J F, Saha P, An J, Demayo F, Xu J, York B, Karpen S, Finegold M, Moore D, Chan L, Newgard C B, O'Malley B W. Science. 2008 Nov. 28; 322(5906):1395). The cells were replated and treated as above followed by luciferase measurements.

Radioligand Receptor Binding Assay.

Ninety nanograms of purified GST-RORα or GST-RORγ was incubated with various concentrations of [$^3$H]-25-hydroxycholesterol in assay buffer (50 mM HEPES, pH 7.4, 0.01% bovine serum albumin, 150 mM NaCl and 5 mM MgCl$_2$) to determine the K$_d$ value (Kumar et al., 2010; Wang Y, Kumar N, Solt L A, Richardson T I, Helvering L M, Crumbley C, Garcia-Ordonez R D, Stayrook K R, Zhang X, Novick S, Chalmers M J, Griffin P R, Burris T P. J Biol Chem. 2010 Feb. 12; 285(7):5013-25).

Non-specific binding was defined in the absence of protein as well as excess of cold 25-hydroxycholesterol and were shown to be identical. The assays were terminated by rapid filtration through pre-soaked Whatman GF/B filters (0.5% PEI in PBS) in Multiscreen plates (Millipore) and were washed (3×0.1 ml) with ice-cold assay buffer. The radioligand binding results were analyzed using GraphPad Prism software. For the competition assay, various concentration of compounds were incubated with receptor in the presence of 3 nM of [$^3$H]-25-hydroxycholesterol.

Reduction of Endogenous Gene Expression by Small Interference RNAs

To reduce endogenous ROR expression, HepG2 cells were seeded into a 12-well plate (2.5×10$^5$/well) and transfected the next day with small interference RNAs (siRNAs) against human RORα (#L-003440-00-0005) and RORγ (#L-003442-00-0005; Dharmacon RNA Technologies, Lafayette, Colo.) at 50 nM following the instructions for DharmaFECT 1 transfection reagent (Kumar et al., 2010). Forty-two hours post transfection, cells were treated with vehicle (DMSO) or T0901319 (10 μM) for 6 hours. Cells were harvested and total RNA was isolated. Quantitative RT-PCR was performed to analyze mRNA levels of human RORα, RORγ, GAPDH, and G6Pase using SYBR Green technology. The primers used for quantitative PCR analysis are:

```
human RORα:
                    (SEQ ID NO: 1; Forward)
GTAGAAACCGCTGCCAACA
and (SEQ ID NO: 2; Reverse)
ATCACCTCCCGCTGCTT;

human RORγ::
                    (SEQ ID NO: 3; Forward)
CCCCTGACCGATGTGGACT
and (SEQ ID NO: 4; Reverse)
CAGGATGCTTTGGCGATGA;

human G6Pase
                    (SEQ ID NO: 5; Forward)
TCATCTTGGTGTCCGTGATCG
and (SEQ ID NO: 6; Reverse)
TTTATCAGGGGCACGGAAGTG;

GAPDH:
                    (SEQ ID NO: 7; Forward)
TGCACCACCAACTGCTTAGC
and (SEQ ID NO: 8; Reverse)
GGCATGGACTGTGGTCATGAG.
```

SPA Protocol.

20 μL of glutathione YSI beads (PE #RPNQ0033: 12.5 μg/μL) were incubated 1 μg of GST-ROR-g protein with the [3H]-T0901317 (5 nM final concentration) in the presence or absence of compounds for 16-18 hrs in a total assay volume of 100 ml. The reaction were carried out in the OptiPlate™-96 (PE#6005290) plate in assay buffer (50 mM HEPES, pH 7.4, 0.01% bovine serum albumin, 150 mM NaCl and 5 mM MgCl2, 10% glycerol, 1 mM DTT, Complete protease inhibitor from Roche). The plates were read in TopCount (Perkin Elmer). The results were analyzed using GraphPad Prism Software (La Jolla, Calif.).

The tables below, 2A, 2B, 2C, and 2D, provide bioassay for results for compounds listed in Table 1, above. Each row of data represents a single compound selected from amongst the exemplary compounds synthesized and evaluated in the bioassays described herein.

TABLE 2A

Bioassay Results for Compounds of the invention

| Ex. | RORγ[1] SPA | RORα[2] | RORγ[2] | VP$_{16}$[2] | LXR[3] |
|---|---|---|---|---|---|
| T0901317 | [4]NT | 2 μM | 1.7 μM | 1 | 200 |
| 1 | 0.15 μM | 1 | 0.4 μM | 1 | 1 |
| 2 | NT[3] | 1.3 | 0.9 | 0.9 | 1.1 |
| 3 | 1 μM | 1 | >1.5 μM | 1 | 1 |
| 11 | NT | 0.5 | 0.5 | 0.35 | 1 |
| 14 | NT | 0.4 | 0.05 | 0.4 | 5 |
| 16 | NT | 0.8 | 0.6 | 0.6 | 1.4 |
| 17 | % bound = 20 | 0.55 | 0.25 | 0.4 | 0.75 |
| 19 | NT | 0.75 | 0.5 | 0.4 | 1.5 |
| 20 | NT | 0.1 | 0.05 | 0.1 | 2.5 |
| 21 | NT | 0.45 | 0.35 | 0.35 | 0.7 |
| 22 | NT | 0.5 | 0.4 | 0.4 | 1.8 |
| 23 | NT | 0.9 | 0.5 | 0.55 | 2 |
| 24 | NT | 0.5 | 0.25 | 0.25 | 1.3 |
| 25 | NT | 0.7 | 0.45 | 0.5 | 1 |
| 26 | NT | 0.9 | 0.8 | 0.7 | 2 |
| 27 | NT | 0.5 | 0.25 | 0.3 | 0.8 |
| 28 | NT | 1.1 | 0.5 | 0.75 | 1.5 |
| 29 | NT | 1 | 0.8 | 0.8 | 1.8 |
| 30 | NT | 1 | 0.75 | 0.75 | 2 |

[1]binding in μM or % bound = % radiolabel bound 10 μM compound SPA assay;
[2]% repression at 10 μM, fold change over DMSO, unless IC$_{50}$'s given;
[3]% activation at 10 μM, fold change over DMSO;
[4]NT = Not Tested.

TABLE 2B

Bioassay Results for Compounds of the invention

| Ex. | RORγ[1] SPA | RORα[2] | RORγ[2] | VP$_{16}$[2] | LXR[3] |
|---|---|---|---|---|---|
| 40 | [4]NT | 0.1 | 0.05 | 0.05 | 1 |
| 41 | NT | 0.5 | 0.3 | 0.3 | 1 |
| 42 | NT | 0.4 | 0.2 | 0.1 | 1 |
| 43 | NT | 0.6 | 0.1 | 0.6 | 1 |
| 44 | NT | 0.5 | 0.4 | 0.3 | 1 |
| 59 | 1.1 μM | 0.4 | 0.05 | 0.4 | 4 |
| 88 | % bound = 35 | 0.6 | 0.2 | 0.3 | 1.3 |
| 91 | 0.43 μM | 0.6 | 0.50 μM | 0.75 | 0.5 |
| 92 | [4]% bound = 25 | 0.7 | 0.1 | 0.6 | 5 |
| 93 | NT | 0.4 | 0.05 | 0.7 | 1.5 |
| 94 | 0.23 μM | 0.5 | 0.05 | 0.8 | 0.8 |
| 95 | NT | 0.5 | 0.05 | 0.7 | 5 |
| 96 | 0.07 μM | 0.5 | 0.05 | 0.6 | 25 |
| 97 | 1.5 μM | 0.5 | 0.05 | 0.5 | 1 |
| 98 | 1.5 μM | 0.8 | 0.05 | 0.65 | 2 |

[1]binding in μM or % bound = % radiolabel bound 10 μM compound SPA assay;
[2]% repression at 10 μM, fold change over DMSO, unless IC$_{50}$'s given;
[3]% activation at 10 μM, fold change over DMSO;
[4]NT = Not Tested.

TABLE 2C

Bioassay Results for Compounds of the Invention

| Ex. | RORγ[1] SPA | RORα[2] | RORγ[2] | VP$_{16}$[2] | LXR[3] |
|---|---|---|---|---|---|
| 100 | 1.7 μM | 0.6 | 0.1 | 0.4 | 0.8 |
| 101 | [4]NT | 0.8 | 0.15 | 0.75 | 4 |
| 104 | % bound = 20 | 0.9 | 0.1 | 0.4 | 1.1 |
| 105 | % bound = 80 | NT | NT | NT | NT |
| 106 | % bound = 40 | NT | NT | NT | NT |
| 107 | % bound = 100 | NT | NT | NT | NT |
| 108 | 0.22 μM | 0.8 | 0.05 | 0.9 | 1 |
| 109 | 0.25 μM | 0.7 | 0.05 | 0.9 | 1 |
| 110 | 0.09 μM | 0.8 | 0.05 | 0.8 | 1 |
| 111 | % bound = 100 | NT | NT | NT | NT |
| 112 | % bound = 48 | NT | NT | NT | NT |
| 113 | % bound = 98 | NT | NT | NT | NT |
| 114 | % bound = 50 | 0.79 | 0.87 | 0.92 | 0.63 |
| 115 | % bound = 75 | 0.61 | 0.31 | 0.69 | 0.76 |

TABLE 2C-continued

Bioassay Results for Compounds of the Invention

| Ex. | RORγ[1] SPA | RORα[2] | RORγ[2] | VP$_{16}$[2] | LXR[3] |
|---|---|---|---|---|---|
| 116 | % bound = 76 | 0.56 | 0.59 | 0.76 | 0.81 |
| 117 | % bound = 20 | NT | NT | NT | NT |
| 118 | % bound = 20 | NT | NT | NT | NT |
| 119 | % bound = 15 | NT | NT | NT | NT |
| 120 | % bound = 15 | NT | NT | NT | NT |

[1]binding in μM or % bound = % radiolabel bound 10 μM compound SPA assay;
[2]% repression at 10 μM, fold change over DMSO, unless IC$_{50}$'s given;
[3]% activation at 10 μM, fold change over DMSO;
[4]NT = Not Tested.

TABLE 2D

Bioassay Results for Compounds of the Invention

| Ex. | RORγ[1] SPA | RORα[2] | RORγ[2] | VP$_{16}$[2] | LXR[3] |
|---|---|---|---|---|---|
| 136 | % bound = 76 | [4]NT | NT | NT | NT |
| 137 | % bound = 81 | NT | NT | NT | NT |
| 138 | % bound = 68 | NT | NT | NT | NT |
| 139 | % bound = 59 | NT | NT | NT | NT |
| 140 | % bound = 74 | NT | NT | NT | NT |
| 141 | % bound = 74 | NT | NT | NT | NT |
| 142 | % bound = 73 | NT | NT | NT | NT |
| 143 | % bound = 74 | NT | NT | NT | NT |
| 144 | % bound = 61 | NT | NT | NT | NT |
| 145 | NT | NT | 3.0 | 3.0 | NT |
| 146 | NT | NT | 0.9 | 0.7 | NT |
| 147 | NT | NT | 0.5 | 0.5 | NT |
| 148 | NT | NT | 0.4 | 1.0 | NT |
| 149 | NT | NT | 0.5 | 0.7 | NT |
| 150 | NT | NT | 0.5 | 0.9 | NT |
| 151 | NT | NT | 0.6 | 0.6 | NT |
| 154 | % bound = 90 | NT | NT | NT | NT |
| 155 | % bound = 100 | NT | NT | NT | NT |
| 156 | % bound = 75 | NT | NT | NT | NT |
| 157 | % bound = 20 | NT | NT | NT | NT |
| 158 | % bound = 10 | NT | NT | NT | NT |
| 159 | % bound = 80 | NT | NT | NT | NT |
| 160 | % bound = 77 | NT | NT | NT | NT |
| 161 | % bound = 95 | NT | NT | NT | NT |
| 162 | % bound = 15 | NT | NT | NT | NT |
| 163 | % bound = 10 | NT | NT | NT | NT |
| 164 | % bound = 10 | NT | NT | NT | NT |

[1]% bound = % radiolabel bound 1 μM compound SPA assay;
[2]% repression at 10 μM, fold change over DMSO, unless IC$_{50}$'s given;
[3]% activation at 10 μM, fold change over DMSO;
[4]NT = Not Tested.

Biological Data for Specific Compounds of the Invention
SR1555 (Compound 3)

T$_H$17 cells are a subset of CD4$^+$ T cells that are critically dependent upon the nuclear receptors (NR) retinoic acid receptor-related orphan receptors alpha and gamma t (RORα and RORγt), and have been demonstrated to produce several proinflammatory cytokines, including IL-17A. IL-17F, IL-21, and IL-22[1-7]. While their normal function is mediating immune defense against extracellular bacteria, aberrant T$_H$17 cell function has been implicated in a variety of autoimmune diseases, including multiple sclerosis (MS) and rheumatoid arthritis (RA). The maintenance of immune homeostasis requires a delicate balance between effector and regulatory T cells. Disruption of this equilibrium can result in the targeting of "self" tissues, leading to the development of autoimmune diseases.

Characterization of T$_H$17 cells has revealed that these cells are generated from naïve precursors in the presence if TGFβ and IL-6 or IL-21 [6]. However, it has been well established that TGFβ is also the critical cytokine regulating the development of Foxp3$^+$ T regulatory cells, with the development of one lineage over the other dependent on the environmental milieu. Given this reciprocal relationship between T regulatory cells and T$_H$17 cells, it is still unclear what factors mediate the expansion of one population over the other. Since T$_H$17 cells play a central role in the development of several autoimmune diseases, identification of synthetic modulators that can inhibit T$_H$17 cell differentiation and function would have significant therapeutic value. We recently identified SR1001, a first-in-class, high affinity synthetic RORα/γ inverse agonist.

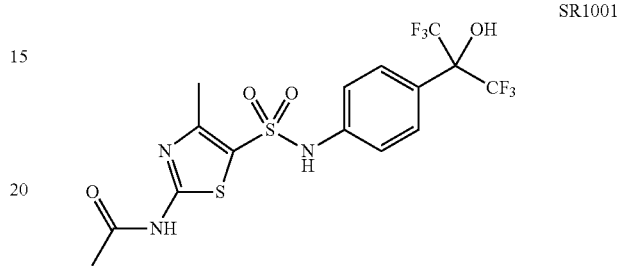

SR1001

SR1001 was effective at suppressing T$_H$17 cell differentiation and function in vitro and in vivo through direct inhibition of RORα and RORγ [8].

Figure 1A:
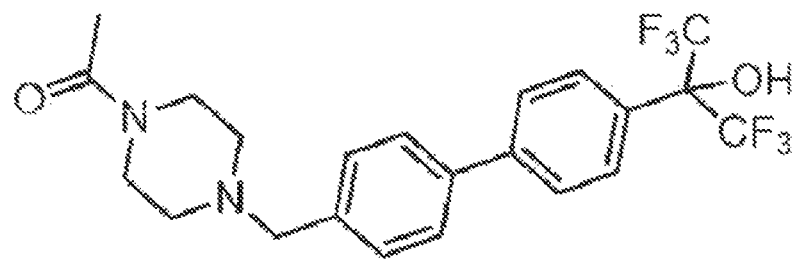
FIG. 1 shows: (a) Structure of SR1555. (b) Full length G6Pase and GAL4-LXRα, RORα, RORγ, and FXR co-transfection assays in HEK293 cells illustrating the specificity SR1555. (n=8). (c) Competition radio-labeled binding assays illustrating the direct binding of SR1555 to the LBD of RORγ only. C.P.M., counts per minute. (n=4). (d) SR1555 dose-dependently inhibits an IL-17 promoter driven luciferase construct only in the presence of RORγ. (n=4). (e) EL4 cells were treated with DMSO or SR1555 (10 μM) for 24 hours followed by mRNA analysis of IL-17A by RTPCR (n=4). (*p<0.05).
Figure 1B:
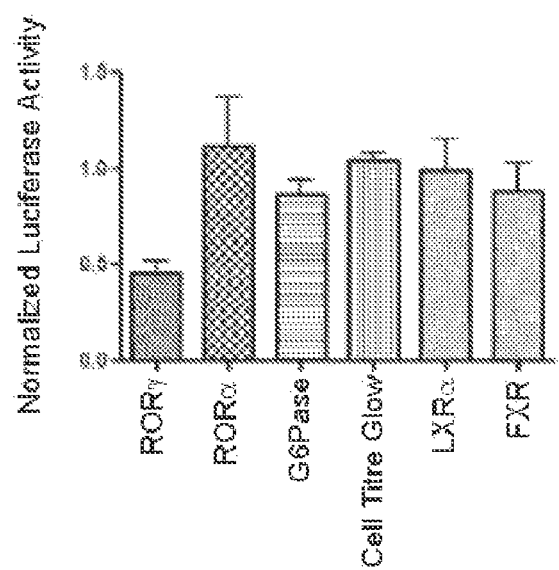
Figure 1C:
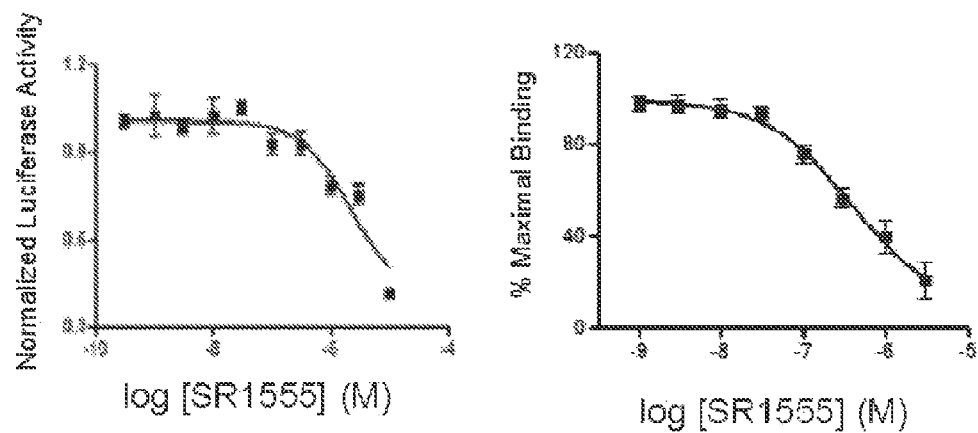

Concurrent with our characterization of SR1001, several other groups identified RORγ-specific inverse agonists[9, 10]. Similar to SR1001, these ligands inhibited T$_H$17 cell development and function. While SR1001 was effective at delaying the onset and reducing the severity of experimental autoimmune encephalomyelitis (EAE), there was some concern that this compound, which modified the activity of RORα, would induce a phenotype similar to that of the staggerer (RORα$^{sg/sg}$) mouse, including ataxia and a disrupted circadian rhythm[11]. Therefore, in order to investigate the specific effects of RORα versus RORγ in T$_H$17 cell development, and alleviate activity at RORα, we performed further modifications to our initial lead compound, T0901317. Previously, we demonstrated that the benzenesulphonamide liver X receptor (LXR) agonist, T0901317, acted as an inverse agonist at RORα and RORγ[12] Due to its mixed pharmacology, it was unsuitable for specifically evaluating ROR effects. Compounds were identified using a screening approach similar to SR1001 and a RORγ-selective inverse agonist. SR1555, was identified (FIG. 1a). Compound SR1555 is shown as compound 3 in Table 1. A screen of SR1555 in a GAL4-NR chimeric co-transfection assay demonstrated that SR1555 was devoid of LXR, FXR, and RORα activity, but it repressed the activity at RORγ in a dose dependent manner (IC$_{50}$~1.5 μM) (FIG. 1b). Next we examined the direct binding of SR1555 to RORα and RORγ in competitive radioligand binding assays. SR1555 was only able to displace [$^3$H]T0901317 from the ligand binding domain (DBD) of RORγ (IC$_{50}$=1 μM; FIG. 1c) and not RORα (data not shown) confirming that SR1555 was indeed specific for RORγ.

Figure 1D:
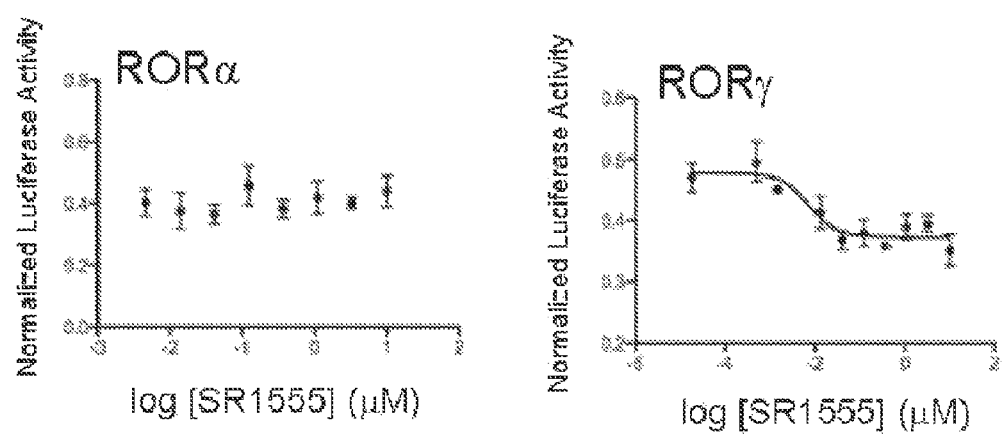
Figure 1E:
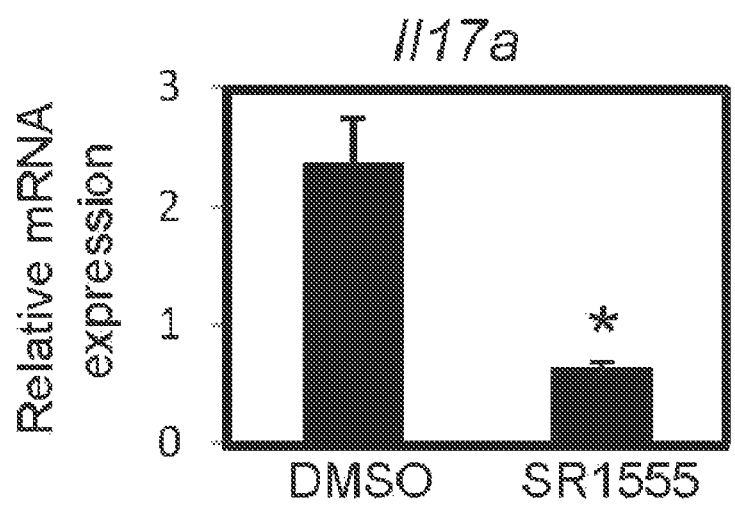

Since RORα and RORγ are critical regulators of IL-17 gene expression, we examined whether SR1555 would affect RORα and RORγ-dependent regulation of an IL-17 promoter driven luciferase reporter construct. HEK293 cells were transiently transfected with an IL-17 reporter, either full-length RORα or RORγ, and treated with an increasing concentration of SR1555[8]. In a dose dependent manner, SR1555 suppressed IL-17 promoter driven activity by RORγ but not RORα, further confirming that SR1555 is indeed a RORγ-specific inverse agonist (FIG. 1d). Finally, using EL4 cells, a murine thymoma which endogenously express RORα, RORγ t, and IL-17A, we examined whether SR1555 affected endogenous IL-17 gene expression[8]. EL4 cells were treated with DMSO or SR1555 for 24 hours and analyzed for Il17a gene expression by quantitative real-time PCR. SR1555 inhibited Il17a gene expression by greater than 70%, demonstrating that SR1555 can inhibit the expression of this $T_H17$ mediated cytokine (FIG. 1e). Together, these data indicate that SR1555 specifically targets RORγ and inhibits its transcriptional activity leading to suppression of IL-17 gene expression.

Figure 2A:
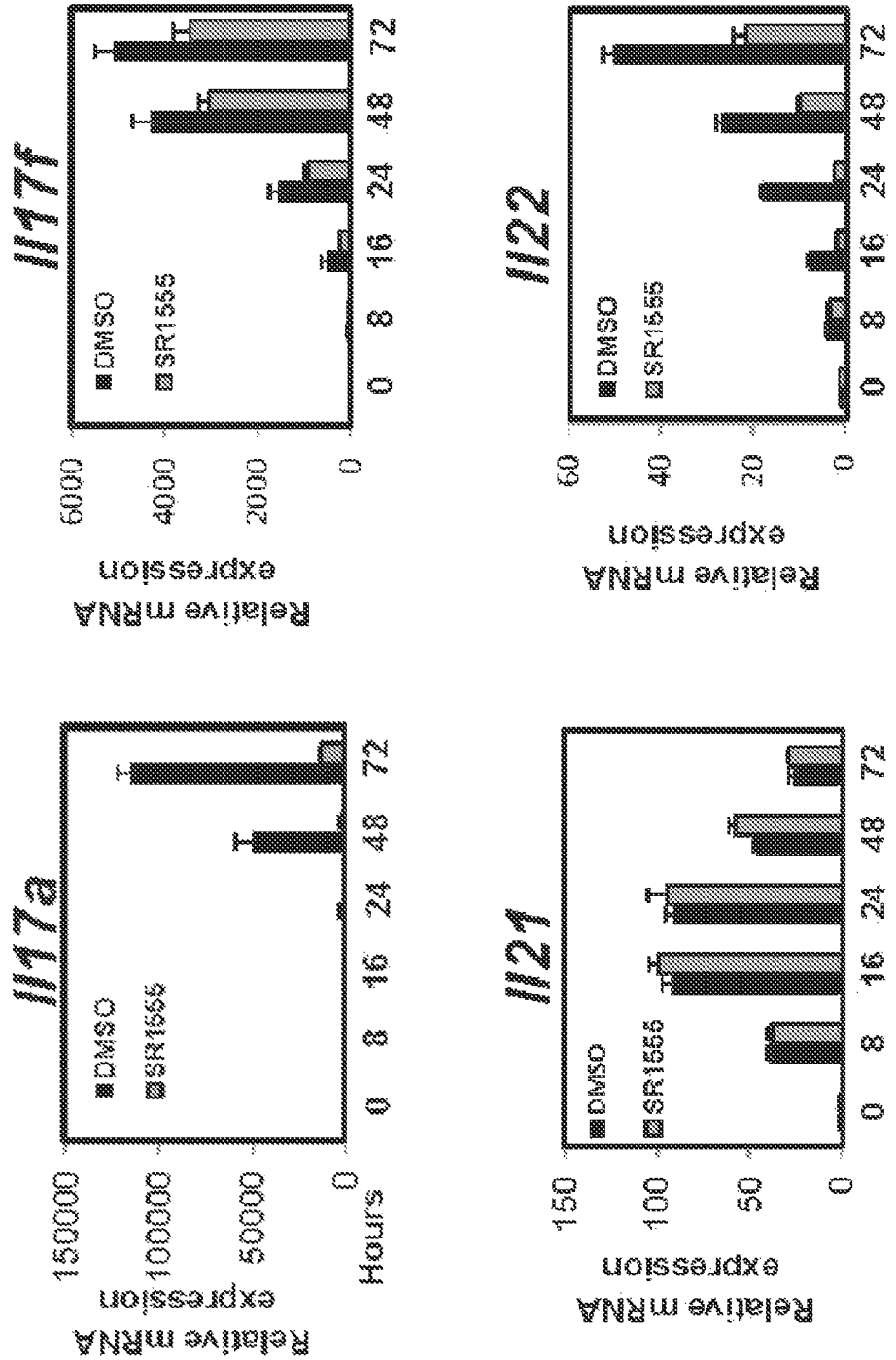
FIG. 2 shows the effects of SR1555 during $T_H17$ cell differentiation: (a) Real time-RTPCR analysis of splenocytes cultured under $T_H17$ polarizing conditions in the presence of DMSO or SR1555 (10 μM) for the duration of the time course. Data are normalized to GAPDH. (n=3). (b) The effect of SR1555 (10 μM) on IL-17A cytokine expression during murine $T_H17$ cell differentiation. Intracellular cytokine staining on splenocytes treated with DMSO or SR1555 for the duration of the experiment. Cells were grated on CD4+ T cells. Graph on the right summarizes IL-17 expression normalized to DMSO. (n=3, *p<0.05). (c) Intracellular cytokine staining on splenocytes treated with DMSO or SR1555 (10☐M) for 24 hours prior to FACS analysis. Cells were grated on CD4+ T cells. Graph on the right summarizes IL-17 expression normalized to DMSO. (n=3, *p<0.05). (d) The effect of SR1555 (10 μM) on the viability of $T_H17$ cells. Cells were gated on AnnexinV and propidium iodide positive cells. Graph depicts percent of positive cells normalized to DMSO. (n=3).

Given that SR1555 was an effective inhibitor of endogenous IL-17 gene expression in EL4 cells, we next examined whether SR1555 would affect the differentiation of $T_H17$ cells in vitro. Murine splenocytes were cultured under $T_H17$ polarizing conditions (TGFβ and IL-6) for three days in the presence of SR1555 or vehicle control (DMSO). Real-time RTPCR analysis revealed that while SR1555 inhibited the mRNA expression of Il17a, it was less effective at inhibiting Il17f, Il21, and Il22 (FIG. 2a). While the effects of SR1555 are distinct from those observed with our dual RORα/γ inverse agonist, SR1001, or other previously published RORγ-ligands, our data suggests that ROR ligands with differing RORα/γ selectivity may display differential effects on $T_H17$ cytokine gene expression. It may also be the case that differential effects may be observed with different chemical classes of ROR ligands as has been observed with other nuclear receptor ligands.

Figure 2D:
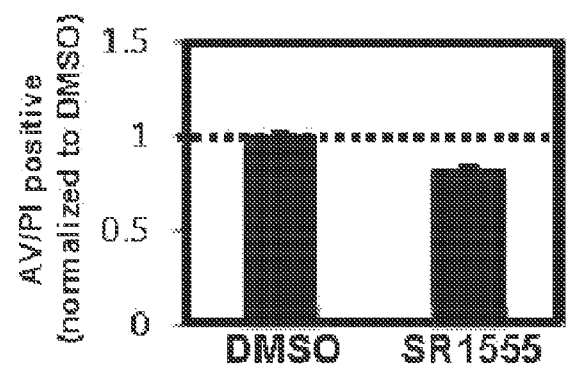

Next, we examined the effects of SR1555 on IL-17 protein expression. Again, splenocytes were cultured under $T_H17$ polarizing conditions for four days in the presence of SR1555 or vehicle control for the full time course (FIG. 2b) or without ligand until 24 hours prior to completion of the experiment (compound added after day 3, FIG. 2c). Using intracellular cytokine FACS analysis, we determined that SR1555 was effective at inhibiting IL-17 protein expression when added at the initiation of $T_H17$ cell differentiation (FIG. 2b) and when SR1555 was added 24 hours prior to the completion of the experiment (FIG. 2c). In order to clarify that the effects observed in the cultures was not due to toxicity of the compounds, we analyzed the cultures for the expression of Annexin V and propidium iodide, markers of cell death, using flow cytometry. SR1555 did not induce cell death during $T_H17$ cell differentiation relative to the DMSO control (FIG. 2d). To date, most RORγ-specific compounds have been evaluated as "preventative" measures. Currently, there is little data evaluating the efficacy of ROR-selective drugs once the initiation of $T_H17$ development has begun. Our data suggests that RORγ-specific inverse agonists will be effective at inhibiting $T_H17$ cell-mediated cytokine responses once the differentiation process has commenced (FIG. 2c).

Figure 3A:
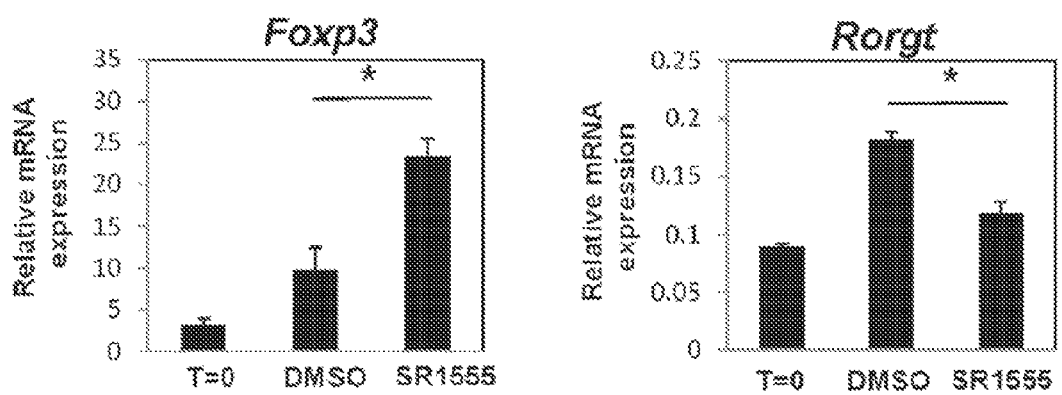
FIG. 3 shows supporting data that SR1555 increases the frequency of iTregs. (a) RTPCR analysis of splenocytes cultured under T regulatory cell polarizing conditions in the presence of DMSO or SR1555 (10 μM) for the duration of the time course. Data are normalized to GAPDH. (n=3). (b) The effect SR1555 (10 μM) on the expression of Foxp3+ cells during the differentiation of iTregulatory cells. Intracellular cytokines staining on splenocytes differentiated under iTreg conditions for 5 days treated with vehicle control (DMSO) or SR1555 for the duration of the experiment. Cells were gated on CD4+ T cells. Graphs to the right of the FACS plots summarize the Foxp3+ expression normalized to DMSO. (n=3, *p<0.05).
Figure 3B:
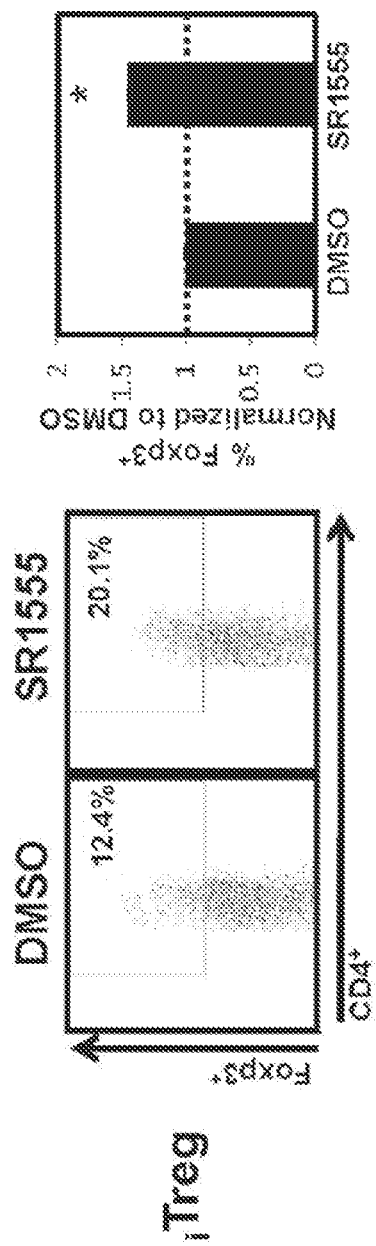

Upon antigen exposure and in the presence of TGFβ both Foxp3 and Rorα/γt are upregulated. Therefore, the environmental cues associated with the concentration of TGFβ dictates the balance between $T_H17$ and T regulatory cell differentiation. In light of the reciprocal relationship between these two cell types, we assessed whether SR1555 affected the development of T regulatory cells in vitro. Splenocytes were cultured under T regulatory cell polarizing conditions (TGFβ and IL-2) for 3 days. Quantitative RTPCR analysis revealed that SR1555 effectively increased the gene expression of Foxp3 while simultaneously suppressing the gene expression of Rorγt (FIG. 3a). To determine whether the gene expression data would correlate with protein expression, we again cultured splenocytes for 5 days under T regulatory cell polarizing conditions in the presence of DMSO or SR1555 and examined the expression of Foxp3 by intracellular cytokine FACS analysis. Similar to the gene expression data, SR1555 treatment increased the frequency of T regulatory cells as evidenced by the almost two-fold increase in the expression of Foxp3$^+$ T cells in the splenocyte culture (FIG. 3b). This result was surprising given that all previously described RORγ ligands have no effect on T regulatory cell population in vitro [8]. Therefore, our data suggests that while inhibition of RORγ alone may be sufficient to inhibit $T_H17$ responses, unique ROR-specific ligands, like SR1555 may hold utility in the generation of T regulatory cells.

Since the nuclear receptors RORα and RORγ t are considered the master regulators of $T_H17$ cell development, generation of synthetic ligands designed to modulate the activity of the RORs is a promising strategy for therapeutics aimed at $T_H17$-mediated diseases. The ultimate goal for the treatment of autoimmune diseases is to not only inhibit the cell type(s) responsible for the disease state, but to help the body regain its immune homeostasis, which may involve increasing the T regulatory cell population. Recently, we and others have reported the identification and characterization of ligands specific to RORα and/or RORγ t that inhibit $T_H17$ cell differentiation and function[8-10, 13]. None of these compounds altered T regulatory cell function. In this report, we identified a RORγ-specific inverse agonist, SR1555, with unique features. Similar to the other ROR-ligands published, SR1555 inhibits $T_H17$ cell differentiation and function. However, SR1555 treatment also enhances the induction of inducible T regulatory cells in vitro. Interestingly, SR1555 is structurally similar to the most recent RORγ selective ligand we recently reported, SR221, but this compound does not alter T regulatory cell proliferation (Supplementary FIG. 1). These data suggest that the $T_H17$ vs. T regulatory effects of RORγ ligands are separable and can likely be optimized individually. Of course, a ROR ligand that affects the $T_H17$/Treg cell ratio by directly targeting both cell types could be of particular benefit in treatment of autoimmunity. Our data suggests that each ROR ligand is unique and may have differential effects at RORα and/or RORγ that could result in some ligands being considered more attractive candidates for therapeutics aimed at treating $T_H17$-mediated diseases.

Methods and Materials

Mice

Male C57BL/6 mice (8 weeks old) were purchased from Jackson Laboratory (Bar Harbor, Me.). All mice were maintained and experiments were performed in specific pathogen free environments in accordance with protocols approved by the Institutional Animal Care and Use Committee.

Cell Culture and Cotransfections

Cotransfection assays were performed as previously described in HEK293 cells (Gal4 cotransfection assay or IL-17 luciferase reporter)[8]. HEK293 and the mouse lymphoma EL4 (ATCC) cells were maintained in DMEM supplemented with 10% FBS plus antibiotics (penicillin and streptomycin; Invitrogen).

Splenocyte Differentiation

Splenocytes were differentiated under the following conditions: iTreg-10 μg/mL anti-IFNγ, 10 μg/mL anti-IL-4, and 2 ng/mL TGFβ (R&D Systems); 20 ug/mL anti-IFNγ, 20 ug/mL anti-IL-4, 1 ng/mL TGFβ, and 10 ng/mL IL-6 (R&D Systems) for $T_H17$ conditions. All cultures were stimulated with 1 μg/mL anti-CD3 (eBiosciences) and 1 μg/mL anti-CD28 (eBiosciences). Four to five days after activation, all cells were restimulated with 5 ng/mL phorbol-12-myristate-13-acetate (PMA) (Sigma) and 500 ng/mL ionomycin (Sigma) for 2 hours with the addition of GolgiStop (BD Bioscience) for an additional 2 hours before intracellular staining. Cells were cultured in RPMI 1640 medium (Invitrogen) with 10% FBS and antibiotics.

Flow Cytometry and Antibodies

Single cell suspensions prepared from spleen were stained with fluorophore-conjugated monoclonal antibodies: FITC anti-CD4 (GK1.5, eBioscience), phycoerythrin-conjugated anti-mouse IL-17A (eBio17B7, eBioscience), and Alexafluor 647 anti-Foxp3 (FJK-16s, eBioscience) along with the Foxp3 staining buffer set (eBioscience). Annexin V and propidium iodide staining was performed using the FITC AnnexinV Apoptosis Detection Kit II (BD Pharmingen). Flow cytometric analysis was performed on a BD LSRII (BD Biosciences) instrument and analyzed using FlowJo software (TreeStar).

Quantitative RT-PCR

RNA extraction and QRT-PCR analysis was performed as previously described[8].

Statistical Analysis

All data are expressed as the mean±s.e.m. (n=3 or more). Statistical analysis was performed using an unpaired Student's t-test.

1. Cua, D. J., et al., *Interleukin-23 rather than interleukin-12 is the critical cytokine for autoimmune inflammation of the brain.* Nature, 2003. 421(6924): p. 744-8.
2. Langrish, C. L., et al., *IL-23 drives a pathogenic T cell population that induces autoimmune inflammation.* J Exp Med, 2005. 201(2): p. 233-40.
3. Veldhoen, M. and B. Stockinger, *TGFbeta1, a "Jack of all trades": the link with pro-inflammatory IL-17-producing T cells.* Trends Immunol, 2006. 27 (8): p. 358-61.
4. Ivanov, I I, et al., *The orphan nuclear receptor RORgammat directs the differentiation program of proinflammatory, IL-17+ T helper cells.* Cell, 2006. 126 (6): p. 1121-33.
5. Weaver, C. T., et al., *Th17: an effector CD4 T cell lineage with regulatory T cell ties.* Immunity, 2006. 24 (6): p. 677-88.
6. Bettelli, E., et al., *Reciprocal developmental pathways for the generation of pathogenic effector TH17 and regulatory T cells.* Nature, 2006. 441 (7090): p. 235-8.
7. Sutton, C., et al., *A crucial role for interleukin (IL)-1 in the induction of IL-17-producing T cells that mediate autoimmune encephalomyelitis.* J Exp Med, 2006. 203 (7): p. 1685-91.
8. Solt, L. A., et al., *Suppression of TH17 differentiation and autoimmunity by a synthetic ROR ligand.* Nature. 472 (7344): p. 491-4.
9. Xu, T., et al., *Ursolic acid suppresses interleukin-17 (IL-17) production by selectively antagonizing the function of RORgamma t protein.* J Biol Chem. 286(26): p. 22707-10.
10. Huh, J. R., et al., *Digoxin and its derivatives suppress TH17 cell differentiation by antagonizing RORgammat activity.* Nature. 472(7344): p. 486-90.
11. Jetten, A. M., S. Kurebayashi, and E. Ueda, *The ROR nuclear orphan receptor subfamily: critical regulators of multiple biological processes.* Prog Nucleic Acid Res Mol Biol, 2001. 69: p. 205-47.
12. Kumar, N., et al., *The benzenesulfoamide T0901317 [N-(2,2,2-trifluoroethyl)-N-[4-[2,2,2-trifluoro-1-hydroxy-1-(trifluoromethyl)ethyl]phenyl]-benzenesulfonamide] is a novel retinoic acid receptor-related orphan receptor-(alpha)/(gamma) inverse agonist.* Mol Pharmacol. 77(2): p. 228-36.
13. Kumar, N., et al., *Identification of SR221: A Potent Synthetic RORgamma-Selective Modulator.* ACS Chem Biol.

SR221 (Compound 108)

The retinoic acid receptor-related orphan receptor γ (RORγ) has been shown to be essential for Interleukin 17 (IL-17) expression and the differentiation of Th17 cells[1]. Th17 cells have been implicated in the pathology of several autoimmune diseases including multiple sclerosis (MS) and rheumatoid arthritis (RA)[2-3]. Genetic ablation of RORγ alone or in combination with RORα in mice led to impaired Th17 cell differentiation and protected the mice from development of experimental autoimmune encephalomyelitis (EAE), a mouse model of MS[1,4]. While the endogenous ligand for RORγ remains controversial, we and others have shown that various oxysterols can bind to RORγ[5-7]. This was followed by a study demonstrating that the synthetic LXR agonist T0901317 (T1317) binds to and modulates the activity of RORα and RORγ[6].

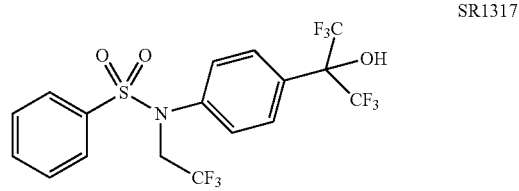 [SMILES: O=S(=O)(c1ccccc1)N(CC(F)(F)F)c1ccc(C(O)(C(F)(F)F)C(F)(F)F)cc1]

SR1317

More recently, we described a synthetic RORα selective inverse agonist, SR3335[8],

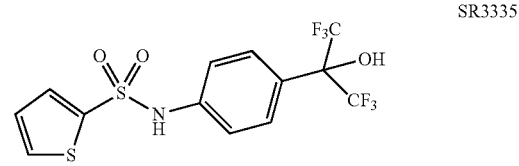 [SMILES: O=S(=O)(Nc1ccc(C(O)(C(F)(F)F)C(F)(F)F)cc1)c1cccs1]

SR3335 and a dual RORα and RORγ inverse agonist, SR1001 (above), which suppresses Th17 cell differentiation and was efficacious at delaying the onset and severity of symptoms in the EAE model[9].

Others have described the natural products digoxin and ursolic acid as RORγ selective modulators and these molecules were capable of inhibiting Th17 cell differentiation[10-11]. However, their utility as candidates for further development is limiting as digoxin displays significant adverse drug reactions with a narrow therapeutic index and ursolic acid activates the glucocorticoid receptor[12-13].

Figure 4:
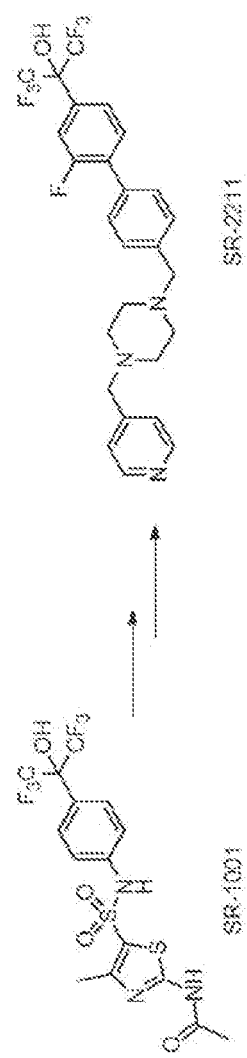
FIG. 4 shows the structure of SR1001 (N-(5-(N-(4-(1,1,1,3,3,3-hexafluoro-2-hydroxypropan-2-yl)phenyl)sulfamoyl)-4-methylthiazol-2-yl)acetamide) and SR2211 (1,1,1,3,3,3-hexafluoro-2-(2-fluoro-4'-((4-(pyridin-4-ylmethyl)piperazin-1-yl)methyl)-[1,1'-biphenyl]-4-yl)propan-2-ol).
Figure 5A:
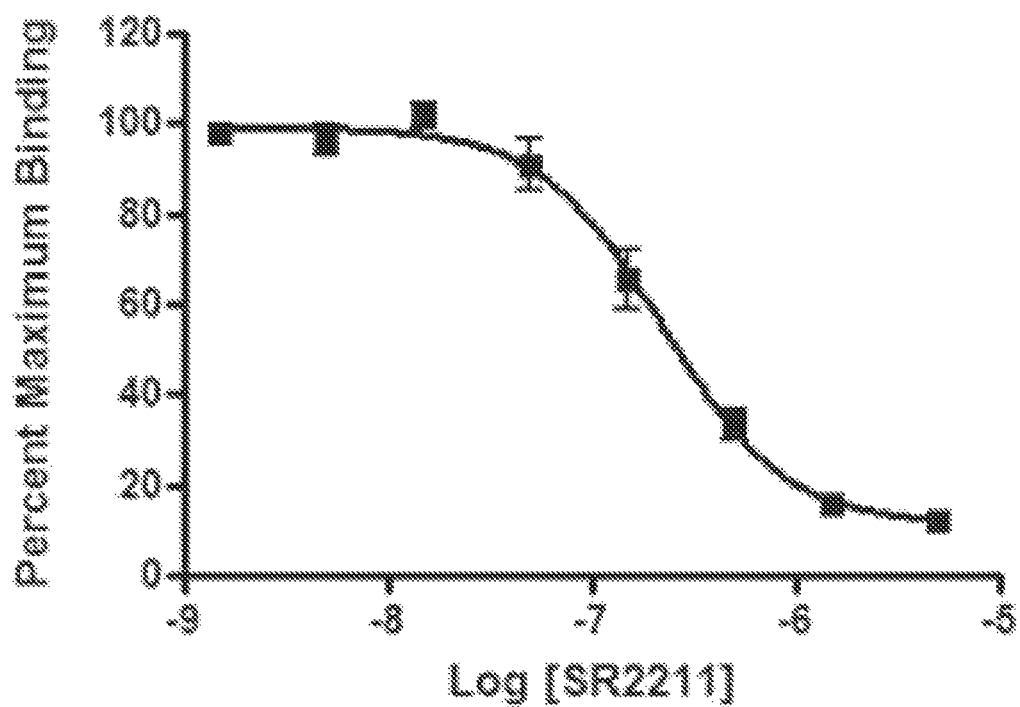
FIG. 5 depicts a demonstration of direct binding of SR2211 to RORγ.
(a) Competition assay was performed to determine IC50 value of SR2211 in a SPA assay. (b) Increasing concentrations of SR2211 were incubated with 5 nM of [3H]-T1317 and 1 μg of GSTRORγ along with Glutathione-YSi beads as detailed in Methods. The percent radioligand bound was calculated at various concentration of SR2211 after 20 hr of incubation. Ki value for SR2211 was calculated to be 105 nM using graphpad prism software. Data shown are representative results from two independent experiments performed in triplicates. HDX perturbation results from SR2211 (right) and T1317 (middle) and digoxin (left) with RORγ. Negative perturbation values means that the exchange rate is slower for these regions within the protein in the ligand-bound protein.
Figure 5B:
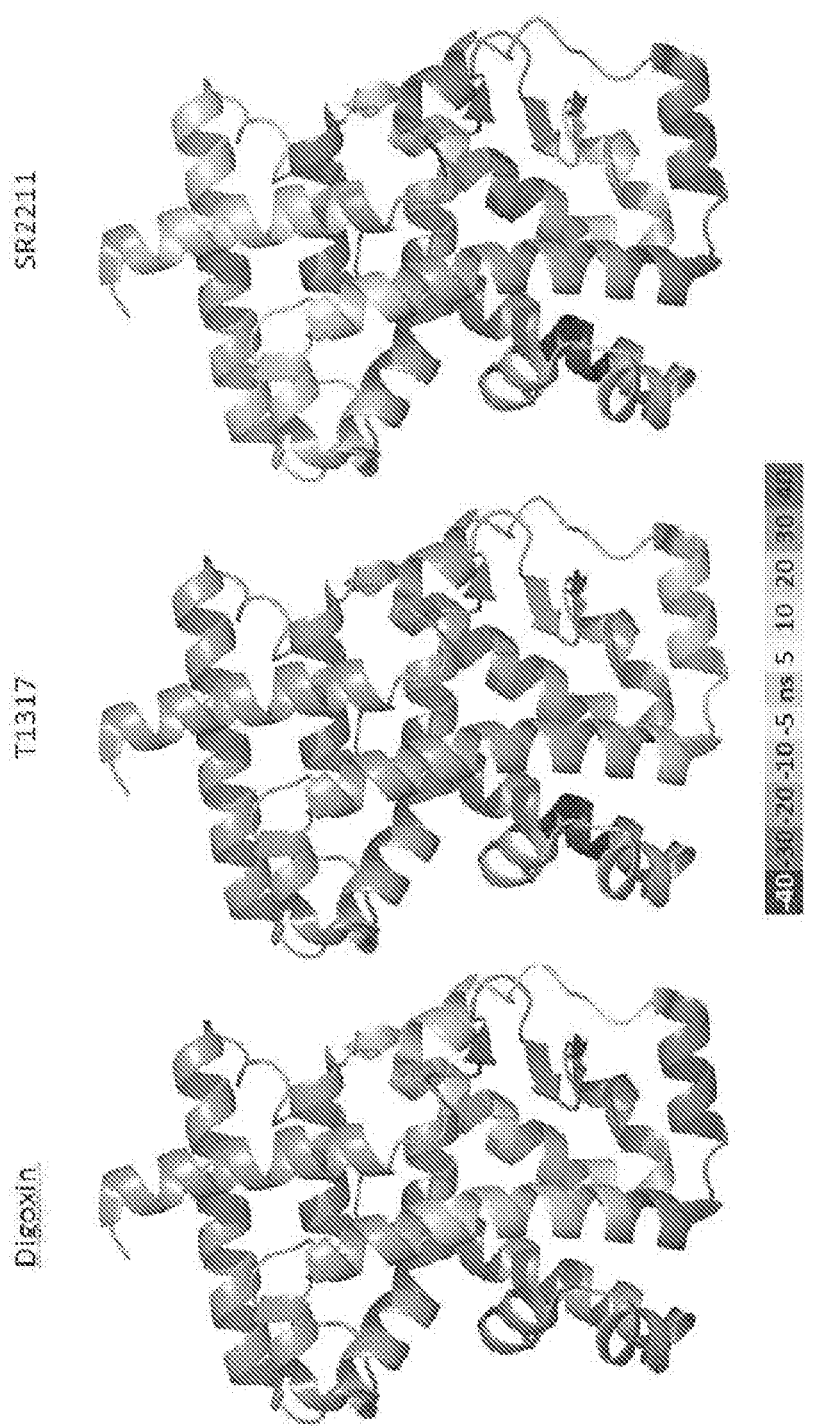

Using a modular chemistry approach, modifications to the SR1001 scaffold were made to develop SAR to diminish RORα activity from the scaffold while maintaining selectivity over LXR. Compounds were profiled using a screening approach based on radioligand binding assay in a Scintillation Proximity Assay (SPA) format. The Kd of [3H]T1317 was ~11.4 nM in the SPA assay. The structure of SR2211 is shown in FIG. 4. As shown in FIG. 5a, the data suggest that SR2211 can bind RORγ and displace radioligand [3H]T1317 in a competition based SPA assay. The calculated Ki value for SR2211 is 105 nM. To further evaluate the nature of the interaction of SR2211 with RORγ, we performed differential hydrogen/deuterium exchange (HDX) mass spectrometry analysis of the RORγ LBD in the presence and absence of digoxin, TI 317, or SR2211. The differential HDX data is shown in FIG. 5b overlaid onto PDB 3KYT where green and blue represent a reduction in HDX as compared with apo receptor. The data shown in FIG. 5b suggests that the conformational mobility of the RORγ LBD is significantly reduced in the presence of SR2211. Comparison of the differential HDX data for SR221 with digoxin or T1317 suggests that SR2211 makes significantly more contacts with the receptor.

Figure 6A:
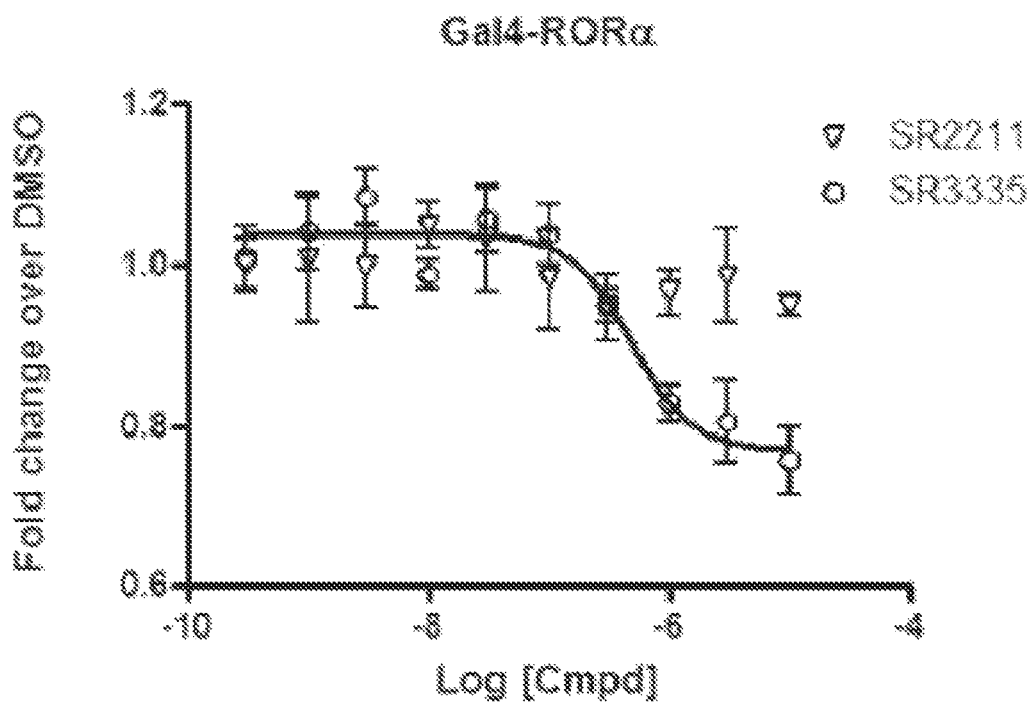
Figure 6B:
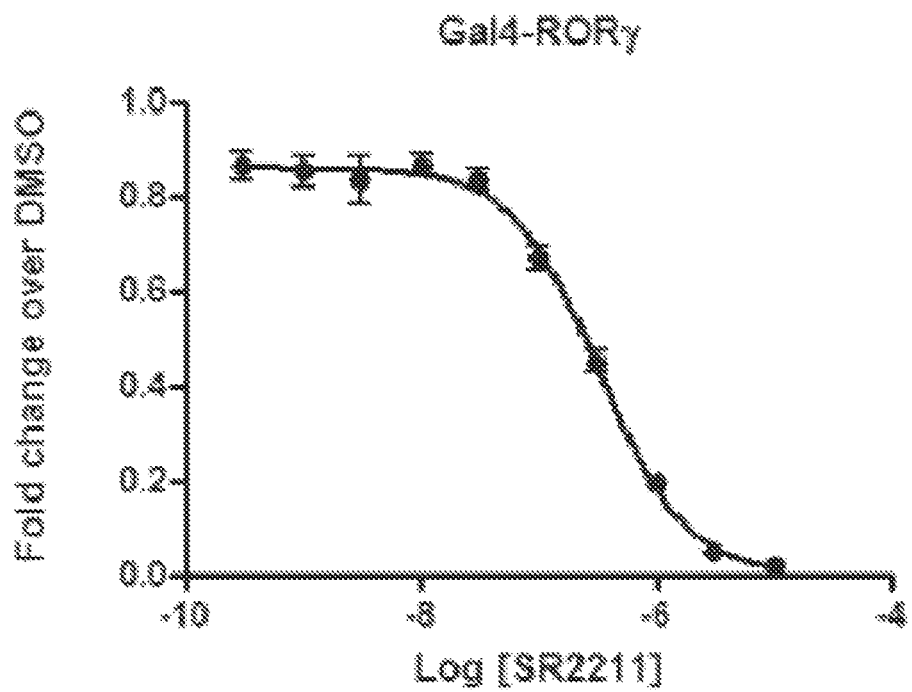
Figure 6C:
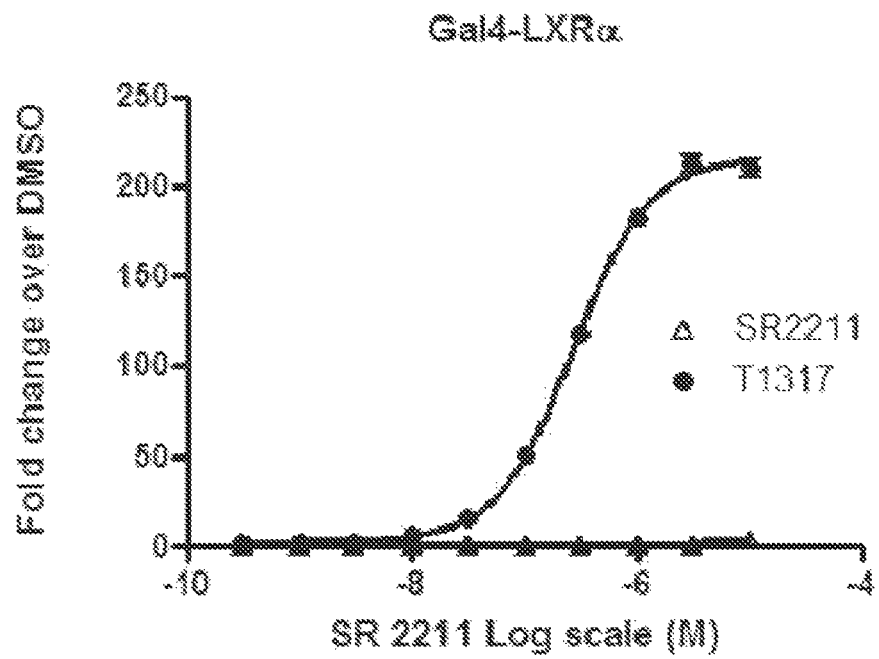
Figure 6D:
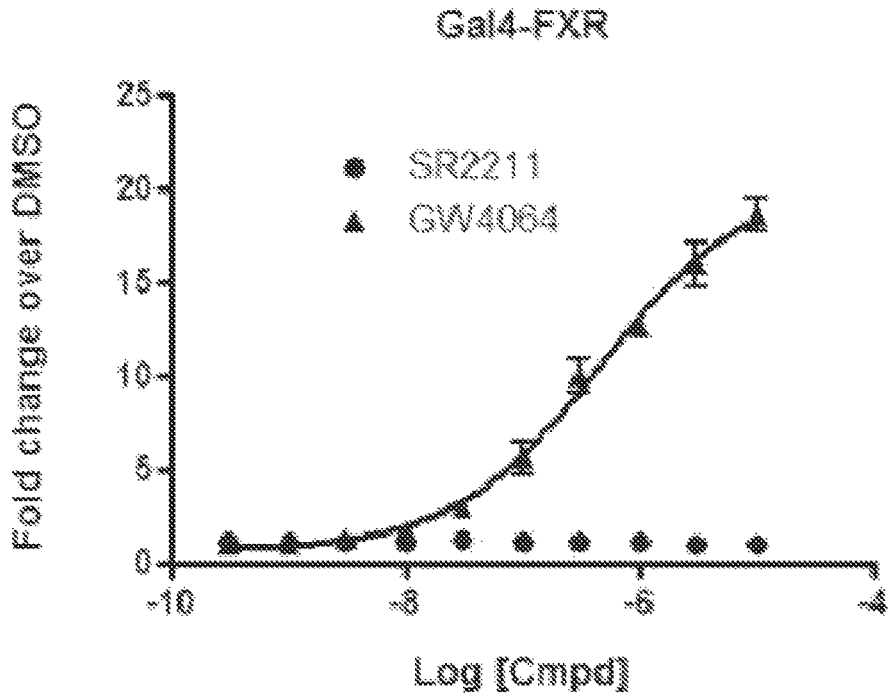
Figure 6E:
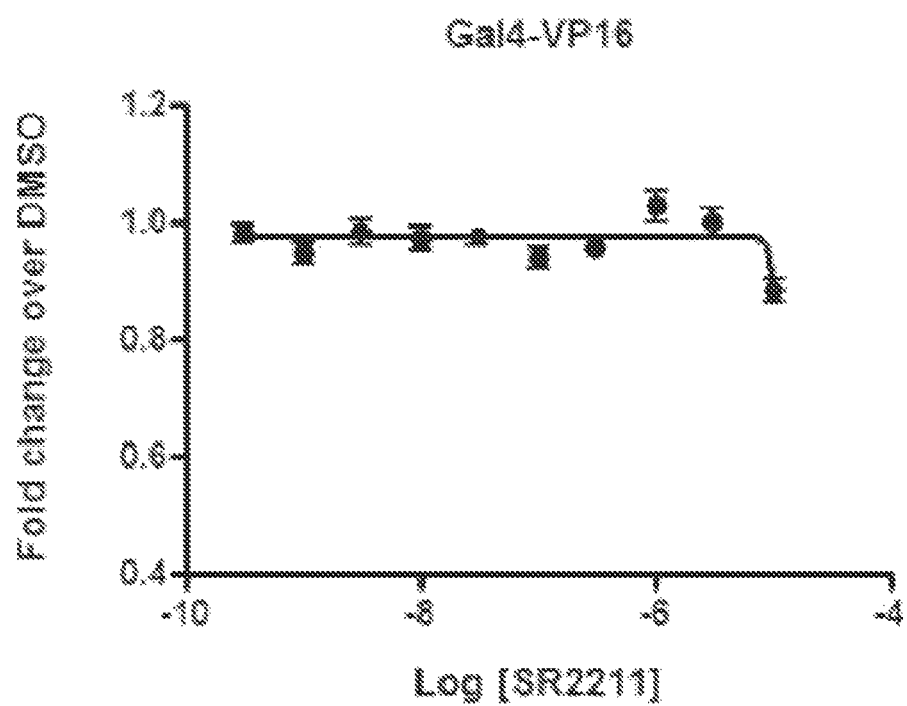
Figure 7A:
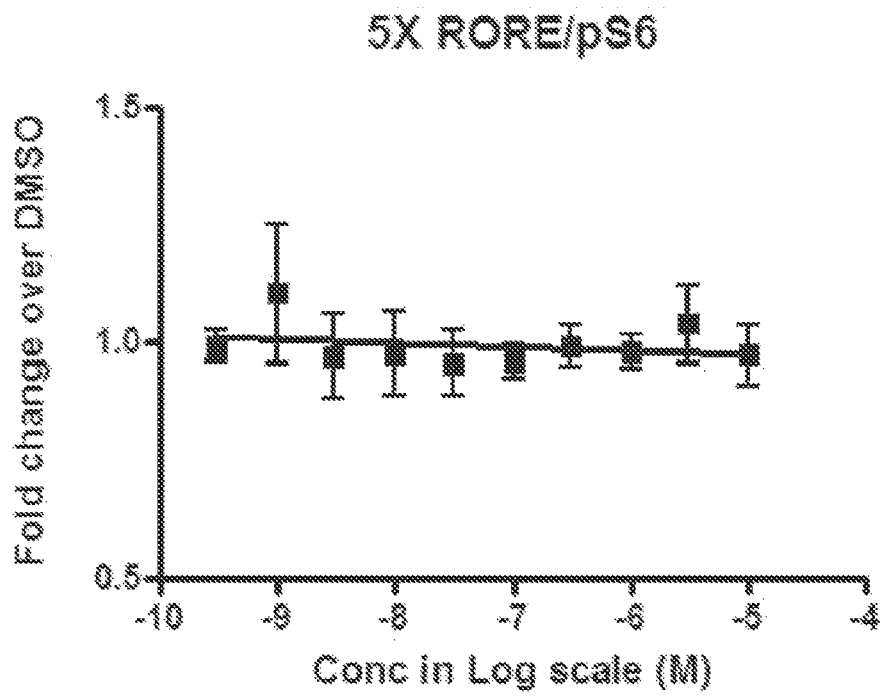
Figure 7B:
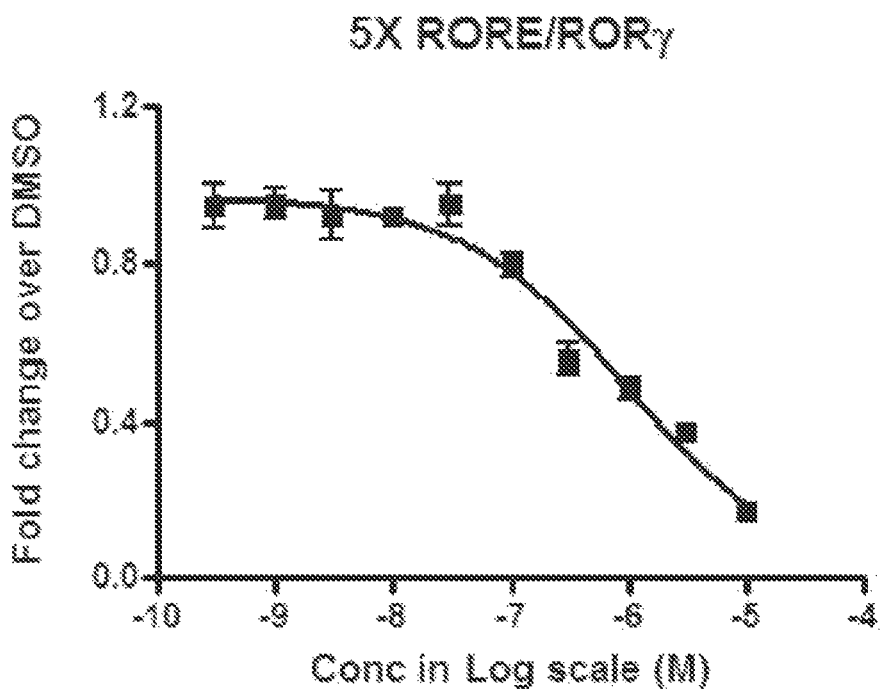
Figure 7C:
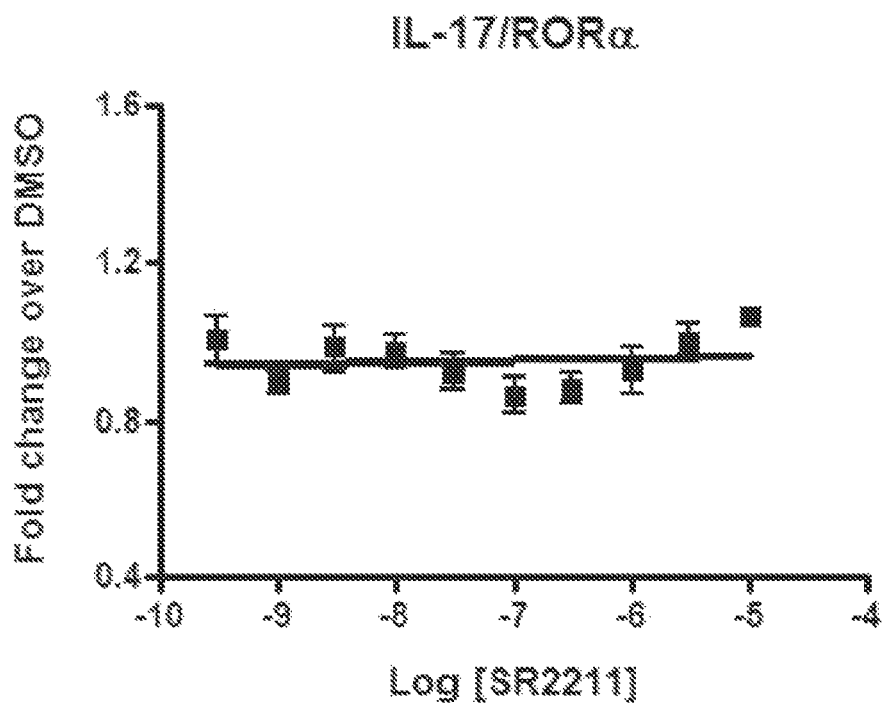
Figure 7D:
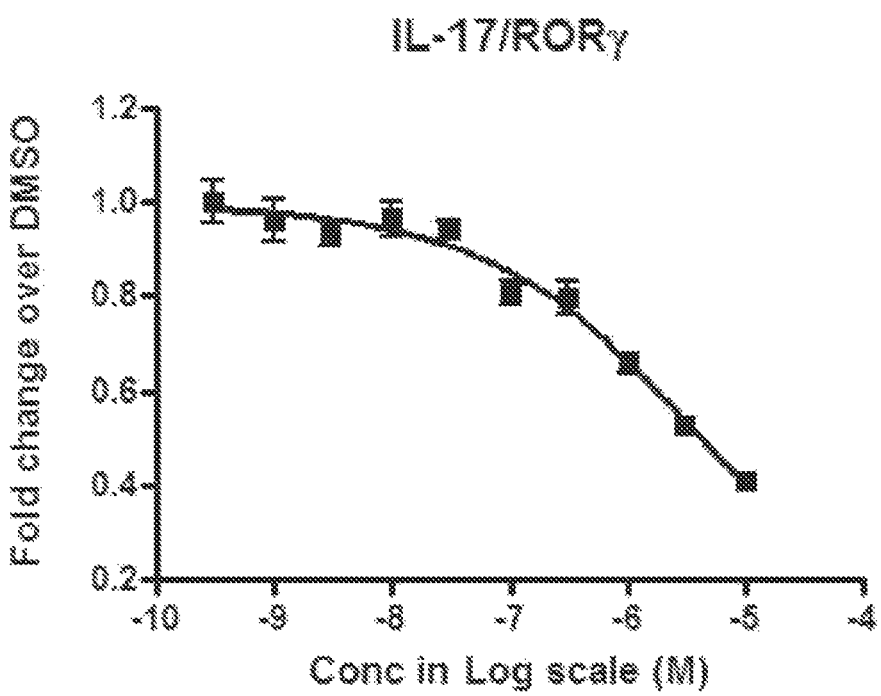
Figure 7E:
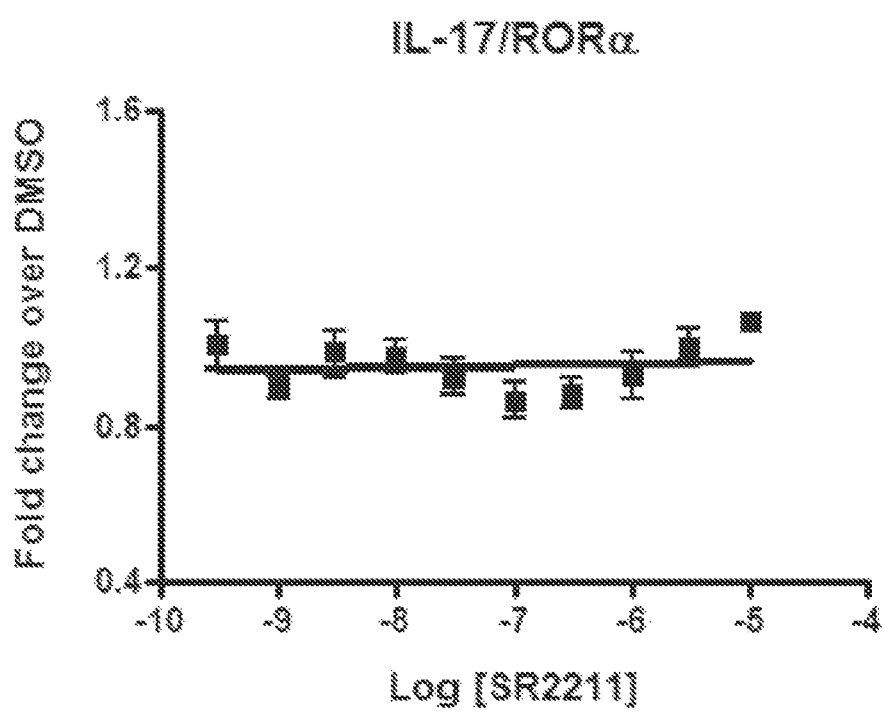

Previously, we had observed that 25-hydroxy cholesterol strongly binds to RORγ, but we were unable to observe any transcriptional activity[6]. To assess the functional transcriptional activity of SR2211, cell based assays using chimeric receptor Gal4 DNA-binding domain (DBD)-NR ligand binding domain cotransfection assay (LBDs of RORα, RORγ, LXRα, FXR and VP-16) were performed. As shown in FIG. 6a, SR2211 treatment did not have any impact on the transcriptional activity of RORα, whereas more than 95% inhibition of RORγ activity was observed at 10 μM (FIG. 6b). Based on the dose response, we calculated the IC50 to be ~320 nM. There is a minimal activation of LXRα by SR2211 at the highest concentration tested (FIG. 6c) and it is less than 5% as compared to T1317. The activity of SR2211 on LXRα is very weak and EC50 is right shifted by more than 100-fold. Moreover we do not observe any activation of ABCA1 promoter when used in conjunction with full length LXRα (FIG. 7e). Additionally, there is no effect on the transcriptional activity of FXR when treated with SR2211 (FIG. 6d) where as a significant increase was seen with the positive control GW4064. We also observed no off-target effects/toxicity as there was no change in the luciferase activity of Gal4 DBD-VP16 (FIG. 6e). These data clearly demonstrate that we have developed a compound that selectively targets RORγ and is potent and efficacious.

To confirm these results that SR2211 can repress the RORγ transcriptional activity, we used a full length receptor along with a multimerized ROR response element (RORE, five repeats of RORE) driving luciferase gene expression. In the absence of RORγ, there was no change in the luciferase activity of 5x-RORE with the treatment of SR2211 (FIG. 7a). SR2211 significantly repressed the 5x-RORE luciferase activity when full length RORγ was added during transfection (FIG. 7b), however, there was no effect of SR2211 on RORα co-transfection with 5x-RORE. To further to examine the activity of SR2211 in more native promoter based assay, we performed additional cotransfection assays where we transfected cells with full-length RORα or RORγ and a luciferase reporter gene driven by a native promoter derived from a known ROR target gene, Il17. Il17 is a well-characterized ROR target gene that plays a critical role in the inflammatory pathway 1. As shown in FIG. 7c, in a RORα cotransfection assay, treatment of cells with SR2211 did not alter the transcription driven by the Il17 promoter. We observed a significant, more than 50%, suppression of transcriptional activity of Il17 promoter in a RORγ dependent manner (FIG. 7d). As previously mentioned, there was no increase in the full length LXRα target gene, ABCA1, promoter activity (FIG. 7e). These results confirm that we have been able to selectively target RORγ.

Figure 8C:
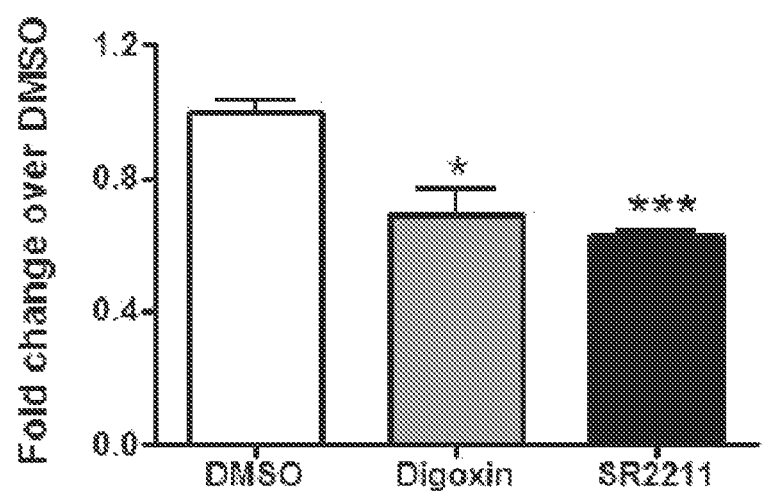

In order to determine whether SR2211 can inhibit the endogenous Il17 gene expression, we used an EL-4 murine T lymphocyte cell line that has been shown to produce IL-17 in response to phorbol myristate acetate (PMA) and ionomycin treatment. The results shown in FIG. 8a demonstrate that pre-treatment of EL-4 cells with 5 μM of either SR2211 or digoxin as control followed by stimulation with PMA/ionomycin leads to a significant reduction in the IL-17 gene expression as measured by quantitative real-time PCR. The treatment of EL4 with SR2211 repressed the Il17 gene expression to a greater extent as compared to digoxin. Similarly, the expression of IL-23 receptor, (Il23r) was significantly inhibited by SR2211 and digoxin (FIG. 8b) as has been previously reported by Fujita-Sato, et al[14]. In order to measure the effect of SR2211 on IL-17 production, we determined the intracellular levels of IL-17 using flow cytometry. After the stimulation of EL-4 cells with PMA/ionomycin for 3 hr, the cells were treated with BD Golgi-Plug™ (protein transport inhibitor) to allow intracellular accumulation of cytokines. After 2 hr, the cells were fixed and stained to analyze the IL-17 by flow cytometry. As shown in FIG. 8c, treatment of EL-4 cells with SR2211 as well as a control digoxin resulted in significant inhibition of IL-17 intracellular staining as compared to vehicle treated cells. These results demonstrate that SR2211 can inhibit the transcriptional activity of RORγ resulting in the suppression of IL-17 production.

Material and Methods

Cell Culture and Cotransfections

HEK293 cells were maintained in Dulbecco's modified Eagle's medium (DMEM) supplemented with 10% fetal bovine serum at 37° C. under 5% CO2. Reverse transfections were performed in bulk using 1×106 cells in 6 cm plates, 3 ug of total DNA in a 1:1 ratio of receptor and reporter and FuGene6 (Roche) in a 1:3 DNA:lipid ratio. Following day, cells re plated in 384 well plates at a density of 10,000 cells/well. After 4 hr, the cells were treated with the compound or DMSO as control. The luciferase levels were assayed following additional 20 hour incubation by one-step addition of BriteLite Plus (Perkin Elmer) and read using an Envision (Perkin Elmer). Data was normalized as fold change over DMSO treated cells.

Radioligand Binding Assay

The assay contains 0.25 mg of beads (Glutathione YSI; PE # RPNQ0033), 1 μg of GST-RORγ-LBD, 5 nM of [3H]T1317 as radioligand and varying concentration of SR2211 in the assay buffer (50 mM HEPES, pH 7.4, 0.010% bovine serum albumin, 150 mM NaCl and 5 mM $MgCl_2$, 10% glycerol, 1 mM DTT, Complete protease inhibitor from Roche). All the components were gently mixed and incubated for 20 hr and were read in TopCount. The radioligand binding results were analyzed using GraphPad Prism software.

HDX Analysis

Solution-phase amide HDX is performed with a fully automated system as described previously (Chalmers, 2006). Briefly, 4 μL of a 10 μM protein solution in HDX buffer was diluted to 20 μL with $D_2O$-containing HDX buffer, and incubated at 25° C. for; 10 s, 30 s, 60 s, 900 s, and 3,600 s. Following on-exchange, unwanted forward or back exchange is minimized and the protein is denatured by dilution to 50 μL with 0.1% TFA in 3M urea (held at 1° C.). Samples are then passed across an immobilized pepsin column (prepared in house) at 50 μL min-1 (0.1% TFA, 1° C.) and the resulting peptides are trapped onto a C8 trap cartridge (Thermo Fisher, Hypersil Gold). Peptides were then gradient eluted (4% $CH_3CN$ to 40% $CH_3CN$, 0.3% formic acid over 5 minutes, 2° C.) across a 1 mm×50 mm $C_{18}$ reverse phase HPLC column (Hypersil Gold, Thermo Fisher) and electrosprayed directly into an Orbitrap mass spectrometer (LTQ Orbitrap with ETD, Thermo Fisher).

Data are processed with in-house software and visualized with pyMOL (DeLano Scientific). To measure the difference in exchange rates we calculated the average percentage deuterium uptake for the apo RORγ LBD following 10, 30, 60, 900 and 3600 seconds of onexchange. From this value, we subtract the average percent deuterium uptake measured for the RORγ LBD+ligand complex. Negative perturbation values means that the exchange rate is slower for these regions within the protein in the ligand-bound protein.

Real-Time PCR Analysis

One million EL-4 cells were seeded in each well of 6 well plate and incubated with 5 uM of digoxin or SR2211 or DMSO for 20 hrs. Cells were then stimulated with phorbol 12-myristate 13-acetate (PMA) (50 ng/ml; Sigma) and Ionomycin (1 ug/ml; Sigma) for 5 hours. Then, RNA was extracted with RNeasy midi kit using DNase I (Qiagen), then cDNA was synthesized with high capacity cDNA Reverse Transcription kits (Applied Biosystems). IL17A gene expression was normalized to the expression of GAPDH. IL17A, IL-23R and GAPDH primer sets were as follows:

```
IL7A:
                           (SEQ ID NO: 9; Forward)
CTCCAGAAGCTCCCTCAGACTAC, (SEQ ID NO: 10; Reverse)
AGCTTTCCCTCCGCATTGACACAG;

IL23R:
                           (SEQ ID NO: 11; Forward)
GCC AAGAAGACC ATT CCCGA, (SEQ ID NO: 12; Reverse)
TCA GTG CTA CAA TCT TCT TCA GAG GAC A GAPDH:
                           (SEQ ID NO: 13; Forward)
ACACATTGGGGGTAGGAACA, (SEQ ID NO: 14; Reverse)
AACTTTGGCATTGTGGAAGG.
```

Flow Cytometry

For intracellular cytokine staining, cells were stimulated with PMA (50 ng/Ml) and Ionomycin (1 ug/ml) for 5 hrs. After 3 hrs of incubation, BD Golgiplug (BD Bioscience) was added and incubated for 2 hrs. Then, cells were fixed, permeabilized, and stained with PEIL17A Ab (BD Biosciences). Cell sorting was performed using LSRII (BD Biosciences).

1. Ivanov, I I; McKenzie, B. S.; Zhou, L.; Tadokoro, C. E.; Lepelley, A.; Lafaille, J. J.; Cua, D. J.; Littman, D. R. (2006) The orphan nuclear receptor RORgammat directs the differentiation program of proinflammatory IL-17+ T helper cells. Cell 126, 1121-1133.
2. Nakae, S.; Nambu, A.; Sudo. K.; Iwakura. Y. (2003) Suppression of immune induction of collagen-induced arthritis in IL-17-deficient mice. J Immunol 171, 6173-6177.
3. Jetten. A. M. (2009) Retinoid-related orphan receptors (RORs): critical roles in development, immunity, circadian rhythm, and cellular metabolism. Nucl Recept Signal 7, e003.
4. Yang, X. O.; Pappu, B. P.; Nurieva, R.; Akimzhanov, A.; Kang, H. S.; Chung, Y.; Ma, L.; Shah, B.; Panopoulos, A. D.; Schluns, K. S.; Watowich, S. S.; Tian, Q.; Jetten, A. M.; Dong, C. (2008) T helper 17 lineage differentiation is programmed by orphan nuclear receptors ROR alpha and ROR gamma. Immunity 28, 29-39.
5. Jin, L.; Martynowski, D.; Zheng, S.; Wada, T.; Xie, W.; Li. Y. (2010) Structural basis for hydroxycholesterols as natural ligands of orphan nuclear receptor RORgamma. Mol Endocrinol 24, 923-929.
6. Kumar, N.; Solt, L. A.; Conkright, J. J.; Wang, Y.; Istrate, M. A.; Busby, S. A.; Garcia-Ordonez, R. D.; Burris, T. P.; Griffin, P. R. (2010) The benzenesulfoamide T0901317 [N-(2,2,2-trifluoroethyl)-N-[4-[2,2,2-trifluoro-1-hydroxy-1-(trifluoromethyl)ethyl]phenyl]-benzenesulfonamide] is a novel retinoic acid receptor-related orphan receptor-alpha/gamma inverse agonist. Mol Pharmacol 77, 228-236.
7. Wang, Y.; Kumar, N.; Solt, L. A.; Richardson, T. I.; Helvering, L. M.; Crumbley, C.; Garcia-Ordonez, R. D.; Stayrook, K. R.; Zhang, X.; Novick, S.; Chalmers, M. J.; Griffin, P. R.; Burris, T. P. (2010) Modulation of retinoic acid receptor-related orphan receptor alpha and gamma activity by 7-oxygenated sterol ligands. J Biol Chem 285, 5013-5025.
8. Kumar, N.; Kojetin, D. J.; Solt, L. A.; Kumar, K. G.; Nuhant, P.; Duckett, D. R.; Cameron, M. D.; Butler, A. A.; Roush, W. R.; Griffin, P. R.; Burris, T. P. (2011) Identification of SR3335 (ML-176): a synthetic RORalpha selective inverse agonist. ACS Chem Biol 6, 218-222.
9. Solt. L. A.; Kumar, N.; Nuhant, P.; Wang. Y.; Lauer, J. L.; Liu, J.; Istrate, M. A.; Kamenecka, T. M.; Roush, W. R.; Vidovic, D.; Schurer, S. C.; Xu, J.; Wagoner, G.; Drew, P. D.; Griffin, P. R.; Burris, T. P. (2011) Suppression of TH17 differentiation and autoimmunity by a synthetic ROR ligand. Nature 472, 491-494.
10. Huh, J. R.; Leung, M. W.; Huang, P.; Ryan, D. A.; Krout, M. R.; Malapaka, R. R.; Chow, J.; Manel, N.; Ciofani, M.; Kim, S. V.; Cuesta, A.; Santori, F. R.; Lafaille, J. J.; Xu, H. E.; Gin, D. Y.; Rastinejad, F.; Littman, D. R. (2011) Digoxin and its derivatives suppress TH17 cell differentiation by antagonizing RORgammat activity. Nature 472, 486-490.
11. Xu, T.; Wang, X.; Zhong, B.; Nurieva, R. I.; Ding, S.; Dong, C. (2011) Ursolic acid suppresses interleukin-17 (IL-17) production by selectively antagonizing the function of RORgamma t protein. J Biol Chem 286, 22707-22710.
12. Kassi, E.; Sourlingas. T. G.; Spiliotaki, M.; Papoutsi, Z.; Pratsinis. H.; Aligiannis, N.; Moutsatsou, P. (2009) Ursolic acid triggers apoptosis and Bcl-2 downregulation in MCF-7 breast cancer cells. Cancer Invest 27, 723-733.
13. Cha, H. J.; Park, M. T.; Chung, H. Y.; Kim, N. D.; Sato, H.; Seiki, M.; Kim, K. W. (1998) Ursolic acid-induced down-regulation of MMP-9 gene is mediated through the nuclear translocation of glucocorticoid receptor in HT1080 human fibrosarcoma cells. Oncogene 16, 771-778.
14. Fujita-Sato, S.; Ito, S.; Isobe, T.; Ohyama, T.; Wakabayashi, K.; Morishita, K.; Ando, O.; Isono, F. (2011) Structural basis of digoxin that antagonizes RORgamma t receptor activity and suppresses Th17 cell differentiation and interleukin (IL)-17 production. J Biol Chem 286, 31409-31417.

All patents and publications referred to herein are incorporated by reference to the same extent as if each individual publication was specifically and individually indicated to be incorporated by reference.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound wherein the compound is any of the following, or a pharmaceutically acceptable salt thereof:

187
-continued
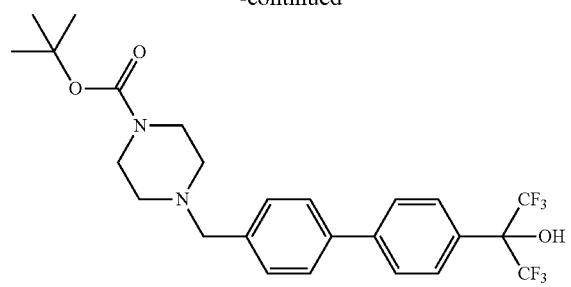
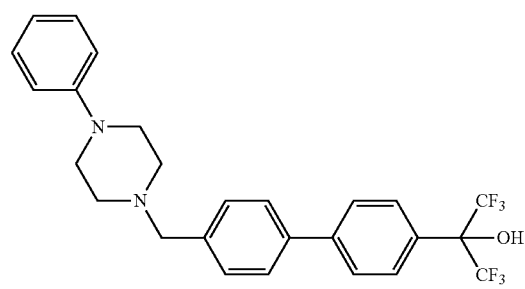
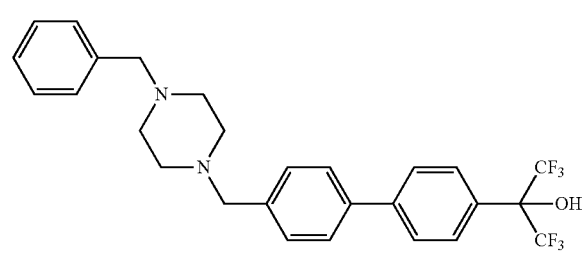
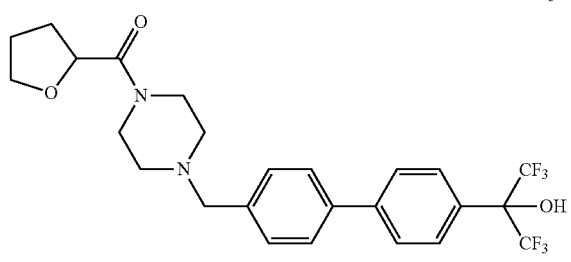
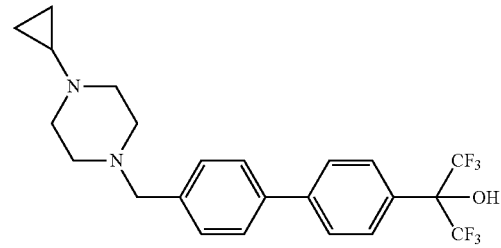
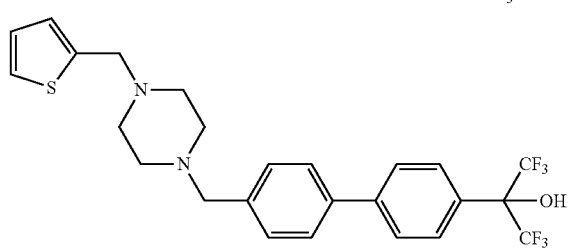
188
-continued
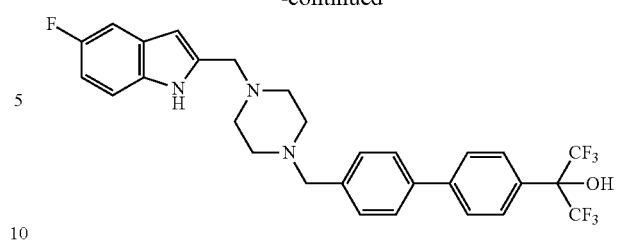
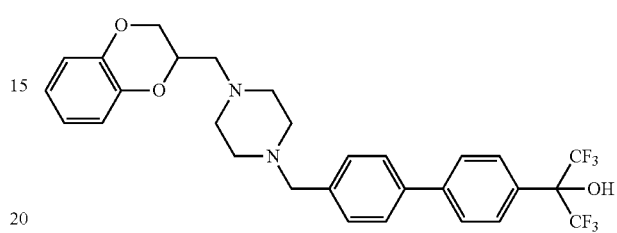
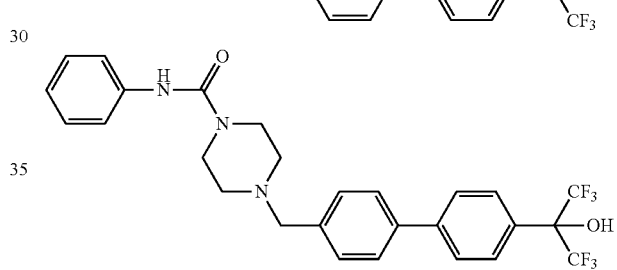
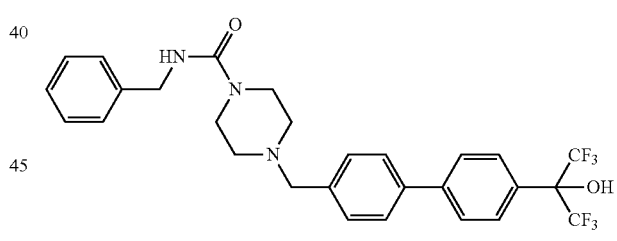
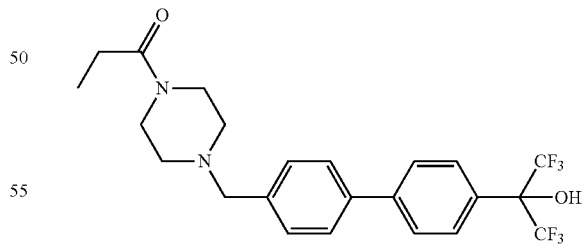
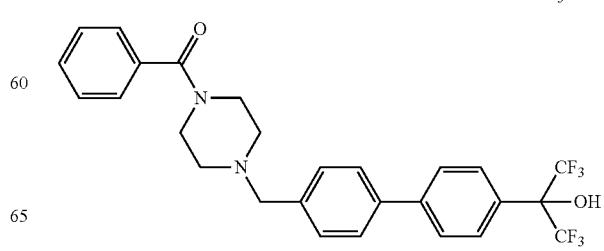

189
-continued
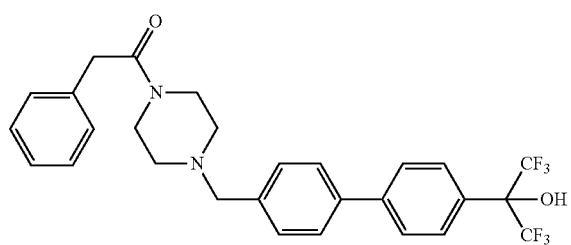 [SMILES: O=C(Cc1ccccc1)N1CCN(Cc2ccc(-c3ccc(C(O)(C(F)(F)F)C(F)(F)F)cc3)cc2)CC1]
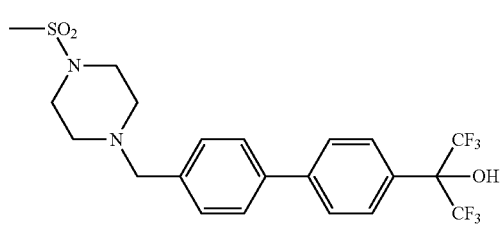
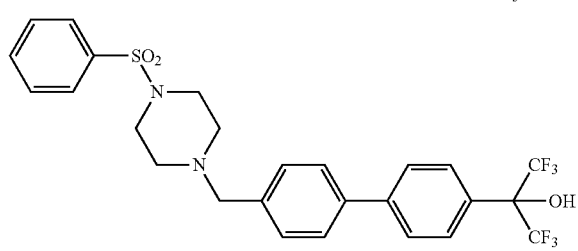
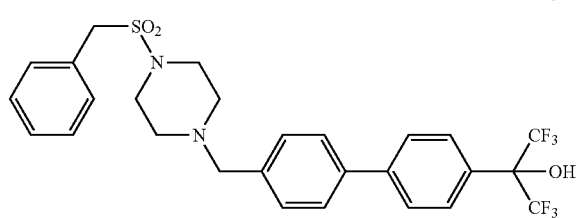
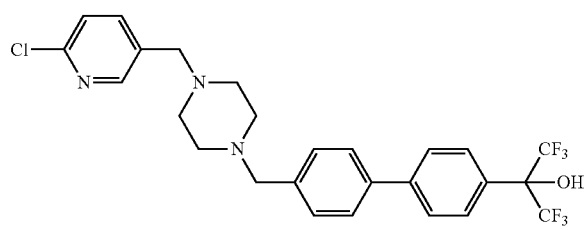
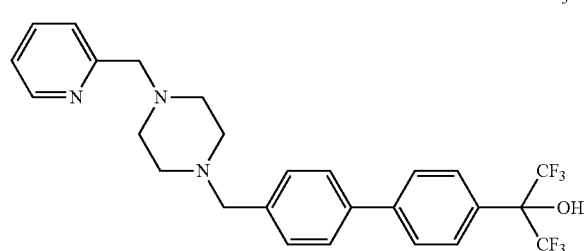
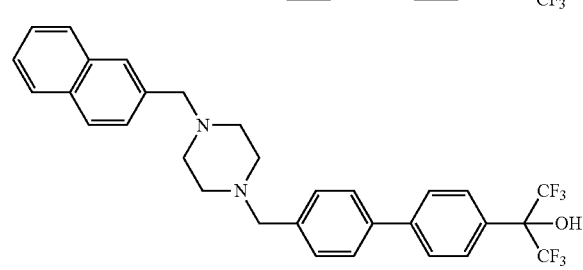
190
-continued
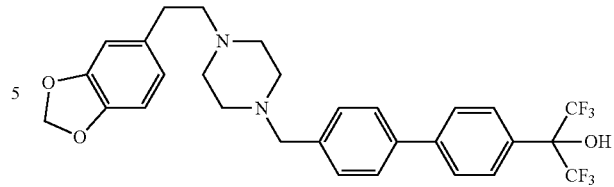
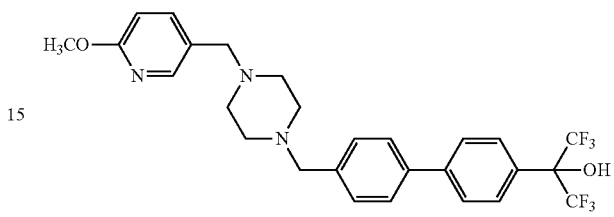
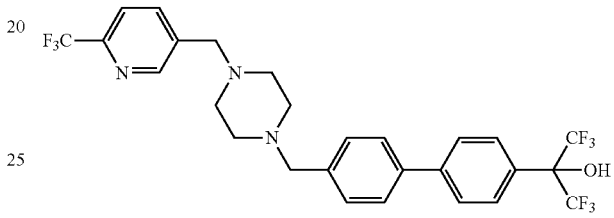
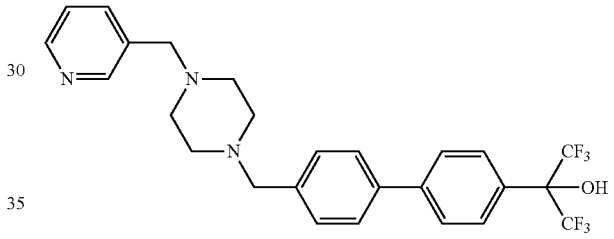
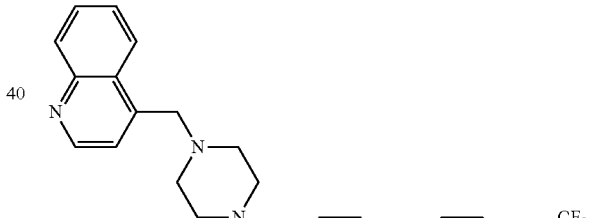
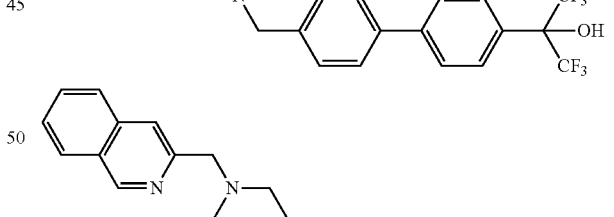
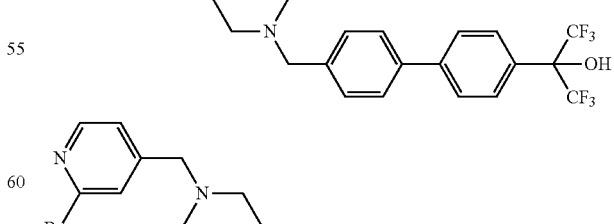
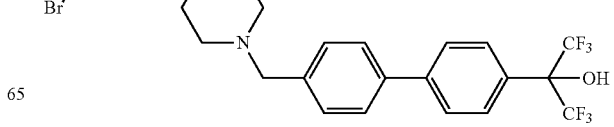

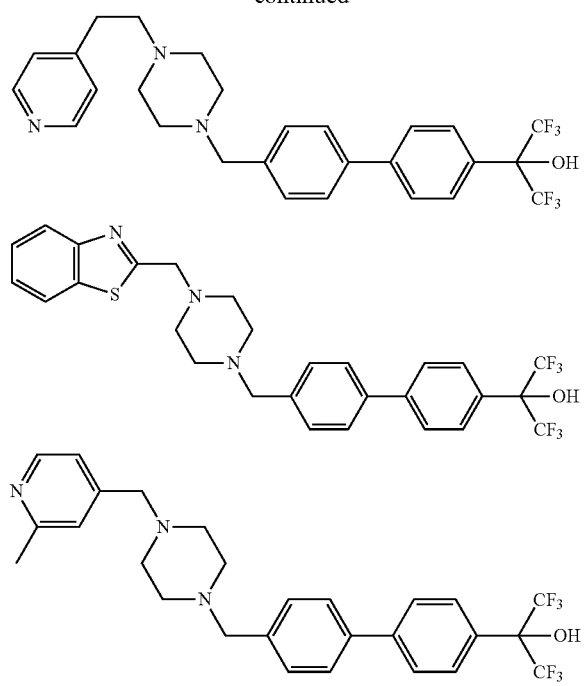
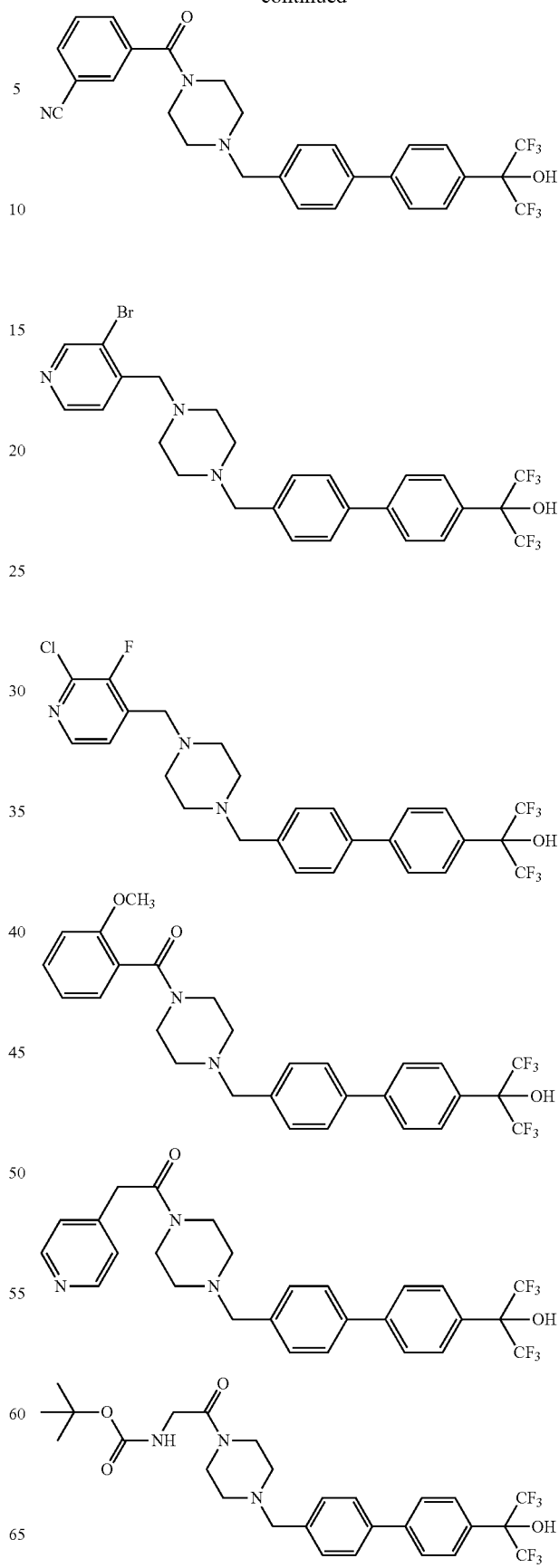

193
-continued
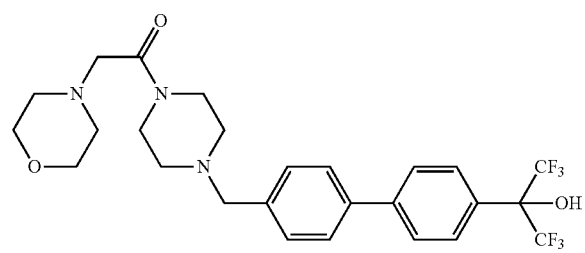
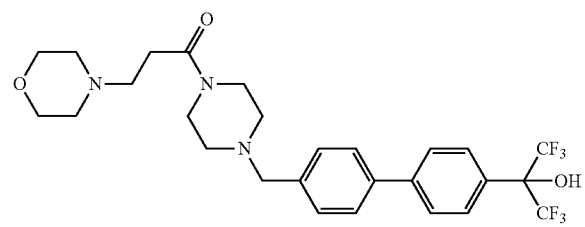
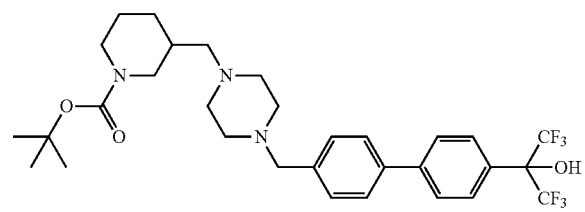
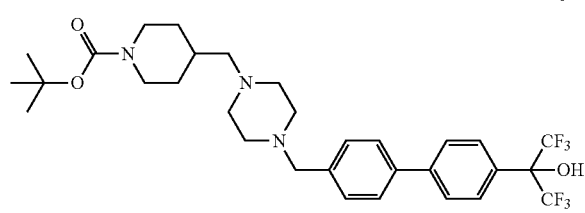
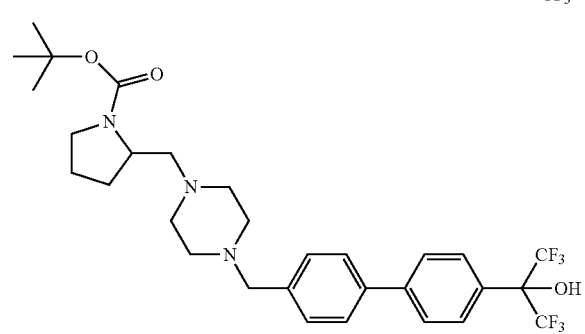
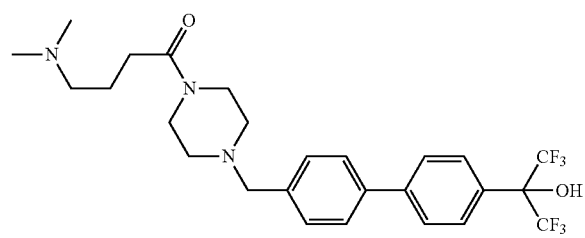
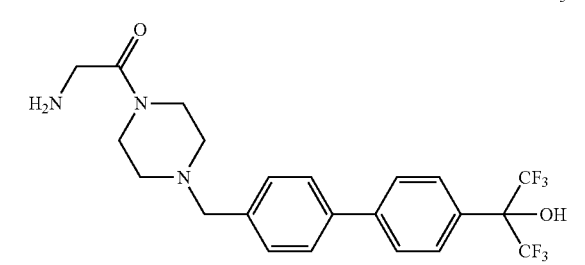
194
-continued
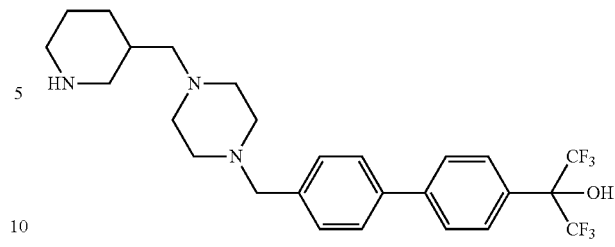
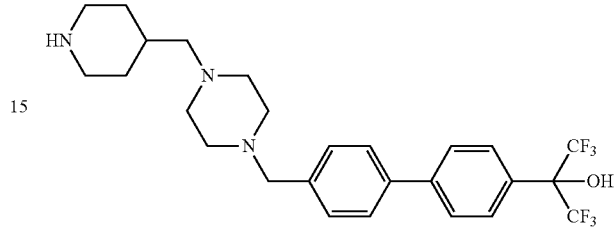
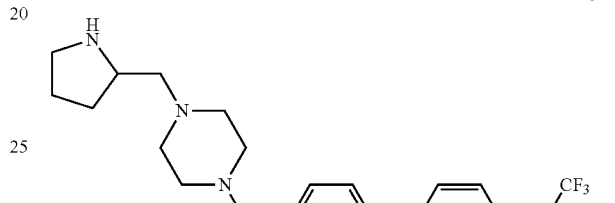
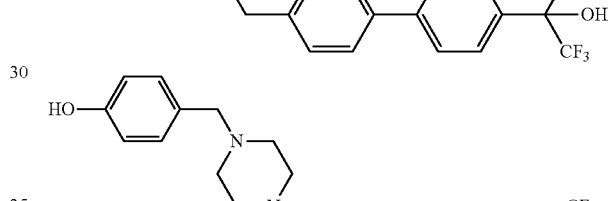
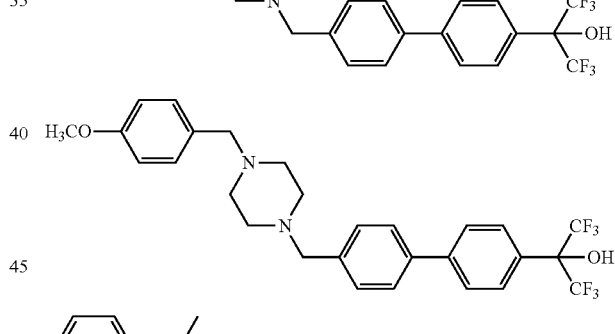
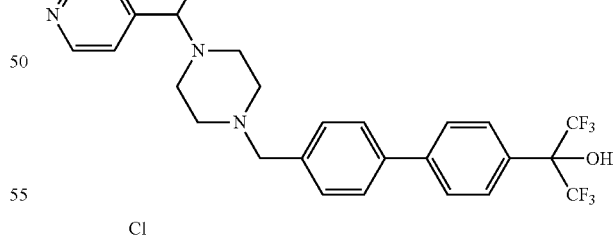
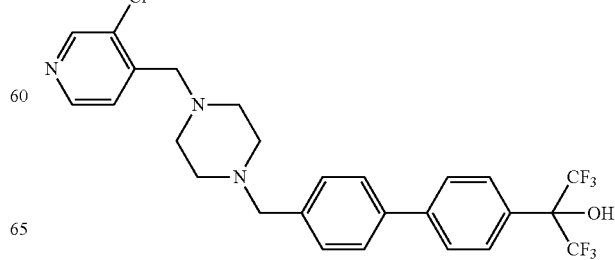

195
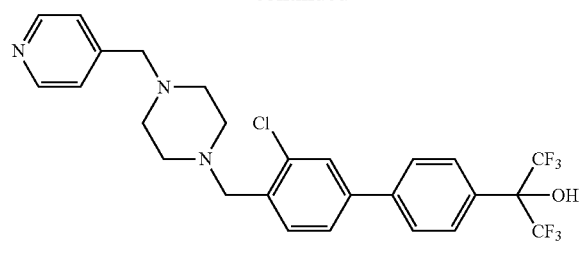
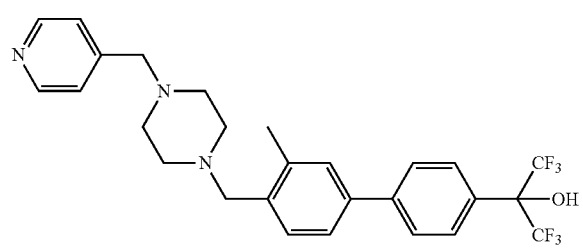
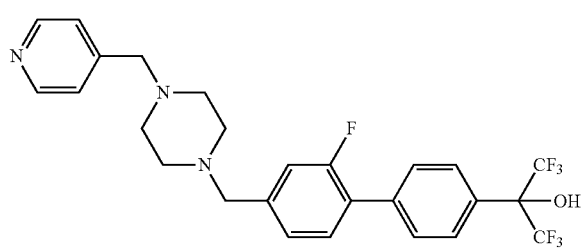
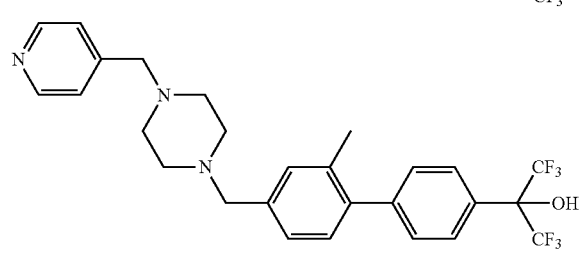
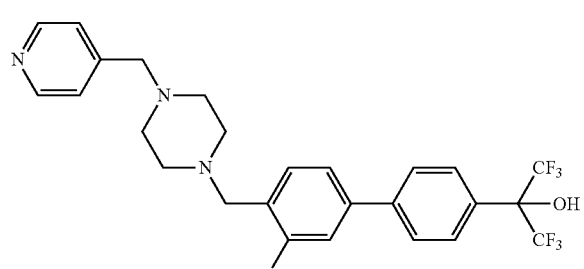
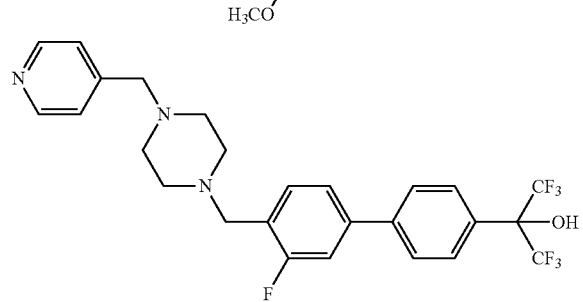
196
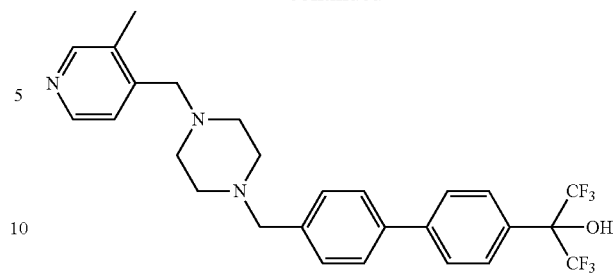
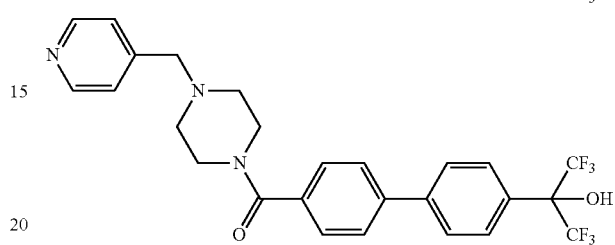
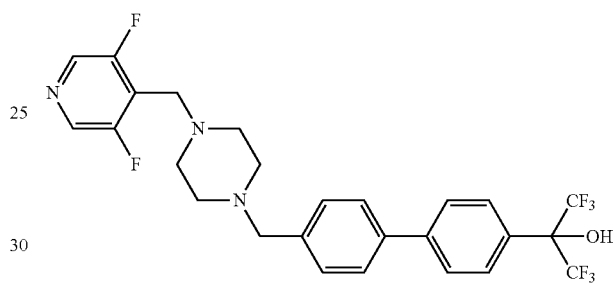
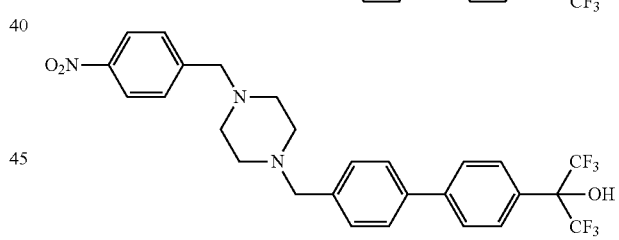
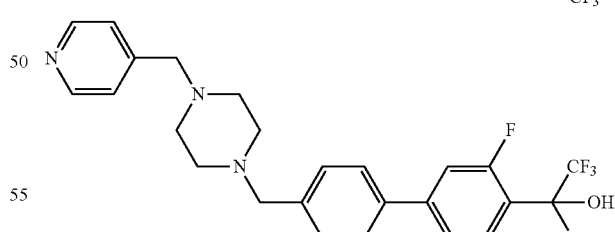
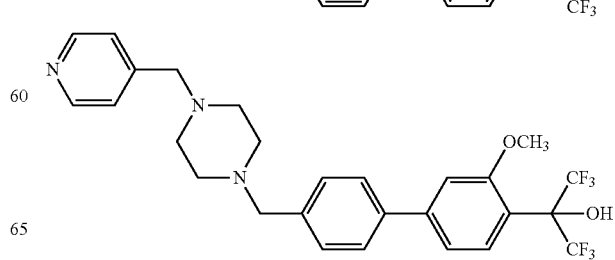

197
-continued
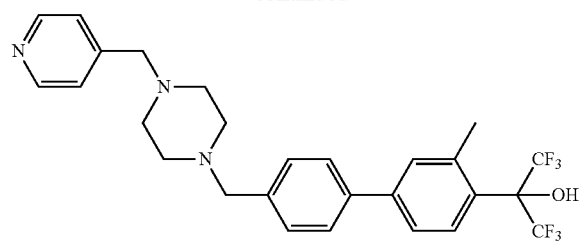
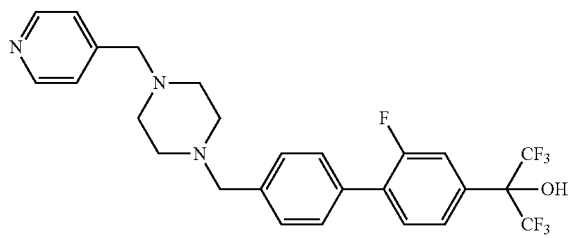
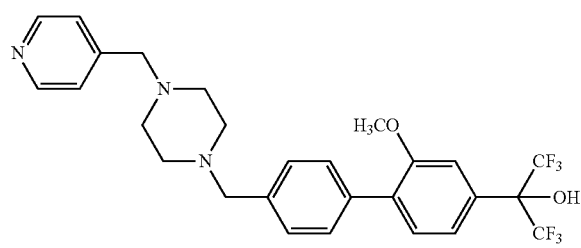
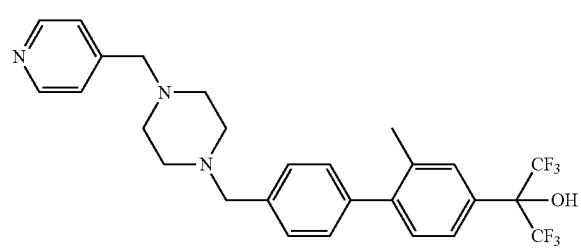
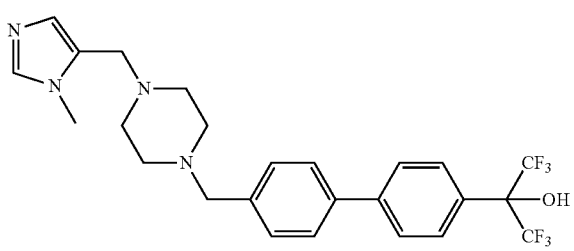
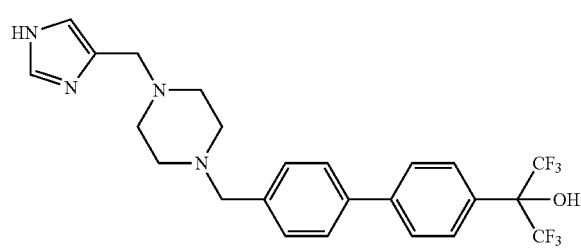
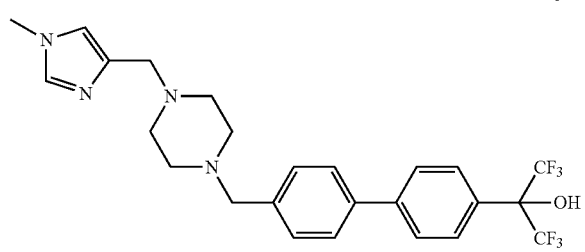
198
-continued
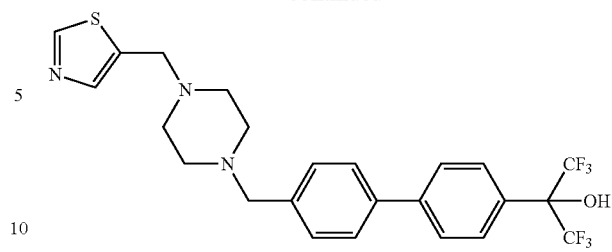
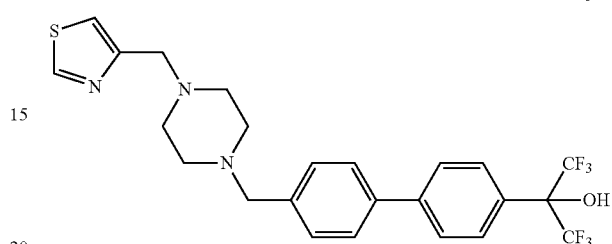
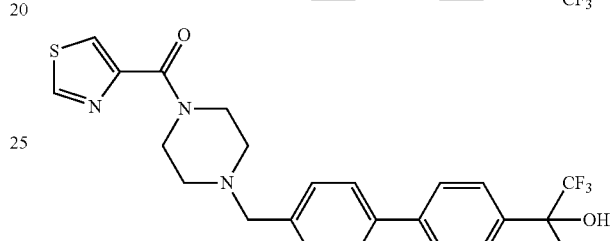
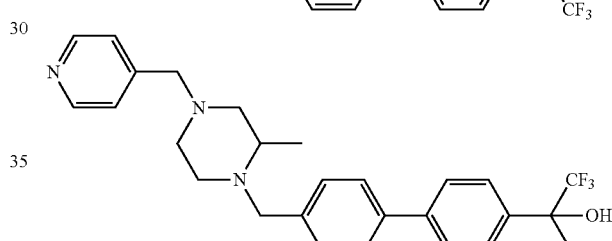
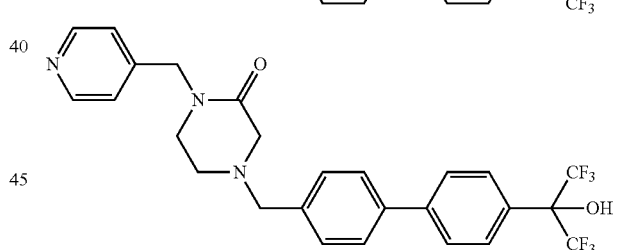
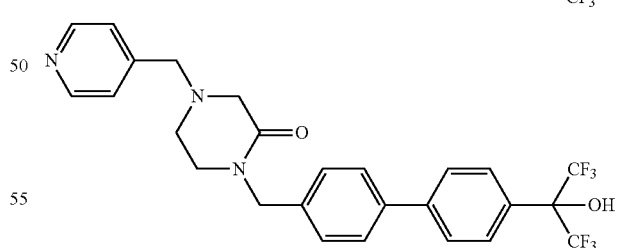
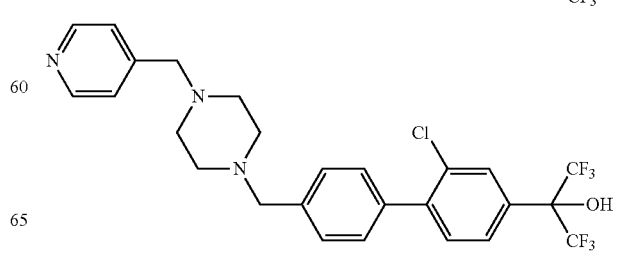

-continued
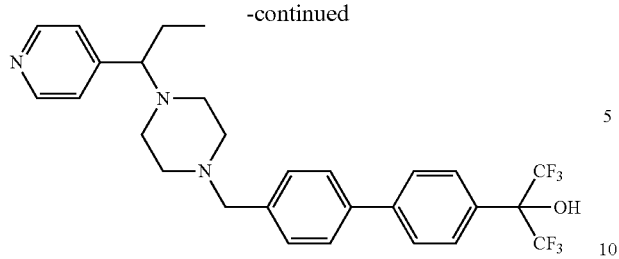
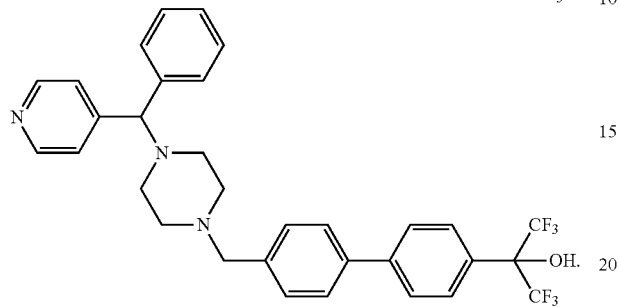
* * * * *

```
                              SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 1
gtagaaaccg ctgccaaca                                                    19

<210> SEQ ID NO 2
<211> LENGTH: 17
<212> TYPE: DNA
<213> ORGANISM: Artificial Sequence
<220> FEATURE:
<223> OTHER INFORMATION: A synthetic oligonucleotide

<400> SEQUENCE: 2
atcacctccc gctgctt                                                      17

<210> SEQ ID NO 3
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 3
cccctgaccg atgtggact                                                    19

<210> SEQ ID NO 4
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 4
caggatgctt tggcgatga                                                    19

<210> SEQ ID NO 5
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 5
tcatcttggt gtccgtgatc g                                                 21

<210> SEQ ID NO 6
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 6
tttatcaggg gcacggaagt g                                                 21
```

<210> SEQ ID NO 7
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 7
tgcaccacca actgcttagc                                              20

<210> SEQ ID NO 8
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 8
ggcatggact gtggtcatga g                                            21

<210> SEQ ID NO 9
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 9
ctccagaagg ccctcagact ac                                           22

<210> SEQ ID NO 10
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 10
agctttccct ccgcattgac acag                                         24

<210> SEQ ID NO 11
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 11
gccaagaaga ccattcccga                                              20

<210> SEQ ID NO 12
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 12
tcagtgctac aatcttcttc agaggaca                                     28

<210> SEQ ID NO 13
<211> LENGTH: 20
<212> TYPE: DNA
<213> ORGANISM: Artificial Sequence
<220> FEATURE:

```
<223> OTHER INFORMATION: A synthetic oligonucleotide

<400> SEQUENCE: 13
acacattggg ggtaggaaca                                        20

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 14
aactttggca ttgtggaagg                                        20
```